United States Patent
Strandwitz et al.

(10) Patent No.: US 11,116,804 B2
(45) Date of Patent: Sep. 14, 2021

(54) MODULATION OF THE GUT MICROBIOME TO TREAT MENTAL DISORDERS OR DISEASES OF THE CENTRAL NERVOUS SYSTEM

(71) Applicant: Holobiome, Inc., South Boston, MA (US)

(72) Inventors: Philip Strandwitz, Medford, MA (US); Kim Lewis, Newton, MA (US)

(73) Assignee: Holobiome, Inc., South Boston, MA (US)

( * ) Notice: Subject to any disclaimer, the term of this patent is extended or adjusted under 35 U.S.C. 154(b) by 125 days.

(21) Appl. No.: 16/084,511

(22) PCT Filed: Mar. 13, 2017

(86) PCT No.: PCT/US2017/022091
§ 371 (c)(1),
(2) Date: Sep. 12, 2018

(87) PCT Pub. No.: WO2017/160711
PCT Pub. Date: Sep. 21, 2017

(65) Prior Publication Data
US 2019/0070225 A1    Mar. 7, 2019

Related U.S. Application Data

(60) Provisional application No. 62/307,991, filed on Mar. 14, 2016.

(51) Int. Cl.
| | |
|---|---|
| *A61K 35/742* | (2015.01) |
| *A61K 35/74* | (2015.01) |
| *C12N 9/02* | (2006.01) |
| *C12N 9/10* | (2006.01) |
| *C12N 9/78* | (2006.01) |
| *C12N 9/88* | (2006.01) |
| *A61K 35/745* | (2015.01) |
| *A61P 25/22* | (2006.01) |
| *A61P 25/18* | (2006.01) |
| *A61P 25/24* | (2006.01) |

(52) U.S. Cl.
CPC ............ *A61K 35/742* (2013.01); *A61K 35/74* (2013.01); *A61K 35/745* (2013.01); *A61P 25/18* (2018.01); *A61P 25/22* (2018.01); *A61P 25/24* (2018.01); *C12N 9/0008* (2013.01); *C12N 9/0069* (2013.01); *C12N 9/1096* (2013.01); *C12N 9/78* (2013.01); *C12N 9/88* (2013.01); *C12Y 102/01019* (2013.01); *C12Y 113/12001* (2013.01); *C12Y 206/01082* (2013.01); *C12Y 305/03011* (2013.01); *C12Y 401/01015* (2013.01); *C12Y 401/01017* (2013.01); *Y02A 50/30* (2018.01)

(58) Field of Classification Search
CPC ........ C12N 9/00; C12N 9/008; C12N 9/0069; C12N 9/1096; C12N 9/78; C12N 9/88; A61K 35/742; A61K 35/74; A61K 35/745; A61K 35/741; C12Y 102/01019; C12Y 113/12001; C12Y 206/01082; C12Y 305/03011; C12Y 401/01015; C12Y 401/01017
See application file for complete search history.

(56) References Cited

U.S. PATENT DOCUMENTS

| | | | |
|---|---|---|---|
| 8,906,668 B2 | 12/2014 | Henn et al. | |
| 9,011,834 B1 | 4/2015 | McKenzie et al. | |
| 9,028,841 B2 | 5/2015 | Henn et al. | |
| 9,408,872 B2 | 8/2016 | Borody | |
| 9,486,487 B2 | 11/2016 | Cutcliffe et al. | |
| 9,533,014 B2 | 1/2017 | Henn et al. | |
| 9,703,929 B2 | 7/2017 | Apte et al. | |
| 2002/0013270 A1 * | 1/2002 | Bolte | A61P 1/00 514/2.9 |
| 2014/0147425 A1 | 5/2014 | Henn et al. | |
| 2014/0328803 A1 | 11/2014 | McKenzie et al. | |
| 2014/0341921 A1 | 11/2014 | Honda et al. | |
| 2015/0265661 A1 * | 9/2015 | Newburg | A23L 33/10 424/93.45 |
| 2016/0375065 A1 | 12/2016 | Mazmanian et al. | |
| 2017/0270268 A1 | 9/2017 | Apte et al. | |

FOREIGN PATENT DOCUMENTS

| | | | | |
|---|---|---|---|---|
| EP | 1 988 155 A1 | 11/2008 | | |
| JP | 2004-357535 A | 12/2004 | | |
| WO | WO-2011137369 A1 * | 11/2011 | ............... | C12N 9/88 |

(Continued)

OTHER PUBLICATIONS

Beye et al., "Careful use of 16S rRNA gene sequence similarity values for the identification of *Mycobacterium* species", New Microbe and New Infect 2018; 22: 24-29 (Year: 2018).*

Edgar et al., "Updating the 97% identity threshold for 16S ribosomal RNA OTUs"Bioinformatics, vol. 34, Issue 14, Jul. 15, 2018, pp. 2371-2375 (Year: 2018).*

(Continued)

*Primary Examiner* — Ruth A Davis
(74) *Attorney, Agent, or Firm* — Cooley LLP; J. Dean Farmer; Jessica D. Cande

(57) ABSTRACT

The present disclosure relates to methods of treating at least one symptom of a mental disorder or disease of the central nervous system in a subject by modulating the amount of GABA produced in the subject's gut. The present disclosure also relates to methods of culturing the bacterial strain new bacterial strains. Also disclosed are methods of identifying bacterial strains capable of producing GABA, and engineering strains to produce GABA.

18 Claims, 18 Drawing Sheets

Specification includes a Sequence Listing.

(56) References Cited

FOREIGN PATENT DOCUMENTS

| WO | WO-2012142605 A1 | * | 10/2012 | | C12N 1/20 |
|---|---|---|---|---|---|
| WO | WO 2012/162496 A1 | | 11/2012 | | |
| WO | WO 2013/107913 A1 | | 7/2013 | | |
| WO | WO-2013154725 A1 | * | 10/2013 | | A23L 33/10 |
| WO | WO 2014/121298 A2 | | 8/2014 | | |
| WO | WO 2014/121301 A1 | | 8/2014 | | |
| WO | WO 2014/121302 A2 | | 8/2014 | | |
| WO | WO 2014/121304 A1 | | 8/2014 | | |
| WO | WO 2014/145958 A2 | | 9/2014 | | |
| WO | WO 2016/069795 A2 | | 5/2016 | | |
| WO | WO 2018/223146 A1 | | 12/2018 | | |

OTHER PUBLICATIONS

Rossi-Tamisier et al., "Cautionary tale of using 16S rRNA gene sequence similarity values in identification of human-associated bacterial species", Int J Syst Evol Microbiol Jun. 2015;65(Pt 6):1929-34. doi: 10.1099/ijs.0.000161. Epub Mar. 3, 2015 (Year: 2015).*
Dhakal et al. "Production of GABA (γ-Aminobutyric Acid) By Microorganisms: A Review", Brazilian Journal of Microbiology (2012): 1230-1241 (Year: 2012).*
Aziz, R. K. et al. "The RAST Server: Rapid Annotations using Subsystems Technology," BMC Genomics 9: 75 (Feb. 8, 2008) doi: 10.1186/1471-2164-9-75 (pp. 1-15 provided).
Bollman, A. et al., "Incubation of Environmental Samples in a Diffusion Chamber Increases the Diversity of Recovered Isolates," Appl Environ Microbiol. Oct. 2007; 73(20):6386-6390.
Buckel, W. et al. "Energy conservation via electron bifurcating ferredoxin reduction and proton/Na(+) translocating ferredoxin oxidation," Biochim Biophys Acta 1827 (2013), 94-113.
Bystrirsky, A. "Treatment-resistant anxiety disorders," Molecular Psychiatry (2006) 11, 805-814.
Carabotti, M. et al., "The gut-brain axis: interactions between enteric microbiota, central and enteric nervous systems," Annals of Gastroenterology (2015) 28, 203-209.
Chang, L. et al., "Magnetic Resonance Spectroscopy Studies of GABA in Neuropsychiatric Disorders," J Clin Psychiatry. 2003;64 (Suppl 3):7-14.
Cho, I. and Blaser, M.J., "The human microbiome: at the interface of health and disease," Nat Rev Genet. Mar. 13, 2012;13(4):260-270; doi:10.1038/nrg3182 (pp. 1-28 provided).
D'Onofrio, A. et al., "Siderophores from Neighboring Organisms Promote the Growth of Uncultured Bacteria," Chemistry & Biology 17, 254-264, Mar. 26, 2010.
Diaz Heijtz, R. et al., "Normal gut microbiota modulates brain development and behavior," PNAS, Feb. 15, 2011, vol. 108, No. 7, 3047-3052.
Dinan, T.G. et al., "Collective unconscious: how gut microbes shape human behavior," Journal of Psychiatric Research 63 (2015) 1-9.
Esel, E. et al., "The Effects of Electroconvulsive Therapy on GABAergic Function in Major Depressive Patients," The Journal of ECT. 24(3):224-228, Sep. 2008.
Feehily, C. et al., "Role of glutamate metabolism in bacterial responses towards acid and other stresses," Journal of Applied Microbiology, 2013, 114, 11-24.
Fodor, A. A. et al., "The 'most wanted' taxa from the human microbiome for whole genome sequencing," PLoS One, Jul. 2012, 7(7): e41294 (pp. 1-11 provided).
Gaetz, W. et al., "GABA estimation in the brains of children on the autism spectrum: measurement precision and regional cortical variation," Neuroimage. Feb. 1, 2014; 86:1-9; doi:10.1016/j.neuroimage. 2013.05.068 (pp. 1-20 provided).
Gareau, M. G. et al., "Bacterial infection causes stress-induced memory dysfunction in mice," Gut, 2011; 60(3):307-317.
Hardman, J. K. and Stadtman T. C., "Metabolism of ω-amino acids. I. Fermentation of γ-aminobutyric acid by *Clostridium aminobutyricum* n. sp.," J Bacteriol., 1960; 79:544-548.
Holm, S., "A Simple Sequentially Rejective Multiple Test Procedure ," Scand J Statist 6: 65-70, 1979.
Hong, S. N. and Rhee, P-L., "Unraveling the ties between irritable bowel syndrome and intestinal microbiota," World J Gastroenterol, Mar. 14, 2014; 20(10): 2470-2481.
Hsiao, E. Y. et al., "Microbiota Modulate Behavioral and Physiological Abnormalities Associated with Neurodevelopmental Disorders," Cell 155, 1451-1463, Dec. 19, 2013.
Howitt, M. R. and Garrett, W. S., "A complex microworld in the gut: gut microbiota and cardiovascular disease connectivity," Nat. Med., 18, 1188-1189 (Aug. 2012).
Kalueff, A. V. and Nutt, D. J., "Role of GABA in anxiety and depression," Depression and Anxiety, 2007; 24: 495-517.
Kaeberlein, T. et al., "Isolating "Uncultivable" Microorganisms in Pure Culture in a Simulated Natural Environment," Science, May 10, 2002, vol. 296, 1127-1129.
Kendell, S. F. et al., "GABA and glutamate systems as therapeutic targets in depression and mood disorders," Expert Opin. Ther. Targets, 2005; 9(1):153-168.
Krystal, J. H. et al., "Glutamate and GABA systems as targets for novel antidepressant and mood-stabilizing treatments," Molecular Psychiatry 7, S71-S80, (2002).
Lagier, J.-C. et al., "The Rebirth of Culture in Microbiology through the Example of Culturomics to Study Human Gut Microbiota," Clin Microbiol Rev 28(1):237-264.
Ling, L. L. et al., "A new antibiotic kills pathogens without detectable resistance," Nature vol. 517, pp. 455-459 (Jan. 22, 2015) (19 pages, including supplement and 1 page erratum, provided).
Mandal, S. et al., "Analysis of composition of microbiomes: a novel method for studying microbial composition," Microb Ecol Health Dis., 2015; 26:27663; dx.doi.org/10.3402/mehd.v26.27663 (pp. 1-7 provided).
Matsumoto, M. et al., "Impact of intestinal microbiota on intestinal luminal metabolome," Sci Rep. 2012; 2:233; doi:10.1038/srep00233 (pp. 1-10 provided).
Mayer, E. A. et al., "Gut microbes and the brain: paradigm shift in neuroscience," The Journal of Neuroscience, Nov. 12, 2014, 34(46):15490-15496.
Moloney, R. D. et al., "Stress-induced visceral pain: toward animal models of irritable-bowel syndrome and associated comorbidities," Front Psychiatry, Feb. 16, 2015, 6:15; doi:10.3389/fpsyt.2015. 00015 (pp. 1-30 provided).
Nielsen, H. B. et al., "Identification and assembly of genomes and genetic elements in complex metagenomic samples without using reference genomes," Nat Biotechnol., Aug. 2014; 32(8):822-828 (and 4 pages supplement provided).
Nutt, D. J and Malizia, A. L., "New insights into the role of the GABA(A)-benzodiazepine receptor in psychiatric disorder," The British Journal of Psychiatry, vol. 179, Issue 5 Nov. 2001, pp. 390-396.
Smith, P. A., "Brain, Meet Gut," Nature, vol. 526, Oct. 15, 2015, pp. 312-314.
Strandwitz, P. et al., "GABA Modulating Bacteria of the Human Gut Microbiome," American Society of Microbiology General Meeting, Boston, Jun. 2016, 14 pages.
Strandwitz, P. et al., "GABA Modulating Bacteria of the Human Gut Microbiome," American Society of Microbiology General Meeting, Boston, Jun. 2016, Abstract, 1 page.
Strandwitz, P., "GABA Modulating Bacteria of the Human Gut Microbiome," Gastronauts Symposium, Duke, Sep. 2016, 14 pages.
Strandwitz, P. et al. "GABA is a Growth Factor for a "Most Wanted" Human Gut Bacterium," Boston Bacterial Meeting, Harvard, Jun. 2015, Poster, 1 page.
Strandwitz, P. et al. "GABA as a Growth Factor for tha Human Gut Microbiota," American Society of Microbiology General Meeting, Boston, Jun. 2014, 11 pages.
Strandwitz, P. et al. "GABA is a Growth Factor for Uncultured Bacteria from the Human Gut Microbiome," American Society of Microbiology General Meeting, Boston, Jun. 2014, Abstract, 1 page.
Strandwitz, P. et al. "GABA as a Growth Factor for the Human Gut Microbiome," American Society of Microbiology General Meeting, Boston, Jun. 2014, Poster, 1 page.

(56) References Cited

OTHER PUBLICATIONS

Strandwitz, P. et al. "GABA as a Growth Factor for an Uncultured Bacterium from the Human Gut Microbiota," Boston Bacterial Meeting, Harvard, Jun. 2014, 12 pages.
Strandwitz, P. et al. "GABA is a Growth Factor for Uncultured Bacteria from the Human Gut Microbiome," Boston Bacterial Meeting, Harvard, Jun. 2014, Abstract, 1 page.
Strandwitz, P. et al. "GABA is a Growth Factor for Uncultured Bacteria from the Human Gut Microbiome," Keystone Symposium, Montana, Mar. 2014, Abstract, 1 page.
Strandwitz, P. et al. "GABA is a Growth Factor for Uncultured Bacteria from the Human Gut Microbiome," Keystone Symposium, Montana, Mar. 2014, Poster, 1 page.
Strandwitz, P. et al. "GABA is a Growth Factor for Uncultured Bacteria from the Human Gut Microbiome," Keystone Symposium, Montana, Apr. 2, 2014, 11 pages.
Strandwitz, P. et al. "The Gut-Brain-Axis: Neurotransmitter Modulation by the Microbiota," Channing Division of Network Medicine, HMS and Brigham, Dec. 2016 23 pages.
Strandwitz, P. et al. "The Gut-Brain-Axis: Neurotransmitter Modulation by the Microbiota," Channing Division of Network Medicine, HMS and Brigham, Dec. 2016, Abstract, 1 page.
Strandwitz, P. et al. "The Gut-Brain-Axis: Neurotransmitter Modulation by the Microbiota," Discovery on Target Conference, Boston, Sep. 2016, 24 pages.
Strandwitz, P. et al. "The Gut-Brain-Axis: Neurotransmitter Modulation by the Microbiota," Vassar College, Nov. 2016, 22 pages.
The UniProt Consortium, "UniProt: a hub for protein information," Nucleic Acids Research, 2015, vol. 43, Database issue, D204-D212.
Wang, D. and Kriegstein, A. R. "Defining the role of GABA in cortical development," J Physiol, 587.9 (2009) pp. 1873-1879.
Wlodarska, M. et al. "An Integrative View of Microbiome-Host Interactions in Inflammatory Bowel Diseases", Cell Host Microbe., 17, 577-591 (May 13, 2015).
Yano, J. M. et al., "Indigenous Bacteria from the Gut Microbiota Regulate Host Serotonin Biosynthesis," Cell 161, 264-276, Apr. 9, 2015.
Zheng, P. et al., "Metabolite signature for diagnosing major depressive disorder in peripheral blood mononuclear cells," J Affect Disord., 2016; links195:75-81.
Backhed, F. et al., "Defining a healthy human gut microbiome: current concepts, future directions, and clinical applications" Cell Host & Microbe, 12, 611-622, (2012).
Barrett, E. et al. "γ-Aminobutyric acid production by culturable bacteria from the human intestine", J Appl Microbiol 113, 411-417 (2012).
Bhagwagar, Z. et al. "Low GABA concentrations in occipital cortex and anterior cingulate cortex in medication-free, recovered depressed patients", Int J Neuropsychopharmacol 11 , 255-260 (2008).
Bravo, J. et al. "Ingestion of Lactobacillus strain regulates emotional behavior and central GABA receptor expression in a mouse via the vagus nerve", PNAS, vol. 108, No. 38, p. 16050-16055 (2011).
Caporaso, J. G. et al. "Ultra-high-throughput microbial community analysis on the Illumina HiSeq and MiSeq platforms" ISME J 6, 1621-1624 (2012).
Caporaso, J. G. et al. "QIIME allows analysis of high-throughput community sequencing data", Nat Methods 7, 335-336 (2010).
Cenit M. C. et al. "Rapidly expanding knowledge on the role of the gut microbiome in health and disease" Biochim Biophys Acta, 1842, 1891-1992 (2014).
Chun, J. et al., "EzTaxon: a web-based tool for the identification of prokaryotes based on 16S ribosomal RNA gene sequences" International journal of Systematic and Evolutionary Microbiology 57, 2259-2261 (2007).
De Biase, D. et al. "Glutamate decarboxylase-dependent acid resistance in orally acquired bacteria: function, distribution and biomedical implications of the gadBC operon" Mol Microbiol 86, 770-786 (2012).
De Palma, G. et al. "Microbiota and host determinants of behavioural phenotype in maternally separated mice", Nature Communications 6, 7735, doi: 10.1038/ncomms8735, pp. 1-13 provided (2015).
Deutscher, J. et al. "How phosphotransferase system-related protein phosphorylation regulates carbohydrate metabolism in bacteria", Microbiol Mol Biol R 70, 939-1031 (and 1 page author's correction provided) (2006).
Dubin, M. J. et al. "Elevated prefrontal cortex GABA in patients with major depressive disorder after TMS treatment measured with proton magnetic resonance spectroscopy", J Psychiatry Neurosci 41, E37-45 (2016).
Enroth, H. et al. "Immunomagnetic separation and PCR for detection of Helicobacter pylori in water and stool specimens", J Clin Microbiol 33, 2162-2165 (1995).
Eckburg et al., "Diversity of the Human Intestinal Microbial Flora", Science, vol. 308, Jun. 10, 2005, pp. 1635-1638.
Fallingborg, J. "Intraluminal pH of the human gastrointestinal tract", Danish Medical Bulletin 46, 183-196 (1999).
Garrett, W. S. "Cancer and the microbiota", Science 348, 80-86 (2015).
Hamilton, M. J. et al. "High-throughput DNA sequence analysis reveals stable engraftment of gut microbiota following transplantation of previously frozen fecal bacteria", Gut Microbes 4, 125-135, (2013).
Hasler, G. et al. "Reduced prefrontal glutamate/glutamine and gamma-aminobutyric acid levels in major depression determined using proton magnetic resonance spectroscopy", Arch Gen Psychiatry 64, 193-200, (2007).
Hyland, N. P. & Cryan, J. F. "A Gut Feeling about GABA: Focus on GABA(B) Receptors", Frontiers in Pharmacology 1, Article 124, doi: 10.3389/fphar.2010.00124 (pp. 1-9 provided) (2010).
Inan, M., Petros, T. J. & Anderson, S. A. "Losing your inhibition: linking cortical GABAergic interneurons to schizophrenia" Neurobiol Dis 53, 36-48, (2013).
Jiang, H. et al. "Altered fecal microbiota composition in patients with major depressive disorder", Brain Behav Immun 48, 186-194, (2015).
Jukes, T. H. "Recent advances in studies of evolutionary relationships between proteins and nucleic acids", Space Life Sciences 1, 469-490 (1969).
Kakee, A. et al. "Efflux of a suppressive neurotransmitter, GABA, across the blood-brain barrier", J Neurochem 79, 110-118 (2001).
Kannampalli, P. & Sengupta, J. N. "Role of principal ionotropic and metabotropic receptors in visceral pain", Journal of Neurogastroenterology and Motility 21, 147-158, (2015).
Kelly, J. R. et al. "Transferring the blues: Depression-associated gut microbiota induces neurobehavioural changes in the rat", J Psychiatr Res 82, 109-118, (2016).
Kitagawa M. et al., "Complete set of ORF clones of Escherichia coli ASKA library (a complete set of E. coli K-12 ORF archive): unique resources for biological research", DNA Research : an international journal for rapid publication of reports on genes and genomes 12, 291-299 (2005).
Komatsuzaki et al., "Production of γ-aminobutyric acid (GABA) by Lactobacillus paracasei isolated from traditional fermented foods", Food Microbiology 22, 497-504 (2005).
Kopylova, E. "SortMeRNA: fast and accurate filtering of ribosomal RNAs in metatranscriptomic data" Bioinformatics 28, 3211-3217 (2012).
Li, Y. et al. "Implications of GABAergic Neurotransmission in Alzheimer's Disease" Front Aging Neurosci 8, Article 31, doi: 10.3389/fnagi.2016.00031 (pp. 1-12 provided) (2016).
Li, H. et al., "Lactic acid bacterial cell factories for gamma-aminobutyric acid", Amino Acids (2010) 39:1107-1116.
Lin, Q. "Submerged fermentation of Lactobacillus rhamnosus YS9 for gamma-aminobutyric acid (GABA) production", Brazilian Journal of Microbiology 44, 183-187 (2013).
Luscher, B. et al. "The GABAergic deficit hypothesis of major depressive disorder", Mol Psychiatry 16, 383-406, (2011).
Lyte, M. "Microbial endocrinology Host-microbiota neuroendocrine interactions influencing brain and behavior", Gut Microbes 5:3, 381-389; May/Jun. 2014.

(56) References Cited

OTHER PUBLICATIONS

Macian, "Lactobacillus rennini 16S rRNA gene, strain CECT 5922", European Nucleotide Archive, Sequence: AJ576007.1, Jul. 16, 2003, 2 pages.

Maldonado-Gomez, M. X. et al. "Stable Engraftment of Bifidobacterium longum AH1206 in the Human Gut Depends on Individualized Features of the Resident Microbiome", Cell Host & Microbe 20, 515-526, (2016).

Marques, T. M. et al. "Influence of GABA and GABA-producing Lactobacillus brevis DPC 6108 on the development of diabetes in a streptozotocin rat model", Beneficial Microbes 7, 409-420, (2016).

Matsumoto, M. et al. "Cerebral low-molecular metabolites influenced by intestinal microbiota: a pilot study", Front Syst Neurosci 7, Article 9, doi: 10.3389/fnsys.2013.00009 (pp. 1-19 provided) (2013).

Mohler, H. "The GABA system in anxiety and depression and its therapeutic potential", Neuropharmacology 62, 42-53, (2012).

Naseribafrouei, A. et al. "Correlation between the human fecal microbiota and depression" Neurogastroent Motil 26, 1155-1162, (2014).

Nemeroff, C. B. "The role of GABA in the pathophysiology and treatment of anxiety disorders", Psychopharmacology Bulletin 37, 133-146 (2003).

Ong, J. & Kerr, D. I. B. "Clinical potential of GABAB receptor modulators", CNS Drug Rev 11, p. 317-334 (2005).

O'Reardon, J. P. et al. "Vagus Nerve Stimulation (VNS) and Treatment of Depression: To the Brainstem and Beyond" Psychiatry (Edgmont) 3, 54-63 (2006).

Overbeek, R. et al., The Seed and the Rapid Annotation of microbial genomes using Subsystems Technology (RAST). Nucleic Acids Research 42, D206-D214 (2014).

Park, K. et al., "Cloning, sequencing and expression of a novel glutamate decarboxylase gene from a newly isolated lactic acid bacterium, Lactobacillus brevis OPK-3", Bioresource Technology 98 (2007) 312-319.

Perez, F. et al. "IPython: A system for interactive scientific computing" Comput Sci Eng 9, 21-29 (2007).

Petty, F. "Plasma concentrations of gamma-aminobutyric acid (GABA) and mood disorders: a blood test for manic depressive disease?" Clinical Chemistry 40, 296-302 (1994).

Pokusaeva, K. et al. "GABA-producing Bifidobacterium dentium modulates visceral sensitivity in the intestine", Neurogastroenterol Motil, 29, e12904, 14 pages, (2017).

Qin, J. et al. "A human gut microbial gene catalogue established by metagenomic sequencing", Nature 464, 59-65 (and 2 pages methods provided), (2010).

Richter, P. J. "On the validity of the Beck Depression Inventory—A review", Psychopathology 31, 160-168 (1998).

Robertson, C. E., Ratai, E. M. & Kanwisher, N. "Reduced GABAergic Action in the Autistic Brain", Curr Biol 26, 80-85, (2016).

Saitou, N. et al. "The neighbor-joining method: a new method for reconstructing phylogenetic trees", Mol Biol Evol 4, 406-425 (1987).

Sanacora, G. et al. "GABAergic contributions to the pathophysiology of depression and the mechanism of antidepressant action" CNS Neurol Disord Drug Targets 6, 127-140 (2007).

Sato et al., "Lactobacillus halophilus gene for 16S r RNA, partial sequence", GenBank, GenBank: AB240455.1, Jan. 7, 2006, 1 page.

Shi, F. et al., "Synthesis of γ-aminobutyric acid by expressing Lactobacillus brevis-derived glutamate decarboxylase in the Corynebacterium glutamicum strain ATCC 13032", Biotechnol Lett (2011) 33:2469-2474.

Sigel, E. & Steinmann, M. E. "Structure, function, and modulation of GABA(A) receptors", J Biol Chem 287, p. 40224-40231, (2012).

Siragusa, S. et al., "Synthesis of γ-Aminobutyric Acid by Lactic Acid Bacteria Isolated from a Variety of Italian Cheeses", Applied and Enviromental Microbiology, vol. 73, No. 22, Nov. 2007, pp. 7283-7290.

Storch, E. A. et al. "Factor structure, concurrent validity, and internal consistency of the Beck Depression Inventory-Second Edition in a sample of college students", Depress Anxiety 19, 187-189 (2004).

Strandwitz, P. et al. "Gaba Modulating Bacteria in the Human Gut Microbiome", Abstract ID#417, 1 page, Research, Innovation and Scholarship Expo (RISE) (2014).

Strandwitz, P. et al. "Gaba Modulating Bacteria—Can Our Bacteria Make Us Depressed?" Abstract ID#947, 1 page, Research, Innovation and Scholarship Expo (RISE) (2015).

Strandwitz, P. et al. "Gaba Modulating Bacteria of the Human Gut Microbiome", 2016, 1 page; online: http://www.abstractsonline.com/pp8/#!/4060/presentation/18619, American Society for Microbiology (2016).

Strandwitz, P. et al. "I'm Not Grumpy, It's My Microbiome", 7 pages, Online: http://americangut.org/im-not-grumpy-its-my-microbiome/ American Gut, (2016).

Szabadi, E. "Drugs for sleep disorders: mechanisms and therapeutic prospects", Br J Clin Pharmacol 61, 761-766, (2006).

Tamura, K. et al. "MEGA6: Molecular Evolutionary Genetics Analysis version 6.0", Mol Biol Evol 30, 2725-2729 (2013).

Tilg, H. et al. "Influence of the human intestinal microbiome on obesity and metabolic dysfunction" Current Opinion in Pediatrics 27, 496-501 (2015).

Treiman, D. M. "GABAergic mechanisms in epilepsy", Epilepsia 42 Suppl 3, 8-12 (2001).

Watson, D. et al. "Development and Validation of Brief Measures of Positive and Negative Affect—the PANAS Scales", J Pers Soc Psychol 54, 1063-1070 (1988).

White, J. P. et al. "Characterization of a {gamma}-aminobutyric acid transport system of Rhizobium leguminosarum bv. viciae 3841" J Bacteriol 191, 1547-1555 (2009).

Wixon, J. et al. "The Kyoto encyclopedia of genes and genomes—KEGG", Yeast 17, 48-55 (2000).

Yarza, P. et al., "Uniting the classification of cultured and uncultured bacteria and archaea using 16S rRNA gene sequences", Nat Rev Microbiol 12, 635-645 (2014).

Zheng, P. et al. "Gut microbiome remodeling induces depressive-like behaviors through a pathway mediated by the host's metabolism" Mol Psychiatry 21, 786-796, (2016).

Kootte, R. S. et al., "Improvement of Insulin Sensitivity after Lean Donor Feces in Metabolic Syndrome Is Driven by Baseline Intestinal Microbiota Composition," Cell Metabolism, Oct. 2017, 26, 611-619, 16 pages.

Machado, R. B. et al., "Sleep deprivation induced by the modified multiple platform technique: quantification of sleep loss and recovery," Brain Research, 2004, 1004: 45-51.

Ni Y. et al., "Molecular-Level Landscape of Diet-Gut Microbiome Interactions: Toward Dietary Interventions Targeting Bacterial Genes," mBio, 2015, 6(6): e01263-15, 14 pages.

Strandwitz, P. et al., "GABA Modulating Bacteria of the Human Gut Microbiota," Nature Microbiology, 2019; 4(3): 396-403, 20 pages.

Thiele, I. et al., "Personalized whole-body models integrate metabolism, physiology, and the gut microbiome," Mol Syst Biol, (2020) 16, e8982, 24 pages.

Dridi et al., "Archaea as emerging organisms in complex human microbiomes," Anaerobe (2011) 17: 56-63.

Leahy et al., "The Genome Sequence of the Rumen Methanogen Methanobrevibacter ruminantium Reveals New Possibilities for Controlling Ruminant Methane Emissions," PLoS One, Jan. 2010, vol. 5, Issue 1, e8926, 17 pages.

Miller et al., "Description of Methanobrevibacter gottschalkii sp. nov., Methanobrevibacter thaueri sp. nov., Methanobrevibacter woesei sp. nov. and Methanobrevibacter wolinii sp. nov.," International Journal of Systematic and Evolutionary Microbiology (2002), 52, 819-822.

Poehlein et al., "Draft Genome Sequences of Methanobrevibacter curvatus DSM11111, Methanobrevibacter cuticularis DSM11139, Methanobrevibacter filiformis DSM11501, and Methanobrevibacter oralis DSM7256," Genome Announcements, May/Jun. 2016, 4(3): e00617-16, 2 pages.

Rea et al., "*Methanobrevibacter millerae* sp. nov. and *Methanobrevibacter olleyae* sp. nov., methanogens from the ovine

(56) References Cited

OTHER PUBLICATIONS and bovine rumen that can utilize formate for growth," International Journal of Systematic and Evolutionary Microbiology (2007), 57, 450-456.

Rinke et al., "Insights into the phylogeny and coding potential of microbial dark matter," Nature, Jul. 2013, vol. 499, pp. 431-437.

Savant et al., "*Methanobrevibacter acididurans* sp. nov., a novel methanogen from a sour anaerobic digester," International Journal of Systematic and Evolutionary Microbiology (2002), 52, 1081-1087.

Van Hul, "From correlation to causality: the case of Subdoligranulum," Gut Microbes, 2020, vol. 12, No. 1, e1849998 (13 pages).

Zeikus et al., "*Methanobacterium arbophilicum* sp. nov. An obligate anaerobe isolated from wetwood of living trees," Antonie van Leeuwenhoek (1975) vol. 41, pp. 543-552.

\* cited by examiner

FIG. 2G

| Compound | Spotted Conc. | Compound | Spotted Conc. | Compound | Spotted Conc. |
|---|---|---|---|---|---|
| γ-amino Butyric Acid (GABA) | 100 mg/mL | Fructose | 100 mg/mL | L-Alanine | 50 mg/mL |
| γ-Butyrolactone | 200 mg/mL | Malate | 100 mg/mL | L-Asparagine monohydrate | 20 mg/mL |
| γ-Hydroxybutryic acid | 100 mg/mL | Sodium nitrate | 100 mg/mL | L-Aspartic Acid | 5 mg/mL |
| Putrescine Dihydrochloride | 100 mg/mL | Sodium pyruvate | 100 mg/mL | L-Cysteine HCl | 50 mg/mL |
| Spermidine Trihydrochloride | 100 mg/mL | Sodium Succinate | 100 mg/mL | L-Glutamic Acid | 5 mg/mL |
| Spermine Tetrahydrochloride | 100 mg/mL | Sodium Acetate | 100 mg/mL | L-Glutamine | 20 mg/mL |
| Succinate Semialdehyde | 15% w/v | Sodium Butyrate | 100 mg/mL | L-Phenylalanine | 20 mg/mL |
| Butyric Acid | 100% soln | Sodium Propionate | 100 mg/mL | L-Proline | 50 mg/mL |
| Lactic Acid | 100 mg/mL | L-Histidine | 40 mg/mL | L-Threonine | 50 mg/mL |
| Malonic Acid | 100 mg/mL | L-Isoleucine | 40 mg/mL | L-Glycine | 20 mg/mL |
| Succinic Acid | 100 mg/mL | L-Leucine | 20 mg/mL | Malic Acid | 100 mg/mL |
| Monosodium Glutamate | 100 mg/mL | L-Lysine | 100 mg/mL | ATCC Mineral Mix | 100% solution |
| Glycerol | 99.9% solution | L-Methionine | 50 mg/mL | ATCC Vitamin Mix | 100% solution |
| Glucose | 100 mg/mL | L-Tryptophan | 10 mg/mL | Induction | |
| Fructose | 100 mg/mL | L-Valine | 50 mg/mL | No induction | |

MODULATION OF THE GUT MICROBIOME TO TREAT MENTAL DISORDERS OR DISEASES OF THE CENTRAL NERVOUS SYSTEM

CROSS REFERENCE TO RELATED APPLICATIONS

This application is a national phase filing under 35 USC § 371 of International PCT Application PCT/US2017/022091, filed on Mar. 13, 2017, which claims priority to, and benefit of, U.S. Provisional Application No. 62/307,991, filed Mar. 14, 2016, the contents of each of which are herein incorporated by reference in their entirety.

GOVERNMENT FUNDING

This invention was made with government support under 3R01HG005824-02S1 awarded by the National Institute of Health. The government has certain rights in the invention.

INCORPORATION OF SEQUENCE LISTING

The contents of the text file named "HOBE-001-01US SeqList.txt," which was created on Sep. 5, 2018 and is 7.6 MB in size, are hereby incorporated by reference in their entirety.

FIELD OF THE DISCLOSURE

The present disclosure relates to compositions and methods for treating at least one symptom of a disease in a subject. In some cases, the disease is a mental disorder or a disease of the central nervous system. The present disclosure teaches treatment of the disease by modulating (e.g., increasing) the amount of endogenous GABA in a subject's body. In some embodiments, the present disclosure teaches modulating (e.g., increasing) the amount of GABA produced in the subject's gut by bacteria in the gut. For example, the present disclosure teaches administration to a subject in need thereof bacteria that are capable of producing GABA (e.g., inside a human gut).

The present disclosure also relates to methods of culturing previously uncultured bacterial strains. For instance, the present disclosure teaches the previously uncultured bacterial strain *Evtepia gabavorous* KLE1738. As set forth herein, newly uncultured bacterial strains such as *Evtepia gabavorous* KLE1738 can be cultured by providing growth factors necessary for the bacteria's growth and reproduction.

Also disclosed are methods of identifying bacterial strains capable of producing certain growth factors. For instance, described herein are methods of identifying bacterial strains capable of producing GABA, for instance under physiologically relevant conditions such as at a physiologically relevant pH.

BACKGROUND

The gut microbiome affects certain gastrointestinal and metabolic disorders, such as irritable bowel syndrome (IBS), Crohn's disease, ulcerative colitis, celiac disease, obesity, heart disease, type I and II diabetes, and colon cancer.

Microbiological studies have so far been limited, by necessity, to cultivable microorganisms. By some estimates, in external environments, 99% of bacteria are thought to be uncultured. The development of new techniques for culturing previously uncultured or unculturable bacteria can thus help to expand the scope of microbiology research.

SUMMARY OF THE INVENTION

The present disclosure provides compositions and methods for treating diseases such as mental illness or diseases of the central nervous system. In some embodiments, the present disclosure teaches therapeutic compositions comprising one or more bacteria (e.g., purified bacteria) that are capable of producing GABA. The bacteria can be capable of producing GABA under physiologically relevant conditions, including within a human gut. The present disclosure also provides methods of treating a subject in need thereof comprising administering to a subject a therapeutic composition comprising GABA-producing bacteria. As set forth herein, the GABA-producing bacteria can produce GABA in the subject's gut. The GABA can diffuse into other systems of the subject's body (e.g., the circulatory and nervous systems). There, the endogenous GABA can act as a neurotransmitter. In some embodiments, increased levels of GABA (e.g., in the nervous system) can improve the symptoms of the mental illness or disease of the central nervous system.

In some embodiments, the present disclosure also provides methods for identifying bacteria that produce GABA in humans at a physiologically relevant pH range and uses for these bacteria to modulate GABA levels in humans to treat mental illness.

The present disclosure also relates to a method of culturing previously uncultivated bacterial species. For instance the present disclosure teaches the isolation and characterization of a bacterial species KLE1738, provisionally named *Evtepia gabavorous*. Growth of *E. gabavorous* requires the presence of the growth factor GABA, which can be supplied by GABA-producing bacteria such as *Bacteroides fragilis* KLE1758.

In one aspect, the present disclosure provides a therapeutic composition comprising at least one purified bacterial population consisting of bacteria capable of producing GABA in a subject in need thereof.

In some embodiments, the at least one bacterial population consists of a bacteria comprising a 16S rDNA sequence at least about 95% identical to a 16S rDNA sequence selected from one of Seq. ID. Nos. 1-31 set forth in Table 1. In some embodiments, the at least one purified bacterial population consists of bacteria selected from the group consisting of: *Bacteroides caccae* KLE1911; *Bacteroides clarus* KLE1930; *Bacteroides dorei* KLE1912; *Bacteroides finegoldii* KLE1931; *Bacteroides fragilis* KLE1958; *Bacteroides massiliensis* KLE1932; *Bacteroides ovatus* KLE1770; *Bacteroides stercoris* KLE1933; *Bacteroides thetaiolaomicron* KLE1934; *Bacteroides uniformis* KLE1913; *Bacteroides vulgatus* KLE1910; *Bacteroides xylanisolvens* KLE1935; *Bifidobacterium adolescentis* KLE1879; *Blautia obeum* KLE1914; *Blautia wexlerae* KLE1916; *Butyricimonas virosa* KLE1938; *Clostridium perfringens* KLE1937; *Clostridium sordellii* KLE1939; *Clostridium* sp. KLE1862; *Clostridium* sp. KLE1918; *Coprobacillus* sp. KLE1779; *Coprococcus* sp. KLE1880; *Dorea longicatena* KLE1917; *Eggerthella lenta* KLE1926; *Eubacterium rectale* KLE1922; *Gordonibacter pamelaeae* KLE1915; *Oscillibacter* sp. KLE1928; *Parabacteroides distasonis* KLE2020; *Parabacteroides merdae* KLE1863; *Ruminococcus gnavus* KLE1940; *Turicibacter sanguinis* KLE1941, and combinations thereof.

In some embodiments, the at least one purified bacterial population consists of a bacteria comprising a 16S rDNA sequence at least about 95% identical to a 16S rDNA sequence selected from one of Seq. ID. Nos. 32-274 set forth in Table 2. In some embodiments, the at least one purified bacterial population consists of bacteria comprising a 16S rDNA sequence having at least 95% similarity to the 16S rDNA sequence selected from one of Seq. ID. Nos. 305-2217 set forth in Table 10. In some embodiments, the at least one purified bacterial population consists of bacteria comprising a DNA sequence which encodes an enzyme selected from: glutamate decarboxylase; putrescine aminotransferase; gamma-aminobutyraldehyde dehydrogenase; arginine decarboxylase; agmatinase; ornithine decarboxylase; or a combination thereof. In some embodiments, the glutamate decarboxylase; putrescine aminotransferase; gamma-aminobutyraldehyde dehydrogenase; arginine decarboxylase; agmatinase; ornithine decarboxylase; or a combination thereof, is encoded by a DNA sequence at least 70% similar in DNA sequence to any one of Seq. ID. Nos. 275-304 set forth in Table 3.

In some embodiments, the glutamate decarboxylase is encoded by a DNA sequence at least 95% similar in DNA sequence to a gene with a EMBL/GENBANK/DDBJ ID found in Table 4. In some embodiments, the putrescine aminotransferase is encoded by a DNA sequence at least 95% similar in DNA sequence to a gene with a EMBL/GENBANK/DDBJ ID found in Table 5. In some embodiments, the gamma-aminobutyraldehyde dehydrogenase is encoded by a DNA sequence at least 95% similar in DNA sequence to a gene with a EMBL/GENBANK/DDBJ ID found in Table 6. In some embodiments, the arginine decarboxylase is encoded by a DNA sequence at least 95% similar in DNA sequence to a gene with a EMBL/GENBANK/DDBJ ID found in Table 7. In some embodiments, the agmatinase is encoded by a DNA sequence at least 95% similar in DNA sequence to a gene with a EMBL/GENBANK/DDBJ ID found in Table 8. In some embodiments, the ornithine decarboxylase is encoded by a DNA sequence at least 95% similar in DNA sequence to a gene with a EMBL/GENBANK/DDBJ ID found in Table 9.

In some embodiments, the at least one purified bacterial population consists of bacteria comprising a 16S rDNA sequence having at least 95% similarity to a reference bacterium selected from the group consisting of: *Escherichia coli* MG1655; *Escherichia coli* Nissle 1917; or a combination thereof.

In some embodiments, the bacterial population consists of bacteria capable of producing GABA at a physiologically relevant pH. In some embodiments, the bacterial population consists of bacteria capable of producing GABA at a pH range between about 4.5 and about 7.5. In some embodiments, the bacterial population consists of bacteria capable of producing GABA inside the human gut.

In some embodiments, the composition is in the form of a probiotic, prebiotic, a capsule, a tablet, a caplet, a pill, a troche, a lozenge, a powders, a granule, a medical food, or a combination thereof. In some embodiments, the composition is administered as a fecal transplant.

In some embodiments, the bacteria are capable of producing GABA via expression of any combination of glutamate decarboxylase, putrescine aminotransferase, gamma-aminobutyraldehyde dehydrogenase, arginine decarboxylase, agmatinase, and/or ornithine decarboxylase.

In some embodiments, the therapeutic composition further comprises a purified bacterial strain that is cytotoxic or cytostatic to a GABA-consuming bacteria. In some embodiments, the GABA-consuming bacteria is *Evtepia gabavorous* or *Firmicutes bacterium* MGS:114.

In some embodiments, the therapeutic composition further comprises a prebiotic capable of stimulating the growth or GABA-production levels of a GABA-producing bacteria.

In one aspect, the present disclosure provides a method of treating a disease or disorder in a subject in need thereof, the method comprising administering to the subject a therapeutic composition comprising at least one purified bacterial population consisting of bacteria capable of producing GABA in a subject in need thereof.

In one aspect, the present disclosure provides the use of a therapeutic composition comprising at least one purified bacterial population consisting of bacteria capable of producing GABA in the manufacture of a medicament for the treatment of a disease.

In one aspect, the present disclosure provides the use of a therapeutic composition comprising at least one purified bacterial population consisting of bacteria capable of producing GABA for the treatment of a disease.

In some embodiments, the disease or disorder is a mental disease or disorder. In some embodiments, the mental disease or disorder is selected from the group consisting of depression, bipolar disorder, schizophrenia, anxiety, anxiety disorders, addiction, social phobia, treatment-resistant major depressive disorder (TR-MDD), major depressive disorder and its subtypes (melancholic depression, atypical depression, catatonic depression, postpartum depression, and seasonal affective disorder), Neurodegenerative amyloid disorders (Parkinson's, Alzheimer's, and Huntington's diseases) orthostatic tremor, Lafora disease, restless leg syndrome, neuropathic pain, pain disorders, dementia, epilepsy, stiff-person syndrome, premenstrual dysphoric disorder, autism spectrum disorder, sleep disorders, and attention deficit hyperactivity disorder (ADHD), and combinations thereof. In some embodiments, treating a disease or disorder comprises decreasing at least one symptom of the disease or disorder, such as fatigue, insomnia, motor dysfunction, stress, persistent anxiety, persistent sadness, social withdrawal, substance withdrawal, irritability, thoughts of suicide, thoughts of self-harm, restlessness, low sex drive, lack of focus, seizures, memory loss, anger, bouts of emotional reactivity, confusion, pain, and muscle spasms, loss of appetite, altered intestine motility, and combinations thereof.

In some embodiments, the at least one bacterial population consists of a bacteria comprising a 16S rDNA sequence at least about 95% identical to a 16S rDNA sequence selected from one of Seq. ID. Nos. of 1-31 set forth in Table 1. In some embodiments, the at least one purified bacterial population consists of bacteria selected from the group consisting of: *Bacteroides caccae* KLE1911; *Bacteroides clarus* KLE1930; *Bacteroides dorei* KLE1912; *Bacteroides finegoldii* KLE1931; *Bacteroides fragilis* KLE1958; *Bacteroides massiliensis* KLE1932; *Bacteroides ovatus* KLE1770; *Bacteroides stercoris* KLE1933; *Bacteroides thetaiotaomicron* KLE1934; *Bacteroides uniformis* KLE1913; *Bacteroides vulgatus* KLE1910; *Bacteroides xylanisolvens* KLE1935; *Bifidobacterium adolescentis* KLE1879; *Blautia obeum* KLE1914; *Blautia wexlerae* KLE1916; *Butyricimonas virosa* KLE1938; *Clostridium perfringens* KLE1937; *Clostridium sordellii* KLE1939; *Clostridium* sp. KLE1862; *Clostridium* sp. KLE1918; *Coprobacillus* sp. KLE1779; *Coprococcus* sp. KLE1880; *Dorea longicatena* KLE1917; *Eggerthella lenta* KLE1926; *Eubacterium rectale* KLE1922; *Gordonibacter pamelaeae* KLE1915; *Oscillibacter* sp. KLE1928; *Parabacteroides distasonis* KLE2020; *Parabacteroides merdae* KLE1863

*Ruminococcus gnavus* KLE1940; *Turicibacter sanguinis* KLE1941, and combinations thereof.

In some embodiments, the at least one purified bacterial population consists of a bacteria comprising a 16S rDNA sequence at least about 95% identical to a 16S rDNA sequence selected from one of Seq. ID. Nos. of 32-274 set forth in Table 2.

In some embodiments, the at least one bacterial population consists of a bacteria comprising a 16S rDNA sequence at least about 95% identical to any one of Seq ID Nos. 305-2217 set forth in Table 10.

In some embodiments, the at least one purified bacterial population consists of bacteria comprising a DNA sequence which encodes an enzyme selected from: glutamate decarboxylase; putrescine aminotransferase; gamma-aminobutyraldehyde dehydrogenase; arginine decarboxylase; agmatinase; ornithine decarboxylase; or a combination thereof.

In some embodiments, the glutamate decarboxylase; putrescine aminotransferase; gamma-aminobutyraldehyde dehydrogenase; arginine decarboxylase; agmatinase; ornithine decarboxylase; or a combination thereof, is encoded by a DNA sequence at least 70% similar to a DNA sequence selected from one of Seq. ID. Nos. 275-304 set forth in Table 3.

In some embodiments, the glutamate decarboxylase is encoded by a DNA sequence at least 95% similar in DNA sequence to a gene with a EMBL/GENBANK/DDBJ ID found in Table 4. In some embodiments, the putrescine aminotransferase is encoded by a DNA sequence at least 95% similar in DNA sequence to a gene with a EMBL/GENBANK/DDBJ ID found in Table 5. In some embodiments, the gamma-aminobutyraldehyde dehydrogenase is encoded by a DNA sequence at least 95% similar in DNA sequence to a gene with a EMBL/GENBANK/DDBJ ID found in Table 6. In some embodiments, the arginine decarboxylase is encoded by a DNA sequence at least 95% similar in DNA sequence to a gene with a EMBL/GENBANK/DDBJ ID found in Table 7. In some embodiments, the agmatinase is encoded by a DNA sequence at least 95% similar in DNA sequence to a gene with a EMBL/GENBANK/DDBJ ID found in Table 8. In some embodiments, the omithine decarboxylase is encoded by a DNA sequence at least 95% similar in DNA sequence to a gene with a EMBL/GENBANK/DDBJ ID found in Table 9.

In some embodiments, the bacteria is genetically engineered to produce GABA. In some embodiments, the bacteria is engineered to produce GABA via expression of glutamate decarboxylase; putrescine aminotransferase; gamma-aminobutyraldehyde dehydrogenase; arginine decarboxylase; agmatinase; ornithine decarboxylase; or a combination thereof.

In some embodiments, wherein the glutamate decarboxylase; putrescine aminotransferase; gamma-aminobutyraldehyde dehydrogenase; arginine decarboxylase; agmatinase; omithine decarboxylase; or a combination thereof, is encoded by a DNA sequence at least 70% similar in DNA sequence selected from one of Seq. ID. Nos. of 275-304 set forth in Table 3.

In some embodiments, the glutamate decarboxylase is encoded by a DNA sequence at least 95% similar in DNA sequence to a gene with a EMBL/GENBANK/DDBJ ID found in Table 4. In some embodiments, the putrescine aminotransferase is encoded by a DNA sequence at least 95% similar in DNA sequence to a gene with a EMBL/GENBANK/DDBJ ID found in Table 5. In some embodiments, the gamma-aminobutyraldehyde dehydrogenase is encoded by a DNA sequence at least 95% similar in DNA sequence to a gene with a EMBL/GENBANK/DDBJ ID found in Table 6. In some embodiments, the arginine decarboxylase is encoded by a DNA sequence at least 95% similar in DNA sequence to a gene with a EMBL/GENBANK/DDBJ ID found in Table 7. In some embodiments, the agmatinase is encoded by a DNA sequence at least 95% similar in DNA sequence to a gene with a EMBL/GENBANK/DDBJ ID found in Table 8. In some embodiments, the omithine decarboxylase is encoded by a DNA sequence at least 95% similar in DNA sequence to a gene with a EMBL/GENBANK/DDBJ ID found in Table 9.

In some embodiments, the at least one purified bacterial population consists of bacteria comprising a 16S rDNA sequence having at least 95% similarity to a reference bacterium selected from the group consisting of: *Escherichia coli* MG1655; *Escherichia coli* Nissle 1917; or a combination thereof.

In some embodiments, the bacterial population consists of bacteria capable of producing GABA at a physiologically relevant pH. In some embodiments, the bacterial population consists of bacteria capable of producing GABA at a pH range between about 4.5 and about 7.5. In some embodiments, bacterial population consists of bacteria capable of producing GABA inside the human gut. In some embodiments, the composition is administered as a fecal transplant. In some embodiments, the composition is administered as a probiotic. In some embodiments, the bacteria are capable of producing GABA via expression any combination of glutamate decarboxylase, putrescine aminotransferase, gamma-aminobutyraldehyde dehydrogenase, arginine decarboxylase, agmatinase, ornithine decarboxylase, and combinations thereof.

In some embodiments, the at least one bacterial strain is cytotoxic or cytostatic to a GABA-consuming bacteria. In some embodiments, the GABA-consuming bacteria is *Evtepia gabavorous* or *Firmicutes bacterium* MGS:114.

In some embodiments, the method of treating a subject further comprises identifying a subject in need of treatment by determining whether the subject would benefit from an increase in endogenous GABA by measuring an initial amount of GABA in the subject's stool. In some embodiments, the initial amount of GABA in the subject's stool is below about 8 µg per gram of wet or dry stool. In some embodiments, the amount of GABA in the subject's stool is increased relative to the initial amount after administering the therapeutic composition.

In some embodiments, the method of treating a subject further comprises identifying a subject in need of treatment by determining whether the subject would benefit from an increase in endogenous GABA by measuring an initial amount of GABA-producing bacteria in the subject's stool. In some embodiments, the initial amount of GABA-producing bacteria in the subject's stool is less than about 10% of total bacteria as measured by 16S sequence mapping. In some embodiments, at least one GABA-producing bacteria is increased in the subject's stool relative to the initial amount of GABA-producing bacteria in the subject's stool after administering the therapeutic composition.

In some embodiments, the method of treating a subject further comprises identifying a subject in need of treatment by determining whether the subject would benefit from an increase in endogenous GABA by measuring an initial amount of GABA in the subject's blood or serum. In some embodiments, the amount of GABA in the subject's blood or serum is below about 10 µg per liter of blood. In some embodiments, the amount of GABA in the subject's blood or serum is increased relative to the initial amount after administering the therapeutic composition.

In some embodiments, the method of treating a subject further comprises identifying a subject in need of treatment by determining whether the subject would benefit from an increase in endogenous GABA by measuring an amount of GABA in the subject's brain. In some embodiments, the amount of GABA in the subject's brain is below about 1.0 mM/kg. In some embodiments, the amount of GABA in the subject's brain is increased relative to the initial amount after administering the therapeutic composition.

In some embodiments, the method of treating a subject further comprises identifying a subject in need of treatment by determining whether the subject would benefit from an increase in endogenous GABA by measuring an initial amount of expression of GABA-producing enzymes in the subject's stool. In some embodiments, the GABA-producing enzymes are selected from glutamate decarboxylase, putrescine aminotransferase, gamma-aminobutyraldehyde dehydrogenase, arginine decarboxylase, agmatinase, ornithine decarboxylase, and combinations thereof. In some embodiments, the initial amount of enzyme expression is measured by qPCR. In some embodiments, the expression of enzymes is increased relative to the initial amount of enzyme expression after administering the therapeutic composition.

In some embodiments, the method of treating a subject further comprises identifying a subject in need of treatment by determining whether the subject would benefit from an increase in endogenous GABA by measuring an initial amount of GABAergic response in the subject's brain. In some embodiments, the amount of the GABAergic response in the subject's brain is increased relative to the initial amount after administering the therapeutic composition. In some embodiments, the therapeutic composition comprises a prebiotic capable of stimulating the growth or GABA production of GABA-producing bacteria.

In one aspect, the present disclosure provides a method of culturing a GABA-dependent bacteria, comprising disposing at least one live GABA-dependent bacterial cell on a suitable substrate, and providing a source of GABA.

In some embodiments, the suitable substrate is agar. In some embodiments, providing a source of GABA comprises co-culturing with another bacterial strain, said strain is capable of producing GABA. In some embodiments, GABA is added to the substrate. In some embodiments, the GABA-dependent bacteria is *E. gabavorous*.

In one aspect, the present disclosure provides a method of identifying a bacterial strain or strains capable of producing GABA at a physiologically relevant pH of the human intestinal tract, comprising:
(a) dispersing a sample believed to contain GABA-producing bacteria within a substrate, the substrate being at least partially permeable to GABA,
(b) contacting the substrate loaded with potential GABA-producing bacteria with a GABA-dependent bacterium; and
(c) identifying a GABA-producing bacteria by observing the formation of a colonies of the GABA-dependent bacteria around potential GABA-producing bacteria in the substrate.

In some embodiments, the substrate is being buffered to maintain the pH at a physiologically range found in the human gastrointestinal tract. In some embodiments, the GABA-dependent bacteria is *E. gabavorous*. In some embodiments, the pH range is between about 4.5 and about 7.5.

The present disclosure provides compositions and methods for treating mental illness or disease of the central nervous system in a subject and therapeutic compositions for the same. The method can comprise administering to the subject a bacterium and/or multiple bacteria capable of producing endogenous GABA in the subject's gut at a physiologically relevant pH. The present technology can have the advantage of alleviating the symptoms of a mental illness or disease of the central nervous system without the aid of synthetic medications (e.g., antidepressants), which can have unwanted side-effects, or in combination with existing medications. Additionally, the present technology can have the advantage of further improving the digestive health of the subject, such as improving intestinal motility and reducing gastrointestinal pain. Additional features and advantages of the present technology will be apparent to one of skill in the art upon reading the Detailed Description of the Invention, below.

BRIEF DESCRIPTION OF THE FIGURES

FIG. 2G shows a table of potential growth factors for *E. gabavorous* KLE1738, with green indicating induction of growth.

DETAILED DESCRIPTION OF THE INVENTION

Figure 1:
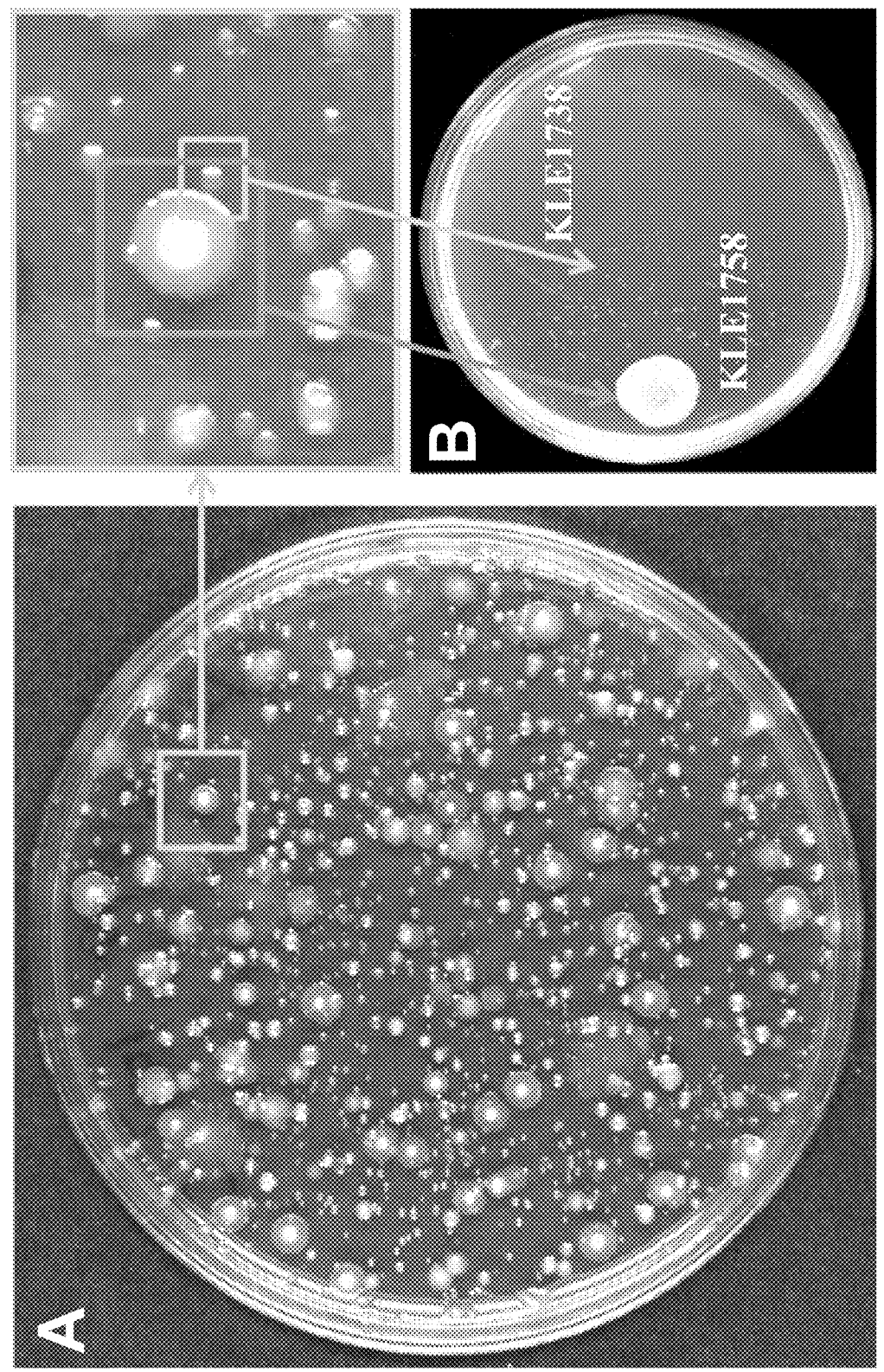
FIG. 1A shows a co-culture assay to grow and identify previously unculturable bacteria.
FIG. 1B shows the growth of *Evtepia gabavorous* KLE1738 in the presence of the helper bacteria *Bacteroides fragilis* KLE1758.

The present disclosure relates to compositions and methods for treating or decreasing a symptom of a disease in a subject. The disease can be a mental illness or a disease of the central nervous system. After identifying a subject with a mental illness or disease of the central nervous system, the method can comprise determining whether the subject would benefit from an increase in endogenous GABA, for instance by measuring the amount of GABA in the subject's stool, blood serum, or other bodily fluids, measuring levels of GABA in different regions of the brain, measuring the GABAergic response in different regions in the brain, measuring activity of GABA producing enzymes in stool, or by measuring the amount of GABA-producing bacteria in the subject's stool. The method can further comprise administering to the subject a GABA-producing bacterium or bacteria that can be capable of producing GABA in the subject's gut. (e.g., at a physiologically relevant pH of the gut).

Some bacteria produce GABA from gamma-aminobutyrate to maintain intracellular pH homoeostasis in order to overcome acid stress. As set forth herein, the production of GABA by microbes (e.g., bacteria) in the human gut can impact the health of a subject. For instance, GABA produced by bacteria in the human gut can act as a neurotransmitter to treat a mental illness, a disease of the central nervous system, or improve gastrointestinal health in a subject.

Definitions

As used herein "administer" and "administration" encompasses embodiments in which one person directs another to consume a bacteria or a bacterial composition in a certain manner and/or for a certain purpose, and also situations in which a user uses bacteria or a bacterial composition in a certain manner and/or for a certain purpose independently of or in variance to any instructions received from a second person. Non-limiting examples of embodiments in which one person directs another to consume a bacteria or bacterial composition in a certain manner and/or for a certain purpose include when a physician prescribes a course of conduct and/or treatment to a patient, when a parent commands a minor user (such as a child) to consume bacteria or a bacterial composition, when a trainer advises a user (such as an athlete) to follow a particular course of conduct and/or treatment, and when a manufacturer, distributer, or marketer recommends conditions of use to an end user, for example through advertisements or labeling on packaging or on other materials provided in association with the sale or marketing of a product.

The term "isolated" encompasses a bacterium or other entity or substance that has been (1) separated from at least some of the components with which it was associated when initially produced (whether in nature, such as human stool, or in an experimental setting, such as a Petri plate consisting of artificial growth medium), and/or (2) produced, prepared, purified, and/or manufactured by the hand of man. Isolated bacteria may be separated from at least about 10%, about 20%, about 30%, about 40%, about 50%, about 60%, about 70%, about 80%, about 90%, or more of the other components with which they were initially associated. In some embodiments, isolated bacteria are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components (such as other bacterial species). The terms "purify," "purifying" and "purified" refer to a bacterium or other material that has been separated from at least some of the components with which it was associated either when initially produced or generated (e.g., whether in nature or in an experimental setting), or during any time after its initial production, as recognized by those skilled in the art of bacterial cultivation. A bacterium or a bacterial population may be considered purified if it is isolated at or after production, such as from a material or environment containing the bacterium or bacterial population, and a purified bacterium or bacterial population may contain other materials up to about 10%, about 20%, about 30%, about 40), about 50%, about 60%, about 70%, about 80%, about 90%, or above about 90% and still be considered "isolated." In some embodiments, purified bacteria and bacterial populations are more than about 80%, about 85%, about 90%, about 91%, about 92%, about 93%, about 94%, about 95%, about 96%, about 97%, about 98%, about 996, or more than about 99% pure. In the instance of bacterial compositions provided herein, the one or more bacterial types present in the composition can be independently purified from one or more other bacteria produced and/or present in the material or environment containing the bacterial type. Bacterial compositions and the bacterial components thereof are generally purified from residual habitat products.

As used herein, "probiotic" is understood to mean "Live microorganisms which when administered in adequate amounts confer a health benefit on the host", as currently defined by the World Health Organization.

As used herein, "prebiotic" is understood to mean an ingredient that allows specific changes, both in the composition and/or activity in the gastrointestinal microbiota that may (or may not) confer benefits upon the host.

As used herein, "medical food" is understood to mean "a food which is formulated to be consumed or administered enterally under the supervision of a physician and which is intended for the specific dietary management of a disease or condition for which distinctive nutritional requirements, based on recognized scientific principles, are established by medical evaluation", as defined by 5(b) of the Orphan Drug Act (21 U.S.C. 360ee (b) (3)).

As used herein "initial amount" is understood to mean the amount of a substance, e.g., GABA in an aliquot of sample prior to administration of GABA-producing bacteria to the subject. Initial amount can be measured in terms of concentration. For instance, an initial amount can be measured in terms of micrograms of substance per milliliter of sample, e.g., micrograms of GABA per milliliter of blood or serum (μg GABA/mL blood or serum). The initial amount of can also be measured, for instance, as the amount of GABA in regions of the brain, such as the prefrontal cortex prior to administration of the GABA-producing bacteria. The amount of GABA can be represented in terms of millimoles of GABA per kg tissue (mmol GABA per kg of brain tissue).

The initial amount can also be measured, for instance, as the amount of GABA in a subject's stool sample prior to administration of GABA-producing bacteria to the subject. The amount of GABA can be represented in terms of micrograms of GABA per gram of stool (μg GABA/g stool). The initial amount can also be the level of expression of GABA producing enzymes in the stool (log change of reads), as measured by qPCR or other appropriate method. Unless otherwise defined herein, stool is weighed when wet or dry. i.e., without active drying, and within one hour of production of the stool. For instance, the stool can be weighed within 45 minutes, 30 minutes, 15 minutes, 10 minutes, or within 5 minutes of production of the stool.

As used herein, a "GABAergic response" means the response of a given organ (e.g., the brain or vagus nerve) to differences in the concentrations of GABA, GABA producing bacteria, or prebiotics to which it is exposed. A GABAergic response can include a change in concentrations of GABA as well as expression levels and/or activity of different $GABA_A$, $GABA_B$, and/or $GABA_C$ receptors.

"GABA-producing bacteria" is understood to mean bacteria that can produce measurable quantities of GABA, as detected by LC/MS, ELISA, or other appropriate analytical assays. In some embodiments, GABA-producing bacteria can produce GABA under the physiological conditions in a human, e.g., under the pH, and temperature of the human gut.

"Physiologically relevant pH" of the human intestinal tract is understood to mean a pH range that exists in the body. For instance, a pH range that is physiologically relevant to the human gut can be in the range of about 4.5 to about 7.5.

The term "gut" is understood to refer to the human gastrointestinal tract, also known as the alimentary canal. The gut includes the mouth, pharynx, oesophagus, stomach, small intestine (duodenum, jejunum, ileum), large intestines (cecum and colon) and rectum.

As used herein, "bacteria" or "bacterial strain" is understood to mean a species of bacteria. A "bacterium" is understood as a single bacterial cell of a given species.

The term "treating" with regard to a subject, refers to improving at least one symptom of the subject's disorder. Treating includes curing, improving, or at least partially ameliorating the disorder.

The term "EMBL/GenBank/DDBJ ID" refers to an accession number, which when used as in input for databases such as the European Molecular Biology Laboratory (EMBL), GenBank, or DNA Data Bank of Japan (DDBJ), via their respective internet websites, enables access to information, such as nucleotide sequence of a gene, and the bacterium encoding that sequence in its genome. The EMBL/GenBank/DDBJ ID is used in this application as a convenient means to access sequence information.

Gamma-Aminobutyric Acid (GABA)

The term "GABA" is understood to mean gamma-aminobutyric acid (γ-aminobutyric acid). GABA has the chemical structure:

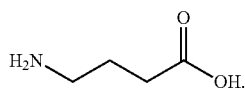

GABA is a major inhibitory neurotransmitter in the mammalian central nervous system. It plays a principal role in reducing neuronal excitability throughout the nervous system. GABA can be a difficult compound to deliver therapeutically due to efflux and half-life limitations. For example, in rodents, the brain efflux rate of GABA was found to be 17 times higher than the influx rate. Additionally, GABA only has a half-life of only 17 minutes in mice. Accordingly, because of the short half-life of GABA in vivo, oral GABA supplementation can be ineffective, as it may require frequent dosing, even with slow release capsules.

The present disclosure provides for delivering a therapeutic composition of one or more bacteria that can produce GABA within the intestinal tract, in order to consistently deliver GABA into systemic circulation (e.g., into the nervous system). The endogenously produced GABA can also activate vagal nerve receptors directly. This can mitigate the inherent half-life of GABA.

In some embodiments, the microbiome can influence GABA levels and the GABAergic response in the brain. For instance, germ-free animals can have substantially reduced luminal and serum levels of GABA. Without wishing to be bound by theory, this suggests the microbiome is important in regulating levels of this important neurotransmitter. As set forth herein, GABAergic modulation by microbiome intervention (e.g., using methods and compositions described herein) can have therapeutic potential.

In some embodiments, GABA can play a role in mental illness or disease of the central nervous system. For instance, in some embodiments, low levels of GABA can be associated with depression, bipolar disorder, schizophrenia, anxiety, anxiety disorders, addiction, social phobia, treatment-resistant major depressive disorder (TR-MDD), major depressive disorder and its subtypes (melancholic depression, atypical depression, catatonic depression, postpartum depression, and seasonal affective disorder), Neurodegenerative amyloid disorders (Parkinson's, Alzheimer's, and Huntington's diseases) orthostatic tremor, Lafora disease, restless leg syndrome, neuropathic pain, pain disorders, dementia, epilepsy, stiff-person syndrome, premenstrual dysphoric disorder, autism spectrum disorder, sleep disorders, and attention deficit hyperactivity disorder (ADHD). As set forth herein, the present disclosure provides increasing the amount of endogenous GABA in a subject can decrease levels of mental illness or disease of the central nervous system in the subject.

In some embodiments, GABA produced by gut bacteria can play a role in mental illness or disease of the central nervous system via the vagus nerve, connecting the intestinal tract to the peripheral and central nervous systems.

In some embodiments, GABA produced by gut bacteria can play a role in mental illness or disease of the central nervous system via affecting circulating levels of systemic GABA in the host, which can influence the peripheral and central nervous systems.

Means of GABA Production by Microbes

Bacteria can produce GABA using a variety of different pathways. Set forth below are exemplary pathways that bacteria and other microbes can use to produce GABA (e.g., in vivo). As set forth below, any of the GABA production pathways described herein can be naturally occurring in a given bacterium. Alternatively, a necessary enzyme or grouping of enzymes can be added to the DNA sequence of a bacteria to enable the bacteria to produce GABA.

Glutamate Pathway

In some embodiments, microbes can produce GABA using the glutamate decarboxylase enzyme (e.g., glutamate decarboxylase EC 4.1.1.15). In some embodiments, glutamate decarboxylase is capable of directly converting glutamate to GABA.

Putrescine to 4-Aminobutanal Pathway

In some embodiments, microbes can produce GABA using the putrescine to 4-aminobutanal pathway. The microbes can then convert 4-aminobutanal to GABA. In some embodiments, putrescine aminotransferase (for instance, putrescine aminotransferase EC 2.6.1.82) can be used to convert putrescine to 4-aminobutanal. The 4-aminobutanal can then be converted in the presence of gamma-aminobutyraldehyde dehydrogenase (e.g., gamma-aminobutyraldehyde dehydrogenase (EC 1.2.1.19)) to GABA.

Arginine to Agmatine to Putrescine Pathway

In some embodiments, microbes can produce GABA using the arginine to agmatine to putrescine Pathway. Once the putrescine is produced, it can be converted as described above (e.g., using the putrescine to 4-aminobutanal pathway) to GABA. In some embodiments, arginine decarboxylase (e.g., arginine decarboxylase (EC 4.1.1.19)) can convert arginine to agmatine. Agmatine can then be converted to putrescine using agmatinase (e.g., agmatinase (EC 3.5.3.11)).

L-Ornithine to Putrescine Pathway

In some embodiments, ornithine decarboxylase (e.g., ornithine decarboxylase (EC 4.1.1.17)) can be used to convert ornithine to putrescine. Once the putrescine is produced, it can be converted as described above (e.g., using the putrescine to 4-aminobutanal pathway) to GABA.

Bacterial Strains

The present disclosure provides bacterial strains (e.g., purified strains) and therapeutic compositions comprising the same for administration to a subject in need thereof. The bacteria can be naturally occurring, or can be engineered (e.g., through strain engineering or selection) to produce GABA. In some embodiments, one strain of GABA-producing bacteria can be administered to a subject. In some embodiments, multiple strains of GABA-producing bacteria can be administered to a subject in need thereof. In some embodiments, the one or more bacteria (e.g., purified bacteria) can act synergistically. For instance, the multiple bacteria can act synergistically to produce high levels of GABA. In some embodiments, the one or more bacteria can also help to reduce the number of GABA-consuming bacteria in a human gut. Accordingly, any one, or any combination of the GABA-producing bacteria taught herein can be administered to a subject in need thereof.

In some embodiments, the bacteria taught herein can produce GABA at physiologically relevant conditions, such as under the conditions of the human gut. In some embodiments, the GABA-producing bacteria taught herein can produce GABA a pH relevant to the human gut is between about 4.5 and about 7.5. For instance, the pH can be about 4.5, 5.0, 5.5, 6.0, 6.5, 7.0, 7.5, or any value between about 4.5 and 7.5.

The ability to produce GABA at physiologically relevant pH is important in view of the pH restrictions of GABA production in many bacteria. For example, E. coli is unable to produce GABA above a pH of 4.5. Instead, without wishing to be bound by theory, it can use conversion of glutamate to GABA coupled with GABA export, for example, as a means to neutralize the intracellular environment. Accordingly the present disclosure bacteria capable of producing GABA at a pH relevant to the host environment, such as the more neutral large intestines (e.g., between about pH 4.5 and about pH 7.5). In some embodiments, the bacteria taught herein can also produce GABA under other relevant conditions that exist within the human gut. That is, the GABA-producing bacteria taught herein can produce GABA in the absence of oxygen, in a nutrient-competitive and fluctuating environment, and in the absence of light.

Natural Strains

In some embodiments, the GABA-producing bacteria can be identified by having a 16S nucleic acid sequence substantially similar to the 16S sequences of reference bacteria listed in Table 1, with a Seq. ID. No. of 1-31. In some embodiments, the GABA-producing bacteria can have at least 90% 16S sequence similarity to the 16S sequences given in Table 1 (e.g., at least 91% similarity, at least 92% similarity, at least 93% similarity, at least 94% similarity, at least 95% similarity, at least 96% similarity, at least 97% similarity, at least 98% similarity, at least 99% similarity, at least 99.5% similarity, at least 99.9% similarity, or 100% similarity).

In some embodiments, the GABA-producing bacteria can be identified by NCBI Taxon ID of the organism they are most related to by 16S sequence. These bacteria include those belonging to the same NCBI Taxon assignment as *Bacteroides caccae* KLE1911; *Bacteroides clarus* KLE1930; *Bacteroides dorei* KLE1912; *Bacteroides finegoldii* KLE1931; *Bacteroides fragilis* KLE1958; *Bacteroides massiliensis* KLE1932; *Bacteroides ovatus* KLE1770; *Bacteroides stercoris* KLE1933; *Bacteroides thetaiotaomicron* KLE1934; *Bacteroides uniformis* KLE1913; *Bacteroides vulgatus* KLE1910; *Bacteroides xylanisolvens* KLE1935; *Bifidobacterium adolescentis* KLE1879; *Blautia obeum* KLE1914; *Blautia wexlerae* KLE1916; *Butyricimonas virosa* KLE1938; *Clostridium perfringens* KLE1937; *Clostridium sordellii* KLE1939; *Clostridium* sp. KLE1862; *Clostridium* sp. KLE1918; *Coprobacillus* sp. KLE1779; *Coprococcus* sp. KLE1880; *Dorea longicatena* KLE1917; *Eggerthella lenta* KLE1926; *Eubacterium rectale* KLE1922; *Gordonibacter pamelaeae* KLE1915; *Oscillibacter* sp. KLE1928; *Parabacteroides distasonis* KLE2020; *Parabacteroides merdae* KLE1863; *Ruminococcus gnavus* KLE1940; *Turicibacter sanguinis* KLE1941, and combinations thereof.

TABLE 1

Strain name of GABA producing bacteria, and their cooresponding Seq. ID No.

| Strain | Seq. ID No. |
| --- | --- |
| *Bacteroides caccae* KLE1911 | 1 |
| *Bacteroides clarus* KLE1930 | 2 |
| *Bacteroides dorei* KLE1912 | 3 |
| *Bacteroides finegoldii* KLE1931 | 4 |
| *Bacteroides fragilis* KLE1958 | 5 |
| *Bacteroides massiliensis* KLE1932 | 6 |
| *Bacteroides ovatus* KLE1770 | 7 |
| *Bacteroides stercoris* KLE1933 | 8 |
| *Bacteroides thetaiotaomicron* KLE1934 | 9 |
| *Bacteroides uniformis* KLE1913 | 10 |
| *Bacteroides vulgatus* KLE1910 | 11 |
| *Bacteroides xylanisolvens* KLE1935 | 12 |
| *Bifidobacterium adolescentis* KLE1879 | 13 |
| *Blautia obeum* KLE1914 | 14 |
| *Blautia wexlerae* KLE1916 | 15 |
| *Butyricimonas virosa* KLE1938 | 16 |
| *Clostridium perfringens* KLE1937 | 17 |
| *Clostridium sordellii* KLE1939 | 18 |
| *Clostridium* sp. KLE1862 | 19 |
| *Clostridium* sp. KLE1918 | 20 |
| *Coprobacillus* sp. KLE1779 | 21 |
| *Coprococcus* sp. KLE1880 | 22 |
| *Dorea longicatena* KLE1917 | 23 |
| *Eggerthella lenta* KLE1926 | 24 |
| *Eubacterium rectale* KLE1922 | 25 |
| *Gordonibacter pamelaeae* KLE1915 | 26 |

TABLE 1-continued

Strain name of GABA producing bacteria, and their cooresponding Seq. ID No.

| Strain | Seq. ID No. |
|---|---|
| Oscillibacter sp. KLE1928 | 27 |
| Parabacteroides distasonis KLE2020 | 28 |
| Parabacteroides merdae KLE1863 | 29 |
| Ruminococcus gnavus KLE1940 | 30 |
| Turicibacter sanguinis KLE1941 | 31 |

Also disclosed herein are bacteria that are predicted to be capable of producing GABA (e.g., under physiologically relevant conditions and/or in the human gut). Bacteria are identified as being candidate GABA producing bacteria if they have encoded in their genome enzymes involved in GABA biosynthesis. In some embodiments, the bacteria that are predicted to be capable of producing GABA can be identified by having a 16S nucleic acid sequence substantially similar to the 16S sequences of reference bacteria listed in Table 2, with a Seq. ID. No. of 32-274. In some embodiments, the predicted GABA-producing bacteria can have at least 90% 16S sequence similarity to the 16S sequences given in Table 2, with a Seq. ID. No. of 32-274 (e.g., at least 91% similarity, at least 92% similarity, at least 93% similarity, at least 94% similarity, at least 95% similarity, at least 96% similarity, at least 97% similarity, at least 98% similarity, at least 99% similarity, at least 99.5% similarity, at least 99.9% similarity, or 100% similarity).

TABLE 2

Predicted GABA producing bacteria and their corresponding Seq. ID No..

| Species | Seq. ID No. |
|---|---|
| Abiotrophia defective | 32 |
| Acetobacter okinawensis | 33 |
| Achromobacter arsenitoxydans | 34 |
| Achromobacter xylosoxidans | 35 |
| Acidovorax sp. | 36 |
| Acidovorax sp. | 37 |
| Acidovorax sp. | 38 |
| Acidovorax sp. | 39 |
| Acidovorax sp. | 40 |
| Actinoplanes friuliensis | 41 |
| Aeromonas enteropelogenes | 42 |
| Aeromonas hydrophila | 43 |
| Afipia birgiae | 44 |
| Afipia clevelandensis | 45 |
| Afipia sp. | 46 |
| Agrobacterium albertimagni | 47 |
| Agrobacterium sp. | 48 |
| Agrobacterium tumefaciens | 49 |
| Akkermansia muciniphila | 50 |
| Alcaligenes faecalis | 51 |
| Alicycliphilus denitrificans | 52 |
| Alistipes finegoldii | 53 |
| Alistipes indistinctus | 54 |
| Alistipes onderdonkii | 55 |
| Alistipes putredinis | 56 |
| Alistipes shahii | 57 |
| Aquamicrobium defluvii | 58 |
| Arenimonas donghaensis | 59 |
| Arthrobacter sp. | 60 |
| Azospirillum sp. | 61 |
| Bacillus bataviensis | 62 |
| Bacillus cereus | 63 |
| Bacillus cereus | 64 |
| Bacillus endophyticus | 65 |
| Bacillus weihenstephanensis | 66 |
| Bacteroidaceae bacterium | 67 |
| Bacteroides acidifaciens | 68 |
| Bacteroides caccae | 69 |

TABLE 2-continued

Predicted GABA producing bacteria and their corresponding Seq. ID No..

| Species | Seq. ID No. |
|---|---|
| Bacteroides cellulosilyticus | 70 |
| Bacteroides dorei | 71 |
| Bacteroides eggerthii | 72 |
| Bacteroides finegoldii | 73 |
| Bacteroides fragilis | 74 |
| Bacteroides gallinarum | 75 |
| Bacteroides intestinalis | 76 |
| Bacteroides massiliensis | 77 |
| Bacteroides oleiciplenus | 78 |
| Bacteroides ovatus | 79 |
| Bacteroides rodentium | 80 |
| Bacteroides salyersiae | 81 |
| Bacteroides sartorii | 82 |
| Bacteroides sp. | 83 |
| Bacteroides sp. | 84 |
| Bacteroides sp. | 85 |
| Bacteroides sp. | 86 |
| Bacteroides stercoris | 87 |
| Bacteroides thetaiotaomicron | 88 |
| Bacteroides uniformis | 89 |
| Bacteroides vulgatus | 90 |
| Bacteroides xylanisolvens | 91 |
| Barnesiella intestinihominis | 92 |
| Bhargavaea cecembensis | 93 |
| Bifidobacterium adolescentis | 94 |
| Bifidobacterium angulatum | 95 |
| Bifidobacterium dentium | 96 |
| Bifidobacterium ruminantium | 97 |
| Blastococcus sp. | 98 |
| Bordetella bronchiseptica | 99 |
| Bordetella trematum | 100 |
| Bosea sp. | 101 |
| Bradyrhizobium sp. | 102 |
| Brevibacillus borstelensis | 103 |
| Brevundimonas diminuta | 104 |
| Brevundimonas naejangsanensis | 105 |
| Brucella abortus | 106 |
| Brucella melitensis | 107 |
| Brucella neotomae | 108 |
| Burkholderia mallei | 109 |
| Burkholderia multivorans | 110 |
| Carnobacterium gallinarum | 111 |
| Caulobacter crescentus | 112 |
| Caulobacter sp. | 113 |
| Cellulomonas flavigena | 114 |
| Cellulomonas sp. | 115 |
| Cellulosimicrobium cellulans | 116 |
| Cetobacterium somerae | 117 |
| Citrobacter amalonaticus | 118 |
| Cloacibacillus evryensis | 119 |
| Clostridium acetobutylicum | 120 |
| Clostridium perfringens | 121 |
| Comamonas granuli | 122 |
| Corynebacterium variabile | 123 |
| Cupriavidus basilensis | 124 |
| Cupriavidus sp. | 125 |
| Dechloromonas agitata | 126 |
| Deinococcus geothermalis | 127 |
| Delftia tsuruhatensis | 128 |
| Desulfovibrio desulfuricans | 129 |
| Desulfovibrio sp. | 130 |
| Devosia riboflavina | 131 |
| Eggerthella sp. | 132 |
| Ensifer adhaerens | 133 |
| Enterococcus casseliflavus | 134 |
| Enterococcus flavescens | 135 |
| Escherichia coli | 136 |
| Eubacterium limosum | 137 |
| Eubacterium nodatum | 138 |
| Eubacterium saphenum | 139 |
| Fusobacterium periodonticum | 140 |
| Gordonia sputi | 141 |
| Gordonia terrae | 142 |
| Gordonibacter pamelaeae | 143 |
| Halomonas stevensii | 144 |
| Halomonas titanicae | 145 |

TABLE 2-continued

Predicted GABA producing bacteria and their corresponding Seq. ID No..

| Species | Seq. ID No. |
|---|---|
| Hoeflea sp. | 146 |
| Intrasporangium calvum | 147 |
| Janibacter hoylei | 148 |
| Kaistia granuli | 149 |
| Kineococcus radiotolerans | 150 |
| Lactobacillus coleohominis | 151 |
| Lactobacillus plantarum | 152 |
| Lactobacillus reuteri | 153 |
| Lactococcus garvieae | 154 |
| Lactococcus lactis | 155 |
| Lautropia mirabilis | 156 |
| Leucobacter salsicius | 157 |
| Luteimonas huabeiensis | 158 |
| Magnetospirillum magnetotacticum | 159 |
| Marinobacter lipolyticus | 160 |
| Marmoricola sp. | 161 |
| Megasphaera micronuciformis | 162 |
| Megasphaera sp. | 163 |
| Mesorhizobium sp. | 164 |
| Methanobrevibacter arboriphilus | 165 |
| Methylobacterium radiotolerans | 166 |
| Methylobacterium sp. | 167 |
| Microbacterium sp. | 168 |
| Micromonospora aurantiaca | 169 |
| Mogibacterium Mogibacterium | 170 |
| Morganella morganii | 171 |
| Mycobacterium smegmatis | 172 |
| Mycobacterium sp. | 173 |
| Mycobacterium sp. | 174 |
| Mycobacterium vanbaalenii | 175 |
| Neisseria sicca | 176 |
| Neorhizobium galegae | 177 |
| Nocardia rhamnosiphila | 178 |
| Nocardiopsis alkaliphila | 179 |
| Nocardiopsis ganjiahuensis | 180 |
| Nocardiopsis synnemataformans | 181 |
| Nocardiopsis valliformis | 182 |
| Novosphingobium nitrogenifigens | 183 |
| Ochrobactrum intermedium | 184 |
| Odoribacter laneus | 185 |
| Odoribacter splanchnicus | 186 |
| Oerskovia turbata | 187 |
| Pannonibacter phragmitetus | 188 |
| Pantoea vagans | 189 |
| Parabacteroides distasonis | 190 |
| Parabacteroides goldsteinii | 191 |
| Parabacteroides johnsonii | 192 |
| Parabacteroides merdae | 193 |
| Parabacteroides sp. | 194 |
| Parabacteroides sp. | 195 |
| Paracoccus denitrificans | 196 |
| Paracoccus sp. | 197 |
| Paracoccus yeei | 198 |
| Parvimonas Parvimonas | 199 |
| Pectobacterium carotovorum | 200 |
| Phyllobacterium sp. | 201 |
| Polaromonas sp. | 202 |
| Porphyromonas bennonis | 203 |
| Proteus mirabilis | 204 |
| Providencia alcalifaciens | 205 |
| Providencia burhodogranariea | 206 |
| Providencia rettgeri | 207 |
| Pseudacidovorax intermedius | 208 |
| Pseudoalteromonas sp. | 209 |
| Pseudochrobactrum sp. | 210 |
| Pseudomonas aeruginosa | 211 |
| Pseudomonas alcaligenes | 212 |
| Pseudomonas chloritidismutans | 213 |
| Pseudomonas chlororaphis | 214 |
| Pseudomonas japonica | 215 |
| Pseudomonas knackmussii | 216 |
| Pseudomonas mendocina | 217 |
| Pseudomonas monteilii | 218 |
| Pseudomonas oleovorans | 219 |
| Pseudomonas putida | 220 |
| Pseudomonas savastanoi | 221 |
| Pseudomonas sp. | 222 |
| Pseudomonas sp. | 223 |
| Pseudomonas sp. | 224 |
| Pseudomonas sp. | 225 |
| Pseudomonas sp. | 226 |
| Pseudomonas sp. | 227 |
| Pseudomonas sp. | 228 |
| Pseudomonas sp. | 229 |
| Pseudomonas sp. | 230 |
| Pseudomonas stutzeri | 231 |
| Pseudomonas synxantha | 232 |
| Pseudomonas syringae | 233 |
| Pseudonocardia sp. | 234 |
| Ralstonia solanacearum | 235 |
| Raoultella planticola | 236 |
| Rhizobium leguminosarum | 237 |
| Rhizobium sp. | 238 |
| Rhodococcus defluvii | 239 |
| Rhodococcus pyridinivorans | 240 |
| Rikenella microfusus | 241 |
| Robinsoniella sp. | 242 |
| Roseomonas cervicalis | 243 |
| Roseomonas sp. | 244 |
| Salmonella enterica | 245 |
| Sanguibacter keddieii | 246 |
| Shewanella baltica | 247 |
| Shewanella sp. | 248 |
| Shinella zoogloeoides | 249 |
| Sphingopyxis alaskensis | 250 |
| Starkeya novella | 251 |
| Stenotrophomonas maltophilia | 252 |
| Stenotrophomonas rhizophila | 253 |
| Streptococcus thermophilus | 254 |
| Streptomyces atroolivaceus | 255 |
| Streptomyces coelicoflavus | 256 |
| Streptomyces olindensis | 257 |
| Streptomyces rimosus | 258 |
| Streptomyces roseoverticillatus | 259 |
| Streptomyces sp. | 260 |
| Streptomyces sp. | 261 |
| Streptomyces sp. | 262 |
| Streptomyces sp. | 263 |
| Streptomyces sp. | 264 |
| Streptomyces sp. | 265 |
| Streptomyces sp. | 266 |
| Streptomyces toyocaensis | 267 |
| Streptomyces turgidiscabies | 268 |
| Synergistes sp. | 269 |
| Tannerella sp. | 270 |
| Thauera terpenica | 271 |
| Variovorax paradoxus | 272 |
| Variovorax sp. | 273 |
| Xanthomonas axonopodis | 274 |

Engineered Strains

In some embodiments, bacteria can be engineered to produce GABA (e.g., under the conditions of the human gut). The bacteria can be engineered using techniques of molecular biology, or can be evolved using the process of selection to produce GABA in the human gut.

As set forth above, GABA can be produced by multiple pathways within a microbial cell. For example, GABA can be produced by the glutamate pathway, the putrescine to 4-aminobutanal pathway, the arginine to agmatine to putrescine pathway, the L-ornithine to putrescine pathway, or by a combination of pathways. In some embodiments, bacteria can be engineered to contain one or more enzymes in any one of the above pathways that can enable the bacteria to produce GABA or a necessary precursor to GABA.

A variety of different host bacteria can be engineered to produce GABA. For instance, in some embodiments, *Escherichia coli* Nissle 1917, can be genetically modified or selected through evolution to produce GABA. In some embodiments, the bacteria (e.g., *Escherichia coli* Nissle 1917) can be modified to express or overexpress glutamate decarboxylase A or glutamate decarboxylase B. The bacteria can also be made to produce GABA by one or more of the other pathways described herein.

Accordingly, in some embodiments, an engineered GABA-producing strain can be identified as having a specific enzyme encoded in its genomes. For example, the enzyme can be glutamate decarboxylase (EC 4.1.1.15); putrescine aminotransferase (EC 2.6.1.82); gamma-aminobutyraldehyde dehydrogenase (EC 1.2.1.19); arginine decarboxylase (EC 4.1.1.19); agmatinase (EC 3.5.3.11); ornithine decarboxylase (EC 4.1.1.17); or a combination thereof. In some embodiments, the GABA-producing strain can be engineered to contain an enzyme that has at least 50% similarity with the representative sequences listed in Table 3 (e.g., at least 60% similarity, at least 70% similarity, at least 80% similarity, at least 90% similarity, at least 91% similarity, at least 92% similarity, at least 93% similarity, at least 94% similarity, at least 95% similarity, at least 96% similarity, at least 97% similarity, at least 98% similarity, at least 99% similarity, at least 99.5% similarity, at least 99.9% similarity, or 100% similarity). The enzyme classes, as identified by their Enzyme Commission (EC) numbers, are listed in Table 3.

TABLE 3

Enzymes involved in GABA-Production Pathways, and Seq. ID No. for representative sequences for each enzyme class

| Enzyme | Seq ID No. |
| --- | --- |
| Glutamate decarboxylase (EC 4.1.1.15) | 275-279 |
| Putrescine aminotransferase (EC 2.6.1.82) | 280-284 |
| Gamma-aminobutyraldehyde dehydrogenase (EC 1.2.1.19) | 285-289 |
| Arginine decarboxylase (EC 4.1.1.19) | 290-294 |
| Agmatinase (EC 3.5.3.11) | 295-299 |
| Ornithine decarboxylase (EC 4.1.1.17) | 300-304 |

Representative examples of glutamate decarboxylase (EC 4.1.1.15) are given below in Table 4 and identified by their EMBL/GENBANK/DDBJ ID numbers. Any of the bacteria given in Table 10 can be engineered with any version of the glutamate decarboxylase set forth in Table 3 or Table 4. For instance, the bacteria can be engineered with a version of the glutamate decarboxylase enzyme that has at least 50% nucleotide similarity with any of the versions of glutamate decarboxylase given in Table 4 (e.g., at least nucleotide 60% similarity, at least 70% nucleotide similarity, at least 80% nucleotide similarity, at least 90% nucleotide similarity, at least 91% nucleotide similarity, at least 92% nucleotide similarity, at least 93% nucleotide similarity, at least 94% nucleotide similarity, at least 95% nucleotide similarity, at least 96% nucleotide similarity, at least 97% nucleotide similarity, at least 98% nucleotide similarity, at least 99% nucleotide similarity, at least 99.5% nucleotide similarity, at least 99.9% nucleotide similarity, or 100% nucleotide similarity).

TABLE 4

Representative Examples of Glutamate Decarboxylase by EMBL/GENBANK/DDBJ ID Number

AAA23833.1
AAA23834.1
AAB18493.1

TABLE 4-continued

Representative Examples of Glutamate Decarboxylase by EMBL/GENBANK/DDBJ ID Number AAC46188.1
AAC74566.1
AAC76542.1
AAG22560.1
AAG22562.1
AAG56275.1
AAG58658.1
AAK05388.1
AAK17187.1
AAK47878.1
AAL54152.1
AAL54153.1
AAN43309.2
AAN45045.2
AAN54823.2
AAN80380.1
AAN82764.1
AAO77677.1
AAP17196.1
AAP19142.1
AAS06807.1
AAS41604.1
AAT42735.1
AAW85387.1
AAW85559.1
AAZ71647.1
AAZ88326.1
AAZ90121.1
ABB61740.1
ABB63509.1
ABB66175.1
ABB68000.1
ABC77952.1
ABD09573.1
ABE07185.1
ABE09478.1
ABE29172.1
ABE36450.1
ABF03896.1
ABF05994.1
ABF08645.1
ABG57877.1
ABG82826.1
ABG85385.1
ABG97793.1
ABI47454.1
ABJ00921.1
ABJ02999.1
ABJ63253.1
ABJ64910.1
ABK67541.1
ABK75920.1
ABK90558.1
ABL03510.1
ABL90375.1
ABM09145.1
ABM12315.1
ABM78546.1
ABP47401.1
ABP56802.1
ABQ62050.1
ABQ75258.1
ABQ85037.1
ABQ85038.1
ABQ85039.1
ABQ85040.1
ABQ85043.1
ABQ85046.1
ABQ85049.1
ABQ85050.1
ABQ85051.1
ABQ85053.1
ABQ85058.1
ABR41498.1
ABR42591.1
ABS42061.1
ABU72013.1

TABLE 4-continued

Representative Examples of Glutamate Decarboxylase by EMBL/GENBANK/DDBJ ID Number

| |
|---|
| ABV20447.1 |
| ABV20705.1 |
| ABV88270.1 |
| ABV98199.1 |
| ABW16238.1 |
| ABY23810.1 |
| ABY39350.1 |
| ABZ77591.1 |
| ABZ87126.1 |
| ACA46668.1 |
| ACA53668.1 |
| ACA88989.1 |
| ACB15780.1 |
| ACB15938.1 |
| ACC39574.1 |
| ACD04211.1 |
| ACD07724.1 |
| ACD82162.1 |
| ACH65664.1 |
| ACJ29997.1 |
| ACL47965.1 |
| ACN16811.1 |
| ACO85906.1 |
| ACR68120.1 |
| ACS81597.1 |
| ACU49468.1 |
| ACU54556.1 |
| ACU77475.1 |
| ACV54143.1 |
| ACV81603.1 |
| ACY51919.1 |
| ACY85701.1 |
| ADA65034.1 |
| ADA74124.1 |
| ADA75905.1 |
| ADB10338.1 |
| ADB51885.1 |
| ADD56429.1 |
| ADD58723.1 |
| ADE69489.1 |
| ADF39290.1 |
| ADG78237.1 |
| ADG96760.1 |
| ADI09031.1 |
| ADJ50560.1 |
| ADM42706.1 |
| ADN37174.1 |
| ADO35975.1 |
| ADP83065.1 |
| ADR26899.1 |
| ADR28903.1 |
| ADT67741.1 |
| ADT75096.1 |
| ADT77123.1 |
| ADU00909.1 |
| ADU26301.1 |
| ADW04875.1 |
| ADY32347.1 |
| ADY58934.1 |
| ADY59978.1 |
| ADZ09662.1 |
| ADZ09880.1 |
| AEA24253.1 |
| AEA24271.1 |
| AEB72391.1 |
| AEE27076.1 |
| AEE56495.1 |
| AEE58814.1 |
| AEF37245.1 |
| AEF40931.1 |
| AEG17214.1 |
| AEH47920.1 |
| AEH93409.1 |
| AEH93479.1 |
| AEI35432.1 |
| AEJ56545.1 |
| AEJ58918.1 |

TABLE 4-continued

Representative Examples of Glutamate Decarboxylase by EMBL/GENBANK/DDBJ ID Number

| |
|---|
| AEK38321.1 |
| AEK47566.1 |
| AEK58322.1 |
| AEM48695.1 |
| AEM88213.1 |
| AEN10737.1 |
| AEN89628.1 |
| AEO05457.1 |
| AEO07341.1 |
| AEO07410.1 |
| AEQ12485.1 |
| AEQ14770.1 |
| AET90796.1 |
| AEU40604.1 |
| AEU40605.1 |
| AEV39535.1 |
| AEV71230.1 |
| AEV85044.1 |
| AEW99357.1 |
| AEY90789.1 |
| AFA40032.1 |
| AFA47141.1 |
| AFA74414.1 |
| AFC23797.1 |
| AFC45457.1 |
| AFG40494.1 |
| AFG42464.1 |
| AFJ28998.1 |
| AFJ31191.1 |
| AFJ37206.1 |
| AFK19988.1 |
| AFK57885.1 |
| AFL79172.1 |
| AFM15894.1 |
| AFN45150.1 |
| AFP38009.1 |
| AFR07193.1 |
| AFR30984.1 |
| AFR47006.1 |
| AFS16303.1 |
| AFS52965.1 |
| AFS74495.1 |
| AFT98587.1 |
| AFV89643.1 |
| AFY29504.1 |
| AFZ52375.1 |
| AGA90199.1 |
| AGB21530.1 |
| AGC43105.1 |
| AGC61247.1 |
| AGE37597.1 |
| AGF77926.1 |
| AGG29530.1 |
| AGJ55746.1 |
| AGK78014.1 |
| AGK95653.1 |
| AGL28896.1 |
| AGL89003.1 |
| AGM10224.1 |
| AGM23454.1 |
| AGM30354.1 |
| AGN85370.1 |
| AGO09336.1 |
| AGP31884.1 |
| AGP56881.1 |
| AGP65818.1 |
| AGR65020.1 |
| AGS70940.1 |
| AGV73208.1 |
| AGY44310.1 |
| AGZ52354.1 |
| AHA64741.1 |
| AHA64994.1 |
| AHA67486.1 |
| AHA67487.1 |
| AHD20397.1 |
| AHE48317.1 |

TABLE 4-continued

Representative Examples of Glutamate Decarboxylase by EMBL/GENBANK/DDBJ ID Number

| |
|---|
| AHE57937.1 |
| AHE60304.1 |
| AHF05109.1 |
| AHF13271.1 |
| AHG20573.1 |
| AHH15398.1 |
| AHH98082.1 |
| AHJ76938.1 |
| AHK29878.1 |
| AHM72117.1 |
| AHW62584.1 |
| AHX21760.1 |
| AHY70401.1 |
| AHY72977.1 |
| AHZ23367.1 |
| AIA01950.1 |
| AIA05032.1 |
| AIA30132.1 |
| AIA55291.1 |
| AIA73764.1 |
| AIC75915.1 |
| AIE75400.1 |
| AIE79640.1 |
| AIG80748.1 |
| AII05027.1 |
| AII76842.1 |
| AIJ07554.1 |
| AIJ15081.1 |
| AIJ26745.1 |
| AIR16227.1 |
| AIS03708.1 |
| AIS31569.1 |
| AIS60683.1 |
| AIS60750.1 |
| AIT09528.1 |
| AIU74973.1 |
| AIX63299.1 |
| AIX65458.1 |
| AIY00711.1 |
| AIY45527.1 |
| AIY83613.1 |
| AIY84119.1 |
| AIZ82546.1 |
| AIZ84546.1 |
| AJA19876.1 |
| AJA25926.1 |
| AJA28548.1 |
| AJA57089.1 |
| AJA79136.1 |
| AJA80033.1 |
| AJC56876.1 |
| AJC60332.1 |
| AJD29942.1 |
| AJD30517.1 |
| AJE06383.1 |
| AJE12001.1 |
| AJE41795.1 |
| AJE55882.1 |
| AJE58075.1 |
| AJE83295.1 |
| AJE87567.1 |
| AJF56325.1 |
| AJF58318.1 |
| AJF66001.1 |
| AJG19558.1 |
| AJG22402.1 |
| AJG22403.1 |
| AJG93936.1 |
| AJH17760.1 |
| AJI06057.1 |
| AJI25468.1 |
| AJI52230.1 |
| AJI53611.1 |
| AJI57942.1 |
| AJI68933.1 |
| AJI74183.1 |
| AJI88044.1 |
| AJJ46763.1 |
| AJK40118.1 |
| AJI45246.1 |
| AJO83482.1 |
| AJO85575.1 |
| AJQ91926.1 |
| AJT65391.1 |
| AJW41655.1 |
| AJY44977.1 |
| AKB18082.1 |
| AKB18368.1 |
| AKB21414.1 |
| AKB22089.1 |
| AKB28570.1 |
| AKB32481.1 |
| AKB36808.1 |
| AKB44521.1 |
| AKB48030.1 |
| AKB51234.1 |
| AKB54327.1 |
| AKB57594.1 |
| AKB78420.1 |
| AKB81570.1 |
| AKC40119.1 |
| AKD98129.1 |
| AKF85158.1 |
| AKG70083.1 |
| AKG72082.1 |
| AKH24178.1 |
| AKH26551.1 |
| AKH83393.1 |
| AKJ11706.1 |
| AKK26454.1 |
| AKK48189.1 |
| AKK50365.1 |
| AKL69083.1 |
| AKM35002.1 |
| AKM37064.1 |
| AKN61935.1 |
| AKN70627.1 |
| AKP77446.1 |
| AKQ55619.1 |
| AKR03347.1 |
| AKS23002.1 |
| ALD25331.1 |
| ALL88386.1 |
| ALL90542.1 |
| ALZ68108.1 |
| AMC47930.1 |
| AMW41208.1 |
| AMW43303.1 |
| AMX13814.1 |
| AMX15691.1 |
| ANK32168.1 |
| ANM82251.1 |
| ANM84279.1 |
| ANO91466.1 |
| ANP18008.1 |
| ANP20338.1 |
| AOM43274.1 |
| AOM46217.1 |
| AOM69863.1 |
| AOM72020.1 |
| AOT30761.1 |
| AOT32983.1 |
| APA40105.1 |
| APA42487.1 |
| APA95425.1 |
| BAA15163.1 |
| BAA17064.1 |
| BAA24585.1 |
| BAA30034.1 |
| BAB35521.1 |
| BAB37820.1 |
| BAB81764.1 |
| BAC71313.1 |
| BAC72367.1 |

TABLE 4-continued

Representative Examples of Glutamate Decarboxylase by EMBL/GENBANK/DDBJ ID Number BAD47203.1
BAD58388.1
BAE77777.1
BAG20906.1
BAG77107.1
BAG79310.1
BAH34246.1
BAH54322.1
BAI25363.1
BAI27772.1
BAI30441.1
BAI32950.1
BAI35784.1
BAI38094.1
BAJ28326.1
BAJ74886.1
BAK43421.1
BAL67532.1
BAL89884.1
BAM06654.1
BAM50779.1
BAN05709.1
BAN07465.1
BAN32855.1
BAO88345.1
CAA44834.1
CAA50736.1
CAB42769.1
CAC97690.1
CAC97755.1
CAC98526.1
CAD00441.1
CAD00512.1
CAE20649.1
CAE33151.1
CAG35114.1
CAG46355.1
CAH06161.1
CAJ13031.1
CAJ13032.1
CAJ50408.1
CAK21799.1
CAK28447.1
CAL13720.1
CAL73487.1
CAL97772.1
CAM63814.1
CAQ78882.1
CAQ89093.1
CAQ90311.1
CAR02896.1
CAR05140.1
CAR07836.2
CAR10182.1
CAR12949.1
CAR15161.1
CAR17889.1
CAR20131.1
CAR42970.1
CAS09168.1
CAS11307.1
CAU97478.1
CAV00414.1
CBG71067.1
CBH50652.1
CBJ01067.1
CBJ03264.1
CBJ13441.1
CBK63002.1
CBK66783.1
CBL04696.1
CBL57837.1
CBW21055.1
CBW86770.1
CBW86835.1
CBY25615.1
CBY25616.1
CBY83732.1
CCA56552.1
CCB79422.1
CCB79423.1
CCC28516.1
CCC45780.1
CCC80401.1
CCF80014.1
CCF80015.1
CCG87871.1
CCG91229.1
CCG98062.1
CCH30995.1
CCH77936.1
CCH93070.1
CCH98079.1
CCI01250.1
CCI09506.1
CCI18860.1
CCI27064.1
CCJ46136.1
CCJ52392.1
CCK19015.1
CCK19016.1
CCK28448.1
CCK46704.1
CCK48823.1
CCK79225.1
CCO09825.2
CCO10173.1
CCO13002.2
CCO24580.1
CCO64903.1
CCO64970.1
CCP46254.1
CCQ12644.1
CCQ14157.1
CCW09328.1
CCW10939.1
CDG05069.1
CDG65008.1
CDI46519.1
CDK01888.1
CDK72542.1
CDK77522.1
CDL24770.1
CDL26737.1
CDL29747.1
CDM06669.1
CDM06670.1
CDN82039.1
CDN84269.1
CDO09876.1
CDO20324.1
CDO27974.1
CDO44733.1
CDO87126.1
CDP84850.1
CDQ46433.1
CDR08766.1
CDU38691.1
CDY74306.1
CDZ89912.1
CEA13064.1
CED70967.1
CEF51573.1
CEG58623.1
CEI23431.1
CEJ51402.1
CEK27848.1
CEK31257.1
CEK34473.1
CEK36954.1
CEL25420.1
CEO38246.1
CEP25754.1
CEP41466.1

TABLE 4-continued

Representative Examples of Glutamate Decarboxylase by EMBL/GENBANK/DDBJ ID Number

| |
|---|
| CEQ04848.1 |
| CEQ04850.1 |
| CFE36737.1 |
| CFE50785.1 |
| CFQ66985.1 |
| CFT98680.1 |
| CFT98693.1 |
| CKO74072.1 |
| CKR41672.1 |
| CKR63720.1 |
| CKR87162.1 |
| CKV41513.1 |
| CNH63762.1 |
| CNN53125.1 |
| CNZ28847.1 |
| COF20080.1 |
| COQ21776.1 |
| COR80523.1 |
| COV15812.1 |
| COV67826.1 |
| COV88060.1 |
| COW22072.1 |
| COW50746.1 |
| COW69018.1 |
| CPR27659.1 |
| CPR27660.1 |
| CQD07112.1 |
| CRF40589.1 |
| CRF42243.1 |
| CRF44683.1 |
| CRF48464.1 |
| CRF50704.1 |
| CRG01912.1 |
| CRH16097.1 |
| CRH16918.1 |
| CRH16922.1 |
| CRI32384.1 |
| CRI34932.1 |
| CRK49247.1 |
| CRK49766.1 |
| CRY53884.1 |
| CRY55938.1 |
| CRY74150.1 |
| CRZ15952.1 |
| CSK83327.1 |
| CSK89516.1 |
| CSN37587.1 |
| CSN43893.1 |
| CSP86321.1 |
| CSS74791.1 |
| CTQ53252.1 |
| CTQ71526.1 |
| CTT09685.1 |
| CTT19248.1 |
| CTT51717.1 |
| CTT83594.1 |
| CTU03723.1 |
| CTU48438.1 |
| CTU63923.1 |
| CTV28671.1 |
| CTV69168.1 |
| CTW64116.1 |
| CTX10177.1 |
| CTZ19187.1 |
| CTZ24614.1 |
| CTZ73544.1 |
| CTZ73631.1 |
| CUJ14933.1 |
| CUK00697.1 |
| CUO21357.1 |
| EAO55448.1 |
| EAQ75094.1 |
| EAQ80748.1 |
| EAR53494.1 |
| EAS62995.1 |
| EAU72855.1 |
| EAV43522.1 |
| EDK88619.1 |
| EDL53816.1 |
| EDL54868.1 |
| EDL56435.1 |
| EDL68777.1 |
| EDM21919.1 |
| EDM65095.1 |
| EDN56728.1 |
| EDN71351.1 |
| EDN82399.1 |
| EDN85024.1 |
| EDO14168.1 |
| EDO51732.1 |
| EDP24277.1 |
| EDP59239.1 |
| EDS02296.1 |
| EDS16532.1 |
| EDS80418.1 |
| EDS92014.1 |
| EDS93501.1 |
| EDT12835.1 |
| EDT15330.1 |
| EDT25330.1 |
| EDT73179.1 |
| EDU36907.1 |
| EDU39421.1 |
| EDU64919.1 |
| EDU66726.1 |
| EDU90194.1 |
| EDU92849.1 |
| EDV04249.1 |
| EDX35836.1 |
| EDX36856.1 |
| EDX42043.1 |
| EDY39693.1 |
| EDY48172.1 |
| EDY57831.1 |
| EDY66556.1 |
| EDZ49153.1 |
| EEA85567.1 |
| EEA92251.1 |
| EEB26629.1 |
| EEB44239.1 |
| EEC53338.1 |
| EEC97976.1 |
| EEE44061.1 |
| EEF92068.1 |
| EEH13682.1 |
| EEI48912.1 |
| EEK47458.1 |
| EEK58881.1 |
| EEK67538.1 |
| EEK74538.1 |
| EEL55986.1 |
| EEL62126.1 |
| EEL64999.1 |
| EEL67614.1 |
| EEM80145.1 |
| EEN88413.1 |
| EEO04360.1 |
| EEO15980.1 |
| EEO27017.1 |
| EEO29218.1 |
| EEO44870.1 |
| EEO51903.1 |
| EEO53210.1 |
| EEO59155.1 |
| EEP21189.1 |
| EEP92210.1 |
| EEQ11471.1 |
| EES66073.1 |
| EET14820.1 |
| EEU03858.1 |
| EEU29590.1 |
| EEU51973.1 |
| EEV32935.1 |
| EEV37488.1 |

TABLE 4-continued

Representative Examples of Glutamate Decarboxylase by EMBL/GENBANK/DDBJ ID Number

| |
|---|
| EEV50802.1 |
| EEV56374.1 |
| EEW54005.1 |
| EEW82128.1 |
| EEX25513.1 |
| EEX36940.1 |
| EEX43978.1 |
| EEY24480.1 |
| EEY27756.1 |
| EEY43805.1 |
| EEY85097.1 |
| EEZ00407.1 |
| EEZ01978.1 |
| EEZ22076.1 |
| EEZ25940.1 |
| EEZ29262.1 |
| EEZ34469.1 |
| EEZ40302.1 |
| EEZ87328.1 |
| EFA19754.1 |
| EFB70565.1 |
| EFC83076.1 |
| EFD80779.2 |
| EFE24383.1 |
| EFE51558.1 |
| EFE61154.2 |
| EFE67958.2 |
| EFE75545.2 |
| EFE80893.2 |
| EFE85357.2 |
| EFF04255.2 |
| EFF12025.2 |
| EFF50165.1 |
| EFF76031.1 |
| EFF93925.2 |
| EFG07494.1 |
| EFG18425.1 |
| EFG35990.2 |
| EFG64869.2 |
| EFG76193.1 |
| EFH79810.1 |
| EFH81299.1 |
| EFH84743.1 |
| EFI02264.1 |
| EFI09603.1 |
| EFI13088.1 |
| EFI38206.1 |
| EFI84887.1 |
| EFI86925.1 |
| EFI90012.1 |
| EFJ64163.1 |
| EFJ67574.1 |
| EFJ67825.1 |
| EFJ70740.1 |
| EFJ74790.1 |
| EFJ79351.1 |
| EFJ83178.1 |
| EFJ84244.1 |
| EFJ97064.1 |
| EFJ99289.1 |
| EFK00002.1 |
| EFK01991.1 |
| EFK04591.1 |
| EFK05907.1 |
| EFK13346.1 |
| EFK13449.1 |
| EFK18567.1 |
| EFK21645.1 |
| EFK25237.1 |
| EFK26359.1 |
| EFK27490.1 |
| EFK28268.1 |
| EFK45013.1 |
| EFK46521.1 |
| EFK48488.1 |
| EFK53224.1 |
| EFK62734.1 |
| EFK65701.1 |
| EFK67634.1 |
| EFK74425.1 |
| EFK74957.1 |
| EFK75509.1 |
| EFK90487.1 |
| EFK90538.1 |
| EFL01709.1 |
| EFL11602.1 |
| EFL25055.1 |
| EFL33863.1 |
| EFL40837.1 |
| EFL51206.1 |
| EFM42529.1 |
| EFM60472.1 |
| EFO55353.1 |
| EFO56156.1 |
| EFO57476.1 |
| EFP68935.1 |
| EFP72276.1 |
| EFP94638.1 |
| EFQ03510.1 |
| EFQ52308.1 |
| EFR14005.1 |
| EFR14897.1 |
| EFR53885.1 |
| EFR56886.1 |
| EFR83644.1 |
| EFR86795.1 |
| EFR86868.1 |
| EFR99235.1 |
| EFS34161.1 |
| EFU32132.1 |
| EFU32541.1 |
| EFU33441.1 |
| EFU33881.1 |
| EFV13462.1 |
| EFV25334.1 |
| EFV31182.1 |
| EFV39052.1 |
| EFV65675.1 |
| EFW48115.1 |
| EFW51528.1 |
| EFW54250.1 |
| EFW54681.1 |
| EFW58324.1 |
| EFW59607.1 |
| EGB59643.1 |
| EGB61475.1 |
| EGB64139.1 |
| EGB66614.1 |
| EGB70190.1 |
| EGB73425.1 |
| EGB88811.1 |
| EGB89514.1 |
| EGB90401.1 |
| EGB91657.1 |
| EGC70448.1 |
| EGC88487.1 |
| EGC95220.1 |
| EGC96302.1 |
| EGD21507.1 |
| EGD55026.1 |
| EGE43685.1 |
| EGF51021.1 |
| EGF52343.1 |
| EGG47377.1 |
| EGI12229.1 |
| EGI13717.1 |
| EGI13978.1 |
| EGI17642.1 |
| EGI19234.1 |
| EGI21026.1 |
| EGI39093.1 |
| EGI43841.1 |
| EGI50973.1 |
| EGI90408.1 |

TABLE 4-continued

Representative Examples of Glutamate Decarboxylase by EMBL/GENBANK/DDBJ ID Number

| |
|---|
| EGI96641.1 |
| EGI99727.1 |
| EGJ08652.1 |
| EGJ75615.1 |
| EGK16006.1 |
| EGK24662.1 |
| EGK37777.1 |
| EGL35452.1 |
| EGM70497.1 |
| EGM97167.1 |
| EGM98872.1 |
| EGN06817.1 |
| EGN63303.1 |
| EGP19624.1 |
| EGQ80440.1 |
| EGU29737.1 |
| EGU35278.1 |
| EGU39626.1 |
| EGU97184.1 |
| EGU98834.1 |
| EGV18719.1 |
| EGV27688.1 |
| EGX55742.1 |
| EHA59342.1 |
| EHB58351.1 |
| EHB91964.1 |
| EHD14624.1 |
| EHE93619.1 |
| EHE94113.1 |
| EHE94521.1 |
| EHG27891.1 |
| EHI10396.1 |
| EHI78992.1 |
| EHJ93424.1 |
| EHK60317.1 |
| EHK80663.1 |
| EHL31595.1 |
| EHL69790.1 |
| EHL73453.1 |
| EHL81956.1 |
| EHM02181.1 |
| EHM25499.1 |
| EHN10689.1 |
| EHN62296.1 |
| EHN62769.1 |
| EHN72080.1 |
| EHO78886.1 |
| EHP50963.1 |
| EHP65728.1 |
| EHQ35549.1 |
| EHS85882.1 |
| EHU04987.1 |
| EHU11189.1 |
| EHU13384.1 |
| EHU15660.1 |
| EHU18453.1 |
| EHU18784.1 |
| EHU21355.1 |
| EHU24375.1 |
| EHU24577.1 |
| EHU31058.1 |
| EHU32272.1 |
| EHU34561.1 |
| EHU41140.1 |
| EHU45989.1 |
| EHU51025.1 |
| EHU59824.1 |
| EHV53301.1 |
| EHV59537.1 |
| EHY69914.1 |
| EIC22952.1 |
| EID17062.1 |
| EID62180.1 |
| EID64225.1 |
| EID65429.1 |
| EID81668.1 |
| EIF28258.1 |
| EIF91592.1 |
| EIG81214.1 |
| EIG83636.1 |
| EIG91092.1 |
| EIG94667.1 |
| EIH12190.1 |
| EIH14542.1 |
| EIH23819.1 |
| EIH24646.1 |
| EIH44138.1 |
| EIH44293.1 |
| EIH77187.1 |
| EIH78539.1 |
| EII21895.1 |
| EII32183.1 |
| EII37008.1 |
| EII44135.1 |
| EII46969.1 |
| EIL45389.1 |
| EIQ03265.1 |
| EIQ09746.1 |
| EIQ16517.1 |
| EIQ21777.1 |
| EIQ23262.1 |
| EIQ25087.1 |
| EIQ31493.1 |
| EIQ33054.1 |
| EIQ41164.1 |
| EIQ56419.1 |
| EIQ60911.1 |
| EIQ65585.1 |
| EIQ73835.1 |
| EIV94746.1 |
| EIY16248.1 |
| EIY32949.1 |
| EIY34626.1 |
| EIY38162.1 |
| EIY53226.1 |
| EIY53668.1 |
| EIY56384.1 |
| EIY56765.1 |
| EIY68174.1 |
| EIY77090.1 |
| EIY82381.1 |
| EIY84200.1 |
| EIY99194.1 |
| EIZ01495.1 |
| EJC61553.1 |
| EJE70343.1 |
| EJE81777.1 |
| EJF49319.1 |
| EJF70133.1 |
| EJI94816.1 |
| EJJ06689.1 |
| EJL12446.1 |
| EJL17356.1 |
| EJO88499.1 |
| EJQ45735.1 |
| EJQ50924.1 |
| EJQ75845.1 |
| EJR29226.1 |
| EJR29527.1 |
| EJR54172.1 |
| EJR72119.1 |
| EJS51805.1 |
| EJS69263.1 |
| EJS76732.1 |
| EJU20276.1 |
| EJV56692.1 |
| EJV88830.1 |
| EJZ11766.1 |
| EJZ58218.1 |
| EJZ61626.1 |
| EJZ66136.1 |
| EJZ66990.1 |
| EKA79028.1 |
| EKA86551.1 |

TABLE 4-continued

Representative Examples of Glutamate Decarboxylase by EMBL/GENBANK/DDBJ ID Number

| |
|---|
| EKA88098.1 |
| EKA94470.1 |
| EKC91611.1 |
| EKC92880.1 |
| EKF24812.1 |
| EKI49243.1 |
| EKI49295.1 |
| EKI49297.1 |
| EKI53609.1 |
| EKI53635.1 |
| EKI53661.1 |
| EKJ88854.1 |
| EKM22885.1 |
| EKN10373.1 |
| EKN12672.1 |
| EKN18388.1 |
| EKN22714.1 |
| EKN32408.1 |
| EKN33078.1 |
| EKN71286.1 |
| EKT54086.1 |
| EKT59853.1 |
| EKT60979.1 |
| EKT61230.1 |
| EKT84064.1 |
| EKU27305.1 |
| EKU87970.1 |
| EKZ99806.1 |
| ELB02396.1 |
| ELB85708.1 |
| ELC09056.1 |
| ELC13735.1 |
| ELC15832.1 |
| ELC19797.1 |
| ELC36081.1 |
| ELC41591.1 |
| ELC88436.1 |
| ELC95019.1 |
| ELD95713.1 |
| ELE00848.1 |
| ELE39573.1 |
| ELE43669.1 |
| ELE52314.1 |
| ELE55503.1 |
| ELE57206.1 |
| ELE60967.1 |
| ELG85654.1 |
| ELG89467.1 |
| ELP68892.1 |
| ELQ79669.1 |
| ELQ90802.1 |
| ELS31036.1 |
| ELS48492.1 |
| ELS55266.1 |
| ELU51445.1 |
| ELV08451.1 |
| ELW26442.1 |
| ELW30245.1 |
| ELW35612.1 |
| ELW38629.1 |
| ELZ99535.1 |
| EMD22949.1 |
| EME15609.1 |
| EME20496.1 |
| EME52937.1 |
| EME64490.1 |
| EMF01384.1 |
| EMF28280.1 |
| EMF57186.1 |
| EMI07274.1 |
| EMI44202.1 |
| EMI57857.1 |
| EMP52368.1 |
| EMQ97025.1 |
| EMS71451.1 |
| EMS81015.1 |
| EMT34264.1 |
| EMU58101.1 |
| EMU62217.1 |
| EMU62585.1 |
| EMU62751.1 |
| EMU66940.1 |
| EMU67068.1 |
| EMU70180.1 |
| EMV16365.1 |
| EMV16410.1 |
| EMV21034.1 |
| EMV21148.1 |
| EMW92532.1 |
| EMW92626.1 |
| EMX05363.1 |
| EMX05478.1 |
| EMX17914.1 |
| EMX21187.1 |
| EMX28781.1 |
| EMX32419.1 |
| EMX35642.1 |
| EMX40966.1 |
| EMX45867.1 |
| EMX49551.1 |
| EMX82482.1 |
| EMX88290.1 |
| ENA02373.1 |
| ENA07939.1 |
| ENA37276.1 |
| ENA37661.1 |
| ENA40409.1 |
| ENA42821.1 |
| ENA44156.1 |
| ENA45677.1 |
| ENA45982.1 |
| ENC88982.1 |
| ENC89168.1 |
| ENC92105.1 |
| END50208.1 |
| END53674.1 |
| END88206.1 |
| END92583.1 |
| END93094.1 |
| ENG91208.1 |
| ENG94444.1 |
| ENG94576.1 |
| ENG97999.1 |
| ENG99381.1 |
| ENG99667.1 |
| ENH03300.1 |
| ENH06479.1 |
| ENH06612.1 |
| ENH09530.1 |
| ENT93039.1 |
| ENZ87560.1 |
| EOA56991.1 |
| EOA59672.1 |
| EOD68466.1 |
| EOD79253.1 |
| EOH72070.1 |
| EOH74810.1 |
| EOH75851.1 |
| EOH76700.1 |
| EOH78743.1 |
| EOH82280.1 |
| EOH83172.1 |
| EOH97586.1 |
| EOI53551.1 |
| EOI58405.1 |
| EOI58566.1 |
| EOM77145.1 |
| EON30602.1 |
| EOO14854.1 |
| EOO21616.1 |
| EOO25486.1 |
| EOO35817.1 |
| EOO41016.1 |
| EOO43604.1 |

TABLE 4-continued

Representative Examples of Glutamate Decarboxylase by EMBL/GENBANK/DDBJ ID Number

| |
|---|
| EOO45684.1 |
| EOO62333.1 |
| EOO80321.1 |
| EOP01042.1 |
| EOP10173.1 |
| EOP26670.1 |
| EOP64330.1 |
| EOP73916.1 |
| EOQ08142.1 |
| EOQ12252.1 |
| EOQ46471.1 |
| EOQ66882.1 |
| EOR96931.1 |
| EOS04353.1 |
| EOS05800.1 |
| EOS12272.1 |
| EOS15404.1 |
| EOS50628.1 |
| EOT40719.1 |
| EOT40879.1 |
| EOT47239.1 |
| EOT48800.1 |
| EOT84227.1 |
| EOT87490.1 |
| EOU43828.1 |
| EOU46128.1 |
| EOU63366.1 |
| EOU68068.1 |
| EOU81074.1 |
| EOU84041.1 |
| EOU87778.1 |
| EOU96296.1 |
| EOV01967.1 |
| EOV09633.1 |
| EOV50262.1 |
| EOV53815.1 |
| EOV63027.1 |
| EOV75070.1 |
| EOV79548.1 |
| EOV87732.1 |
| EOV92823.1 |
| EOW02331.1 |
| EOW07796.1 |
| EOW18421.1 |
| EOW20754.1 |
| EOW24078.1 |
| EOW28567.1 |
| EOW59950.1 |
| EOW65871.1 |
| EOW93464.1 |
| EOW98321.1 |
| EPD56434.1 |
| EPH07228.1 |
| EPH19749.1 |
| EPH46070.1 |
| EPH62839.1 |
| EPH66025.1 |
| EPH93813.1 |
| EPI24085.1 |
| EPJ40403.1 |
| EPJ94947.1 |
| EPZ46100.1 |
| EPZ53654.1 |
| EPZ62416.1 |
| EPZ62425.1 |
| EPZ62435.1 |
| EPZ62442.1 |
| EPZ62447.1 |
| EQC78775.1 |
| EQC92431.1 |
| EQI12458.1 |
| EQK38915.1 |
| EQK38916.1 |
| EQK38918.1 |
| EQK41183.1 |
| EQK41185.1 |
| EQK41187.1 |
| EQK44497.1 |
| EQK44499.1 |
| EQM30718.1 |
| EQM34161.1 |
| EQM76570.1 |
| EQN22922.1 |
| EQN27974.1 |
| EQN90009.1 |
| EQN99753.1 |
| EQO57355.1 |
| EQO68196.1 |
| EQP45261.1 |
| EQP56441.1 |
| EQQ01715.1 |
| EQQ13272.1 |
| EQV93401.1 |
| EQV95026.1 |
| EQX25160.1 |
| EQX28194.1 |
| EQX84913.1 |
| EQX88348.1 |
| EQY14917.1 |
| EQY25002.1 |
| EQY56854.1 |
| EQY62408.1 |
| EQZ97993.1 |
| ERA02674.1 |
| ERB52265.1 |
| ERB55118.1 |
| ERI40669.1 |
| ERK10135.1 |
| ERK12938.1 |
| ERK13614.1 |
| ERK41051.1 |
| ERK66628.1 |
| ERK71783.1 |
| ERL43390.1 |
| ERM89976.1 |
| ERN40441.1 |
| ERP96019.1 |
| ERT35460.1 |
| ERT41208.1 |
| ERT49556.1 |
| ERT62990.1 |
| ESA62393.1 |
| ESA65687.1 |
| ESA66394.1 |
| ESA93675.1 |
| ESC98980.1 |
| ESD24585.1 |
| ESD76492.1 |
| ESE01639.1 |
| ESE85174.1 |
| ESK09396.1 |
| ESK17280.1 |
| ESK32677.1 |
| ESK37118.1 |
| ESL01761.1 |
| ESN63984.1 |
| ESQ03366.1 |
| ESS01667.1 |
| EST27229.1 |
| EST29520.1 |
| EST30199.1 |
| EST38278.1 |
| ESU48041.1 |
| ESW58026.1 |
| ETA03730.1 |
| ETA07612.1 |
| ETA90193.1 |
| ETB03602.1 |
| ETB08300.1 |
| ETB10179.1 |
| ETB16733.1 |
| ETB35297.1 |
| ETB47280.1 |
| ETD05566.1 |

TABLE 4-continued

Representative Examples of Glutamate Decarboxylase by EMBL/GENBANK/DDBJ ID Number ETD33178.1
ETD61117.1
ETE20971.1
ETE21708.1
ETE42297.1
ETI67406.1
ETO95552.1
ETT01291.1
ETT07691.1
ETT26644.1
ETW26102.1
ETY41349.1
ETY48295.1
ETY71896.1
ETZ28153.1
ETZ53554.1
ETZ64519.1
EUA15396.1
EUA21463.1
EUA28413.1
EUA53026.1
EUA67104.1
EUA75069.1
EUA92002.1
EUB26488.1
EUB31643.1
EUB36799.1
EUC52448.1
EUC78743.1
EUD07003.1
EUJ23680.1
EUJ28388.1
EUJ30749.1
EUJ31401.1
EUJ40784.1
EUJ40792.1
EUJ41071.1
EUJ42403.1
EUJ43336.1
EUJ51856.1
EWC60294.1
EWM15117.1
EWM60131.1
EWS92576.1
EWT00088.1
EXG78068.1
EXJ13320.1
EXU65898.1
EXU86004.1
EXU92348.1
EXY29077.1
EXY29706.1
EXY30556.1
EXY42580.1
EXY67115.1
EXY71894.1
EXY75839.1
EXY86423.1
EXY92402.1
EXZ07152.1
EXZ21187.1
EXZ30272.1
EXZ46400.1
EXZ75157.1
EXZ80321.1
EXZ85038.1
EXZ96661.1
EYA21095.1
EYA40854.1
EYB10940.1
EYD86105.1
EYE48014.1
EYE57289.1
EYT59609.1
EYT64496.1
EYT82998.1
EYU71182.1
EYV06431.1
EYZ98625.1
EZA00512.1
EZA34652.1
EZA36855.1
EZD95411.1
EZE53483.1
EZE53678.1
EZJ35629.1
EZJ35909.1
EZJ42565.1
EZJ48607.1
EZJ48835.1
EZJ52118.1
EZJ52194.1
EZJ63265.1
EZJ68808.1
EZJ76944.1
EZJ82498.1
EZJ83430.1
EZJ85518.1
EZJ86304.1
EZJ86635.1
EZJ86695.1
EZK23505.1
GAA03253.1
GAA12812.1
GAA58630.1
GAA65880.1
GAA68572.1
GAA78749.1
GAA78750.1
GAB03735.1
GAB11197.1
GAB17583.1
GAB22060.1
GAB34314.1
GAB40201.1
GAB42886.1
GAB44706.1
GAB56771.1
GAB57270.1
GAB87450.1
GAB93700.1
GAC00312.1
GAC07309.1
GAC16640.1
GAC19112.1
GAC24811.1
GAC28020.1
GAC32436.1
GAC47684.1
GAC52174.1
GAC57015.1
GAC62570.1
GAC65427.1
GAC68386.1
GAC80779.1
GAC84962.1
GAD02073.1
GAD32959.1
GAD74177.1
GAD82821.1
GAF38011.1
GAP50854.1
GAJ68231.1
GAJ81697.1
GAK24408.1
GAK28408.1
GAK83740.1
GAK86157.1
GAK86158.1
GAK86159.1
GAK86194.1
GAK86195.1
GAL07170.1
GAL07171.1

TABLE 4-continued

Representative Examples of Glutamate Decarboxylase by EMBL/GENBANK/DDBJ ID Number GAL12019.1
GAL12020.1
GAL12022.1
GAL20988.1
GAL20989.1
GAL29483.1
GAL29484.1
GAL31575.1
GAL31576.1
GAL34169.1
GAL35839.1
GAL35840.1
GAL35841.1
GAL87714.1
GAL92165.1
GAM51354.1
GAM53981.1
GAM59058.1
GAM59059.1
GAM60805.1
GAM66966.1
GAM66967.1
GAM71689.1
GAM71690.1
GAM71691.1
GAM74761.1
GAM76677.1
GAM76678.1
GAM76679.1
GAM80335.1
GAM80336.1
GAM95569.1
GAO06850.1
GAP74509.1
KBR62640.1
KBZ68706.1
KCV62158.1
KDA43821.1
KDA56308.1
KDA58506.1
KDD64269.1
KDE11380.1
KDE98800.1
KDG91983.1
KDG95757.1
KDN16332.1
KDN21808.1
KDN77775.1
KDN85633.1
KDO93455.1
KDP03104.1
KDP04362.1
KDQ00107.1
KDQ03697.1
KDQ68019.1
KDR43957.1
KDS10818.1
KDS15451.1
KDS30703.1
KDS50373.1
KDS51190.1
KDS54295.1
KDS68998.1
KDU28500.1
KDV27639.1
KDV35035.1
KDV65274.1
KDW28640.1
KDW31269.1
KDX16969.1
KDX18273.1
KDX19058.1
KDX19100.1
KDX37004.1
KEF97907.1
KEG40867.1
KEI69530.1
KEI99750.1
KEJ44146.1
KEJ48094.1
KEJ57806.1
KEJ63339.1
KEJ72299.1
KEJ77438.1
KEJ77524.1
KEJ87021.1
KEK13730.1
KEK28691.1
KEL66215.1
KEL67246.1
KEL68023.1
KEL70025.1
KEN52247.1
KEN57490.1
KEN61954.1
KEN64216.1
KEN69872.1
KEN70466.1
KEN96761.1
KEN96869.1
KEO01826.1
KEO06704.1
KEO12265.1
KEO12361.1
KEO27842.1
KEO34740.1
KEO53821.1
KEQ19823.1
KER51036.1
KER76820.1
KES06427.1
KEY62213.1
KEZ81504.1
KFA95398.1
KFA95888.1
KFC84707.1
KFC90678.1
KFD42951.1
KFD43242.1
KFD74162.1
KFD78258.1
KFE40611.1
KFF59575.1
KFF94854.1
KFF96973.1
KFI71515.1
KFI90825.1
KFI97074.1
KFJ42086.1
KFJ73865.1
KFK85587.1
KFK95245.1
KFX75687.1
KFZ83979.1
KGA45423.1
KGA59562.1
KGA94282.1
KGE62311.1
KGI67105.1
KGI75049.1
KGJ48506.1
KGJ48508.1
KGL37357.1
KGL37365.1
KGL42766.1
KGL45419.1
KGL45426.1
KGM61473.1
KGM61755.1
KGM69566.1
KGM78904.1
KGM81894.1
KGM84341.1
KGM85121.1

TABLE 4-continued

Representative Examples of Glutamate Decarboxylase by EMBL/GENBANK/DDBJ ID Number KGP43353.1
KGQ70005.1
KGR34277.1
KHE42794.1
KHI28202.1
KHJ22054.1
KHJ71931.1
KHJ73332.1
KHK01750.1
KHK96657.1
KHK97208.1
KHL05645.1
KHM48596.1
KHO23213.1
KHO27057.1
KHS42788.1
KIA60405.1
KIA71170.1
KIC39052.1
KIC69438.1
KIC99691.2
KID43237.1
KID43894.1
KIE05689.1
KIE57897.1
KIF05904.1
KIF45347.1
KIF54655.1
KIF68652.1
KIG96197.1
KII76501.1
KIM01026.1
KIM15962.1
KIO34904.1
KIO44976.1
KIO94387.1
KIO96271.1
KIP30337.1
KIP53570.1
KIP73611.1
KIQ19345.1
KIQ45943.1
KIQ62037.1
KIQ77066.1
KIQ77348.1
KIS21947.1
KIS23847.1
KIU16352.1
KIV73177.1
KIX49302.1
KIZ19716.1
KJE46656.1
KJE22572.1
KJE77520.1
KJF18813.1
KJF19781.1
KJF19871.1
KJF23624.1
KJF79218.1
KJF79887.1
KJF93058.1
KJF96745.1
KJG19354.1
KJG35319.1
KJG55556.1
KJK37053.1
KJK56361.1
KJL18343.1
KJL32904.1
KJL38091.1
KJL44323.1
KJS62465.1
KJU70415.1
KJW12820.1
KJW22772.1
KJW44373.1
KJY18848.1

TABLE 4-continued

Representative Examples of Glutamate Decarboxylase by EMBL/GENBANK/DDBJ ID Number KJY30329.1
KJY38629.1
KJY39390.1
KJY40940.1
KJY43460.1
KKA40192.1
KKB46833.1
KKB57083.1
KKB58027.1
KKC03154.1
KKD05819.1
KKD45841.1
KKD49597.1
KKD62061.1
KKE98190.1
KKI22291.1
KKI42113.1
KKI50839.1
KKW62398.1
KKX97583.1
KKY01177.1
KKY01179.1
KKY69347.1
KLA29488.1
KLA31120.1
KLD60995.1
KLE26826.1
KLI09651.1
KLI91468.1
KLI98112.1
KLJ05152.1
KLN34163.1
KLN95712.1
KLO25668.1
KLO35668.1
KLO43396.1
KLO51710.1
KLR49798.1
KLR60461.1
KLU05222.1
KLU19162.1
KLU58975.1
KLU69060.1
KLV28432.1
KLX53926.1
KLX61120.1
KLX94454.1
KLX97537.1
KME63659.1
KME67053.1
KME68735.1
KMM25249.1
KMM34481.1
KMM81854.1
KMM85123.1
KMM89123.1
KMN03094.1
KMN10907.1
KMN15408.1
KMN18102.1
KMN42082.1
KMN99021.1
KMO68962.1
KMO71467.1
KMO77249.1
KMO96783.1
KMQ76627.1
KMS68506.1
KMS83576.1
KMT54476.1
KMV17260.1
KMV23624.1
KMW38818.1
KMW82598.1
KNA39120.1
KNA42305.1
KNA42530.1

TABLE 4-continued

Representative Examples of Glutamate Decarboxylase by EMBL/GENBANK/DDBJ ID Number KNB52133.1
KNC11996.1
KND28891.1
KND38179.1
KND38376.1
KND61615.1
KNF63080.1
KNF82369.1
KNH21214.1
KNZ42189.1
KOA33258.1
KOA34702.1
KOG31486.1
KOG36523.1
KOG41666.1
KOG45278.1
KOG56200.1
KOG63866.1
KOG67868.1
KOG82155.1
KON11130.1
KON74404.1
KON83792.1
KOP74641.1
KOR26641.1
KOS58051.1
KOT30645.1
KOT53033.1
KOT88922.1
KOT94882.1
KOU20397.1
KOU22686.1
KOU33149.1
KOU50755.1
KOU54733.1
KOU56607.1
KOV13964.1
KOV45494.1
KOV48801.1
KOV52774.1
KOV57805.1
KOV68117.1
KOV68430.1
KOV76057.1
KOV97628.1
KOX01174.1
KOX37867.1
KOX47623.1
KOY49525.1
KOY53494.1
KOY54178.1
KPA51275.1
KPC66018.1
KPC77424.1
KPC82004.1
KPD04524.1
KPG33268.1
KPH96934.1
KPI04468.1
KPI10516.1
KPI15295.1
KPI19262.1
KPI20012.1
KPI26485.1
KPL33203.1
KPM51038.1
KPN18694.1
KPN43081.1
KPN48420.1
KPO13719.1
KPO16265.1
KPO16391.1
KPO17089.1
KPO34510.1
KPO35845.1
KPO37368.1
KPO41178.1

TABLE 4-continued

Representative Examples of Glutamate Decarboxylase by EMBL/GENBANK/DDBJ ID Number KPO44233.1
KPO51751.1
KPO52539.1
KPO58193.1
KPQ02829.1
KPV45380.1
KQB54807.1
KQJ27665.1
KST35322.1
KST82806.1
KST89062.1
KSU11406.1
KSU16536.1
KXL66213.1
KYR53955.1
KYV67232.1
KYV71371.1
OAJ87252.1
OAJ89593.1
OAO63316.1
OCL17438.1
OEI61147.1
OEN35083.1
OEN35408.1
OIX26336.1

Representative examples of putrescine aminotransferase (EC 2.6.1.82) are given below in Table 5 and identified by their EMBL/GenBank/DDBJ ID numbers. Any of the bacteria given in Table 10 can be engineered with any version of the putrescine aminotransferase (EC 2.6.1.82) set forth in Table 3 and Table 5. For instance, the bacteria can be engineered with a version of the putrescine aminotransferase enzyme that has at least 50% nucleotide similarity with any of the versions of putrescine aminotransferase given in Table 5 (e.g., at least nucleotide 60% similarity, at least 70% nucleotide similarity, at least 80% nucleotide similarity, at least 90% nucleotide similarity, at least 91% nucleotide similarity, at least 92% nucleotide similarity, at least 93% nucleotide similarity, at least 94% nucleotide similarity, at least 95% nucleotide similarity, at least 96% nucleotide similarity, at least 97% nucleotide similarity, at least 98% nucleotide similarity, at least 99% nucleotide similarity, at least 99.5% nucleotide similarity, at least 99.9% nucleotide similarity, or 100% nucleotide similarity).

TABLE 5

Representative Examples of Putrescine Aminotransferase by EMBL/GenBank/DDBJ ID Number AAA57874.1
AAA89152.1
AAC36832.1
AAC45301.1
AAC74384.1
AAC75709.1
AAC76108.3
AAF10980.1
AAG03522.1
AAG03688.1
AAG58206.1
AAK15486.1
AAL22091.1
AAN44587.2
AAN82273.1
AAO70680.1
AAP18399.1
AAV78920.1
AAX67071.1
AAZ89792.1

TABLE 5-continued

Representative Examples of Putrescine Aminotransferase by EMBL/GenBank/DDBJ ID Number

| |
|---|
| ABA89323.1 |
| ABB67447.1 |
| ABE08957.1 |
| ABF05173.1 |
| ABG71145.1 |
| ABJ02583.1 |
| ABJ15261.1 |
| ABO88369.1 |
| ABP62186.1 |
| ABR78896.1 |
| ABU78707.1 |
| ABV07484.1 |
| ABV15541.1 |
| ABV20592.1 |
| ABX24187.1 |
| ABX64022.1 |
| ABX69344.1 |
| ABX75605.1 |
| ABY42524.1 |
| ACA76303.1 |
| ACB04157.1 |
| ACB17060.1 |
| ACF64513.1 |
| ACF70070.1 |
| ACF88918.1 |
| ACH48710.1 |
| ACH77510.1 |
| ACI09453.1 |
| ACI18235.1 |
| ACI36066.1 |
| ACI77901.1 |
| ACI77902.1 |
| ACI77903.1 |
| ACI77904.1 |
| ACI77905.1 |
| ACN47379.1 |
| ACO02631.1 |
| ACO80985.1 |
| ACR65342.1 |
| ACS85106.1 |
| ACT07527.1 |
| ACT12462.1 |
| ACT27738.1 |
| ACX87602.1 |
| ACY90298.1 |
| ACZ77451.1 |
| ADA75444.1 |
| ADD58285.1 |
| ADF63987.1 |
| ADM97796.1 |
| ADO46913.1 |
| ADO70560.1 |
| ADR28470.1 |
| ADT76707.1 |
| ADX19008.1 |
| AEA71912.1 |
| AEE58362.1 |
| AEE97629.1 |
| AEG95705.1 |
| AEI06121.1 |
| AEI45944.1 |
| AEJ41147.1 |
| AEJ58471.1 |
| AEN66465.1 |
| AEQ14325.1 |
| AEW04404.1 |
| AEW63332.1 |
| AEW75317.1 |
| AEX02383.1 |
| AFC33584.1 |
| AFG42020.1 |
| AFH65907.1 |
| AFI89823.1 |
| AFJ30752.1 |
| AFJ45596.1 |
| AFJ57021.1 |
| AFM41617.1 |
| AFM61662.1 |
| AFN34266.1 |
| AFR02837.1 |
| AFS72647.1 |
| AFT85698.1 |
| AFU12013.1 |
| AGB76663.1 |
| AGF56701.1 |
| AGH86154.1 |
| AGM28805.1 |
| AGN85841.1 |
| AGQ74484.1 |
| AGR60480.1 |
| AHA09869.1 |
| AHA67171.1 |
| AHA67172.1 |
| AHB72039.1 |
| AHE60723.1 |
| AHE69148.1 |
| AHF76631.1 |
| AHJ76496.2 |
| AHM77480.1 |
| AHM83064.1 |
| AHN81979.1 |
| AHY10460.1 |
| AHY72510.1 |
| AID92376.1 |
| AII63595.1 |
| AIP96878.1 |
| AIR04884.1 |
| AIR60611.1 |
| AIR68505.1 |
| AIS03494.1 |
| AIS53235.1 |
| AIT00514.1 |
| AIU72158.1 |
| AIW78685.1 |
| AIW86257.1 |
| AIX66695.1 |
| AIZ84136.1 |
| AJA28077.1 |
| AJB64485.1 |
| AJC52685.1 |
| AJC61854.1 |
| AJC65876.1 |
| AJE19840.1 |
| AJE57644.1 |
| AJE82594.1 |
| AJF57894.1 |
| AJF75010.1 |
| AJH17424.1 |
| AJK49269.1 |
| AJO86687.1 |
| AJQ98395.1 |
| AJY76773.1 |
| AJZ91824.1 |
| AKE62036.1 |
| AKE93437.1 |
| AKH08854.1 |
| AKH23767.1 |
| AKK34697.1 |
| AKK40619.1 |
| AKK49917.1 |
| AKL15453.1 |
| AKL34316.1 |
| AKL96946.1 |
| AKM18742.1 |
| AKM36624.1 |
| AKP48388.1 |
| AKP75846.1 |
| AKZ54414.1 |
| ALA75381.1 |
| ALB43935.1 |
| ALB53581.1 |
| ALB68770.1 |
| ALB72871.1 |
| ALC72125.1 |

TABLE 5-continued

Representative Examples of Putrescine Aminotransferase by EMBL/GenBank/DDBJ ID Number

| |
|---|
| ALD27706.1 |
| ALK33515.1 |
| ALL90941.1 |
| ALO12800.1 |
| ALO15071.1 |
| ALR25918.1 |
| ALR78149.1 |
| ALX80070.1 |
| ALY14616.1 |
| ALZ69902.1 |
| AMA74351.1 |
| AMJ41057.1 |
| AMJ69166.1 |
| AMK11196.1 |
| AMW45996.1 |
| AMX16618.1 |
| ANK35521.1 |
| ANM83865.1 |
| ANO24137.1 |
| ANO91000.1 |
| ANP19910.1 |
| ANZ85526.1 |
| AOM43730.1 |
| APA44613.1 |
| BAA14871.1 |
| BAA16525.1 |
| BAA94599.1 |
| BAA94600.1 |
| BAB37378.1 |
| BAD88710.1 |
| BAE77123.1 |
| BAG78878.1 |
| BAI27353.1 |
| BAI32529.1 |
| BAI37675.1 |
| BAK33480.1 |
| BAM00748.1 |
| BAN45963.1 |
| BAN57107.1 |
| BAS27610.1 |
| BAS27927.1 |
| BAT36548.1 |
| BAT40862.1 |
| BAT45090.1 |
| BAU25986.1 |
| BAU53092.1 |
| CAB99164.1 |
| CAD07742.1 |
| CAD55516.1 |
| CAG74449.1 |
| CAJ90253.1 |
| CAQ90518.1 |
| CAR00034.1 |
| CAR04699.1 |
| CAR09890.2 |
| CAR14711.1 |
| CAR19687.1 |
| CAR34636.1 |
| CAR38915.1 |
| CAR61129.1 |
| CAS10914.1 |
| CAU99632.1 |
| CBA27530.1 |
| CBG36194.1 |
| CBG91495.1 |
| CBH75900.1 |
| CBI02339.1 |
| CBI02439.1 |
| CBJ02843.1 |
| CBL20779.1 |
| CBW19289.1 |
| CCC31907.1 |
| CCF65898.1 |
| CCI78933.1 |
| CCJ45694.1 |
| CCJ72687.1 |
| CCJ77939.1 |
| CCJ80840.1 |
| CCJ87365.1 |
| CCJ91133.1 |
| CCK00585.1 |
| CCK05055.1 |
| CCK09612.1 |
| CCK25971.1 |
| CCK48380.1 |
| CCO07408.1 |
| CCO08483.1 |
| CCY61522.1 |
| CDB46597.1 |
| CDC39173.1 |
| CDD12313.1 |
| CDK69254.1 |
| CDK78180.1 |
| CDL09266.1 |
| CDL16320.1 |
| CDL21785.1 |
| CDL24460.1 |
| CDL41008.1 |
| CDL43466.1 |
| CDL49947.1 |
| CDL54548.1 |
| CDL60105.1 |
| CDN08464.1 |
| CDN83823.1 |
| CDO12367.1 |
| CDQ16366.1 |
| CDQ55161.1 |
| CDS92449.1 |
| CDU33631.1 |
| CDU41038.1 |
| CDW60669.1 |
| CDZ85955.1 |
| CDZ90589.1 |
| CEG33484.1 |
| CEH27897.1 |
| CEH28958.1 |
| CEJ63776.1 |
| CEK06962.1 |
| CEL88139.1 |
| CEO89736.1 |
| CEP33002.1 |
| CFW77176.1 |
| CJF89882.1 |
| CKG89699.1 |
| CNQ38822.1 |
| CNT85510.1 |
| CNU20511.1 |
| CNU75336.1 |
| CPR21341.1 |
| CPR52929.1 |
| CPR70581.1 |
| CPS20475.1 |
| CPU47210.1 |
| CPU50448.1 |
| CPU63604.1 |
| CPV69500.1 |
| CPW19061.1 |
| CPW19086.1 |
| CPW42553.1 |
| CQA01107.1 |
| CQA05377.1 |
| CQR59780.1 |
| CQR65737.1 |
| CQR76108.1 |
| CRF31866.1 |
| CRK82822.1 |
| CRL90015.1 |
| CSL03976.1 |
| CSN57331.1 |
| CSP97983.1 |
| CSS48268.1 |
| CST07703.1 |
| CTQ00194.1 |
| CTQ01408.1 |

TABLE 5-continued

Representative Examples of Putrescine Aminotransferase by EMBL/GenBank/DDBJ ID Number

| |
|---|
| CTQ06965.1 |
| CTQ10470.1 |
| CTQ20562.1 |
| CTQ78696.1 |
| CTR79713.1 |
| CTR96904.1 |
| CTS73379.1 |
| CTS73419.1 |
| CTT28505.1 |
| CTT56172.1 |
| CTT69475.1 |
| CTU79150.1 |
| CTU88023.1 |
| CTU94690.1 |
| CTV09894.1 |
| CTV11053.1 |
| CTX20702.1 |
| CTZ29307.1 |
| CTZ49322.1 |
| CUI62304.1 |
| CUJ87125.1 |
| CUK19452.1 |
| CUV19889.1 |
| CUV29759.1 |
| CUV44247.1 |
| CUW27398.1 |
| CUX83295.1 |
| CVK16600.1 |
| EAU62914.1 |
| EDL55484.1 |
| EDO56632.1 |
| EDQ32965.1 |
| EDS93910.1 |
| EDU66756.1 |
| EDU92373.1 |
| EDX36107.1 |
| EDX43683.1 |
| EDX70173.1 |
| EDY23644.1 |
| EDY55948.1 |
| EDY58150.2 |
| EDY59830.2 |
| EEH12859.1 |
| EEI19352.1 |
| EEI70764.1 |
| EEI93920.1 |
| EEK74306.1 |
| EEL07176.1 |
| EEL35424.1 |
| EEL41357.1 |
| EEL47872.1 |
| EEL58542.1 |
| EEL71807.1 |
| EEL84498.1 |
| EEM06318.1 |
| EEM17585.1 |
| EEP53384.1 |
| EEP61904.1 |
| EEQ93121.1 |
| EEW41109.1 |
| EFC54109.1 |
| EFE05843.1 |
| EFE61929.2 |
| EFF04850.2 |
| EFF11713.2 |
| EFI88372.1 |
| EFJ64643.1 |
| EFJ70989.1 |
| EFJ81337.1 |
| EFJ85921.1 |
| EFJ98691.1 |
| EFK04657.1 |
| EFK09659.1 |
| EFK13604.1 |
| EFK21010.1 |
| EFK23876.1 |
| EFK46876.1 |
| EFK49689.1 |
| EFK57463.1 |
| EFK70624.1 |
| EFK75383.1 |
| EFK91732.1 |
| EFL03670.1 |
| EFL18682.1 |
| EFL30368.1 |
| EFL33839.1 |
| EFL36249.1 |
| EFO59858.1 |
| EFP71978.1 |
| EFP71979.1 |
| EFR14711.1 |
| EFU36955.1 |
| EFV42072.1 |
| EFW49740.1 |
| EFW54280.1 |
| EFW57755.1 |
| EGB14251.1 |
| EGB62034.1 |
| EGB65436.1 |
| EGB73934.1 |
| EGB87427.1 |
| EGC96496.1 |
| EGE35595.1 |
| EGH58156.1 |
| EGI09466.1 |
| EGI14765.1 |
| EGI20132.1 |
| EGI39453.1 |
| EGI44536.1 |
| EGI49547.1 |
| EGI91691.1 |
| EGI91882.1 |
| EGI91908.1 |
| EGJ05807.1 |
| EGK18274.1 |
| EGK35042.1 |
| EGK57964.1 |
| EGU98422.1 |
| EHB43515.1 |
| EHC32088.1 |
| EHC32777.1 |
| EHC32780.1 |
| EHC32793.1 |
| EHC45475.1 |
| EHC45503.1 |
| EHC52082.1 |
| EHC52087.1 |
| EHC52088.1 |
| EHC61796.1 |
| EHC61797.1 |
| EHC67244.1 |
| EHC67259.1 |
| EHC75056.1 |
| EHC75092.1 |
| EHC81432.1 |
| EHC81436.1 |
| EHC81453.1 |
| EHC82194.1 |
| EHC82200.1 |
| EHC87537.1 |
| EHC87548.1 |
| EHC99340.1 |
| EHC99346.1 |
| EHC99347.1 |
| EHC99662.1 |
| EHC99665.1 |
| EHC99666.1 |
| EHD22256.1 |
| EHJ00584.1 |
| EHJ80884.1 |
| EHJ80892.1 |
| EHM38093.1 |
| EHM49393.1 |
| EHP66038.1 |

TABLE 5-continued

Representative Examples of Putrescine Aminotransferase by EMBL/GenBank/DDBJ ID Number EHT11055.1
EHU06080.1
EHU06383.1
EHU09521.1
EHU19477.1
EHU22647.1
EHU26084.1
EHU36390.1
EHU39097.1
EHU51516.1
EHV54826.1
EHY68818.1
EID63416.1
EID68002.1
EIG80589.1
EIG93735.1
EIH10970.1
EIH24433.1
EIH45756.1
E1H76113.1
EII21076.1
EII37121.1
EII44330.1
EIK73551.1
EIL52772.1
EIQ05705.1
EIQ18685.1
EIQ33923.1
EIQ57498.1
EIQ69925.1
EIQ70386.1
EJE66457.1
EJE84374.1
EJF29639.1
EJK89144.1
EJL13039.1
EJL42219.1
EJP95200.1
EJQ09156.1
EJQ42479.1
EJQ53619.1
EJQ73265.1
EJQ76215.1
EJR03070.1
EJR30137.1
EJR37137.1
EJR56655.1
EJR60363.1
EJS01188.1
EJS10133.1
EJS12547.1
EJS52655.1
EJS66726.1
EJS74470.1
EJU35674.1
EJV59704.1
EJV88337.1
EJZ63610.1
EKB48854.1
EKI50350.1
EKN69369.1
EKY15805.1
ELC14392.1
ELC16479.1
ELC36432.1
ELC95414.1
ELD97045.1
ELE40056.1
ELE53047.1
ELE57708.1
ELG86056.1
ELI22530.1
ELJ68100.1
ELK42117.1
ELS58123.1
ELV07387.1
ELW30847.1
EMD08043.1
EMR53712.1
EMT38915.1
EMT53291.1
EMU59120.1
EMU68070.1
EMV17890.1
EMW94343.1
EMX18799.1
EMX29635.1
EMX36855.1
EMX47016.1
EMX83385.1
EMZ13604.1
ENA04805.1
ENA37997.1
ENA43345.1
ENC89529.1
END51354.1
END88908.1
ENG94980.1
ENH00344.1
ENH06977.1
ENZ36084.1
ENZ85363.1
EOB13036.1
EOO15443.1
EOO21808.1
EOO40793.1
EOO75774.1
EOO78537.1
EOP16122.1
EOP27458.1
EOP41686.1
EOP56689.1
EOP57538.1
EOP72097.1
EOP74673.1
EOQ14051.1
EOQ45898.1
EOQ51737.1
EOU48296.1
EOU64078.1
EOU77605.1
EOU89114.1
EOV03214.1
EOV47394.1
EOV55537.1
EOV76073.1
EOV93686.1
EOW03648.1
EOW19479.1
EOW29746.1
EOW62005.1
EOW94128.1
EPF20607.1
EPF23810.1
EPF68941.1
EPH43618.1
EPI71152.1
EPI71726.1
EPI91450.1
EPI98428.1
EPI99620.1
EPJ05539.1
EPJ10674.1
EQD48086.1
EQN24196.1
EQN91238.1
EQO58637.1
EQP45856.1
EQQ02030.1
EQV89459.1
EQX26002.1
EQX85393.1
EQY15934.1
EQY57475.1

TABLE 5-continued

Representative Examples of Putrescine Aminotransferase by EMBL/GenBank/DDBJ ID Number

| |
|---|
| EQZ98152.1 |
| ERI03907.1 |
| ERI09683.1 |
| ERI93353.1 |
| ERK29115.1 |
| ERO58336.1 |
| ERO59766.1 |
| ERP00368.1 |
| ESA64895.1 |
| ESA65448.1 |
| ESA65917.1 |
| ESA75128.1 |
| ESA87456.1 |
| ESA87933.1 |
| ESB01012.1 |
| ESC94775.1 |
| ESD11433.1 |
| ESD19507.1 |
| ESD37227.1 |
| ESD63043.1 |
| ESD69311.1 |
| ESD77797.1 |
| ESE00825.1 |
| ESE81665.1 |
| ESE84032.1 |
| ESF53913.1 |
| ESG67336.1 |
| ESJ20736.1 |
| ESK15909.1 |
| ESK33462.1 |
| ESL70275.1 |
| ESM13806.1 |
| ESN17365.1 |
| ESN64633.1 |
| ESS57289.1 |
| ESS68083.1 |
| EST52466.1 |
| ESU79725.1 |
| ESU79726.1 |
| ETA87938.1 |
| ETC31011.1 |
| ETD63590.1 |
| ETE17194.1 |
| ETE48332.1 |
| ETI91426.1 |
| ETJ22905.1 |
| ETJ36492.1 |
| ETT76699.1 |
| ETY41938.1 |
| EUA69680.1 |
| EUA84046.1 |
| EWG73522.1 |
| EWG77224.1 |
| EWS95005.1 |
| EWS95811.1 |
| EYD83647.1 |
| EYE21343.1 |
| EYV13884.1 |
| EYV14671.1 |
| EYZ94185.1 |
| EZA39087.1 |
| EZD30976.1 |
| EZE08113.1 |
| EZE58040.1 |
| EZJ36257.1 |
| EZJ49055.1 |
| EZJ70721.1 |
| EZJ83281.1 |
| EZK20097.1 |
| EZP34120.1 |
| EZP69273.1 |
| GAB53792.1 |
| GAD66768.1 |
| GAF37976.1 |
| GAK71556.1 |
| GAL45775.1 |
| GAL51546.1 |
| GAL57703.1 |
| GAM01523.1 |
| GAP71067.1 |
| GAQ24599.1 |
| GAQ52594.1 |
| GAQ62824.1 |
| GAR76344.1 |
| GAS78753.1 |
| KCZ71192.1 |
| KDA56524.1 |
| KDE35397.1 |
| KDF12097.1 |
| KDF12267.1 |
| KDG92710.1 |
| KDM54636.1 |
| KDN97932.1 |
| KDU32581.1 |
| KDV36696.1 |
| KDV41290.1 |
| KDV63554.1 |
| KDW29512.1 |
| KDX22072.1 |
| KDX46941.1 |
| KEA53701.1 |
| KEF36300.1 |
| KEJ44729.1 |
| KEJ58710.1 |
| KEJ72834.1 |
| KEL69605.1 |
| KEN52983.1 |
| KEN65251.1 |
| KEN97872.1 |
| KEO07702.1 |
| KEO29548.1 |
| KEO37679.1 |
| KER50700.1 |
| KER78502.1 |
| KEY61249.1 |
| KEY61542.1 |
| KEY61632.1 |
| KEY61720.1 |
| KEY62070.1 |
| KEY62211.1 |
| KEY62248.1 |
| KEY62600.1 |
| KEY62750.1 |
| KEY62777.1 |
| KEY63154.1 |
| KEY63197.1 |
| KEY63491.1 |
| KEY63621.1 |
| KEY63666.1 |
| KEZ84112.1 |
| KEZ91498.1 |
| KFB98795.1 |
| KFC77618.1 |
| KFC87779.1 |
| KFC92200.1 |
| KFC94055.1 |
| KFD40864.1 |
| KFD77810.1 |
| KFF72766.1 |
| KFI56278.1 |
| KFI63760.1 |
| KFI64199.1 |
| KFI81170.1 |
| KFX06880.1 |
| KFX14235.1 |
| KFX74939.1 |
| KGA35360.1 |
| KGA42964.1 |
| KGF09343.1 |
| KGM62239.1 |
| KGM72003.1 |
| KGM83624.1 |
| KGM85554.1 |
| KGT96644.1 |

TABLE 5-continued

Representative Examples of Putrescine Aminotransferase by EMBL/GenBank/DDBJ ID Number

| |
|---|
| KHD16675.1 |
| KHG17857.1 |
| KHG23880.1 |
| KHG24026.1 |
| KHG25621.1 |
| KHI36730.1 |
| KHJ14566.1 |
| KHN51965.1 |
| KHN62432.1 |
| KHN91314.1 |
| KHO61939.1 |
| KHS46174.1 |
| KHS75073.1 |
| KHT32808.1 |
| KHT39972.1 |
| KID02664.2 |
| KIH05031.1 |
| KIL36988.1 |
| KIL37280.1 |
| KIL75881.1 |
| KIL78121.1 |
| KIQ46533.1 |
| KIQ55575.1 |
| KIS45828.1 |
| KIU31395.1 |
| KIV76534.1 |
| KJC02074.1 |
| KJC05752.1 |
| KJC10953.1 |
| KJF38320.1 |
| KJH07563.1 |
| KJM39013.1 |
| KJM95208.1 |
| KJN23016.1 |
| KJS00574.1 |
| KJS11246.1 |
| KJS12052.1 |
| KJS23079.1 |
| KJS48202.1 |
| KJW31626.1 |
| KJW48653.1 |
| KJX12962.1 |
| KJX35546.1 |
| KJZ82908.1 |
| KJZ83822.1 |
| KKA53732.1 |
| KKB33451.1 |
| KKB37484.1 |
| KKC61647.1 |
| KKI48768.1 |
| KKI89815.1 |
| KKJ26361.1 |
| KKK45477.1 |
| KKM10135.1 |
| KKY41353.1 |
| KKY86484.1 |
| KLQ22117.1 |
| KLT72735.1 |
| KLU65949.1 |
| KLV42517.1 |
| KLV56190.1 |
| KLV64988.1 |
| KLV65484.1 |
| KLV74220.1 |
| KLW86671.1 |
| KLX58084.1 |
| KLX94977.1 |
| KLY12232.1 |
| KLY33021.1 |
| KME67644.1 |
| KMI32966.1 |
| KMK12937.1 |
| KML66598.1 |
| KMM34304.1 |
| KMM41841.1 |
| KMN46751.1 |
| KMN64361.1 |
| KMN93720.1 |
| KMO70017.1 |
| KMO73567.1 |
| KMO79473.1 |
| KMV34687.1 |
| KMV71410.1 |
| KMY52755.1 |
| KMY52867.1 |
| KNA43034.1 |
| KNB70753.1 |
| KNB70796.1 |
| KNC12151.1 |
| KNC91419.1 |
| KNF71262.1 |
| KNF81324.1 |
| KNH23702.1 |
| KNN86024.1 |
| KNW78813.1 |
| KNY77855.1 |
| KNZ99940.1 |
| KOA27411.1 |
| KON69897.1 |
| KON90844.1 |
| KON96751.1 |
| KOP04345.1 |
| KOP73204.1 |
| KOP92853.1 |
| KOR79514.1 |
| KOR86809.1 |
| KPA87633.1 |
| KPA87634.1 |
| KPB72987.1 |
| KPL77404.1 |
| KPO05706.1 |
| KPO33063.1 |
| KPO54643.1 |
| KPP86588.1 |
| KPP90487.1 |
| KPQ06635.1 |
| KPQ07802.1 |
| KPQ17574.1 |
| KPQ18521.1 |
| KPQ21853.1 |
| KPQ48969.1 |
| KPR56433.1 |
| KPU43824.1 |
| KPW09941.1 |
| KPW15746.1 |
| KPW54438.1 |
| KPW91211.1 |
| KPX42861.1 |
| KPX63485.1 |
| KPY30896.1 |
| KPY55802.1 |
| KPY81707.1 |
| KPY97724.1 |
| KQB77808.1 |
| KQC84343.1 |
| KQJ43040.1 |
| KQL34770.1 |
| KQL45807.1 |
| KQL49683.1 |
| KQU20541.1 |
| KQU25399.1 |
| KRD84748.1 |
| KRE10236.1 |
| KRF52830.1 |
| KRF58868.1 |
| KRF60614.1 |
| KRF63503.1 |
| KRK41016.1 |
| KRM06091.1 |
| KRM11195.1 |
| KRQ86107.1 |
| KRT40898.1 |
| KSB12379.1 |
| KSB60709.1 |

TABLE 5-continued

Representative Examples of Putrescine Aminotransferase by EMBL/GenBank/DDBJ ID Number KSB77569.1
KST26609.1
KST80109.1
KSU03228.1
KSU11825.1
KSU28121.1
KSX62841.1
KSX94554.1
KSY24943.1
KSZ14257.1
KTH73029.1
KTI23444.1
KTK26313.1
KTK78251.1
KTM84786.1
KTO49964.1
KTO73181.1
KTP65662.1
KTZ06525.1
KUB34136.1
KUE74614.1
KUH45954.1
KUH57572.1
KUO48919.1
KUQ85390.1
KWU61736.1
KWU68561.1
KWW11355.1
KXG99471.1
KXH99505.1
KXL57621.1
KXQ38659.1
KYR51641.1
KYS98061.1
KYV66420.1
KZJ62467.1
OAC42867.1
OAJ90061.1
OAO74321.1
OCL20194.1
OCS62224.1
OCV69030.1
ODH23946.1
OEH16092.1
OEN36946.1
OFD09909.1
SAE79353.1
SBL80466.1
SBZ09436.1

Representative examples of gamma-aminobutyraldehyde dehydrogenase (EC 1.2.1.19) are given below in Table 6 and identified by their EMBL/GENBANK/DDBJ ID numbers. Any of the bacteria given in Table 10 can be engineered with any version of the gamma-aminobutyraldehyde dehydrogenase (EC 1.2.1.19) set forth in Table 3 and Table 6. For instance, the bacteria can be engineered with a version of the gamma-aminobutyraldehyde dehydrogenase enzyme that has at least 50% nucleotide similarity with any of the versions of gamma-aminobutyraldehyde dehydrogenase given in Table 6 (e.g., at least nucleotide 60% similarity, at least 70% nucleotide similarity, at least 80% nucleotide similarity, at least 90% nucleotide similarity, at least 91% nucleotide similarity, at least 92% nucleotide similarity, at least 93% nucleotide similarity, at least 94% nucleotide similarity, at least 95% nucleotide similarity, at least 96% nucleotide similarity, at least 97% nucleotide similarity, at least 98% nucleotide similarity, at least 99% nucleotide similarity, at least 99.5% nucleotide similarity, at least 99.9% nucleotide similarity, or 100% nucleotide similarity).

TABLE 6

Representative Examples of Gamma-Aminobutyraldehyde Dehydrogenase by EMBL/GENBANK/DDBJ ID Number AAA23428.1
AAC74382.1
AAC74526.1
AAG56331.1
AAL20515.1
AAN43345.1
AAN54343.1
AAN68409.1
AAN80331.1
AAO69141.1
AAP17225.1
AAV77220.1
AAX65500.1
AAY35300.1
AAY91615.1
AAZ88386.1
ABA73866.1
ABA76670.1
ABA77271.1
ABA81134.1
ABB06719.1
ABB09933.1
ABB61850.1
ABC35115.1
ABE07141.1
ABE33447.1
ABE35009.1
ABE58543.1
ABF03934.1
ABF07563.1
ABF08506.1
ABF77276.1
ABG69453.1
ABI88593.1
ABI91617.1
ABJ00886.1
ABO56067.1
ABP60799.1
ABP83011.1
ABQ62162.1
ABQ79255.1
ABQ81306.1
ABR77355.1
ABR80823.1
ABU77182.1
ABV05856.1
ABV12611.1
ABV19407.1
ABV19711.1
ABV42738.1
ABV94754.1
ABX21278.1
ABX67082.1
ACA77853.1
ACB02660.1
ACB16069.1
ACB17411.1
ACD08717.1
ACF65188.1
ACH48735.1
ACI07089.1
ACI11169.1
ACI11654.1
ACI38546.1
ACI83776.1
ACI83777.1
ACI83778.1
ACI83779.1
ACI83780.1
ACI84176.1
ACI84177.1
ACI84178.1
ACI84179.1
ACI84180.1
ACI98856.1
ACL96708.1
ACN46267.1

TABLE 6-continued

Representative Examples of Gamma-Aminobutyraldehyde Dehydrogenase by EMBL/GENBANK/DDBJ ID Number

| |
|---|
| ACR63729.1 |
| ACS85105.1 |
| ACT07528.1 |
| ACT12461.1 |
| ACX87601.1 |
| ACY88405.1 |
| ACZ77452.1 |
| ACZ84797.1 |
| ACZ84868.1 |
| ADA74159.1 |
| ADD56229.1 |
| ADD56381.1 |
| ADF61409.1 |
| ADF61777.1 |
| ADI12862.1 |
| ADJ47943.1 |
| ADM97795.1 |
| ADN75355.1 |
| ADO48635.1 |
| ADP16410.1 |
| ADR26852.1 |
| ADT74882.1 |
| ADT75049.1 |
| ADV53576.1 |
| ADX17297.1 |
| AEC17673.1 |
| AEE56233.1 |
| AEE56444.1 |
| AEG95612.1 |
| AEG98095.1 |
| AEG98933.1 |
| AEH78268.1 |
| AEH79912.1 |
| AEI77057.1 |
| AEI81569.1 |
| AEJ11708.1 |
| AEJ41144.1 |
| AEJ56308.1 |
| AEJ56491.1 |
| AEK44843.1 |
| AEN65037.1 |
| AEQ12441.1 |
| AEV61105.1 |
| AEW60590.1 |
| AEW61596.1 |
| AEW61597.1 |
| AEW73833.1 |
| AEW96833.1 |
| AEX05106.1 |
| AEX05672.1 |
| AEX21381.1 |
| AEY02655.1 |
| AFG40539.1 |
| AFG40645.1 |
| AFI68614.1 |
| AFI89822.1 |
| AFJ28854.1 |
| AFJ28952.1 |
| AFJ47105.1 |
| AFK56420.1 |
| AFK67163.1 |
| AFL53103.1 |
| AFM59735.1 |
| AFM60144.1 |
| AFN32345.1 |
| AFO48697.1 |
| AFO86070.1 |
| AFO92872.1 |
| AFR02836.1 |
| AFR27692.1 |
| AFR30100.1 |
| AFR31023.1 |
| AFS74542.1 |
| AFS74651.1 |
| AFT90302.1 |
| AFT90471.1 |
| AFY18239.1 |

TABLE 6-continued

Representative Examples of Gamma-Aminobutyraldehyde Dehydrogenase by EMBL/GENBANK/DDBJ ID Number

| |
|---|
| AFY18244.1 |
| AGB72506.1 |
| AGB72704.1 |
| AGB74580.1 |
| AGB75454.1 |
| AGB78252.1 |
| AGE94564.1 |
| AGG75097.1 |
| AGI23954.1 |
| AGI25578.1 |
| AGK03386.1 |
| AGM29868.1 |
| AGN78797.1 |
| AGN78800.1 |
| AGN79081.1 |
| AGN81120.1 |
| AGN84096.1 |
| AGO56529.1 |
| AGO56534.1 |
| AGP45636.1 |
| AGP48796.1 |
| AGP52381.1 |
| AGP54692.1 |
| AGP54697.1 |
| AGP60625.1 |
| AGQ73200.1 |
| AGR58814.1 |
| AGS23468.1 |
| AGS72121.1 |
| AGZ34904.1 |
| AGZ34909.1 |
| AGZ36730.1 |
| AHA65135.1 |
| AHA65444.1 |
| AHA65445.1 |
| AHB59062.1 |
| AHB70534.1 |
| AHB70670.1 |
| AHC33991.1 |
| AHC33996.1 |
| AHC38640.1 |
| AHC86568.1 |
| AHC90526.1 |
| AHC99932.1 |
| AHD03574.1 |
| AHD13184.1 |
| AUD17058.1 |
| AHE51105.1 |
| AHE57975.1 |
| AHE58040.1 |
| AHE70444.1 |
| AHF76632.1 |
| AHF85737.1 |
| AHG19057.1 |
| AHG19062.1 |
| AHG38795.1 |
| AHH95453.1 |
| AHH96134.1 |
| AHI31496.1 |
| AHJ73863.1 |
| AHK28152.1 |
| AHK28260.1 |
| AHK29047.1 |
| AHK29048.1 |
| AHK29235.1 |
| AHK29423.1 |
| AHK34315.1 |
| AHL32427.1 |
| AHM79287.1 |
| AHM80280.1 |
| AHM84957.1 |
| AHM85917.1 |
| AHN80401.1 |
| AHW62955.1 |
| AHX59431.1 |
| AHY13380.1 |
| AHY70456.1 |

TABLE 6-continued

Representative Examples of Gamma-Aminobutyraldehyde Dehydrogenase by EMBL/GENBANK/DDBJ ID Number

| |
|---|
| AHZ69437.1 |
| AHZ75601.1 |
| AHZ75934.1 |
| AIA06216.1 |
| AIC18252.1 |
| AIC18257.1 |
| AIC29053.1 |
| AID34200.1 |
| AID90110.1 |
| AIG78005.1 |
| AIG79529.1 |
| AII03300.1 |
| AII05641.1 |
| AII06622.1 |
| AII07903.1 |
| AII88152.1 |
| AIJ13059.1 |
| AIJ13068.1 |
| AIL63307.1 |
| AIN56881.1 |
| AIN58220.1 |
| AIO70590.1 |
| AIO83941.1 |
| AIP25746.1 |
| AIP94956.1 |
| AIR03200.1 |
| AIR62232.1 |
| AIR68506.1 |
| AIS00809.1 |
| AIS00819.1 |
| AIT03707.1 |
| AIU71844.1 |
| AIU71849.1 |
| AIW48087.1 |
| AIW76907.1 |
| AIX63251.1 |
| AIZ82499.1 |
| AJA14625.1 |
| AJA25872.1 |
| AJC55682.1 |
| AJC65875.1 |
| AJC81199.1 |
| AJD42887.1 |
| AJE42771.1 |
| AJE55657.1 |
| AJE55826.1 |
| AJE81228.1 |
| AJF56173.1 |
| AJF56280.1 |
| AJF67554.1 |
| AJF67987.1 |
| AJF73013.1 |
| AJG15382.1 |
| AJK47164.1 |
| AJO83449.1 |
| AJP04064.1 |
| AJQ48790.1 |
| AJQ89920.1 |
| AJT64083.1 |
| AJX74179.1 |
| AJY44820.1 |
| AJZ89630.1 |
| AKA21608.1 |
| AKA25271.1 |
| AKA26423.1 |
| AKA26428.1 |
| AKA26652.1 |
| AKC39739.1 |
| AKE96156.1 |
| AKF49081.1 |
| AKG67805.1 |
| AKG67810.1 |
| AKH07208.1 |
| AKH08765.1 |
| AKH26598.1 |
| AKH26766.1 |
| AKH85122.1 |

TABLE 6-continued

Representative Examples of Gamma-Aminobutyraldehyde Dehydrogenase by EMBL/GENBANK/DDBJ ID Number

| |
|---|
| AKJ10458.1 |
| AKJ98810.1 |
| AKK26535.1 |
| AKK48033.1 |
| AKK48134.1 |
| AKL12092.1 |
| AKL36390.1 |
| AKM34859.1 |
| AKM34956 1 |
| AKM45294.1 |
| AKN71659.1 |
| AKR56664.1 |
| AKR58199.1 |
| AKS06052.1 |
| AKS06057.1 |
| ALD25372.1 |
| ALL90586.1 |
| ALQ29888.1 |
| ALR27562.1 |
| ALY13061.1 |
| ALY13176.1 |
| ALZ65876.1 |
| ALZ66856.1 |
| AMW41259.1 |
| AMW41352.1 |
| AMX15658.1 |
| ANK32128.1 |
| ANM82203.1 |
| ANP17955.1 |
| ANZ87342.1 |
| AOM46387.1 |
| AOM69814.1 |
| AOT33034.1 |
| APA42536.1 |
| APA42696.1 |
| BAA14869.1 |
| BAA15073.1 |
| BAB35471.1 |
| BAD88708.1 |
| BAG42223.1 |
| BAG77050.1 |
| BAI25150.1 |
| BAI25318.1 |
| BAI30293.1 |
| BAI30398.1 |
| BAI35600.1 |
| BAI35738.1 |
| BAL95971.1 |
| BAN47691.1 |
| BAN47978.1 |
| BAN50325.1 |
| BAN50330.1 |
| BAN56084.1 |
| CAC47084.1 |
| CAD01728.1 |
| CAG74448.1 |
| CAQ89037.1 |
| CAQ98298.1 |
| CAR02855.1 |
| CAR07796.1 |
| CAR12812.1 |
| CAR12894.1 |
| CAR17782.1 |
| CAR37392.1 |
| CAR50912.1 |
| CAS09132.1 |
| CAU97432.1 |
| CAZ86962.1 |
| CBA30725.1 |
| CBG87141.1 |
| CBG88353.1 |
| CBJ00907.1 |
| CBJ01019.1 |
| CBW17622.1 |
| CCB65972.1 |
| CCB67003.1 |
| CCB67169.1 |

TABLE 6-continued

Representative Examples of Gamma-Aminobutyraldehyde Dehydrogenase by EMBL/GENBANK/DDBJ ID Number

| |
|---|
| CCC30509.1 |
| CCE10783.1 |
| CCF61531.1 |
| CCH28399.1 |
| CCH31748.1 |
| CCH72874.1 |
| CCH76962.1 |
| CCH77412.1 |
| CCH79600.1 |
| CCI52108.1 |
| CCI77183.1 |
| CCJ43834.1 |
| CCJ43945.1 |
| CCJ80233.1 |
| CCK02487.1 |
| CCK27139.1 |
| CCK27147.1 |
| CCK46650.1 |
| CCM79078.1 |
| CCM79926.1 |
| CCN44439.1 |
| CCQ17877.1 |
| CCT59175.1 |
| CCV08313.1 |
| CCV10163.1 |
| CCV14388.1 |
| CCV15291.1 |
| CCW32353.1 |
| CDF82476.1 |
| CDF82481.1 |
| CDF83258.1 |
| CDG13595.1 |
| CDG17619.1 |
| CDH77402.1 |
| CDK71151.1 |
| CDK74582.1 |
| CDL26553.1 |
| CDL56081.1 |
| CDL81552.1 |
| CDL81886.1 |
| CDM87455.1 |
| CDN05905.1 |
| CDN06835.1 |
| CDN82002.1 |
| CDO06723.1 |
| CDO11198.1 |
| CDO20175.1 |
| CDO27859.1 |
| CDP84626.1 |
| CDQ13701.1 |
| CDQ14695.1 |
| CDR01601.1 |
| CDR17539.1 |
| CDU36030.1 |
| CDU38743.1 |
| CDW92927.1 |
| CDX11539.1 |
| CDX11561.1 |
| CDX14815.1 |
| CDX15464.1 |
| CDX15608.1 |
| CDX15708.1 |
| CDX18128.1 |
| CDX23952.1 |
| CDX24321.1 |
| CDX24344.1 |
| CDX24795.1 |
| CDX26102.1 |
| CDX30033.1 |
| CDX30137.1 |
| CDX32833.1 |
| CDX33250.1 |
| CDX33780.1 |
| CDX35494.1 |
| CDX39763.1 |
| CDX50647.1 |
| CDX52898.1 |
| CDX53624.1 |
| CDX58882.1 |
| CDX59913.1 |
| CDX61300.1 |
| CDX61327.1 |
| CDX61366.1 |
| CDX62732.1 |
| CDZ83389.1 |
| CEG54345.1 |
| CEI20766.1 |
| CEJ64257.1 |
| CEL27766.1 |
| CEL27771.1 |
| CEL84834.1 |
| CEL86039.1 |
| CEP29887.1 |
| CFU00610.1 |
| CPR21343.1 |
| CQD06815.1 |
| CQR61483.1 |
| CRI57441.1 |
| CRI58732.1 |
| CRL88003.1 |
| CRP27791.1 |
| CRQ48403.1 |
| CRZ15796.1 |
| CSK40308.1 |
| CSK40325.1 |
| CSL03164.1 |
| CSM54609.1 |
| CSM54649.1 |
| CSN55245.1 |
| CSP80178.1 |
| CSP84594.1 |
| CSP99410.1 |
| CSS89574.1 |
| CTP99211.1 |
| CTQ00586.1 |
| CTQ03890.1 |
| CTQ10217.1 |
| CTQ15467.1 |
| CTQ16305.1 |
| CTQ16977.1 |
| CTQ17997.1 |
| CTQ25284.1 |
| CTR39889.1 |
| CTS37133.1 |
| CTS49511.1 |
| CTS54984.1 |
| CTT37563.1 |
| CTT55391.1 |
| CTT62054.1 |
| CTT65179.1 |
| CTT92436.1 |
| CTT92613.1 |
| CTT97100.1 |
| CTU01835.1 |
| CTU36153.1 |
| CTU72845.1 |
| CTV40159.1 |
| CTV56108.1 |
| CTV74457.1 |
| CTW04360.1 |
| CTW29476.1 |
| CTW61879.1 |
| CTW77542.1 |
| CTX33307.1 |
| CTY24484.1 |
| CTZ61796.1 |
| CTZ76546.1 |
| CTZ79234.1 |
| CTZ96800.1 |
| CUI28728.1 |
| CUJ66815.1 |
| CUJ82879.1 |
| CUZ08279.1 |
| EDM61330.1 |

TABLE 6-continued

Representative Examples of Gamma-Aminobutyraldehyde Dehydrogenase by EMBL/GENBANK/DDBJ ID Number EDS91265.1
EDS92029.1
EDU65292.1
EDU90202.1
EDU90317.1
EDX34020.1
EDX35915.1
EDX46872.1
EDY24930.1
EDY65642.1
EED35505.1
EED97074.1
EEE03881.1
EEE05415.1
EEP49475.1
EEP84228.1
EET48351.1
EET48956.1
EEW39317.1
EEW60473.1
EEX16532.1
EFC56792.1
EFE08792.1
EFE63903.2
EFE64066.2
EFF07668.2
EFF07812.2
EFF12655.2
EFF12736.2
EFG35656.2
EFH33353.1
EFI90126.1
EFJ64881.1
EFJ72274.1
EFJ83495.1
EFJ89608.1
EFJ98868.1
EFK05124.1
EFK15965.1
EFK19444.1
EFK26532.1
EFK45262.1
EFK52086.1
EFK66278.1
EFK74995.1
EFK91145.1
EFL88470.1
EFM58433.1
EFO59324.1
EFP69095.1
EFP69402.1
EFR14050.1
EFU33457.1
EFV41685.1
EFV42196.1
EFV44308.1
EGB59482.1
EGB68820.1
EGB72004.1
EGB90260.1
EGB98679.1
EGC95168.1
EGD06231.1
EGE34132.1
EGE48689.1
EGE61394.1
EGF89341.1
EGG47793.1
EGI10883.1
EGI11039.1
EGI17601.1
EGI21877.1
EGI22685.1
EGI41263.1
EGI41264.1
EGI46454.1
EGI47073.1
EGI51604.1
EGI51699.1
EGI96778.1
EGI99670.1
EGI99749.1
EGJ03157.1
EGJ05085.1
EGJ74429.1
EGK24148.1
EGK24149.1
EGK24615.1
EGK24616.1
EGK37820.1
EGK60394.1
EGO94631.1
EGU95611.1
EGW40786.1
EGX55949.1
EHB41733.1
EHD22257.1
EHH02231.1
EHH09516.1
EHH11988.1
EHJ94704.1
EHJ94844.1
EHK52408.1
EHK54788.1
EHK66824.1
EHK74830.1
EHM27681.1
EHM47677.1
EHN75593.1
EHP43848.1
EHP62718.1
EHP64017.1
EHT05663.1
EHT13683.1
EHU11201.1
EHU13340.1
EHU15614.1
EHU24532.1
EHU29232.1
EHU31012.1
EHU41094.1
EHU45943.1
EHU59778.1
EHV59483.1
EIC82100.1
EID61817.1
EID62214.1
EID65440.1
EID65521.1
EID73534.1
EIE52002.1
EIF92872.1
EIG83929.1
EIG94831.1
EIH12409.1
EIH21939.1
EIH44123.1
EIH77056.1
EII23324.1
EII32616.1
EII44042.1
EIK70381.1
EIK70690.1
EIK97767.1
EIK97772.1
EIL50217.1
EIL50351.1
EIM73619.1
EIQ09709.1
EIQ75858.1
EJE59098.1
EJE61181.1
EJE85045.1
EJE96318.1

TABLE 6-continued

Representative Examples of Gamma-Aminobutyraldehyde Dehydrogenase by EMBL/GENBANK/DDBJ ID Number

| |
|---|
| EJF29138.1 |
| EJF32265.1 |
| EJF68495.1 |
| EJF68500.1 |
| EJI90289.1 |
| EJI93345.1 |
| EJI93407.1 |
| EJI95486.1 |
| EJI95544.1 |
| EJI96663.1 |
| EJI98843.1 |
| EJJ00315.1 |
| EJJ07858.1 |
| EJK91259.1 |
| EJK91378.1 |
| EJL01279.1 |
| EJL02848.1 |
| EJL08255.1 |
| EJL08816.1 |
| EJL08880.1 |
| EJL16742.1 |
| EJL17014.1 |
| EJO32261.1 |
| EJT03922.1 |
| EJU29480.1 |
| EJZ04156.1 |
| EJZ05782.1 |
| EJZ07520.1 |
| EJZ11850.1 |
| EJZ13633.1 |
| EJZ18209.1 |
| EJZ22729.1 |
| EJZ67420.1 |
| EJZ67421.1 |
| EKE69095.1 |
| EKF44031.1 |
| EKF58906.1 |
| EKI53765.1 |
| EKI53852.1 |
| EKT77536.1 |
| EKU47209.1 |
| EKU47702.1 |
| EKX82560.1 |
| EKX83133.1 |
| EKX83138.1 |
| EKX85141.1 |
| EKZ96977.1 |
| EKZ99926.1 |
| ELB93420.1 |
| ELC09512.1 |
| ELC09701.1 |
| ELC19003.1 |
| ELC41369.1 |
| ELC41538.1 |
| ELC88918.1 |
| ELC89051.1 |
| ELE01126.1 |
| ELE01606.1 |
| ELE44498.1 |
| ELE44659.1 |
| ELE56019.1 |
| ELE56114.1 |
| ELE60912.1 |
| ELE61186.1 |
| ELG89411.1 |
| ELG90335.1 |
| ELI30197.1 |
| ELI31157.1 |
| ELJ74005.1 |
| ELQ84051.1 |
| ELQ90577.1 |
| ELV07386.1 |
| ELW35774.1 |
| ELX11035.1 |
| EMD12755.1 |
| EMD12954.1 |
| EMD13067.1 |
| EMF25251.1 |
| EMP54680.1 |
| EMP54686.1 |
| EMR54447.1 |
| EMU62810.1 |
| EMU70199.1 |
| EMV21190.1 |
| EMX05854.1 |
| EMX21136.1 |
| EMX32353.1 |
| EMX40913.1 |
| EMX51161.1 |
| EMX88242.1 |
| EMY35234.1 |
| ENA08671.1 |
| ENA40359.1 |
| ENA45932.1 |
| ENC92169.1 |
| END53755.1 |
| END93044.1 |
| ENG98074.1 |
| ENH03358.1 |
| ENH09610.1 |
| ENY73407.1 |
| ENY78290.1 |
| ENZ86937.1 |
| EOD53374.1 |
| EOQ49232.1 |
| EOQ49914.1 |
| EOQ61470.1 |
| EOQ65631.1 |
| EOU43508.1 |
| EOU43864.1 |
| EOU68015.1 |
| EOU70063.1 |
| EOU79907.1 |
| EOU81119.1 |
| EOU96152.1 |
| EOU96255.1 |
| EOV09796.1 |
| EOV10270.1 |
| EOV49578.1 |
| EOV63174.1 |
| EOV63548.1 |
| EOV79497.1 |
| EOV79860.1 |
| EOV87779.1 |
| EOW08077.1 |
| EOW08486.1 |
| EOW21036.1 |
| EOW21374.1 |
| EOW24870.1 |
| EOW26044.1 |
| EOW65040.1 |
| EOW98830.1 |
| EPB97616.1 |
| EPC03794.1 |
| EPE95228.1 |
| EPF16860.1 |
| EPH43419.1 |
| EPH43431.1 |
| EPI73506.1 |
| EPI73882.1 |
| EPI87463.1 |
| EPJ00727.1 |
| EPJ01132.1 |
| EPJ03992.1 |
| EPJ12747.1 |
| EPJ38971.1 |
| EPJ38980.1 |
| EPJ81214.1 |
| EPJ81219.1 |
| EPJ89017.1 |
| EPL05218.1 |
| EPR07720.1 |
| EQD81697.1 |
| EQD82324.1 |

TABLE 6-continued

Representative Examples of Gamma-Aminobutyraldehyde Dehydrogenase by EMBL/GENBANK/DDBJ ID Number EQD83794.1
EQD87767.1
EQL44300.1
EQM34719.1
EQM69852.1
EQM71564.1
EQM71569.1
EQM75964.1
EQM77609.1
EQM78485.1
EQM79321.1
EQM80144.1
EQN28573.1
EQN28672.1
EQN99840.1
EQN99841.1
EQO00250.1
EQO68143.1
EQO71509.1
EQP56400.1
EQQ14012.1
EQQ14796.1
EQV92076.1
EQV93438.1
EQX28154.1
EQX88295.1
EQX88882.1
EQY25054.1
EQY25162.1
EQY62629.1
EQY63166.1
EQZ93705.1
ERA03230.1
ERB51269.1
ERE03382.1
ERF62800.1
ERF79994.1
ERF80025.1
ERF86678.1
ERH52669.1
ERH54945.1
ERH56364.1
ERH56369.1
ERI50841.1
ERI52992.1
ERK06991.1
ERK14296.1
ERK98773.1
ERK98876.1
ERL53130.1
ERO58335.1
ERO62836.1
ERO63658.1
ERP07702.1
ERP86472.1
ERS89090.1
ERT55553.1
ESA66810.1
ESA77122.1
ESA78274.1
ESA83620.1
ESA83744.1
ESA95270.1
ESB01449.1
ESD02695.1
ESD09814.1
ESD21218.1
ESD33644.1
ESD67552.1
ESD75875.1
ESD88637.1
ESD99184.1
ESE82501.1
ESE84822.1
ESF48176.1
ESG58184.1
ESJ13234.1
ESJ21013.1
ESK09882.1
ESK10485.1
ESK37171.1
ESK37414.1
ESL81948.1
ESL82348.1
ESM14498.1
ESN13440.1
ESQ05398.1
ESQ76607.1
ESQ77377.1
ESQ81731.1
ESQ83104.1
ESQ91911.1
ESQ93897.1
ESQ98710.1
ESS14987.1
ESS59788.1
EST30101.1
EST30107.1
EST33761.1
EST33892.1
EST36063.1
EST39150.1
ESU49379.1
ESU76946.1
ESU81649.1
ESU81650.1
ESW36007.1
ESW41503.1
ESW64252.1
ESW66425.1
ESW68009.1
ESW86999.1
ESW87442.1
ESW90408.1
ESW91937.1
ESX01731.1
ESX14872.1
ESX15364.1
ESX27250.1
ESX43501.1
ESX52337.1
ESX56930.1
ESX58061.1
ESX60692.1
ESX73443.1
ESX77081.1
ESX81416.1
ESX87236.1
ESX88150.1
ESX88342.1
ESY00266.1
ESY04276.1
ESY06338.1
ESY12861.1
ESY17564.1
ESY18933.1
ESY26034.1
ESY28484.1
ESY30944.1
ESY33527.1
ESY37324.1
ESY52717.1
ESY60955.1
ESY66683.1
ESY68060.1
ESY74421.1
ESY80296.1
ESY83492.1
ESY84782.1
ESY90437.1
ESY93751.1
ESZ00304.1
ESZ01923.1
ESZ09540.1

TABLE 6-continued

Representative Examples of Gamma-Aminobutyraldehyde Dehydrogenase by EMBL/GENBANK/DDBJ ID Number

| |
|---|
| ESZ09896.1 |
| ESZ13256.1 |
| ESZ14738.1 |
| ESZ24600.1 |
| ESZ25961.1 |
| ESZ27305.1 |
| ESZ28042.1 |
| ESZ34731.1 |
| ESZ35713.1 |
| ESZ39312.1 |
| ESZ47365.1 |
| ESZ49754.1 |
| ESZ50191.1 |
| ESZ51262.1 |
| ESZ60420.1 |
| ESZ62981.1 |
| ESZ63558.1 |
| ESZ67001.1 |
| ESZ70861.1 |
| ESZ73525.1 |
| ESZ73952.1 |
| ESZ75665.1 |
| ETA08782.1 |
| ETA86576.1 |
| ETC29664.1 |
| ETD30716.1 |
| ETD31105.1 |
| ETD62961.1 |
| ETE19722.1 |
| ETE53115.1 |
| ETF04172.1 |
| ETF05232.1 |
| ETF07523.1 |
| ETI61741.1 |
| ETK22368.1 |
| ETK22373.1 |
| ETK33993.1 |
| ETK35735.1 |
| ETM65117.1 |
| ETM65275.1 |
| ETM67859.1 |
| ETM67864.1 |
| ETM68681.1 |
| ETY48139.1 |
| ETY48243.1 |
| ETZ11507.1 |
| EUB74063.1 |
| EUB83842.1 |
| EWC42375.1 |
| EWG76330.1 |
| EWH00701.1 |
| EWM12655.1 |
| EXF91839.1 |
| EXF93299.1 |
| EXF94820.1 |
| EXF94825.1 |
| EXF96398.1 |
| EXJ51305.1 |
| EXL03099.1 |
| EXU69106.1 |
| EXU88516.1 |
| EYC51688.1 |
| EYD86031.1 |
| EYR82110.1 |
| EYT83596.1 |
| EYU66295.1 |
| EYV04090.1 |
| EYV10968.1 |
| EZA00470.1 |
| EZA36281.1 |
| EZD25558.1 |
| EZD99900.1 |
| EZE53557.1 |
| EZH78629.1 |
| EZH78632.1 |
| EZI29263.1 |
| EZI29268.1 |
| EZJ43273.1 |
| EZJ52521.1 |
| EZJ77242.1 |
| EZJ87004.1 |
| EZK23644.1 |
| EZP27312.1 |
| EZP41476.1 |
| EZP45031.1 |
| EZP62483.1 |
| GAB53548.1 |
| GAB56017.1 |
| GAD63079.1 |
| GAD63084.1 |
| GAK29357.1 |
| GAK29362.1 |
| GAL43981.1 |
| GAL48526.1 |
| GAL58082.1 |
| GAM50401.1 |
| GAO07729.1 |
| GAP56165.1 |
| GAP56166.1 |
| GAP56167.1 |
| KDA58453.1 |
| KDD67292.1 |
| KDD68894.1 |
| KDD69165.1 |
| KDD69170.1 |
| KDE38101.1 |
| KDE98698.1 |
| KDF06849.1 |
| KDF18076.1 |
| KDF20685.1 |
| KDG95704.1 |
| KDG97056.1 |
| KDM67929.1 |
| KDN76233.1 |
| KDN83114.1 |
| KDN83117.1 |
| KDO01521.1 |
| KDQ69796.1 |
| KDS87067.1 |
| KDU28283.1 |
| KDV34603.1 |
| KDV38010.1 |
| KDV65222.1 |
| KDW32558.1 |
| KDX18550.1 |
| KDX47161.1 |
| KEA05640.1 |
| KEA51004.1 |
| KEC74664.1 |
| KEC77821.1 |
| KEG39710.1 |
| KEH13576.1 |
| KEJ48744.1 |
| KEJ63425.1 |
| KEJ77549.1 |
| KEJ95365.1 |
| KEL69022.1 |
| KEN57716.1 |
| KEN70496.1 |
| KEO01987.1 |
| KEO12714.1 |
| KEO35027.1 |
| KEO51439.1 |
| KEO53693.1 |
| KEO57514.1 |
| KER68883.1 |
| KES06595.1 |
| KES20242.1 |
| KES21942.1 |
| KES22773.1 |
| KES22778.1 |
| KEX91709.1 |
| KEX92394.1 |
| KEY87097.1 |

TABLE 6-continued

Representative Examples of Gamma-Aminobutyraldehyde Dehydrogenase by EMBL/GENBANK/DDBJ ID Number KEZ76822.1
KFB89554.1
KFB89559.1
KFC10517.1
KFC67945.1
KFC70569.1
KFC75085.1
KFC81786.1
KFC91913.1
KFC95867.1
KFC99397.1
KFD74218.1
KFE44941.1
KFE53051.1
KFF88438.1
KFF88443.1
KFF99222.1
KFG67154.1
KFG73420.1
KFG77433.1
KFI29656.1
KFK85449.1
KFK97286.1
KFK97291.1
KFL25738.1
KFL29966.1
KFL38046.1
KFN19465.1
KFN41111.1
KFN46900.1
KFN49964.1
KFN51535.1
KFX06879.1
KFX69867.1
KGA35361.1
KGA42963.1
KGD59263.1
KGD94090.1
KGE65706.1
KGE65711.1
KGF68263.1
KGF72312.1
KGI67195.1
KGI94899.1
KGJ03236.1
KGK24105.1
KGM32302.1
KGM44306.1
KGM58952.1
KGM69324.1
KGM78828.1
KGM81944.1
KGP01633.1
KGQ21090.1
KGR84694.1
KGT96645.1
KGU84905.1
KGU85044.1
KGW16883.1
KHA75030.1
KHA75035.1
KHD08750.1
KHD11829.1
KHI27478.1
KHJ12630.1
KHK63949.1
KHK63954.1
KHL04063.1
KHL17238.1
KHL18800.1
KHL69724.1
KHN51966.1
KHN62433.1
KHN91313.1
KHO23301.1
KHO27139.1
KHO65650.1
KHS48549.1
KHS48554.1
KHS75072.1
KHT32807.1
KHT39971.1
KIC09090.1
KIC40995.1
KIC41133.1
KIC83744.1
KIC99939.2
KIC99947.1
KID09632.1
KIF07001.1
KIF26716.1
KIF43517.1
KIF59716.1
KIF59721.1
KIF67705.1
KIH01614.1
KIK89863.1
KIK89868.1
KIQ45546.1
KIQ47862.1
KIQ55257.1
KIQ59125.1
KIQ63814.1
KIU18518.1
KIU34636.1
KIU47422.1
KIU53338.1
KIU53341.1
KIX41539.1
KIX76475.1
KIY37490.1
KIY39817.1
KIY42118.1
KIY42676.1
KIZ13851.1
KIZ24787.1
KJC00426.1
KJC06180.1
KJC11238.1
KJE36612.1
KJE78198.1
KJF18418.1
KJF21349.1
KJF69984.1
KJF70827.1
KJH08553.1
KJH75518.1
KJH75523.1
KJH76614.1
KJH78831.1
KJH87663.1
KJH87668.1
KJK01996.1
KJK02001.1
KJK03668.1
KJK05212.1
KJK08131.1
KJK20451.1
KJK37817.1
KJK52206.1
KJK58811.1
KJL20365.1
KJL23069.1
KJL30351.1
KJL31602.1
KJL33666.1
KJL48804.1
KJM37801.1
KJM97308.1
KJN29799.1
KJQ55807.1
KJQ55948.1
KJW23607.1
KJW25580.1

TABLE 6-continued

Representative Examples of Gamma-Aminobutyraldehyde Dehydrogenase by EMBL/GENBANK/DDBJ ID Number

| |
|---|
| KJW52220.1 |
| KJX08981.1 |
| KJX38421.1 |
| KJY22909.1 |
| KJY33089.1 |
| KJY33790.1 |
| KJY43331.1 |
| KJZ10920.1 |
| KJZ37958.1 |
| KJZ37963.1 |
| KJZ40441.1 |
| KJZ40446.1 |
| KJZ45327.1 |
| KJZ45333.1 |
| KJZ66226.1 |
| KJZ66231.1 |
| KKA04889.1 |
| KKA04894.1 |
| KKA09911.1 |
| KKA37777.1 |
| KKA42030.1 |
| KKA53217.1 |
| KKB78257.1 |
| KKB82836.1 |
| KKC63115.1 |
| KKD05136.1 |
| KKD60858.1 |
| KKE99588.1 |
| KKF00080.1 |
| KKF03311.1 |
| KKI46974.1 |
| KKI46979.1 |
| KKJ25486.1 |
| KKO14271.1 |
| KKW63834.1 |
| KKX63769.1 |
| KKX64098.1 |
| KKY43260.1 |
| KKY88574.1 |
| KKZ17922.1 |
| KKZ17927.1 |
| KKZ88372.1 |
| KLI09733.1 |
| KLI88767.1 |
| KLI99518.1 |
| KLK91133.1 |
| KLO51629.1 |
| KLQ25311.1 |
| KLT72736.1 |
| KLU27310.1 |
| KLV08340.1 |
| KLV50364.1 |
| KLV67254.1 |
| KLV72352.1 |
| KLW92152.1 |
| KLX61073.1 |
| KLX97485.1 |
| KLY16841.1 |
| KLY40951.1 |
| KME63607.1 |
| KMI30519.1 |
| KMK11631.1 |
| KML66599.1 |
| KMM42844.1 |
| KMM79980.1 |
| KMM79984.1 |
| KMM93815.1 |
| KMN10712.1 |
| KMN10715.1 |
| KMN35503.1 |
| KMN66213.1 |
| KMN83689.1 |
| KMO68456.1 |
| KMO68855.1 |
| KMO70407.1 |
| KMO71981.1 |
| KMO77030.1 |
| KMO77166.1 |
| KMO78179.1 |
| KMO83081.1 |
| KMO84977.1 |
| KMO98166.1 |
| KMQ75593.1 |
| KMS67055.1 |
| KMS84091.1 |
| KMV13999.1 |
| KMV35767.1 |
| KNA39386.1 |
| KNC09274.1 |
| KNC93864.1 |
| KND34924.1 |
| KND39332.1 |
| KND42278.1 |
| KNF62763.1 |
| KNF78118.1 |
| KNF82323.1 |
| KNG95257.1 |
| KNH18859.1 |
| KNH37980.1 |
| KNH43304.1 |
| KNN88316.1 |
| KNW77292.1 |
| KNY72567.1 |
| KNZ31302.1 |
| KNZ82970.1 |
| KNZ97006.1 |
| KOA33208.1 |
| KOF21370.1 |
| KOG30324.1 |
| KOG34758.1 |
| KOG38875.1 |
| KOG44119.1 |
| KOG60686.1 |
| KOG65984.1 |
| KOG73930.1 |
| KOG84617.1 |
| KOP04486.1 |
| KOP81781.1 |
| KOT34360.1 |
| KOT54726.1 |
| KOT89785.1 |
| KOT93096.1 |
| KOU23107.1 |
| KOU32059.1 |
| KOU37064.1 |
| KOU48313.1 |
| KOU68154.1 |
| KOU76809.1 |
| KOV10064.1 |
| KOV34566.1 |
| KOV38826.1 |
| KOV52198.1 |
| KOV66117.1 |
| KOV74373.1 |
| KOV87450.1 |
| KOX03723.1 |
| KOX05951.1 |
| KOX35809.1 |
| KOX51055.1 |
| KOY03131.1 |
| KOY03136.1 |
| KOY58167.1 |
| KPA89964.1 |
| KPA90118.1 |
| KPB70152.1 |
| KPC25344.1 |
| KPC62377.1 |
| KPC63412.1 |
| KPC68317.1 |
| KPC80506.1 |
| KPC83739.1 |
| KPC92801.1 |
| KPF46210.1 |
| KPF61380.1 |

TABLE 6-continued

Representative Examples of Gamma-Aminobutyraldehyde Dehydrogenase by EMBL/GENBANK/DDBJ ID Number KPG35216.1
KPG89320.1
KPG89325.1
KPG90595.1
KPG90600.1
KPG95593.1
KPG96003.1
KPH06793.1
KPL32866.1
KPL68330.1
KPN71959.1
KPN74360.1
KPN92591.1
KPN92596.1
KPO09259.1
KPO42565.1
KPO48511.1
KPO53785.1
KPP88272.1
KPP99458.1
KPQ21464.1
KPQ21534.1
KPQ21854.1
KPR53957.1
KPW26103.1
KPW26988.1
KPW67069.1
KPW74859.1
KPY59757.1
KPY87595.1
KQJ17275.1
KQJ36447.1
KQJ45372.1
KSH07068.1
KST34997.1
KSY01459.1
KTH76882.1
KTZ11478.1
KUN93478.1
KUU42596.1
KWZ91965.1
KXG93510.1
KXH01990.1
KXI02527.1
KXL57426.1
KXL65443.1
KXQ40269.1
KYR44624.1
KYR46262.1
KYS89391.1
KYV69812.1
KYV69919.1
KZJ61423.1
OAC44376.1
OAJ89643.1
OAJ89801.1
OAO73826.1
OCB47501.1
OCS64471.1
OCS99847.1
OCV46435.1
OCV69750.1
ODH20373.1
ODN18141.1
OEG95421.1
OEH12679.1
OEH17081.1
OEI60939.1
OEN32142.1
OEN32392.1
OIR52348.1
OJF09290.1
SAD98048.1
SAZ48890.1
SBX26203.1

Representative examples of arginine decarboxylase (EC 4.1.1.19) are given below in Table 7 and identified by their EMBL/GENBANK/DDBJ ID numbers. Any of the bacteria given in Table 10 can be engineered with any version of the arginine decarboxylase (EC 4.1.1.19) set forth in Table 3 and Table 7. For instance, the bacteria can be engineered with a version of the arginine decarboxylase enzyme that has at least 50% nucleotide similarity with any of the versions of arginine decarboxylase given in Table 7 (e.g., at least nucleotide 60% similarity, at least 70% nucleotide similarity, at least 80% nucleotide similarity, at least 90% nucleotide similarity, at least 91% nucleotide similarity, at least 92% nucleotide similarity, at least 93% nucleotide similarity, at least 94% nucleotide similarity, at least 95% nucleotide similarity, at least 96% nucleotide similarity, at least 97% nucleotide similarity, at least 98% nucleotide similarity, at least 99% nucleotide similarity, at least 99.5% nucleotide similarity, at least 99.9% nucleotide similarity, or 100% nucleotide similarity).

TABLE 7

Representative Examples of Arginine Decarboxylase by EMBL/GENBANK/DDBJ ID Number AAA23481.1
AAA24646.1
AAA62686.1
AAA69105.1
AAA97017.1
AAC24937.1
AAC75975.1
AAC77078.2
AAD06541.1
AAD07486.1
AAF09826.1
AAF40905.1
AAF82957.1
AAF96713.1
AAG08224.1
AAG58069.1
AAK03466.1
AAK65018.1
AAK65019.2
AAL21961.1
AAL23120.1
AAM38760.1
AAM43099.1
AAM86863.1
AAN44412.1
AAN54922.1
AAN66194.1
AAN81972.1
AAN83546.1
AAO10730.2
AAO28012.1
AAO58271.1
AAO70551.1
AAO71667.1
AAO78500.1
AAP07133.1
AAP10882.1
AAP18235.1
AAP27896.1
AAP77830.1
AAP99095.1
AAQ60544.1
AAQ61700.1
AAR35910.1
AAS63667.1
AAS81619.1
AAS94900.1
AAT33294.1
AAT56175.1
AAU16546.1
AAU26114.1
AAU91686.1

TABLE 7-continued

Representative Examples of Arginine Decarboxylase by EMBL/GENBANK/DDBJ ID Number AAV78788.1
AAV81611.1
AAV82053.1
AAV93917.1
AAW73474.1
AAW87910.1
AAW90125.1
AAX66932.1
AAY39411.1
AAY50992.1
AAY96086.1
AAZ33811.1
AAZ58866.1
AAZ89679.1
ABA21777.1
ABA23030.1
ABA48961.1
ABA57077.1
ABA72371.1
ABA89337.1
ABB10893.1
ABB26344.1
ABB27130.1
ABB31146.1
ABB35370.1
ABB36243.1
ABB37372.1
ABB44410.1
ABB49107.1
ABB50154.1
ABB56739.1
ABB57067.1
ABB63148.1
ABB67557.1
ABB74343.1
ABC18380.1
ABC20552.1
ABC33051.1
ABC81667.1
ABC98358.1
ABD03703.1
ABD80860.1
ABE08775.1
ABE10119.1
ABE55560.1
ABE57906.1
ABF05062.1
ABF09627.1
ABF46066.1
ABF85039.1
ABF88624.1
ABG12304.1
ABG12881.1
ABG19102.1
ABG19453.1
ABG42373.1
ABG50504.1
ABG50611.1
ABG58847.1
ABI38635.1
ABI42627.1
ABI46161.1
ABI55429.1
ABI60410.1
ABI68665.1
ABI71549.1
ABJ02367.1
ABJ14223.1
ABJ88595.1
ABK15308.1
ABK38605.1
ABK43242.1
ABK47857.1
ABK75092.1
ABK82178.1
ABK86821.1
ABL00211.1

TABLE 7-continued

Representative Examples of Arginine Decarboxylase by EMBL/GENBANK/DDBJ ID Number ABL82864.1
ABL89457.1
ABM00169.1
ABM02703.1
ABM13722.1
ABM17621.1
ABM25203.1
ABM29533.1
ABM63175.1
ABM69334.1
ABM71261.1
ABM74623.1
ABM79561.1
ABN07206.1
ABN61275.1
ABN69317.1
ABO16671.1
ABO23486.1
ABO48608.1
ABO50340.1
ABO90758.1
ABP62006.1
ABP75372.1
ABP78675.1
ABP83495.1
ABQ05833.1
ABQ19043.1
ABQ25189.1
ABQ76774.1
ABQ91208.1
ABR39026.1
ABR71752.1
ABR78771.1
ABR85787.1
ABR88619.1
ABS07904.1
ABS26167.1
ABS44765.1
ABS51948.1
ABU58554.1
ABU74620.1
ABU75700.1
ABV15373.1
ABV17227.1
ABV17863.1
ABV37216.1
ABV43068.1
ABV49674.1
ABV67224.1
ABV87800.1
ABW26679.1
ABX07146.1
ABX07983.1
ABX24332.1
ABX48976.1
ABX69181.1
ABX73818.1
ABY34333.1
ABY96523.1
ABZ76368.1
ACA11160.1
ACA16086.1
ACA35608.1
ACA67146.1
ACA75078.1
ACA86341.1
ACA99796.1
ACB15562.1
ACB16864.1
ACB59509.1
ACB76743.1
ACB91563.1
ACC79266.1
ACC84558.1
ACD05477.1
ACD08093.1
ACD08437.1

TABLE 7-continued

Representative Examples of Arginine Decarboxylase
by EMBL/GENBANK/DDBJ ID Number

| |
|---|
| ACD22470.1 |
| ACD56878.1 |
| ACD84161.1 |
| ACD95391.1 |
| ACE82746.1 |
| ACF30404.1 |
| ACF53467.1 |
| ACF61369.1 |
| ACF63192.1 |
| ACF69056.1 |
| ACF90655.1 |
| ACG73211.1 |
| ACH39919.1 |
| ACH51462.1 |
| ACH52106.1 |
| ACH64501.1 |
| ACH76229.1 |
| ACH83424.1 |
| ACI09897.1 |
| ACI17330.1 |
| ACI27705.1 |
| ACI37609.1 |
| ACI78401.1 |
| ACI78402.1 |
| ACI78403.1 |
| ACI78404.1 |
| ACI78405.1 |
| ACJ08154.1 |
| ACJ29742.1 |
| ACJ78722.1 |
| ACK47011.1 |
| ACK63941.1 |
| ACK65701.1 |
| ACK72412.1 |
| ACK80041.1 |
| ACK89576.1 |
| ACK93714.1 |
| ACL08484.1 |
| ACL10977.1 |
| ACL24678.1 |
| ACL46250.1 |
| ACL48808.1 |
| ACL65409.1 |
| ACL74193.1 |
| ACL75477.1 |
| ACM20036.1 |
| ACM64074.1 |
| ACM92229.1 |
| ACN13264.1 |
| ACN47236.1 |
| ACO16949.1 |
| ACO18249.1 |
| ACO45270.1 |
| ACO74026.1 |
| ACO74435.1 |
| ACO76955.1 |
| ACP07734.1 |
| ACQ68147.1 |
| ACQ92008.1 |
| ACQ95950.1 |
| ACR12004.2 |
| ACR67553.1 |
| ACR70511.1 |
| ACS84361.1 |
| ACT05390.1 |
| ACT14721.1 |
| ACT17369.1 |
| ACT94637.1 |
| ACU04524.1 |
| ACU08698.1 |
| ACU63629.1 |
| ACU90402.1 |
| ACU93413.1 |
| ACV26547.1 |
| ACV27755.1 |
| ACV29034.1 |
| ACX84176.1 |
| ACX89634.1 |
| ACX98134.1 |
| ACX99534.1 |
| ACY12668.1 |
| ACY40093.1 |
| ACY48301.1 |
| ACY53514.1 |
| ACY85796.1 |
| ACY90136.1 |
| ACZ12309.1 |
| ACZ78457.1 |
| ADA75259.1 |
| ADB16530.1 |
| ADB41493.1 |
| ADB95292.1 |
| ADC70718.1 |
| ADD58093.1 |
| ADD69353.1 |
| ADD78376.1 |
| ADE16426.1 |
| ADE54552.1 |
| ADE68385.1 |
| ADE82828.1 |
| ADF38194.1 |
| ADF54509.1 |
| ADF63801.1 |
| ADG05247.1 |
| ADG69601.1 |
| ADG90777.1 |
| ADG93622.1 |
| ADH59926.1 |
| ADH64946.1 |
| ADH85917.1 |
| ADI13223.1 |
| ADI31741.1 |
| ADI35097.1 |
| ADI63948.1 |
| ADJ27548.1 |
| ADJ64931.1 |
| ADK13228.1 |
| ADK82353.1 |
| ADK95316.1 |
| ADL08911.1 |
| ADL25363.1 |
| ADL33935.1 |
| ADM42795.1 |
| ADN00148.1 |
| ADN01531.1 |
| ADN09145.1 |
| ADN13212.1 |
| ADN74820.1 |
| ADN80145.1 |
| ADO02588.1 |
| ADO07215.1 |
| ADO10713.1 |
| ADO30989.1 |
| ADO47091.1 |
| ADO50285.1 |
| ADO71288.1 |
| ADP11444.1 |
| ADP85550.1 |
| ADP96036.1 |
| ADQ16388.1 |
| ADQ41297.1 |
| ADQ80979.1 |
| ADR18999.1 |
| ADR23218.1 |
| ADR28298.1 |
| ADR33896.1 |
| ADT68877.1 |
| ADT69825.1 |
| ADT76573.1 |
| ADT88845.1 |
| ADU23228.1 |
| ADU27690.1 |
| ADU41306.1 |
| ADU61911.1 |

TABLE 7-continued

Representative Examples of Arginine Decarboxylase by EMBL/GENBANK/DDBJ ID Number ADU65890.1
ADU70509.1
ADU80224.1
ADU81854.1
ADU83415.1
ADU84974.1
ADU91399.1
ADV04673.1
ADV26011.1
ADV42555.1
ADV46298.1
ADV49133.1
ADV54125.1
ADV64798.1
ADV66885.1
ADW14248.1
ADW16260.1
ADW22931.1
ADW75122.1
ADX18873.1
ADX68773.1
ADY13324.1
ADY25759.1
ADY29884.1
ADY33564.1
ADY37564.1
ADY51339.1
ADY54539.1
ADY57443.1
ADY59760.1
ADZ04173.1
ADZ79550.1
ADZ81772.1
ADZ83276.1
ADZ90751.1
AEA21246.1
AEA43924.1
AEA66789.1
AEA80789.1
AEA82850.1
AEB00023.2
AEB11372.1
AEB28348.1
AEB56841.1
AEB69458.1
AEB99114.1
AEC00221.1
AEC17309.1
AEE18245.1
AEE24780.1
AEE58171.1
AEE70651.1
AEE81155.1
AEE81156.1
AEE97250.1
AEF05606.1
AEF16136.1
AEF16227.1
AEF17164.1
AEF23959.1
AEF90677.1
AEF92944.1
AEF93776.1
AEF98646.1
AEG11827.1
AEG13685.1
AEG34055.1
AEG95551.1
AEH00504.1
AEH34628.1
AEH46105.1
AEH48741.1
AEI50098.1
AEI66195.1
AEI78192.1
AEI99981.1
AEJ04159.1

TABLE 7-continued

Representative Examples of Arginine Decarboxylase by EMBL/GENBANK/DDBJ ID Number AEJ11150.1
AEJ19738.1
AEJ58269.1
AEJ60865.1
AEK23616.1
AEK58300.1
AEK61259.1
AEL05345.1
AEL27626.1
AEM47745.1
AEM53114.1
AEM69221.1
AEN15598.1
AEN17163.1
AEN18717.1
AEN66325.1
AEN73395.1
AEO44056.1
AEP12819.1
AEP31437.1
AEP37160.1
AEP84802.1
AEP86444.1
AEQ14110.1
AEQ98316.1
AER31405.1
AER40829.1
AER54676.1
AET65493.1
AEU09127.1
AEV15411.1
AEV30675.1
AEV33398.1
AEV37643.1
AEV60701.1
AEV60704.1
AEV60707.1
AEV67344.1
AEV70467.1
AEV98535.1
AEW03722.1
AEW50294.1
AEW63140.1
AEW75168.1
AEW84926.1
AEX02268.1
AEX23688.1
AEX24950.1
AEX53406.1
AEY01954.1
AEY67109.1
AFA47332.1
AFA73970.1
AFC23734.1
AFC87564.1
AFD07122.1
AFD26775.1
AFD56867.1
AFE10378.1
AFE59771.1
AFF19873.1
AFG36749.1
AFG41864.1
AFH38314.1
AFH68776.1
AFH99689.1
AFI02753.1
AFI04761.1
AFI06437.1
AFI07649.1
AFI84424.1
AFI92112.1
AFJ01340.1
AFJ07943.1
AFJ30621.1
AFJ45704.1
AFJ58120.1

TABLE 7-continued

Representative Examples of Arginine Decarboxylase by EMBL/GENBANK/DDBJ ID Number AFJ81937.1
AFJ90992.1
AFK03753.1
AFK51272.1
AFK70099.1
AFL54808.1
AFL66748.1
AFL68607.1
AFL74612.1
AFL79082.1
AFL80326.1
AFL84801.1
AFL98027.1
AFM03193.1
AFM14860.1
AFM34600.1
AFM61484.1
AFN34158.1
AFO49567.1
AFP36739.1
AFR05095.1
AFR34769.1
AFS72870.1
AFS76505.1
AFS77190.1
AFS77221.1
AFS78772.1
AFT72428.1
AFT76388.1
AFT80129.1
AFT97219.1
AFU69082.1
AFU98562.1
AFV06009.1
AFV13045.1
AFV75467.1
AFW94965.1
AFX90032.1
AFX91360.1
AFY00064.1
AFY17769.1
AFY19232.1
AFY20072.1
AFY29829.1
AFY31564.1
AFY33433.1
AFY36612.1
AFY38143.1
AFY42927.1
AFY43519.1
AFY49150.1
AFY53502.1
AFY58942.1
AFY60143.1
AFY62113.1
AFY66936.1
AFY67481.1
AFY68642.1
AFY69655.1
AFY74051.1
AFY79174.1
AFY80035.1
AFY81634.1
AFY88446.1
AFY89952.1
AFY96160.1
AFZ00099.1
AFZ00140.1
AFZ04829.1
AFZ05210.1
AFZ13691.1
AFZ14945.1
AFZ19310.1
AFZ19658.1
AFZ23331.1
AFZ25951.1
AFZ28979.1
AFZ29238.1
AFZ34486.1
AFZ35910.1
AFZ44576.1
AFZ45212.1
AFZ47363.1
AFZ47406.1
AFZ52083.1
AFZ53867.1
AFZ55178.1
AFZ56231.1
AFZ58381.1
AFZ68543.1
AGA32088.1
AGA64911.1
AGA71585.1
AGA78721.1
AGA87856.1
AGA91287.1
AGB27428.1
AGB76810.1
AGB83896.1
AGC44465.1
AGC68230.1
AGC68780.1
AGC77086.1
AGD97973.1
AGE21541.1
AGE28840.1
AGE63314.1
AGF46648.1
AGF47390.1
AGF48115.1
AGF48812.1
AGF58399.1
AGF77157.1
AGF98737.1
AGG02742.1
AGG32139.1
AGG70048.1
AGG70049.1
AGG90911.1
AGH42699.1
AGH79375.1
AGH84838.1
AGH96448.1
AGH98733.1
AGI26195.1
AGK04961.1
AGK18815.1
AGL50812.1
AGL70280.1
AGL71083.1
AGN36083.1
AGN77656.1
AGN85662.1
AGO56879.1
AGP45919.1
AGP60451.1
AGP79570.1
AGP99328.1
AGQ75011.1
AGQ75715.1
AGQ92959.1
AGR60292.1
AGR77271.1
AGS39310.1
AGT10955.1
AGT74287.1
AGU60604.1
AGW85841.1
AGX41788.1
AGX44838.1
AGY58242.1
AGY75546.1
AGY76455.1
AGY88583.1

TABLE 7-continued

Representative Examples of Arginine Decarboxylase by EMBL/GENBANK/DDBJ ID Number AGZ37216.1
AHA67006.1
AHA68178.1
AHA90255.1
AHB58530.1
AHB69077.1
AHB88451.1
AHC15721.1
AHC33269.1
AHC86082.1
AHD06174.1
AHD12720.1
AHE48922.1
AHE59627.1
AHE60910.1
AHE67762.1
AHE69334.1
AHE94171.1
AHE99491.1
AHF02503.1
AHF12870.1
AHF14205.1
AHF64905.1
AHF69813.1
AHF75852.1
AHF89946.1
AHG19399.1
AHG42876.1
AHG91184.1
AHI04766.1
AHJ12914.1
AHJ98606.1
AHK03030.1
AHK76683.1
AHK78070.1
AHL31986.1
AHL74294.1
AHM04085.1
AHM04146.1
AHM55552.1
AHM55591.1
AHM56089.1
AHM57413.1
AHM72257.1
AHM77671.1
AHM83263.1
AHN36471.1
AHN42175.1
AHN78631.1
AHN81853.1
AHW76536.1
AHX13501.1
AHX15381.1
AHX61830.1
AHY10273.1
AHY11503.1
AHY41739.1
AHY57313.1
AHY72294.1
AHY73771.1
AHZ25697.1
AHZ27049.1
AHZ69904.1
AHZ75105.1
AIA25262.1
AIA55267.1
AIA73814.1
AIC09292.1
AIC13270.1
AIC17824.1
AID43715.1
AID92227.1
AIE59498.1
AIE72691.1
AIE73587.1
AIE80613.1
AIF46276.1
AIF53874.1
AIG00462.1
AIG04575.1
AIG24465.1
AIG27859.1
AIG32739.1
AIG34894.1
AIG39523.1
AII14684.1
AII44730.1
AII46407.1
AII48194.1
AII53131.1
AIJ07653.1
AIJ37593.1
AIK36959.1
AIL47042.1
AIL63848.1
AIM36252.1
AIN60343.1
AIO35913.1
AIO46079.1
AIO86595.1
AIP97923.1
AIP98185.1
AIQ93098.1
AIQ94087.1
AIQ96154.1
AIR06030.1
AIR59441.1
AIR70547.1
AIR78811.1
AIR89334.1
AIS17530.1
AIS18369.1
AIS51300.1
AIS52271.1
AIT00342.1
AIU71685.1
AIU74296.1
AIU75005.1
AIW15710.1
AIW78499.1
AIX49204.1
AIX64799.1
AIX64838.1
AIX66185.1
AIX72613.1
AIY05985.1
AIY42499.1
AIY44410.1
AIY64168.1
AIY65959.1
AIZ35463.1
AIZ41262.1
AIZ46633.1
AIZ64390.1
AIZ80755.1
AIZ83995.1
AJA12982.1
AJA27933.1
AJA50204.1
AJA51748.1
AJC46830.1
AJC63707.1
AJC67765.1
AJC84641.1
AJC86256.1
AJC87691.1
AJC89173.1
AJC90641.1
AJC94047.1
AJD01709.1
AJD06276.1
AJD49796.1
AJD72328.1
AJD90845.1

TABLE 7-continued

Representative Examples of Arginine Decarboxylase by EMBL/GENBANK/DDBJ ID Number AJE04066.1
AJE22826.1
AJE57486.1
AJE58684.1
AJF05803.1
AJF57742.1
AJF57774.1
AJF58959.1
AJF74877.1
AJG15944.1
AJG20615.1
AJG76397.1
AJG96579.1
AJH06775.1
AJH14965.1
AJH21997.1
AJH79563.1
AJI04447.1
AJI11123.1
AJI18133.1
AJI20378.1
AJI21783.1
AJI51649.1
AJI68839.1
AJI86574.1
AJJ47448.1
AJJ79421.1
AJJ80961.1
AJK45428.1
AJK84596.1
AJO76357.1
AJO84926.1
AJO86233.1
AJQ25834.1
AJQ49239.1
AJQ86078.1
AJQ92951.1
AJQ96966.1
AJR02566.1
AJR08104.1
AJW64789.1
AJY49487.1
AJY68826.1
AJZ41720.1
AJZ91147.1
AKA26859.1
AKA35243.1
AKA84246.1
AKA84438.1
AKB79206.1
AKB84150.1
AKC79848.1
AKC82482.1
AKC86571.1
AKD03611.1
AKD24893.1
AKD38345.1
AKD58010.1
AKE51966.1
AKE61219.1
AKE61764.1
AKE62865.1
AKE94625.1
AKF03665.1
AKF25158.1
AKF49695.1
AKF81025.1
AKG68123.1
AKH08725.1
AKH09890.1
AKH17278.1
AKH20941.1
AKH23616.1
AKH24763.1
AKH64396.1
AKH69186.1
AKI01113.1
AKI01416.1
AKJ05268.1
AKJ41195.1
AKJ53541.1
AKJ64714.1
AKJ94106.1
AKJ97406.1
AKK00568.1
AKK49722.1
AKK66313.1
AKK71642.1
AKL10485.1
AKL34468.1
AKL93588.1
AKL93616.1
AKM01921.1
AKM17405.1
AKM18378.1
AKM36436.1
AKM38713.1
AKM39687.1
AKM41511.1
AKM92041.1
AKN25889.1
AKN61444.1
AKN68937.1
AKO77003.1
AKO96332.1
AKP45430.1
AKP46702.1
AKP53234.1
AKP75073.1
AKP76339.1
AKQ46065.1
AKQ54037.1
AKQ67372.1
AKS06605.1
ALD23720.1
ALD23755.1
ALD27245.1
ALL39775.1
ALL89048.1
ALR26077.1
ALV75857.1
ALV77901.1
ALY14442.1
ALY15746.1
ALZ68230.1
ALZ68795.1
AMC46980.1
AMJ69296.1
AMW42739.1
AMX13191.1
AMX14483.1
ANC21029.1
ANH43655.1
ANK33675.1
ANK34958.1
ANM83718.1
ANM84924.1
ANO92070.1
ANP19758.1
ANP20955.1
AOE77376.1
AOM43879.1
AOM48592.1
AOM71331.1
AOM71367.1
AOM72743.1
AOT31396.1
AOT34840.1
AOZ73672.1
AOZ75058.1
APA40674.1
BAA16587.1
BAA18683.1
BAB06359.1

TABLE 7-continued

Representative Examples of Arginine Decarboxylase by EMBL/GENBANK/DDBJ ID Number BAB37237.1
BAB75100.1
BAC09359.1
BAC61513.1
BAC92011.1
BAC94750.1
BAD46988.1
BAD64942.1
BAD71463.1
BAD78700.1
BAE75293.1
BAE77001.1
BAE78119.1
BAF69929.1
BAF72313.1
BAG04503.1
BAG78731.1
BAG83373.1
BAH39093.1
BAH44872.1
BAH46155.1
BAI27222.1
BAI32252.1
BAI37476.1
BAI80755.1
BAI92054.1
BAJ02496.1
BAJ55572.1
BAJ56452.1
BAJ57954.1
BAJ60069.1
BAK12516.1
BAK33766.1
BAK70627.1
BAK73092.1
BAK76369.1
BAK98463.1
BAL81291.1
BAL84001.1
BAM04828.1
BAM33479.1
BAM50284.1
BAM53453.1
BAM96903.1
BAM98361.1
BAM99840.1
BAN02878.1
BAN50817.1
BAN52492.1
BAN70003.1
BAO54359.1
BAO98678.1
BAP18257.1
BAP32992.1
BAP43154.1
BAP57483.1
BAP58680.1
BAU72598.1
BAU76793.1
CAA41337.1
CAA65422.1
CAB13336.1
CAD02911.1
CAD09281.1
CAD16072.1
CAD73363.1
CAE08874.1
CAE09688.1
CAE16054.1
CAE18504.1
CAE22324.1
CAE31349.1
CAE40174.1
CAE40569.1
CAE78014.1
CAG45065.1
CAG76815.1

CAH05973.1
CAH14236.1
CAH20481.1
CAH22440.1
CAI86150.1
CAI87882.1
CAJ25769.1
CAJ48085.1
CAJ50298.1
CAJ67721.1
CAJ70455.1
CAJ94006.1
CAJ99421.1
CAK17500.1
CAK24815.1
CAK29281.1
CAL13443.1
CAL17846.1
CAL19596.1
CAL34892.1
CAL43775.1
CAL68563.1
CAM09122.1
CAM10863.1
CAN92612.1
CAO97871.1
CAP44435.1
CAP53422.1
CAQ47743.1
CAQ70346.1
CAQ81008.1
CAQ83180.1
CAQ83413.1
CAQ90371.1
CAR04456.1
CAR05775.1
CAR09410.1
CAR10810.1
CAR14453.1
CAR15764.1
CAR19475.1
CAR20645.1
CAR38786.1
CAR39908.1
CAR42872.1
CAR44185.1
CAR54969.1
CAS10739.1
CAU99219.1
CAV01446.1
CAV18374.1
CAX29520.1
CAX61193.1
CAY46894.1
CAY75592.1
CAZ96112.1
CBA07513.1
CBA14903.1
CBA19555.1
CBA33565.1
CBG39474.1
CBG91721.1
CBH20174.1
CBI42666.1
CBI66029.1
CBJ02631.1
CBJ10334.1
CBJ81373.1
CBJ82759.1
CBJ89096.1
CBJ90126.1
CBK62911.1
CBK67757.1
CBK75517.1
CBK76873.1
CBK79250.1
CBK89692.1

TABLE 7-continued

Representative Examples of Arginine Decarboxylase by EMBL/GENBANK/DDBJ ID Number

| |
|---|
| CBK93443.1 |
| CBK95550.1 |
| CBK97421.1 |
| CBK98076.1 |
| CBK99239.1 |
| CBL02265.1 |
| CBL06429.1 |
| CBL06632.1 |
| CBL08498.1 |
| CBL11309.1 |
| CBL17760.1 |
| CBL18279.1 |
| CBL18584.1 |
| CBL22837.1 |
| CBL25542.1 |
| CBL33751.1 |
| CBL33969.1 |
| CBL41416.1 |
| CBL46386.1 |
| CBN55346.1 |
| CBV43889.1 |
| CBW19161.1 |
| CBW20794.1 |
| CBW26940.1 |
| CBW74145.1 |
| CBY25861.1 |
| CBY83075.1 |
| CCA53939.1 |
| CCA57465.1 |
| CCB69668.1 |
| CCB80486.1 |
| CCB85396.1 |
| CCB88488.1 |
| CCC31740.1 |
| CCC32782.1 |
| CCC57896.1 |
| CCD40282.1 |
| CCE19088.1 |
| CCE19708.1 |
| CCE25072.1 |
| CCF69259.1 |
| CCF81308.1 |
| CCG18048.1 |
| CCG19863.1 |
| CCG39483.1 |
| CCG45166.1 |
| CCG53314.1 |
| CCG86051.1 |
| CCG93076.1 |
| CCG93934.1 |
| CCG98515.1 |
| CCH32647.1 |
| CCH47920.1 |
| CCH56597.1 |
| CCH64504.1 |
| CCH66661.1 |
| CCH73037.1 |
| CCH92456.1 |
| CCH95671.1 |
| CCH97887.1 |
| CCH98535.1 |
| CCI02124.1 |
| CCI02703.1 |
| CCI05752.1 |
| CCI08081.1 |
| CCI12608.1 |
| CCI13269.1 |
| CCI17237.1 |
| CCI21360.1 |
| CCI26537.1 |
| CCI26557.1 |
| CCI27928.1 |
| CCI31841.1 |
| CCI35741.1 |
| CCI36837.1 |
| CCI78870.1 |
| CCJ33001.1 |
| CCJ37191.1 |
| CCJ45542.1 |
| CCJ46772.1 |
| CCJ48129.1 |
| CCJ54509.1 |
| CCJ71908.1 |
| CCJ80969.1 |
| CCJ86077.1 |
| CCJ89761.1 |
| CCJ99408.1 |
| CCK02016.1 |
| CCK08384.1 |
| CCK48228.1 |
| CCK49456.1 |
| CCK74876.1 |
| CCK76603.1 |
| CCK78280.1 |
| CCK88893.1 |
| CCK89714.1 |
| CCK96041.1 |
| CCK96850.1 |
| CCK99990.1 |
| CCL00838.1 |
| CCL21002.1 |
| CCL24016.1 |
| CCL28925.1 |
| CCL31787.1 |
| CCO04884.1 |
| CCO08560.1 |
| CCO12883.1 |
| CCP12708.1 |
| CCP13614.1 |
| CCP17046.1 |
| CCP18758.1 |
| CCP24686.1 |
| CCP27538.1 |
| CCQ09200.1 |
| CCQ09658.1 |
| CCQ91054.1 |
| CCQ92417.1 |
| CCQ95938.1 |
| CCU62281.1 |
| CCU62303.1 |
| CCW05309.1 |
| CCW08807.1 |
| CCW14223.1 |
| CCW18613.1 |
| CCW31446.1 |
| CCW32107.1 |
| CDF57172.1 |
| CDF57711.1 |
| CDF63223.1 |
| CDF80723.1 |
| CDF86470.1 |
| CDF92784.1 |
| CDF94833.1 |
| CDF95827.1 |
| CDG13951.1 |
| CDG17974.1 |
| CDG18838.1 |
| CDG20298.1 |
| CDG21576.1 |
| CDG29398.1 |
| CDG34413.1 |
| CDG41242.1 |
| CDG57553.1 |
| CDG92785.1 |
| CDG93659.1 |
| CDG98742.1 |
| CDG98818.1 |
| CDG99561.1 |
| CDG99621.1 |
| CDH04673.1 |
| CDH05982.1 |
| CDH19229.1 |
| CDH21449.1 |
| CDH24501.1 |

TABLE 7-continued

Representative Examples of Arginine Decarboxylase by EMBL/GENBANK/DDBJ ID Number CDH25327.1
CDH33018.1
CDH35045.1
CDH79904.1
CDK72226.1
CDK72598.1
CDK73473.1
CDL10509.1
CDL10510.1
CDL14319.1
CDL23452.1
CDL25124.1
CDL25589.1
CDL37867.1
CDL39140.1
CDL46170.1
CDL58441.1
CDL62104.1
CDL78959.1
CDL81271.1
CDL85577.1
CDL87375.1
CDL90268.1
CDL90667.1
CDM04050.1
CDM25489.1
CDM39225.1
CDM40785.1
CDM61201.1
CDM66630.1
CDM69239.1
CDM89651.1
CDM91302.1
CDN08348.1
CDN19844.1
CDN43705.1
CDN75234.1
CDN83562.1
CDO12490.1
CDO59353.1
CDP53980.1
CDQ16188.1
CDR28964.1
CDR33456.1
CDR89846.1
CDR91413.1
CDS49197.1
CDS55845.1
CDS84399.1
CDS84845.1
CDS89935.1
CDS90150.1
CDT62112.1
CDT66706.1
CDU33290.1
CDU33786.1
CDU40272.1
CDU41159.1
CDY74095.1
CDZ24843.1
CDZ77476.1
CDZ85766.1
CDZ95756.1
CEA06065.1
CEA15542.1
CED57568.1
CED79730.1
CEE01723.1
CEF27490.1
CEF30990.1
CEF31449.1
CEF32542.1
CEF33945.1
CEG51568.1
CEG53321.1
CEG53340.1
CEG55497.1
CEG60275.1
CEI12237.1
CEI20008.1
CEJ65415.1
CEJ67509.1
CEJ70957.1
CEK09860.1
CEK22005.1
CEK22994.1
CEK27007.1
CEK36677.1
CEK37311.1
CEL27366.1
CEL28884.1
CEL88254.1
CEN32690.1
CEN35796.1
CEN40472.1
CEN48259.1
CEN49444.1
CEN51746.1
CEN53336.1
CEO37650.1
CEO37783.1
CEO37785.1
CEO37787.1
CEO37789.1
CEO39707.1
CEO41667.1
CEP33357.1
CEP41494.1
CEQ02610.1
CEV48346.1
CEX91433.1
CEY68596.1
CFB65687.1
CFC48275.1
CFE47017.1
CFQ52871.1
CFT90862.1
CFT92467.1
CFW00234.1
CGF82653.1
CIO61989.1
CIU00001.1
CIX12577.1
CIY95083.1
CJA23818.1
CJC39705.1
CJF41584.1
CJF88893.1
CJF99117.1
CJK22396.1
CJM58301.1
CJP89135.1
CJU40070.1
CJV39857.1
CJV78922.1
CJW30609.1
CKB02318.1
CKE35363.1
CKE99011.1
CKF04495.1
CKI15512.1
CKQ74340.1
CKR21949.1
CKS03825.1
CKS26945.1
CKU60545.1
CNA50506.1
CNG15293.1
CNU29954.1
CNU37560.1
CNY76236.1
CNZ37408.1
COB87482.1
COB97035.1

TABLE 7-continued

Representative Examples of Arginine Decarboxylase by EMBL/GENBANK/DDBJ ID Number COC15604.1
COC27925.1
COC38808.1
COC67187.1
COE22069.1
COE68225.1
COE79226.1
COE80568.1
COE81104.1
COE89634.1
COF13698.1
COL35053.1
COO42015.1
COP44209.1
COP71525.1
COQ07912.1
COQ86754.1
COQ96585.1
COS68670.1
COV97320.1
COW18997.1
COW22156.1
CPR16817.1
CPR28569.1
CPR28570.1
CQH27992.1
CQR55269.1
CQR76248.1
CRF41170.1
CRF42208.1
CRF43922.1
CRF48690.1
CRF51588.1
CRF97350.1
CRG01188.1
CRG01880.1
CRG01892.1
CRG49571.1
CRG51097.1
CRH09188.1
CRH15043.1
CRH30682.1
CRH35400.1
CRH39703.1
CRH76554.1
CRH80270.1
CRH99218.1
CRI32264.1
CRI34231.1
CRI55296.1
CRL61081.1
CRL62210.1
CRL87965.1
CRL89510.1
CRL90918.1
CRL92324.1
CRN95722.1
CRO14030.1
CRQ27226.1
CRQ69552.1
CRQ76426.1
CRR63643.1
CRV31623.1
CRX68631.1
CRY53197.1
CRY55323.1
CRY79285.1
CRY93389.1
CSA21308.1
CSA60188.1
CSB08393.1
CSB25865.1
CSB40644.1
CSB44143.1
CSB49667.1
CSB66054.1
CSB75406.1

TABLE 7-continued

Representative Examples of Arginine Decarboxylase by EMBL/GENBANK/DDBJ ID Number CSB76184.1
CSB95854.1
CSB98158.1
CSC34871.1
CSC73993.1
CSD22235.1
CSI57174.1
CSK13615.1
CSK81683.1
CSM45986.1
CSN19117.1
CSP73797.1
CSR75551.1
CSS00410.1
CSS26808.1
CSS59054.1
CTF84311.1
CTO24990.1
CTP86128.1
CTP91660.1
CTP92036.1
CTQ00822.1
CTQ01840.1
CTQ07393.1
CTQ11016.1
CTQ21388.1
CTR60186.1
CTR88293.1
CTS05226.1
CTS30710.1
CTT02231.1
CTT12868.1
CTT68786.1
CTT71981.1
CTT77614.1
CTT83391.1
CTT94455.1
CTT95016.1
CTU31752.1
CTU43794.1
CTU68580.1
CTU79219.1
CTV10378.1
CTV16830.1
CTV23368.1
CTV42489.1
CTV60594.1
CTV70893.1
CTW39538.1
CTW91358.1
CTX50053.1
CTZ18208.1
CTZ55606.1
CTZ68780.1
CTZ88923.1
CUB10138.1
CUB14550.1
CUB17378.1
CUB19225.1
CUB20007.1
CUB20037.1
CUB21150.1
CUB24943.1
CUB26441.1
CUB28066.1
CUB30863.1
CUB32254.1
CUB38825.1
CUB42267.1
CUB42609.1
CUB42690.1
CUB45694.1
CUB49762.1
CUB50111.1
CUB52004.1
CUB53555.1
CUB55220.1

TABLE 7-continued

Representative Examples of Arginine Decarboxylase by EMBL/GENBANK/DDBJ ID Number

| |
|---|
| CUB55706.1 |
| CUH92886.1 |
| CUH95441.1 |
| CUI26621.1 |
| CUI32013.1 |
| CUI43235.1 |
| CUI77995.1 |
| CUI82617.1 |
| CUI97214.1 |
| CUJ01273.1 |
| CUJ29137.1 |
| CUJ59072.1 |
| CUJ84510.1 |
| CUJ95389.1 |
| CUK18245.1 |
| CUR47999.1 |
| CUS48382.1 |
| CUX80760.1 |
| CVA34089.1 |
| CVE90640.1 |
| CVQ04108.1 |
| CVT44067.1 |
| CVV27730.1 |
| CWE46408.1 |
| CWM52080.1 |
| CYJ06643.1 |
| CYL65762.1 |
| CYN07819.1 |
| CYO72927.1 |
| CZQ34128.1 |
| CZX12172.1 |
| CZX80218.1 |
| EAL52385.1 |
| EAO12990.1 |
| EAO54355.1 |
| EAP73812.1 |
| EAP87194.1 |
| EAP93054.1 |
| EAQ32906.1 |
| EAQ43377.1 |
| EAQ50085.1 |
| EAQ66911.1 |
| EAQ70464.1 |
| EAQ72344.1 |
| EAQ76582.1 |
| EAQ77591.1 |
| EAQ97815.1 |
| EAR09325.1 |
| EAR13003.1 |
| EAR16281.1 |
| EAR17315.1 |
| EAR22580.1 |
| EAR30279.1 |
| EAR53966.1 |
| EAS21033.1 |
| EAS45733.1 |
| EAS66651.1 |
| EAT02109.1 |
| EAT04436.1 |
| EAT12991.1 |
| EAT16635.1 |
| EAT98614.1 |
| EAU54879.1 |
| EAU62359.1 |
| EAU71335.1 |
| EAU75144.1 |
| EAW26171.1 |
| EAW26965.1 |
| EAW38293.1 |
| EAZ83215.2 |
| EAZ92702.1 |
| EAZ94470.1 |
| EBA47554.1 |
| EDK22114.1 |
| EDK27087.1 |
| EDK35189.1 |
| EDK35781.1 |
| EDL55745.1 |
| EDM19339.1 |
| EDM24091.1 |
| EDM28695.1 |
| EDM34238.1 |
| EDM43630.1 |
| EDM47206.1 |
| EDM59952.1 |
| EDM72867.1 |
| EDM78148.1 |
| EDN58210.1 |
| EDN69139.1 |
| EDN84738.1 |
| EDO12412.1 |
| EDO55269.1 |
| EDP57831.1 |
| EDP96203.1 |
| EDP99652.1 |
| EDR32346.1 |
| EDR33302.1 |
| EDS04311.1 |
| EDS14810.1 |
| EDS90152.1 |
| EDS94131.1 |
| EDU60243.1 |
| EDU61801.1 |
| EDU64180.1 |
| EDU66731.1 |
| EDU92574.1 |
| EDU93429.1 |
| EDV02459.1 |
| EDV06321.1 |
| EDW23582.1 |
| EDX35590.1 |
| EDX36036.1 |
| EDX36066.1 |
| EDX46577.1 |
| EDX47180.1 |
| EDX68999.1 |
| EDX75316.1 |
| EDX86149.1 |
| EDX90404.1 |
| EDY20546.1 |
| EDY23711.1 |
| EDY26729.1 |
| EDY39883.1 |
| EDY80770.1 |
| EDY87242.1 |
| EDY97001.1 |
| EDZ51155.1 |
| EDZ64094.1 |
| EDZ92135.1 |
| EEA96461.1 |
| EEB25237.1 |
| EEB32660.1 |
| EEB44175.1 |
| EEB45162.1 |
| EEB65951.1 |
| EEC22705.1 |
| EEC52457.1 |
| EEC95655.1 |
| EED08084.1 |
| EED09856.1 |
| EED26047.1 |
| EED37169.1 |
| EED40881.1 |
| EEE02695.1 |
| EEE38554.1 |
| EEE39911.1 |
| EEF12870.1 |
| EEF60316.1 |
| EEF76458.1 |
| EEF78531.1 |
| EEF90887.1 |
| EEG08845.1 |
| EEG09028.1 |
| EEG41374.1 |

TABLE 7-continued

Representative Examples of Arginine Decarboxylase
by EMBL/GENBANK/DDBJ ID Number EEG42545.1
EEG85449.1
EEI48480.1
EEI89760.1
EEJ52636.1
EEK14623.1
EEO01851.1
EEO17497.1
EEO24268.1
EEO26226.1
EEO46786.1
EEO48467.1
EEO55967.1
EEO62202.1
EEP52908.1
EEP83814.1
EEP91273.1
EEQ09356.1
EEQ47662.1
EEQ48939.1
EEQ63558.1
EES50668.1
EES65191.1
EES68952.1
EES72773.1
EES89131.1
EET13958.1
EET79835.1
EEV18063.1
EEV88514.1
EEW07548.1
EEW09243.1
EEW41138.1
EEX09883.1
EEX12420.1
EEX18739.1
EEX36091.1
EEX44127.1
EEX49425.1
EEX52952.1
EEX72486.1
EEX77148.1
EEY45420.1
EEY72539.1
EEY99071.1
EEZ05434.1
EEZ20306.1
EEZ25742.1
EEZ39280.1
EEZ41342.1
EEZ42255.1
EEZ84117.1
EEZ88011.1
EFA19997.1
EFA24542.1
EFA45160.1
EFA68566.1
EFA72660.1
EFA93091.1
EFA97054.1
EFB31818.1
EFB33967.1
EFB71688.1
EFB72852.1
EFC32879.1
EFC53930.1
EFC68230.1
EFC70407.1
EFC74158.1
EFC76178.1
EFE04794.2
EFE06567.1
EFE24315.1
EFE28188.2
EFE52717.1
EFE53196.1
EFE61789.2

TABLE 7-continued

Representative Examples of Arginine Decarboxylase
by EMBL/GENBANK/DDBJ ID Number EFE96242.1
EFF05372.2
EFF11562.2
EFF44939.1
EFF46228.1
EFF52960.1
EFF65456.1
EFF72972.1
EFG19573.1
EFG77890.1
EFH74644.1
EFI14920.1
EFI17631.1
EFI38855.1
EFI48237.1
EFI71796.1
EFI85175.1
EFI87349.1
EFI90947.1
EFJ68585.1
EFJ68633.1
EFJ72102.1
EFJ74584.1
EFJ78630.1
EFJ81431.1
EFJ85215.1
EFJ85317.1
EFJ95126.1
EFJ95461.1
EFK02094.1
EFK02694.1
EFK07237.1
EFK16317.1
EFK16401.1
EFK17953.1
EFK18112.1
EFK25144.1
EFK27352.1
EFK33114.1
EFK43745.1
EFK47161.1
EFK50509.1
EFK52583.1
EFK58701.1
EFK66137.1
EFK66442.1
EFK71309.1
EFK73843.1
EFK91754.1
EFK92718.1
EFL44876.1
EFM01444.1
EFM05245.1
EFM19909.1
EFM22067.1
EFN90887.1
EFN94455.1
EFN97184.1
EFO54374.1
EFO56780.1
EFO59695.1
EFO79517.1
EFP71829.1
EFP73330.1
EFQ63652.1
EFQ65858.1
EFR17600.1
EFR18234.1
EFR54063.1
EFR58692.1
EFS20507.1
EFS31465.1
EFS98153.1
EFU31591.1
EFU33766.1
EFU36797.1
EFU69462.1

TABLE 7-continued

Representative Examples of Arginine Decarboxylase by EMBL/GENBANK/DDBJ ID Number EFU72568.1
EFV04322.1
EFV27725.1
EFV30929.1
EFV39452.1
EFV43819.1
EFV63706.1
EFV69380.1
EFW49235.1
EFW49274.1
EFW54088.1
EFW57052.1
EFW58445.1
EFW59098.1
EFX42291.1
EFX56847.1
EFX59483.1
EFZ38208.1
EGA66011.1
EGA71636.1
EGB13397.1
EGB61889.1
EGB66940.1
EGB73846.1
EGB86369.1
EGB86483.1
EGC01298.1
EGC21337.1
EGC85605.1
EGC96357.1
EGD13828.1
EGD20671.1
EGD33620.1
EGD47799.1
EGD49452.1
EGE35466.1
EGE46318.1
EGF27184.1
EGF51940.1
EGF55092.1
EGG29616.1
EGG38296.1
EGG53968.1
EGG94813.1
EGH07763.1
EGH20626.1
EGH41959.1
EGH53302.1
EGH60244.1
EGH92632.1
EGH94776.1
EGI01301.1
EGI09326.1
EGI14581.1
EGI19909.1
EGI39909.1
EGI45082.1
EGI49388.1
EGI71763.1
EGI73765.1
EGI74585.1
EGI88322.1
EGI88695.1
EGI89525.1
EGI92003.1
EGI92757.1
EGJ06067.1
EGJ06595.1
EGJ31789.1
EGJ32358.1
EGJ48895.1
EGJ70523.1
EGK01810.1
EGK05202.1
EGK08599.1
EGK19270.1
EGK29801.1
EGK32128.1
EGK32129.1
EGK34621.1
EGK58218.1
EGK87545.1
EGK89608.1
EGL19747.1
EGL54944.1
EGL86229.1
EGL91485.1
EGM69611.1
EGM77628.1
EGM98072.1
EGN04092.1
EGN06621.1
EGN55947.1
EGN75140.1
EGP08625.1
EGP18125.1
EGP70309.1
EGP70453.1
EGQ13522.1
EGQ14735.1
EGQ16803.1
EGQ61183.1
EGU34333.1
EGU40288.1
EGU44011.1
EGU51392.1
EGU98977.1
EGV18080.1
EGV30721.1
EGV36706.1
EGV43418.1
EGW22905.1
EGW38512.1
EGW45479.1
EGW47999.1
EGW49793.1
EGW53900.1
EGY26117.1
EGY52145.1
EGY52303.1
EGY80801.1
EGZ43857.1
EGZ47008.1
EHA13596.1
EHA29720.1
EHA61904.1
EHA63133.1
EHB43287.1
EHB92177.1
EHC12856.1
EHC15115.1
EHC32562.1
EHC33284.1
EHC45854.1
EHC52500.1
EHC67678.1
EHC67688.1
EHC82045.1
EHC82811.1
EHC84879.1
EHC87972.1
EHC99842.1
EHC99945.1
EHC99946.1
EHD20027.1
EHG15746.1
EHG22758.1
EHH01677.1
EHI48137.1
EHI97907.1
EHJ01371.1
EHJ04424.1
EHJ37076.1
EHJ81032.1

TABLE 7-continued

Representative Examples of Arginine Decarboxylase by EMBL/GENBANK/DDBJ ID Number

| |
|---|
| EHJ81054.1 |
| EHJ93009.1 |
| EHK60802.1 |
| EHK70010.1 |
| EHL81981.1 |
| EHL91407.1 |
| EHM45586.1 |
| EHM49306.1 |
| EHM52790.1 |
| EHO08337.1 |
| EHO11855.1 |
| EHO68606.1 |
| EHO71565.1 |
| EHP31153.1 |
| EHP45502.1 |
| EHP66625.1 |
| EHQ02439.1 |
| EHQ24721.1 |
| EHQ40902.1 |
| EHQ44550.1 |
| EHQ51868.1 |
| EHR41063.1 |
| EHT11453.1 |
| EHT99387.1 |
| EHU03082.1 |
| EHU03351.1 |
| EHU05505.1 |
| EHU07105.1 |
| EHU07471.1 |
| EHU10272.1 |
| EHU19741.1 |
| EHU20407.1 |
| EHU20988.1 |
| EHU23878.1 |
| EHU27439.1 |
| EHU29624.1 |
| EHU34399.1 |
| EHU35766.1 |
| EHU37211.1 |
| EHU40410.1 |
| EHU49113.1 |
| EHU52686.1 |
| EHV51291.1 |
| EHV55180.1 |
| EHY68649.1 |
| EHY76875.1 |
| EIA07694.1 |
| EIA38800.1 |
| EIB51628.1 |
| EIC22362.1 |
| EIC28827.1 |
| EIC82504.1 |
| EID32911.1 |
| EID63306.1 |
| EID67828.1 |
| EID72224.1 |
| EIE30102.1 |
| EIF06919.1 |
| EIF52011.1 |
| EIG78691.1 |
| EIG93478.1 |
| EIH12869.1 |
| EIH21876.1 |
| EIH45560.1 |
| EIH76673.1 |
| EII24830.1 |
| EII34710.1 |
| EII46184.1 |
| EIJ34481.1 |
| EIJ40219.1 |
| EIJ41403.1 |
| EIK43927.1 |
| EIK45786.1 |
| EIK46160.1 |
| EIK53544.1 |
| EIK63187.1 |
| EIK68334.1 |
| EIK69996.1 |
| EIK96535.1 |
| EIL52554.1 |
| EIL87847.1 |
| EIL89177.1 |
| EIL96389.1 |
| EIL96460.1 |
| EIM32597.1 |
| EIP99569.1 |
| EIQ05168.1 |
| EIQ05557.1 |
| EIQ17816.1 |
| EIQ18546.1 |
| EIQ26062.1 |
| EIQ30073.1 |
| EIQ34463.1 |
| EIQ55519.1 |
| EIQ57190.1 |
| EIQ64791.1 |
| EIQ65835.1 |
| EIQ71328.1 |
| EIQ78421.1 |
| EIT71762.1 |
| EIW88565.1 |
| EIW91670.1 |
| EIY17637.1 |
| EIY32545.1 |
| EIY36788.1 |
| EIY37052.1 |
| EIY53920.1 |
| EIY54279.1 |
| EIY58813.1 |
| EIY66667.1 |
| EIY70029.1 |
| EIY74616.1 |
| EIY79988.1 |
| EIY85347.1 |
| EIZ00158.1 |
| EIZ01825.1 |
| EJB14848.1 |
| EJB16556.1 |
| EJB19827.1 |
| EJB23702.1 |
| EJB23977.1 |
| EJB26400.1 |
| EJB29229.1 |
| EJB29946.1 |
| EJB30033.1 |
| EJB32499.1 |
| EJB35336.1 |
| EJB37017.1 |
| EJB37646.1 |
| EJB39924.1 |
| EJB42939.1 |
| EJB43406.1 |
| EJB45027.1 |
| EJB45391.1 |
| EJB49839.1 |
| EJB50034.1 |
| EJB51708.1 |
| EJB53907.1 |
| EJB55025.1 |
| EJB56551.1 |
| EJB57975.1 |
| EJB59811.1 |
| EJB60409.1 |
| EJB63120.1 |
| EJB65622.1 |
| EJB65702.1 |
| EJB68991.1 |
| EJB70910.1 |
| EJB71404.1 |
| EJB74413.1 |
| EJB74966.1 |
| EJB75595.1 |
| EJB77218.1 |
| EJB80849.1 |

TABLE 7-continued

Representative Examples of Arginine Decarboxylase by EMBL/GENBANK/DDBJ ID Number

| |
|---|
| EJB81088.1 |
| EJB81799.1 |
| EJB84950.1 |
| EJB87126.1 |
| EJB88385.1 |
| EJB90467.1 |
| EJB90548.1 |
| EJB92801.1 |
| EJB94869.1 |
| EJB95273.1 |
| EJB96496.1 |
| EJB99121.1 |
| EJC02347.1 |
| EJC02425.1 |
| EJC04636.1 |
| EJC08570.1 |
| EJC08694.1 |
| EJC08709.1 |
| EJC11811.1 |
| EJC11826.1 |
| EJC14043.1 |
| EJC15845.1 |
| EJC18371.1 |
| EJC19409.1 |
| EJC21392.1 |
| EJC22985.1 |
| EJC23357.1 |
| EJC26559.1 |
| EJC27448.1 |
| EJC29756.1 |
| EJC32969.1 |
| EJC33159.1 |
| EJC34883.1 |
| EJC37288.1 |
| EJC37890.1 |
| EJC39690.1 |
| EJC42076.1 |
| EJC43069.1 |
| EJC44761.1 |
| EJC46949.1 |
| EJC48994.1 |
| EJC51269.1 |
| EJC51645.1 |
| EJC52741.1 |
| EJC55221.1 |
| EJC57220.1 |
| EJC60490.1 |
| EJE70688.1 |
| EJE72667.1 |
| EJF07261.1 |
| EJF10819.1 |
| EJF28963.1 |
| EJF35650.1 |
| EJF67926.1 |
| EJF99356.1 |
| EJG45313.1 |
| EJI86684.1 |
| EJI92286.1 |
| EJK90497.1 |
| EJL05765.1 |
| EJL07513.1 |
| EJL10780.1 |
| EJL13646.1 |
| EJL59252.1 |
| EJL74965.1 |
| EJL86651.1 |
| EJL93876.1 |
| EJM01555.1 |
| EJM14551.1 |
| EJM16866.1 |
| EJM18376.1 |
| EJM29803.1 |
| EJM31718.1 |
| EJM47413.1 |
| EJM51011.1 |
| EJM64276.1 |
| EJM73569.1 |

TABLE 7-continued

Representative Examples of Arginine Decarboxylase by EMBL/GENBANK/DDBJ ID Number

| |
|---|
| EJM76313.1 |
| EJM80112.1 |
| EJM80845.1 |
| EJM90007.1 |
| EJM95558.1 |
| EJN26255.1 |
| EJN28670.1 |
| EJN35237.1 |
| EJN38607.1 |
| EJP75284.1 |
| EJP79470.1 |
| EJU30245.1 |
| EJU35714.1 |
| EJU55911.1 |
| EJW20856.1 |
| EJZ56337.1 |
| EJZ62656.1 |
| EJZ62989.1 |
| EJZ63479.1 |
| EKA78857.1 |
| EKA86757.1 |
| EKA88055.1 |
| EKB08191.1 |
| EKB20130.1 |
| EKB20483.1 |
| EKB29486.1 |
| EKB43813.1 |
| EKB47023.1 |
| EKB50524.1 |
| EKB56886.1 |
| EKB59777.1 |
| EKD09436.1 |
| EKE75917.1 |
| EKE80497.1 |
| EKE80736.1 |
| EKE81635.1 |
| EKE84692.1 |
| EKE87132.1 |
| EKE88767.1 |
| EKE92179.1 |
| EKE92371.1 |
| EKE94894.1 |
| EKE95013.1 |
| EKF04077.1 |
| EKF56035.1 |
| EKF75530.1 |
| EKG30394.1 |
| EKG35718.1 |
| EKI47752.1 |
| EKI50663.1 |
| EKJ91033.1 |
| EKK03341.1 |
| EKM19532.1 |
| EKM27369.1 |
| EKM33123.1 |
| EKM97272.1 |
| EKN06246.1 |
| EKN13589.1 |
| EKQ59703.1 |
| EKQ67050.1 |
| EKQ70123.1 |
| EKQ72452.1 |
| EKT55066.1 |
| EKT55968.1 |
| EKT57267.1 |
| EKT60399.1 |
| EKT65146.1 |
| EKU11723.1 |
| EKU90730.1 |
| EKU99609.1 |
| EKV02611.1 |
| EKX85043.1 |
| EKX91099.1 |
| EKY02026.1 |
| EKY07478.1 |
| EKY10219.1 |
| EKY13803.1 |

TABLE 7-continued

Representative Examples of Arginine Decarboxylase by EMBL/GENBANK/DDBJ ID Number EKY21196.1
ELC14266.1
ELC16837.1
ELC37938.1
ELC95207.1
ELD97322.1
ELE41731.1
ELE53629.1
ELE58435.1
ELG86731.1
ELI22619.1
ELJ68848.1
ELP32817.1
ELP53718.1
ELP56620.1
ELQ06726.1
ELQ17703.1
ELR67226.1
ELR68531.1
ELR73634.1
ELR80702.1
ELR96270.1
ELS03888.1
ELS26426.1
ELS26899.1
ELS33992.1
ELS34647.1
ELS45534.1
ELT80942.1
ELU52902.1
ELW29101.1
ELW31523.1
ELX08395.1
ELX67235.1
ELY20188.1
EMB16639.1
EMD05366.1
EMD08744.1
EMD99302.1
EMG29941.1
EMG36518.1
EMG80552.1
EMG81375.1
EMG83328.1
EMG85067.1
EMG90353.1
EMG92202.1
EMG92921.1
EMG95880.1
EMG97280.1
EMG97371.1
EMH01414.1
EMH01598.1
EMH05152.1
EMH05692.1
EMH07062.1
EMH07880.1
EMH11608.1
EMH20676.1
EMH23184.1
EMH23218.1
EMH24922.1
EMH27240.1
EMH31442.1
EMH32228.1
EMH36381.1
EMH36815.1
EMH37015.1
EMH40386.1
EMH40500.1
EMH44660.1
EMH49506.1
EMH59432.1
EMH69334.1
EMH71508.1
EMI08652.1
EMT13553.1
EMI19018.1
EMI25919.1
EMI45208.1
EMI58017.1
EMJ41880.1
EMJ41986.1
EMJ43448.1
EMJ45150.1
EMP51370.1
EMP54150.1
EMQ95230.1
EMQ99308.1
EMR04830.1
EMR05081.1
EMR07653.1
EMR12041.1
EMR52882.1
EMR55723.1
EMR57703.1
EMR59166.1
EMR59894.1
EMS33700.1
EMS70703.1
EMS73603.1
EMU56968.1
EMU59687.1
EMU65357.1
EMU68327.1
EMV15078.1
EMV17996.1
EMW91062.1
EMW96728.1
EMW97461.1
EMX15494.1
EMX18621.1
EMX29476.1
EMX33528.1
EMX34251.1
EMX36711.1
EMX46865.1
EMX56824.1
EMX81299.1
EMX83206.1
EMY81020.1
EMZ41287.1
EMZ50395.1
ENA01016.1
ENA04654.1
ENA32193.1
ENA35846.1
ENA38210.1
ENA41620.1
ENA43837.1
ENC88200.1
ENC90023.1
END49167.1
END51201.1
END87069.1
END90132.1
ENG93781.1
ENG95643.1
ENG97959.1
ENH01175.1
ENH05522.1
ENH07606.1
ENH60192.1
ENN97706.1
ENN99012.1
ENO14664.1
ENY70479.1
ENY75181.1
ENZ85539.1
ENZ95106.1
EOA53659.1
EOA60059.1
EOC16725.1
EOD01056.1

TABLE 7-continued

Representative Examples of Arginine Decarboxylase by EMBL/GENBANK/DDBJ ID Number EOD01708.1
EOD55293.1
EOD78016.1
EON77899.1
EON87503.1
EON89205.1
EON91172.1
EOQ46177.1
EOQ52663.1
EOR94186.1
EOR98455.1
EOS02472.1
EOS11079.1
EOS14650.1
EOU48069.1
EOU65288.1
EOU78387.1
EOU89741.1
EOV04150.1
EOV47240.1
EOV55388.1
EOV76751.1
EOV94391.1
EOW04341.1
EOW16263.1
EOW19942.1
EOW61852.1
EOW95132.1
EOZ93556.1
EPA96712.1
EPB93485.1
EPC02883.1
EPD31850.1
EPD98827.1
EPF13751.1
EPF17537.1
EPF21605.1
EPF68350.1
EPF68473.1
EPH07536.1
EPH21580.1
EPI67044.1
EPI70349.1
EPI90403.1
EPJ00323.1
EPJ02080.1
EPJ05850.1
EPJ12078.1
EPJ79656.1
EPJ90215.1
EPJ93745.1
EPL04978.1
EPL63254.1
EPN64426.1
EPP23941.1
EPR12129.1
EPR26288.1
EPR32845.1
EPR44697.1
EPR66995.1
EPR73837.1
EPT33373.1
EPX63361.1
EPX75972.1
EPX79893.1
EPX85529.1
EPZ50793.1
EPZ68373.1
EPZ69904.1
EPZ70096.1
EPZ71437.1
EPZ73670.1
EPZ93539.1
EPZ96226.1
EPZ96901.1
EPZ97559.1
EQB40349.1
EQB91601.1
EQC00900.1
EQC06150.1
EQC46203.1
EQC46450.1
EQC51959.1
EQC66601.1
EQD88409.1
EQD91604.1
EQD92375.1
EQD93814.1
EQD96580.1
EQD96886.1
EQD99945.1
EQL43170.1
EQL47661.1
EQL50895.1
EQL54133.1
EQL57441.1
EQL59958.1
EQL63991.1
EQL67045.1
EQL70097.1
EQL73574.1
EQL75680.1
EQL75690.1
EQL75717.1
EQM66263.1
EQM78326.1
EQM87861.1
EQN24782.1
EQN91650.1
EQO59512.1
EQP47195.1
EQQ03971.1
EQV89276.1
EQX25773.1
EQX86242.1
EQY17583.1
EQY57339.1
EQZ99176.1
ERA59136.1
ERE06409.1
ERF66688.1
ERF77295.1
ERG07873.1
ERG11044.1
ERG17091.1
ERG24593.1
ERG26262.1
ERG36314.1
ERG36846.1
ERG42423.1
ERG44637.1
ERG53669.1
ERG54725.1
ERH47769.1
ERH53106.1
ERH97657.1
ERI03748.1
ERI53864.1
ERI61622.1
ERI81690.1
ERJ19318.1
ERJ22052.1
ERJ22898.1
ERJ26266.1
ERJ29171.1
ERJ30739.1
ERJ32256.1
ERJ59126.1
ERJ59423.1
ERJ76012.1
ERJ79618.1
ERJ98652.1
ERK00664.1
ERK06334.1

TABLE 7-continued

Representative Examples of Arginine Decarboxylase by EMBL/GENBANK/DDBJ ID Number ERK11302.1
ERK12084.1
ERK40558.1
ERL00460.1
ERL46829.1
ERL52081.1
ERL56578.1
ERM21676.1
ERM81855.1
ERM89954.1
ERN40958.1
ERO57040.1
ERO62594.1
ERP09069.1
ERP91471.1
ERP99142.1
ERS04711.1
ERS86390.1
ERS87232.1
ERS91854.1
ERT06712.1
ERT14070.1
ERT56956.1
ESA33218.1
ESA61592.1
ESA67358.1
ESA68724.1
ESA72702.1
ESA84976.1
ESA92507.1
ESB01863.1
ESC99189.1
ESD05521.1
ESD21415.1
ESD37527.1
ESD70934.1
ESD76699.1
ESD90268.1
ESE04816.1
ESE42704.1
ESE82023.1
ESE83037.1
ESE85318.1
ESE86258.1
ESF53718.1
ESF55412.1
ESG63282.1
ESG73913.1
ESJ12988.1
ESJ19423.1
ESK15533.1
ESK34335.1
ESL70097.1
ESM15736.1
ESN17180.1
ESN61562.1
ESP91266.1
ESQ72659.1
ESQ98506.1
ESR23196.1
ESR27061.1
ESS57492.1
ESS71276.1
EST40648.1
EST58096.1
ESU18866.1
ESU25453.1
ESU27166.1
ESU77439.1
ESU78126.1
ESW37563.1
ESW52929.1
ETA89391.1
ETB63778.1
ETC27700.1
ETC31135.1
ETC85052.1
ETD18804.1
ETD22871.1
ETD26440.1
ETD27161.1
ETD59989.1
ETD64469.1
ETE22281.1
ETE27053.1
ETE36278.1
ETE47321.1
ETE48159.1
ETE50251.1
ETF10350.1
ETI62472.1
ETK18845.1
ETK24212.1
ETK27546.1
ETM65380.1
ETN88238.1
ETN95568.1
ETS33246.1
ETT00960.1
ETT02263.1
ETT07388.1
ETT28858.1
ETW99192.1
ETX06515.1
ETX09877.1
ETY41684.1
ETZ09940.1
ETZ11400.1
ETZ11401.1
ETZ20997.1
ETZ22197.1
EUB71843.1
EUB87538.1
EUD05822.1
EVU13225.1
EVU13226.1
EWC41146.1
EWC58917.1
EWC60810.1
EWG73749.1
EWH03492.1
EWH03493.1
EWH04198.1
EWH06793.1
EWH11550.1
EWH15068.1
EWS59738.1
EWS77356.1
EWS97918.1
EWS99002.1
EXF46432.1
EXF51063.1
EXF91547.1
EXG78764.1
EXG84733.1
EXJ09881.1
EXJ13081.1
EXU67280.1
EXU74155.1
EXY29211.1
EXY33704.1
EXY43202.1
EXY67304.1
EXY72022.1
EXY75943.1
EXY86437.1
EXY92714.1
EXZ07363.1
EXZ21227.1
EXZ30510.1
EXZ46466.1
EXZ75334.1
EXZ80412.1
EXZ80749.1

TABLE 7-continued

Representative Examples of Arginine Decarboxylase by EMBL/GENBANK/DDBJ ID Number EXZ81010.1
EXZ81185.1
EXZ82079.1
EXZ83185.1
EXZ83435.1
EXZ84050.1
EXZ84907.1
EXZ85059.1
EXZ85221.1
EXZ85313.1
EXZ85634.1
EXZ85863.1
EXZ86207.1
EXZ86241.1
EXZ86725.1
EXZ91489.1
EXZ92090.1
EXZ92345.1
EXZ96372.1
EXZ96517.1
EXZ96775.1
EXZ96947.1
EXZ97324.1
EYA21384.1
EYA41181.1
EYB11611.1
EYB68441.1
EYD71048.1
EYD71269.1
EYD77132.1
EYD83103.1
EYD83144.1
EYE47819.1
EYE59402.1
EYF00414.1
EYU15774.1
EYU15950.1
EYV07474.1
EYV09937.1
EYV12182.1
EYV18353.1
EYZ99020.1
EYZ99540.1
EZA32955.1
EZA36513.1
EZD27285.1
EZD33881.1
EZE09296.1
EZE12279.1
EZE47844.1
EZE49623.1
EZH71533.1
EZH79132.1
EZI29906.1
EZJ34131.1
EZJ36632.1
EZJ47817.1
EZJ49365.1
EZJ65986.1
EZJ71202.1
EZJ81000.1
EZJ83511.1
EZK16071.1
EZK19946.1
EZP28490.1
EZP44002.1
EZP56652.1
EZP66078.1
EZQ19254.1
GAA05804.1
GAA59698.1
GAA61579.1
GAA62825.1
GAA65644.1
GAA68204.1
GAA68485.1
GAA80936.1

TABLE 7-continued

Representative Examples of Arginine Decarboxylase by EMBL/GENBANK/DDBJ ID Number GAA81294.1
GAB51337.1
GAB55910.1
GAB59559.1
GAB61720.1
GAC05867.1
GAC16515.1
GAC19153.1
GAC24840.1
GAC27365.1
GAC31749.1
GAC65340.1
GAD19562.1
GAD32505.1
GAD63345.1
GAD68291.1
GAD77234.1
GAE14826.1
GAE17566.1
GAE20934.1
GAE50743.1
GAE50744.1
GAE54881.1
GAE64745.1
GAE82642.1
GAF02272.1
GAJ47652.1
GAJ68143.1
GAJ70028.1
GAJ74711.1
GAK15505.1
GAK22285.1
GAK28095.1
GAK35190.1
GAK75264.1
GAK75265.1
GAK86393.1
GAK92926.1
GAK92927.1
GAK97921.1
GAL04346.1
GAL04347.1
GAL04804.1
GAL05072.1
GAL11044.1
GAL16861.1
GAL30713.1
GAL36801.1
GAL45647.1
GAL50933.1
GAL56699.1
GAL62431.1
GAL66822.1
GAL70388.1
GAL75241.1
GAL79181.1
GAL86673.1
GAL90465.1
GAL93717.1
GAM07869.1
GAM14623.1
GAM16409.1
GAM57915.1
GAM65554.1
GAM65555.1
GAM68525.1
GAM76288.1
GAO04477.1
GAO31699.1
GAO33666.1
GAO45653.1
GAO91678.1
GAO91679.1
GAP37055.1
GAP61915.1
GAP72423.1
GAP76842.1

TABLE 7-continued

Representative Examples of Arginine Decarboxylase by EMBL/GENBANK/DDBJ ID Number

| |
|---|
| GAR75750.1 |
| KAJ56674.1 |
| KCU95650.1 |
| KCW98899.1 |
| KDA24159.1 |
| KDA35749.1 |
| KDA37931.1 |
| KDA55394.1 |
| KDA56762.1 |
| KDA92360.1 |
| KDC48914.1 |
| KDC51679.1 |
| KDD67072.1 |
| KDD69088.1 |
| KDE33950.1 |
| KDE39162.1 |
| KDE41001.1 |
| KDE90314.1 |
| KDF12960.1 |
| KDF13307.1 |
| KDG93657.1 |
| KDM49648.1 |
| KDM68718.1 |
| KDM68719.1 |
| KDN30189.1 |
| KDN56291.1 |
| KDN73057.1 |
| KDN99663.1 |
| KDR44432.1 |
| KDR51619.1 |
| KDR94681.1 |
| KDR94730.1 |
| KDR96264.1 |
| KDS17972.1 |
| KDS22344.1 |
| KDS33124.1 |
| KDS52278.1 |
| KDS56812.1 |
| KDU29239.1 |
| KDU31861.1 |
| KDV26776.1 |
| KDV28114.1 |
| KDV40156.1 |
| KDV41543.1 |
| KDV62400.1 |
| KDV63793.1 |
| KDW27169.1 |
| KDW29868.1 |
| KDX21121.1 |
| KDX22110.1 |
| KDX42786.1 |
| KDX45707.1 |
| KEA46535.1 |
| KEA54562.1 |
| KEA61551.1 |
| KEA62619.1 |
| KEF30262.1 |
| KEF33353.1 |
| KEI67085.1 |
| KEI68609.1 |
| KEI72809.1 |
| KEJ43225.1 |
| KEJ44938.1 |
| KEJ56396.1 |
| KEJ59126.1 |
| KEJ70817.1 |
| KEJ73415.1 |
| KEK28674.1 |
| KEL65109.1 |
| KEL72014.1 |
| KEN50130.1 |
| KEN53759.1 |
| KEN65627.1 |
| KEN81913.1 |
| KEN95683.1 |
| KEN98031.1 |
| KEO05580.1 |
| KEO08161.1 |
| KEO24816.1 |
| KEO30080.1 |
| KEO72498.1 |
| KEQ11859.1 |
| KEQ16618.1 |
| KEQ28307.1 |
| KER03202.1 |
| KER51206.1 |
| KER72322.1 |
| KER76638.1 |
| KES24091.1 |
| KEX90562.1 |
| KEX95184.1 |
| KEY18642.1 |
| KEY39601.1 |
| KEY59238.1 |
| KEY84828.1 |
| KEZ01477.1 |
| KEZ03267.1 |
| KEZ78110.1 |
| KEZ92071.1 |
| KFA04678.1 |
| KFA36836.1 |
| KFA89275.1 |
| KFA97526.1 |
| KFB01609.1 |
| KFB86395.1 |
| KFC05463.1 |
| KFC07098.1 |
| KFC18775.1 |
| KFC20875.1 |
| KFC39603.1 |
| KFC59091.1 |
| KFC78158.1 |
| KFC79267.1 |
| KFC83040.1 |
| KFC87306.1 |
| KFC87307.1 |
| KFC88523.1 |
| KFC89970.1 |
| KFC90672.1 |
| KFC95288.1 |
| KFC98497.1 |
| KFD07809.1 |
| KFD17131.1 |
| KFD39669.1 |
| KFD75087.1 |
| KFD78853.1 |
| KFD81164.1 |
| KFE26842.1 |
| KFE29849.1 |
| KFE38039.1 |
| KFE40407.1 |
| KFE50878.1 |
| KFE51463.1 |
| KFE51926.1 |
| KFE53529.1 |
| KFE64790.1 |
| KFF00394.1 |
| KFF03918.1 |
| KFF04643.1 |
| KFF13425.1 |
| KFF13691.1 |
| KFF15603.1 |
| KFF24492.1 |
| KFF24725.1 |
| KFF33206.1 |
| KFF49430.1 |
| KFF67537.1 |
| KFF75398.1 |
| KFF88090.1 |
| KFG77442.1 |
| KFH26796.1 |
| KFI20485.1 |
| KFJ74929.1 |
| KFJ92088.1 |

TABLE 7-continued

Representative Examples of Arginine Decarboxylase by EMBL/GENBANK/DDBJ ID Number KFK53898.1
KFK84555.1
KFK92733.1
KFL36101.1
KFL54829.1
KFL92212.1
KFN02659.1
KFN09730.1
KFN20471.1
KFN41529.1
KFN43972.1
KFN46384.1
KFN49579.1
KFX05154.1
KFX10605.1
KFX71524.1
KFX75866.1
KFZ27800.1
KFZ30182.1
KFZ38533.1
KGA31718.1
KGA43478.1
KGA48786.1
KGA58341.1
KGA92942.1
KGB23003.1
KGB92031.1
KGD52658.1
KGD62570.1
KGD63593.1
KGD67727.1
KGD74930.1
KGD75028.1
KGE12918.1
KGE50810.1
KGE68364.1
KGE71433.1
KGE78509.1
KGF16727.1
KGF26636.1
KGF34522.1
KGF43280.1
KGF45725.1
KGF49777.1
KGF52178.1
KGF56050.1
KGF63655.1
KGF63738.1
KGF88277.1
KGF91126.1
KGF94746.1
KGF98813.1
KGG02043.1
KGG06694.1
KGG08515.1
KGG13342.1
KGG16902.1
KGG20690.1
KGG25301.1
KGI22183.1
KGI51761.1
KGI53124.1
KGI59215.1
KGI60343.1
KGI79227.1
KGI87491.1
KGI91964.1
KGJ93972.1
KGJ99825.1
KGK02508.1
KGK02667.1
KGK11102.1
KGK23554.1
KGK41898.1
KGK59739.1
KGK66000.1
KGK82506.1

TABLE 7-continued

Representative Examples of Arginine Decarboxylase by EMBL/GENBANK/DDBJ ID Number KGL06861.1
KGL11309.1
KGL13567.1
KGL15463.1
KGL17335.1
KGL29400.1
KGL30461.1
KGL33804.1
KGL37280.1
KGL61019.1
KGL63589.1
KGM06101.1
KGM21402.1
KGM27648.1
KGM27861.1
KGM51253.1
KGM53981.1
KGM56140.1
KGM58508.1
KGM62446.1
KGM67544.1
KGM71413.1
KGM76900.1
KGM78995.1
KGM83357.1
KGM85011.1
KGN81341.1
KGO11905.1
KGO35136.1
KGO83427.1
KGO86156.1
KGO90041.1
KGO94762.1
KGO96620.1
KGO98326.1
KGP46487.1
KGP63789.1
KGQ20140.1
KGQ21232.2
KGQ31157.1
KGQ42404.1
KGQ44023.1
KGQ45908.1
KGQ50253.1
KGQ57330.1
KGQ59395.1
KGQ63142.1
KGR36637.1
KGR59419.1
KGT92074.1
KGT93839.1
KGT99163.1
KGU86824.1
KGY09804.1
KGY14273.1
KHA74142.1
KHD07149.1
KHD11120.1
KHD26207.1
KHD65185.1
KHE42876.1
KHE71266.1
KHF26633.1
KHF28513.1
KHF28514.1
KHF29887.1
KHF33712.1
KHF33713.1
KHF36661.1
KHG33418.1
KHG41692.1
KHG64539.1
KHI35431.1
KHI37340.1
KHJ15087.1
KHJ20005.1
KHJ37179.1

TABLE 7-continued

Representative Examples of Arginine Decarboxylase by EMBL/GENBANK/DDBJ ID Number KHJ49938.1
KHJ65217.1
KHK62458.1
KHL08583.1
KHL11564.1
KHL18640.1
KHL59754.1
KHL70867.1
KHL78786.1
KHL79579.1
KHL80012.1
KHL81128.1
KHL83404.1
KHL85844.1
KHL86355.1
KHL87974.1
KHL89471.1
KHL90211.1
KHM48729.1
KHM49647.1
KHM50824.1
KHM92424.1
KHN50316.1
KHN57161.1
KHN63730.1
KHN93577.1
KHO63712.1
KHO63713.1
KHO64416.1
KHS42892.1
KHS44852.1
KHS51059.1
KHS53269.1
KHS73061.1
KHT30841.1
KHT42018.1
KHT50744.1
KHT65210.1
KIA76173.1
KIA79535.1
KIA84354.1
KIA86664.1
KIA88155.1
KIA96246.1
KIA97247.1
KIC20030.1
KIC34193.1
KIC41765.1
KIC41860.1
KIC47910.1
KIC63479.1
KIC80370.1
KIC91903.1
KIC93749.1
KIC99323.2
KID01690.1
KID06608.2
KID09915.1
KID53399.1
KID55412.1
KIE10977.1
KIE41615.1
KIE47462.1
KIE57848.1
KIF05806.1
KIF16862.1
KIF29318.1
KIF31064.1
KIF41875.1
KIF44860.1
KIF47532.1
KIF56410.1
KIF65759.1
KIG15607.1
KIH01698.1
KIH04248.1
KIH77871.1

TABLE 7-continued

Representative Examples of Arginine Decarboxylase by EMBL/GENBANK/DDBJ ID Number KIH85503.1
KII76310.1
KIJ73823.1
KIJ80520.1
KIK87497.1
KIL06168.1
KIL10730.1
KIL19543.1
KIL44729.1
KIL47560.1
KIL50316.1
KIM02995.1
KIM08543.1
KIM08702.1
KIM10584.1
KIM13067.1
KIN12773.1
KIO35234.1
KIO44426.1
KIO52490.1
KIO64044.1
KIO64828.1
KIO64880.1
KIO74024.1
KIO75181.1
KIP20469.1
KIP22393.1
KIP30082.1
KIP63626.1
KIP77624.1
KIP86694.1
KIP92292.1
KIP99462.1
KIQ14588.1
KIQ28277.1
KIQ33154.1
KIQ47084.1
KIQ47216.1
KIQ55660.1
KIQ56619.1
KIQ60207.1
KIQ79728.1
KIQ93208.1
KIQ93267.1
KIQ96608.1
KIR02360.1
KIR20554.1
KIR21483.1
KIR22223.1
KIS42545.1
KIS78068.1
KIT53654.1
KIU32905.1
KIU53521.1
KIV63259.1
KIV65004.1
KIV66814.1
KIV70624.1
KIV70876.1
KIX22820.1
KIX48438.1
KIY14042.1
KIY14047.1
KIY40969.1
KIZ15345.1
KIZ36062.1
KIZ50625.1
KJC02191.1
KJC03662.1
KJC05650.1
KJC06414.1
KJC11070.1
KJD22009.1
KJD31599.1
KJD36996.1
KJE41320.1
KJE51611.1

TABLE 7-continued

Representative Examples of Arginine Decarboxylase
by EMBL/GENBANK/DDBJ ID Number

| |
|---|
| KJF82239.1 |
| KJF92896.1 |
| KJF94545.1 |
| KJF95976.1 |
| KJF96788.1 |
| KJF97649.1 |
| KJF99814.1 |
| KJG15312.1 |
| KJG17565.1 |
| KJG26623.1 |
| KJG26708.1 |
| KJG34980.1 |
| KJG38239.1 |
| KJG40540.1 |
| KJG52887.1 |
| KJG53015.1 |
| KJG53489.1 |
| KJG56948.1 |
| KJH06976.1 |
| KJH08954.1 |
| KJH71848.1 |
| KJH75936.1 |
| KJH77340.1 |
| KJH83755.1 |
| KJH88029.1 |
| KJJ39829.1 |
| KJJ74678.1 |
| KJJ86656.1 |
| KJJ97023.1 |
| KJK09157.1 |
| KJK17930.1 |
| KJK39268.1 |
| KJL17379.1 |
| KJL19924.1 |
| KJL32283.1 |
| KJL32721.1 |
| KJL47944.1 |
| KJM40294.1 |
| KJM94811.1 |
| KJN20030.1 |
| KJR24918.1 |
| KJS62014.1 |
| KJU76259.1 |
| KJV08099.1 |
| KJV28421.1 |
| KJV33512.1 |
| KJV50178.1 |
| KJW32727.1 |
| KJW37560.1 |
| KJW52381.1 |
| KJW52975.1 |
| KJX12328.1 |
| KJX37016.1 |
| KJY36082.1 |
| KJY40855.1 |
| KJY40903.1 |
| KJY81951.1 |
| KJY87010.1 |
| KJY91596.1 |
| KJY96966.1 |
| KJZ05971.1 |
| KJZ06664.1 |
| KJZ14999.1 |
| KJZ15059.1 |
| KJZ18625.1 |
| KJZ33665.1 |
| KJZ36032.1 |
| KJZ46139.1 |
| KJZ47590.1 |
| KJZ49128.1 |
| KJZ60809.1 |
| KJZ64968.1 |
| KJZ83739.1 |
| KJZ85288.1 |
| KKA06404.1 |
| KKA09841.1 |
| KKA50887.1 |
| KKA53937.1 |
| KKB03410.1 |
| KKC56343.1 |
| KKC64605.1 |
| KKC65426.1 |
| KKC79309.1 |
| KKD31624.1 |
| KKD58709.1 |
| KKD62046.1 |
| KKE81684.1 |
| KKF37789.1 |
| KKI42107.1 |
| KKI44372.1 |
| KKI47461.1 |
| KKI52239.1 |
| KKJ26482.1 |
| KKJ98306.1 |
| KKK99989.1 |
| KKO13447.1 |
| KKO45109.1 |
| KKO48310.1 |
| KKO64897.1 |
| KKO88680.1 |
| KKP30172.1 |
| KKP36843.1 |
| KKP40578.1 |
| KKP72963.1 |
| KKP75581.1 |
| KKP88656.1 |
| KKP98423.1 |
| KKQ21504.1 |
| KKQ47851.1 |
| KKQ55697.1 |
| KKR39473.1 |
| KKR41999.1 |
| KKR62922.1 |
| KKR69783.1 |
| KKS05164.1 |
| KKS12144.1 |
| KKS23019.1 |
| KKS72573.1 |
| KKS83788.1 |
| KKT00885.1 |
| KKT03015.1 |
| KKT10692.1 |
| KKT19966.1 |
| KKT24904.1 |
| KKU39856.1 |
| KKU48195.1 |
| KKU49767.1 |
| KKU75779.1 |
| KKU87068.1 |
| KKW45691.1 |
| KKW50514.1 |
| KKX49557.1 |
| KKX58062.1 |
| KKX63732.1 |
| KKX66458.1 |
| KKY43327.1 |
| KKY43878.1 |
| KKY65107.1 |
| KKY79845.1 |
| KKZ13187.1 |
| KKZ18899.1 |
| KKZ98376.1 |
| KKZ99926.1 |
| KLA23800.1 |
| KLA25117.1 |
| KLA31027.1 |
| KLA31452.1 |
| KLA96304.1 |
| KLA99369.1 |
| KLB01232.1 |
| KLB11267.1 |
| KLB14716.1 |
| KLB22478.1 |
| KLB23603.1 |

TABLE 7-continued

Representative Examples of Arginine Decarboxylase
by EMBL/GENBANK/DDBJ ID Number

| |
|---|
| KLB27709.1 |
| KLB31750.1 |
| KLB41291.1 |
| KLC01821.1 |
| KLC03447.1 |
| KLC04907.1 |
| KLC18880.1 |
| KLC19575.1 |
| KLC24598.1 |
| KLC34817.1 |
| KLC35928.1 |
| KLC38727.1 |
| KLC42228.1 |
| KLC42317.1 |
| KLC49000.1 |
| KLC54631.1 |
| KLC62972.1 |
| KLC63061.1 |
| KLC63907.1 |
| KLC72357.1 |
| KLC80920.1 |
| KLC81056.1 |
| KLC86009.1 |
| KLC90423.1 |
| KLC94053.1 |
| KLC98220.1 |
| KLD01509.1 |
| KLD01730.1 |
| KLD13508.1 |
| KLD20683.1 |
| KLD21311.1 |
| KLD25825.1 |
| KLD31524.1 |
| KLD34072.1 |
| KLD38665.1 |
| KLD63515.1 |
| KLD63554.1 |
| KLD66193.1 |
| KLD71246.1 |
| KLD80177.1 |
| KLE01246.1 |
| KLE03460.1 |
| KLE09177.1 |
| KLE26682.1 |
| KLI68356.1 |
| KLI99305.1 |
| KLJ14455.1 |
| KLN47468.1 |
| KLN96569.1 |
| KLQ26951.1 |
| KLQ27291.1 |
| KLS52971.1 |
| KLT65350.1 |
| KLT70448.1 |
| KLT72986.1 |
| KLU04484.1 |
| KLU62082.1 |
| KLU63827.1 |
| KLU67158.1 |
| KLU99121.1 |
| KLV00218.1 |
| KLV01109.1 |
| KLV04650.1 |
| KLV04732.1 |
| KLV10775.1 |
| KLV43183.1 |
| KLV47021.1 |
| KLV65167.1 |
| KLV65610.1 |
| KLV87502.1 |
| KLW86530.1 |
| KLX50943.1 |
| KLX57834.1 |
| KLX90366.1 |
| KLX95655.1 |
| KLY12052.1 |
| KLY34066.1 |
| KME68569.1 |
| KMI32840.1 |
| KMJ44158.1 |
| KMJ45198.1 |
| KMJ53196.1 |
| KMK12312.1 |
| KMK12388.1 |
| KMK65741.1 |
| KML20789.1 |
| KML20912.1 |
| KML48083.1 |
| KML65003.1 |
| KMM17341.1 |
| KMM40283.1 |
| KMM44209.1 |
| KMM74668.1 |
| KMM79436.1 |
| KMM83437.1 |
| KMM87484.1 |
| KMM91807.1 |
| KMM98149.1 |
| KMN11315.1 |
| KMN13443.1 |
| KMN18851.1 |
| KMN35621.1 |
| KMN52211.1 |
| KMN58862.1 |
| KMN64506.1 |
| KMN81232.1 |
| KMN92035.1 |
| KMO78898.1 |
| KMO80014.1 |
| KMP13875.1 |
| KMP92251.1 |
| KMQ23559.1 |
| KMQ62276.1 |
| KMQ65521.1 |
| KMQ67933.1 |
| KMQ72280.1 |
| KMQ73391.1 |
| KMQ80007.1 |
| KMS77340.1 |
| KMS90246.1 |
| KMT22151.1 |
| KMT22950.1 |
| KMT55834.1 |
| KMT66157.1 |
| KMT67645.1 |
| KMT68464.1 |
| KMU66082.1 |
| KMV32029.1 |
| KMV34547.1 |
| KMV67940.1 |
| KMV68973.1 |
| KMV72040.1 |
| KMW72260.1 |
| KMW73819.1 |
| KMW79566.1 |
| KMY85028.1 |
| KMZ12404.1 |
| KMZ45161.1 |
| KMZ45733.1 |
| KMZ47283.1 |
| KMZ48992.1 |
| KMZ49221.1 |
| KNA43180.1 |
| KNA60505.1 |
| KNB61204.1 |
| KNC06722.1 |
| KNC12046.1 |
| KNC16749.1 |
| KNC68501.1 |
| KNC94639.1 |
| KND51979.1 |
| KND54388.1 |
| KND59806.1 |
| KNE03726.1 |

TABLE 7-continued

Representative Examples of Arginine Decarboxylase by EMBL/GENBANK/DDBJ ID Number

| |
|---|
| KNE05809.1 |
| KNE07439.1 |
| KNE07808.1 |
| KNE08827.1 |
| KNE10687.1 |
| KNE13318.1 |
| KNE14112.1 |
| KNE16939.1 |
| KNE17736.1 |
| KNE24464.1 |
| KNE76189.1 |
| KNF09795.1 |
| KNF09831.1 |
| KNF69262.1 |
| KNF70644.1 |
| KNF79445.1 |
| KNF81883.1 |
| KNH02424.1 |
| KNH10085.1 |
| KNH14365.1 |
| KNH26156.1 |
| KNH46145.1 |
| KNN84556.1 |
| KNN85899.1 |
| KNW70656.1 |
| KNW74427.1 |
| KNX43865.1 |
| KNX46584.1 |
| KNX47560.1 |
| KNX49078.1 |
| KNX80210.1 |
| KNX94009.1 |
| KNY27166.1 |
| KNY27231.1 |
| KNY29154.1 |
| KNY73335.1 |
| KNY78421.1 |
| KNZ84104.1 |
| KNZ85960.1 |
| KNZ96652.1 |
| KNZ97917.1 |
| KOA18143.1 |
| KOA19093.1 |
| KOA27317.1 |
| KOA35716.1 |
| KOA70224.1 |
| KOB20841.1 |
| KOC89710.1 |
| KOC93511.1 |
| KOE81619.1 |
| KOE86500.1 |
| KOE98088.1 |
| KOF02803.1 |
| KOG62614.1 |
| KOH46400.1 |
| KOO07593.1 |
| KOO13952.1 |
| KOO59694.1 |
| KOO65836.1 |
| KOO83034.1 |
| KOP01917.1 |
| KOP04218.1 |
| KOP26957.1 |
| KOP33536.1 |
| KOP34817.1 |
| KOP36989.1 |
| KOP96620.1 |
| KOQ72056.1 |
| KOQ79259.1 |
| KOR18913.1 |
| KOR38747.1 |
| KOR43231.1 |
| KOR44320.1 |
| KOR71845.1 |
| KOS05070.1 |
| KOS31558.1 |
| KOS31918.1 |
| KOS33911.1 |
| KOU24174.1 |
| KOU67934.1 |
| KOV81195.1 |
| KOV90464.1 |
| KOV92694.1 |
| KOX28823.1 |
| KOX89259.1 |
| KOY02434.1 |
| KOY04397.1 |
| KOY33063.1 |
| KOY42334.1 |
| KOY42343.1 |
| KOY45863.1 |
| KOY50204.1 |
| KOY52585.1 |
| KOY61140.1 |
| KOY61821.1 |
| KOY85392.1 |
| KPA10472.1 |
| KPA52388.1 |
| KPA53393.1 |
| KPA53642.1 |
| KPA88888.1 |
| KPA90439.1 |
| KPA92636.1 |
| KPB67773.1 |
| KPB69211.1 |
| KPB79158.1 |
| KPB81326.1 |
| KPC07003.1 |
| KPC14008.1 |
| KPC35485.1 |
| KPC49975.1 |
| KPC57075.1 |
| KPC99496.1 |
| KPD01309.1 |
| KPD03211.1 |
| KPD11155.1 |
| KPD20872.1 |
| KPD32893.1 |
| KPE49813.1 |
| KPG83065.1 |
| KPG95064.1 |
| KPG99865.1 |
| KPH01642.1 |
| KPH13642.1 |
| KPH55638.1 |
| KPH58606.1 |
| KPH60167.1 |
| KPI00128.1 |
| KPI21829.1 |
| KPI28804.1 |
| KPL49155.1 |
| KPL85176.1 |
| KPL99048.1 |
| KPM32213.1 |
| KPM49141.1 |
| KPM63679.1 |
| KPM65064.1 |
| KPM81369.1 |
| KPM81389.1 |
| KPM84874.1 |
| KPM96730.1 |
| KPN17561.1 |
| KPN64870.1 |
| KPN71852.1 |
| KPN73933.1 |
| KPN76064.1 |
| KPN88872.1 |
| KPN90573.1 |
| KPN90601.1 |
| KPO18579.1 |
| KPO32516.1 |
| KPO36865.1 |
| KPO46576.1 |
| KPO56914.1 |

TABLE 7-continued

Representative Examples of Arginine Decarboxylase by EMBL/GENBANK/DDBJ ID Number KPP89788.1
KPP99272.1
KPQ04554.1
KPQ14293.1
KPQ25476.1
KPQ26228.1
KPQ27964.1
KPQ28712.1
KPQ35007.1
KPQ40221.1
KPQ42687.1
KPR47334.1
KPR54754.1
KPR57621.1
KPU43059.1
KPU45374.1
KPU53302.1
KPU59624.1
KPV48774.1
KPW00046.1
KPW04292.1
KPW13659.1
KPW16726.1
KPW17184.1
KPW23692.1
KPW27562.1
KPW34805.1
KPW42050.1
KPW48373.1
KPW51442.1
KPW62237.1
KPW62967.1
KPW66391.1
KPW77493.1
KPW79725.1
KPW85370.1
KPW97437.1
KPX00575.1
KPX06301.1
KPX09224.1
KPX14980.1
KPX22033.1
KPX30196.1
KPX31760.1
KPX38634.1
KPX43708.1
KPX44429.1
KPX56237.1
KPX65518.1
KPX66339.1
KPX73444.1
KPX75665.1
KPX84858.1
KPX85936.1
KPX98179.1
KPY01178.1
KPY03822.1
KPY16964.1
KPY20911.1
KPY29392.1
KPY38577.1
KPY41782.1
KPY47144.1
KPY54488.1
KPY56327.1
KPY64080.1
KPY70158.1
KPY74009.1
KPY80616.1
KPY90395.1
KPY92798.1
KPY99398.1
KPZ05993.1
KPZ14794.1
KPZ14841.1
KPZ23429.1
KPZ24832.1
KPZ30414.1
KPZ42886.1
KPZ47275.1
KPZ49946.1
KPZ52051.1
KPZ54935.1
KPZ63333.1
KPZ63441.1
KPZ64594.1
KPZ67736.1
KPZ72598.1
KPZ74870.1
KQA98214.1
KQB40657.1
KQB42336.1
KQB52498.1
KQB89823.1
KQB94067.1
KQJ13933.1
KQJ19480.1
KQJ38967.1
KQJ46044.1
KRG50855.1
KRV51537.1
KRV54923.1
KSG98439.1
KST27457.1
KST30748.1
KSX90037.1
KSX90873.1
KSZ13905.1
KTH73164.1
KTI23271.1
KTM92464.1
KTP62443.1
KUG62774.1
KUH45679.1
KUQ52564.1
KUR40671.1
KUU48152.1
KWS16060.1
KWS38521.1
KWS79043.1
KWV37200.1
KWV39942.1
KWX82425.1
KWZ89005.1
KXA39294.1
KXG92416.1
KXG97350.1
KXH00368.1
KXH98343.1
KXI03206.1
KXL66971.1
KXQ41321.1
KXQ42780.1
KXY17951.1
KXY86957.1
KYR44969.1
KYR45993.1
KYS91454.1
KYS97775.1
KYV67950.1
KYV73707.1
KZD84079.1
KZD88271.1
KZE54774.1
KZJ50109.1
KZJ59532.1
OAC39173.1
OAC43114.1
OAE94114.1
OAH32121.1
OAI64384.1
OAJ86653.1
OAJ87922.1
OAN24058.1

TABLE 7-continued

Representative Examples of Arginine Decarboxylase by EMBL/GENBANK/DDBJ ID Number OAO68286.1
OAO72924.1
OBS13167.1
OCL17286.1
OCQ74268.1
OCS74958.1
OCS76529.1
OCS95943.1
OCS96129.1
OCV53558.1
OCV69154.1
OCW73841.1
OCX56897.1
ODH24470.1
ODJ92889.1
ODN20234.1
ODR86790.1
OEB17588.1
OEC25471.1
OEH12480.1
OEH95894.1
OEI62511.1
OEI65537.1
OEN36599.1
OFJ25861.1
OIN26436.1
OIN31202.1
SAD71382.1
SAE32738.1
SAY76613.1
SBX90614.1
SBZ90867.1

Representative examples of agmatinase (EC 3.5.3.11) are given below in Table 8 and identified by their EMBL/GENBANK/DDBJ ID numbers. Any of the bacteria given in Table 10 can be engineered with any version of the agmatinase (EC 3.5.3.11) set forth in Table 3 and Table 8. For instance, the bacteria can be engineered with a version of the agmatinase enzyme that has at least 50% nucleotide similarity with any of the versions of agmatinase given in Table 8 (e.g., at least nucleotide 60% similarity, at least 70% nucleotide similarity, at least 80% nucleotide similarity, at least 90% nucleotide similarity, at least 91% nucleotide similarity, at least 92% nucleotide similarity, at least 93% nucleotide similarity, at least 94% nucleotide similarity, at least 95% nucleotide similarity, at least 96% nucleotide similarity, at least 97% nucleotide similarity, at least 98% nucleotide similarity, at least 99% nucleotide similarity, at least 99.5% nucleotide similarity, at least 99.9% nucleotide similarity, or 100% nucleotide similarity).

TABLE 8

Representative Examples of Agmatinase by EMBL/GENBANK/DDBJ ID Number

AAA24647.1
AAA69104.1
AAA83909.1
AAB98295.1
AAC75974.1
AAF40906.1
AAG58067.1
AAK40769.1
AAK42842.1
AAL21953.1
AAL51292.1
AAL52351.1
AAM30619.1
AAN44408.1

TABLE 8-continued

Representative Examples of Agmatinase by EMBL/GENBANK/DDBJ ID Number

AAN67809.1
AAN81970.1
AAO70550.1
AAO90262.1
AAP12232.1
AAP18231.1
AAP29255.1
AAQ00893.1
AAQ58167.1
AAQ87313.1
AAQ87384.1
AAT34764.1
AAT57507.1
AAT63474.1
AAU15214.1
AAU45759.1
AAV44785.1
AAV46799.1
AAV78787.1
AAV93914.1
AAV95718.1
AAV95721.1
AAV97369.1
AAW87909.1
AAW90124.1
AAX66926.1
AAY90871.2
AAZ22133.1
AAZ24263.1
AAZ54096.1
AAZ58777.1
AAZ65050.1
AAZ69672.1
AAZ89678.1
ABA19753.1
ABA52140.1
ABA53789.1
ABA73200.1
ABA74317.1
ABA79070.1
ABA81349.1
ABB07975.1
ABB10482.1
ABB11261.1
ABB12898.1
ABB27188.1
ABB37375.1
ABB50840.1
ABB63153.1
ABB67558.1
ABC20115.1
ABC35193.1
ABC36254.1
ABC90370.1
ABC90927.1
ABC99063.1
ABD02701.1
ABD10232.1
ABD53194.1
ABD54884.1
ABD55257.1
ABD68100.1
ABD68348.1
ABE08773.1
ABE29546.1
ABE35008.1
ABE43955.1
ABE52778.1
ABE55558.1
ABE60184.1
ABE75327.1
ABF05058.1
ABF41119.1
ABF53436.1
ABF63671.1
ABF63672.1
ABF77979.1

TABLE 8-continued

Representative Examples of Agmatinase
by EMBL/GENBANK/DDBJ ID Number

| |
|---|
| ABF78588.1 |
| ABG05817.1 |
| ABG32253.1 |
| ABG32638.1 |
| ABG32639.1 |
| ABG62558.1 |
| ABG70915.1 |
| ABG82607.1 |
| ABG87141.1 |
| ABI47535.1 |
| ABI59683.1 |
| ABI60409.1 |
| ABI67996.1 |
| ABI89619.1 |
| ABI90194.1 |
| ABJ02365.1 |
| ABK02249.1 |
| ABK16419.1 |
| ABK71425.1 |
| ABK71845.1 |
| ABK73126.1 |
| ABK75016.1 |
| ABK78003.1 |
| ABK88044.1 |
| ABL69259.1 |
| ABL73176.1 |
| ABL77915.1 |
| ABL82726.1 |
| ABL82883.1 |
| ABL88073.1 |
| ABL91072.1 |
| ABL91501.1 |
| ABL91972.1 |
| ABL92277.1 |
| ABM02702.1 |
| ABM10897.1 |
| ABM11012.1 |
| ABM11652.1 |
| ABM13827.1 |
| ABM29529.1 |
| ABM37937.1 |
| ABM56124.1 |
| ABM71179.1 |
| ABM73084.1 |
| ABM76715.1 |
| ABM79681.1 |
| ABM79929.1 |
| ABM94848.1 |
| ABM98665.2 |
| ABN06601.1 |
| ABN56898.1 |
| ABN70230.1 |
| ABN76664.1 |
| ABN78567.1 |
| ABN87189.1 |
| ABN87725.1 |
| ABN92921.1 |
| ABN92962.1 |
| ABO09043.1 |
| ABO18500.1 |
| ABO23488.1 |
| ABO36121.1 |
| ABO49035.1 |
| ABO56523.1 |
| ABO58149.1 |
| ABP42590.1 |
| ABP43281.1 |
| ABP45780.1 |
| ABP51374.1 |
| ABP62005.1 |
| ABP70012.1 |
| ABP86798.1 |
| ABP94673.1 |
| ABP96350.1 |
| ABQ18665.1 |
| ABQ26532.1 |
| ABQ31960.1 |
| ABQ33008.1 |
| ABQ60179.1 |
| ABQ77546.1 |
| ABQ79666.1 |
| ABQ87081.1 |
| ABQ91371.1 |
| ABR78770.1 |
| ABR81216.1 |
| ABR81751.1 |
| ABS77512.1 |
| ABU75701.1 |
| ABV07331.1 |
| ABV15371.1 |
| ABV21194.1 |
| ABV43067.1 |
| ABV51572.1 |
| ABV67817.1 |
| ABV93477.1 |
| ABX09748.1 |
| ABX69169.1 |
| ABX74248.1 |
| ABX81911.1 |
| ABY21971.1 |
| ACA38569.1 |
| ACA76446.1 |
| ACB04033.1 |
| ACB18855.1 |
| ACC84325.1 |
| ACD06722.1 |
| ACD24294.1 |
| ACE90614.1 |
| ACE91158.1 |
| ACE94809.1 |
| ACF30403.1 |
| ACF61915.1 |
| ACF67727.1 |
| ACF91868.1 |
| ACH50852.1 |
| ACH63482.1 |
| ACH77920.1 |
| ACI10057.1 |
| ACI11642.1 |
| ACI18698.1 |
| ACI35219.1 |
| ACI78406.1 |
| ACI78407.1 |
| ACI78408.1 |
| ACI78409.1 |
| ACI78410.1 |
| ACJ29740.1 |
| ACK73593.1 |
| ACM05018.1 |
| ACM06157.1 |
| ACN13261.1 |
| ACN47228.1 |
| ACO74132.1 |
| ACP07733.1 |
| ACP21851.1 |
| ACP21922.1 |
| ACP26294.1 |
| ACP35785.1 |
| ACP36686.1 |
| ACR61943.1 |
| ACR70510.1 |
| ACS32933.1 |
| ACS41939.1 |
| ACS89313.1 |
| ACU08695.1 |
| ACV76715.1 |
| ACV81107.1 |
| ACY53515.1 |
| ACY85795.1 |
| ACY90127.1 |
| ACZ87232.1 |
| ADA75255.1 |
| ADB74457.1 |
| ADC90860.1 |

TABLE 8-continued

Representative Examples of Agmatinase
by EMBL/GENBANK/DDBJ ID Number

| |
|---|
| ADD45355.1 |
| ADD58091.1 |
| ADD78375.1 |
| ADE04586.1 |
| ADE37357.1 |
| ADE39009.1 |
| ADE40257.1 |
| ADE40278.1 |
| ADE67897.1 |
| ADE69284.1 |
| ADE72169.1 |
| ADE85469.1 |
| ADE86001.1 |
| ADF37727.1 |
| ADF39062.1 |
| ADF41976.1 |
| ADF63800.1 |
| ADG91441.1 |
| ADG91991.1 |
| ADI14533.1 |
| ADJ63231.1 |
| ADK07910.1 |
| ADL07911.1 |
| ADL18546.1 |
| ADL44534.1 |
| ADM42794.1 |
| ADN75943.1 |
| ADO10712.1 |
| ADO30990.1 |
| ADO47092.1 |
| ADP11446.1 |
| ADP83855.1 |
| ADQ66311.1 |
| ADR28296.1 |
| ADT68876.1 |
| ADT70429.1 |
| ADT76571.1 |
| ADT96768.1 |
| ADT97392.1 |
| ADT99263.1 |
| ADU52417.1 |
| ADU70503.1 |
| ADV49134.1 |
| ADV64546.1 |
| ADV66173.1 |
| ADX18864.1 |
| ADX72077.1 |
| ADY13321.1 |
| ADY27253.1 |
| ADY29885.1 |
| ADY33548.1 |
| ADY55312.1 |
| ADY72884.1 |
| ADZ04172.1 |
| ADZ08379.1 |
| ADZ10562.1 |
| ADZ27749.1 |
| ADZ83109.1 |
| ADZ91927.1 |
| AEA33345.1 |
| AEA45611.1 |
| AEA47221.1 |
| AEA80791.1 |
| AEA80792.1 |
| AEB08603.1 |
| AEB10992.1 |
| AEB12421.1 |
| AEC00219.1 |
| AEE58170.1 |
| AEE96159.1 |
| AEF17260.1 |
| AEF54342.1 |
| AEF88522.1 |
| AEF93913.1 |
| AEF93919.1 |
| AEF95254.1 |
| AEF97223.1 |
| AEG03799.1 |
| AEG05228.1 |
| AEG14656.1 |
| AEG17355.1 |
| AEG33547.1 |
| AEG44996.1 |
| AEG44997.1 |
| AEG95549.1 |
| AEH00503.1 |
| AEH06103.1 |
| AEH08712.1 |
| AEH11147.1 |
| AEH22925.1 |
| AEH36766.1 |
| AEH48221.1 |
| AEH49662.1 |
| AEH50623.1 |
| AEI14843.1 |
| AEI94329.1 |
| AEI94330.1 |
| AEJ58268.1 |
| AEK22524.1 |
| AEK23614.1 |
| AEK61616.1 |
| AEK64195.1 |
| AEM40724.1 |
| AEM58024.1 |
| AEM69220.1 |
| AEN05459.1 |
| AEN05763.1 |
| AEN06930.1 |
| AEN66324.1 |
| AEP88702.1 |
| AEQ14108.1 |
| AER31406.1 |
| AEV37646.1 |
| AEV38161.1 |
| AEV61529.1 |
| AEV87262.1 |
| AEV97888.1 |
| AEW04403.1 |
| AEW06905.1 |
| AEW63139.1 |
| AEW75167.1 |
| AEX02267.1 |
| AEX23687.1 |
| AFA38334.1 |
| AFA38752.1 |
| AFA47334.1 |
| AFC24160.1 |
| AFD00687.1 |
| AFG41863.1 |
| AFI84427.1 |
| AFJ01337.1 |
| AFJ30619.1 |
| AFJ45705.1 |
| AFJ59747.1 |
| AFJ63961.1 |
| AFK19996.1 |
| AFL51309.1 |
| AFL51840.1 |
| AFM19977.1 |
| AFM61483.1 |
| AFO87859.1 |
| AFO87860.1 |
| AFO91682.1 |
| AFO91683.1 |
| AFP37519.1 |
| AFP39918.1 |
| AFP40726.1 |
| AFP40804.1 |
| AFQ48622.1 |
| AFQ49589.1 |
| AFQ50194.1 |
| AFQ51687.1 |
| AFR09275.1 |
| AFS72872.1 |

TABLE 8-continued

Representative Examples of Agmatinase
by EMBL/GENBANK/DDBJ ID Number

| |
|---|
| AFS77227.1 |
| AFV11211.1 |
| AFY19072.1 |
| AFY19668.1 |
| AFY21148.1 |
| AFY36898.1 |
| AFY39232.1 |
| AFY40247.1 |
| AFY66803.1 |
| AFY87223.1 |
| AFZ10381.1 |
| AFZ31237.1 |
| AFZ34586.1 |
| AFZ37423.1 |
| AFZ44104.1 |
| AFZ47238.1 |
| AFZ54331.1 |
| AFZ55267.1 |
| AGA67678.1 |
| AGA72691.1 |
| AGB21222.1 |
| AGB76811.1 |
| AGB83895.1 |
| AGC68778.1 |
| AGC77085.1 |
| AGD97972.1 |
| AGE22498.1 |
| AGE23989.1 |
| AGG04209.1 |
| AGG32138.1 |
| AGG73823.1 |
| AGG75093.1 |
| AGH87553.1 |
| AGI26201.1 |
| AGI47257.1 |
| AGI68304.1 |
| AGI68305.1 |
| AGI72348.1 |
| AGI72349.1 |
| AGI84982.1 |
| AGJ55062.1 |
| AGJ58747.1 |
| AGJ59299.1 |
| AGK77294.1 |
| AGN38302.1 |
| AGO56878.1 |
| AGP45918.1 |
| AGQ74348.1 |
| AGQ92958.1 |
| AGR60291.1 |
| AGR77854.1 |
| AGS21412.1 |
| AGS21940.1 |
| AGS26045.1 |
| AGS39313.1 |
| AGT07309.1 |
| AGT11108.1 |
| AGX41862.1 |
| AGY56862.1 |
| AGZ34567.1 |
| AHA67015.1 |
| AHB69078.1 |
| ARC15724.1 |
| AHD07591.1 |
| AHD07965.1 |
| AHD07966.1 |
| AHD09199.1 |
| AHD09200.1 |
| AHE60912.1 |
| AHE69335.1 |
| AHF69002.1 |
| AHF73775.1 |
| AHF75853.1 |
| AHG19398.1 |
| AHK01119.1 |
| AHK03741.1 |
| AHM05195.1 |

TABLE 8-continued

Representative Examples of Agmatinase
by EMBL/GENBANK/DDBJ ID Number

| |
|---|
| AHM05332.1 |
| AHM57412.1 |
| AHM77673.1 |
| AHM83265.1 |
| AHN81844.1 |
| AHW76535.1 |
| AHY10272.1 |
| AHY72292.1 |
| AHZ23375.1 |
| AIA74065.1 |
| AIC26759.1 |
| AIC27350.1 |
| AID41526.1 |
| AID92226.1 |
| AIE61595.1 |
| AIE72946.1 |
| AIE75743.1 |
| AIE81817.1 |
| AIF82761.1 |
| AIF84264.1 |
| AIF84945.1 |
| AIG28743.1 |
| AIG32998.1 |
| AIG35154.1 |
| AIG39783.1 |
| AIG97525.1 |
| AII87322.1 |
| AII87324.1 |
| AIJ07652.1 |
| AIJ37317.1 |
| AIK37348.1 |
| AIK38502.1 |
| AIM26660.1 |
| AIM28333.1 |
| AIO30916.1 |
| AIO31498.1 |
| AIO35681.1 |
| AIO35975.1 |
| AIO36489.1 |
| AIO44724.1 |
| AIO46049.1 |
| AIO46224.1 |
| AIO49720.1 |
| AIO70072.1 |
| AIO70112.1 |
| AIO82805.1 |
| AIO84618.1 |
| AIP28881.1 |
| AIP29149.1 |
| AIP96985.1 |
| AIQ96062.1 |
| AIQ98336.1 |
| AIR06031.1 |
| AIR59440.1 |
| AIS52428.1 |
| AIU71687.1 |
| AIW15709.1 |
| AIW78498.1 |
| AIX49199.1 |
| AIX64797.1 |
| AIX72614.1 |
| AIY06411.1 |
| AIY17255.1 |
| AIY19826.2 |
| AIY19931.2 |
| AIY44086.1 |
| AIY47278.1 |
| AIY65960.1 |
| AIZ56989.1 |
| AIZ83993.1 |
| AJA15226.1 |
| AJA27931.1 |
| AJA92009.1 |
| AJC63708.1 |
| AJC78797.1 |
| AJC79353.1 |
| AJD40791.1 |

TABLE 8-continued

Representative Examples of Agmatinase by EMBL/GENBANK/DDBJ ID Number

AJD44781.1
AJD44817.1
AJD52273.1
AJD92404.1
AJE47384.1
AJE57484.1
AJF57741.1
AJF74876.1
AJG14739.1
AJG17918.1
AJG79170.1
AJG94738.1
AJH06394.1
AJH17306.1
AJH80029.1
AJI07021.1
AJI11177.1
AJI18362.1
AJI19711.1
AJI21563.1
AJI23861.1
AJI24944.1
AJK42294.1
AJK48584.1
AJO84924.1
AJQ48197.1
AJW70766.1
AJX73400.1
AJX73637.1
AJY10662.1
AJY38564.1
AJY39189.1
AJY39634.1
AJY49045.1
AJY49192.1
AJY49305.1
AJZ58787.1
AJZ61461.1
AJZ62973.1
AJZ91146.1
AKA25996.1
AKA85572.1
AKB13293.1
AKB16072.1
AKB17277.1
AKB20676.1
AKB23916.1
AKB30046.1
AKB33946.1
AKB38310.1
AKB39394.1
AKB45534.1
AKB49003.1
AKB49561.1
AKB56266.1
AKB59739.1
AKB60366.1
AKB63578.1
AKB66937.1
AKB70291.1
AKB73823.1
AKB76958.1
AKB83790.1
AKB84178.1
AKD38344.1
AKE61765.1
AKE63966.1
AKE65066.1
AKE94626.1
AKG68119.1
AKG91930.1
AKH08717.1
AKH23614.1
AKH64397.1
AKH98312.1
AKH99850.1
AKI01044.1

AKJ41197.1
AKJ64711.1
AKK49720.1
AKL10486.1
AKL34469.1
AKL94121.1
AKM00856.1
AKM03663.1
AKM20612.1
AKM36435.1
AKM38930.1
AKM44683.1
AKM92040.1
AKO77002.1
AKO96563.1
AKO98269.1
AKP48868.1
AKP80163.1
AKV73628.1
AKV75131.1
AKV75868.1
AKV77369.1
AKV78118.1
AKV79620.1
AKV80363.1
AKV81865.1
AKV82611.1
AKV84100.1
ALD23757.1
ALG82706.1
ALL39774.1
ALV77276.1
ALV81183.1
ALY14440.1
ALZ68232.1
AMJ69304.1
AMW42737.1
AMX08364.1
AMX14485.1
ANC16538.1
ANC22333.1
ANM83716.1
ANO90761.1
ANP19756.1
ANZ85663.1
AOM43881.1
AOM71329.1
AOT31398.1
APA40676.1
BAA16710.1
BAA17298.1
BAA80638.2
BAB07529.1
BAB37235.1
BAB51449.1
BAB65332.1
BAC14507.1
BAD63716.1
BAD66428.1
BAD77689.1
BAD85071.1
BAE75292.1
BAE77000.1
BAG30482.1
BAG45193.1
BAG46924.1
BAG78729.1
BAH31284.1
BAH46484.1
BAH50915.1
BAH51568.1
BAI27220.1
BAI32251.1
BAI37474.1
BAI75018.1
BAI75040.1
BAI75047.1

TABLE 8-continued

Representative Examples of Agmatinase
by EMBL/GENBANK/DDBJ ID Number

| |
|---|
| BAI80439.1 |
| BAJ82447.1 |
| BAK12515.1 |
| BAK34589.1 |
| BAK98432.1 |
| BAK98465.1 |
| BAL95958.1 |
| BAN02875.1 |
| BAN46237.1 |
| BAN54991.1 |
| BAN90497.1 |
| BAU72144.1 |
| BAU75360.1 |
| BAU76701.1 |
| CAB02517.1 |
| CAB15776.1 |
| CAC45820.1 |
| CAC47080.1 |
| CAD02910.1 |
| CAD18729.1 |
| CAD83324.1 |
| CAD85058.1 |
| CAE07927.1 |
| CAE08937.1 |
| CAE16053.1 |
| CAE20145.1 |
| CAE22388.1 |
| CAE33200.1 |
| CAE38071.1 |
| CAE78008.1 |
| CAE78232.1 |
| CAF31141.1 |
| CAH37930.1 |
| CAH39062.1 |
| CAI86151.1 |
| CAI89357.1 |
| CAJ10765.1 |
| CAJ11914.1 |
| CAJ35086.1 |
| CAJ53446.1 |
| CAJ67724.1 |
| CAK07164.1 |
| CAK09940.1 |
| CAK10592.1 |
| CAK16253.1 |
| CAK16639.1 |
| CAK24880.1 |
| CAK29338.1 |
| CAK29381.1 |
| CAL44270.1 |
| CAL68562.1 |
| CAL80391.1 |
| CAM05191.1 |
| CAM09121.1 |
| CAM10862.1 |
| CAN90200.1 |
| CAN99327.1 |
| CAO97869.1 |
| CAP14282.1 |
| CAQ83181.1 |
| CAQ90364.1 |
| CAQ99884.1 |
| CAR04454.1 |
| CAR09553.2 |
| CAR14451.1 |
| CAR19473.1 |
| CAR34499.1 |
| CAR38778.1 |
| CAR44182.1 |
| CAR51520.1 |
| CAR54274.1 |
| CAR56347.1 |
| CAR60989.1 |
| CAS10737.1 |
| CAU99217.1 |
| CAV18375.1 |
| CAX26528.1 |
| CAX58939.1 |
| CAX61192.1 |
| CAY51214.1 |
| CAY75590.1 |
| CAZ86945.1 |
| CAZ96113.1 |
| CBA07510.1 |
| CBA19557.1 |
| CBA33563.1 |
| CBG91722.1 |
| CBH20171.1 |
| CBI44700.1 |
| CBJ02630.1 |
| CBJ36000.1 |
| CBJ41226.1 |
| CBJ80582.1 |
| CBJ89098.1 |
| CBK43642.1 |
| CBK64440.1 |
| CBK76875.1 |
| CBK99237.1 |
| CBL02267.1 |
| CBL06427.1 |
| CBL17762.1 |
| CBL18586.1 |
| CBL22839.1 |
| CBL25540.1 |
| CBL28295.1 |
| CBL41552.1 |
| CBV41181.1 |
| CBW19153.1 |
| CCB64763.1 |
| CCB65171.1 |
| CCB70695.1 |
| CCB85395.1 |
| CCB88489.1 |
| CCC19821.1 |
| CCC31739.1 |
| CCC41606.1 |
| CCC82222.1 |
| CCD03081.1 |
| CCD03343.1 |
| CCD89954.1 |
| CCD93845.1 |
| CCE01319.1 |
| CCE10074.1 |
| CCE15097.1 |
| CCE17011.1 |
| CCE95457.1 |
| CCE96893.1 |
| CCF18965.1 |
| CCF20747.1 |
| CCG46987.1 |
| CCG52586.1 |
| CCG86053.1 |
| CCH00037.1 |
| CCH71227.1 |
| CCH91980.1 |
| CCH94031.1 |
| CCH97873.1 |
| CCH98110.1 |
| CCH99362.1 |
| CCI04256.1 |
| CCI06792.1 |
| CCI07869.1 |
| CCI14209.1 |
| CCI14551.1 |
| CCI18636.1 |
| CCI20568.1 |
| CCI26509.1 |
| CCI27381.1 |
| CCI27656.1 |
| CCI29463.1 |
| CCI33484.1 |
| CCI33643.1 |
| CCI38967.1 |
| CCI52514.1 |

TABLE 8-continued

Representative Examples of Agmatinase
by EMBL/GENBANK/DDBJ ID Number

| |
|---|
| CCI78869.1 |
| CCJ06579.1 |
| CCJ36819.1 |
| CCJ45540.1 |
| CCJ49843.1 |
| CCJ52441.1 |
| CCJ71907.1 |
| CCJ80970.1 |
| CCJ86076.1 |
| CCJ89760.1 |
| CCJ99407.1 |
| CCK02015.1 |
| CCK08383.1 |
| CCK48226.1 |
| CCK74894.1 |
| CCK78277.1 |
| CCK89717.1 |
| CCK96853.1 |
| CCL00841.1 |
| CCL21005.1 |
| CCL28928.1 |
| CCM75184.1 |
| CCM77037.1 |
| CCM78508.1 |
| CCM79193.1 |
| CCM80257.1 |
| CCO04886.1 |
| CCO05578.1 |
| CCO05593.1 |
| CCO06200.1 |
| CCO08237.1 |
| CCP10570.1 |
| CCQ09657.1 |
| CCQ10974.1 |
| CCQ34449.1 |
| CCQ35689.1 |
| CCQ36200.1 |
| CCQ47332.1 |
| CCQ74550.1 |
| CCQ94339.1 |
| CCQ95023.1 |
| CCQ95940.1 |
| CCV06472.1 |
| CCV13247.1 |
| CCV63725.1 |
| CCV65581.1 |
| CCW06091.1 |
| CCW16005.1 |
| CCW31444.1 |
| CDF80722.1 |
| CDF85323.1 |
| CDF86475.1 |
| CDF92525.1 |
| CDG13942.1 |
| CDG18839.1 |
| CDG20299.1 |
| CDG31563.1 |
| CDG92784.1 |
| CDG98743.1 |
| CDG99622.1 |
| CDH05986.1 |
| CDH21445.1 |
| CDH24733.1 |
| CDH33017.1 |
| CDH74672.1 |
| CDH78253.1 |
| CDI05863.1 |
| CDI08139.1 |
| CDI40700.1 |
| CDK71508.1 |
| CDK72224.1 |
| CDK72597.1 |
| CDK98654.1 |
| CDL10508.1 |
| CDL11618.1 |
| CDL16097.1 |
| CDL17208.1 |

TABLE 8-continued

Representative Examples of Agmatinase
by EMBL/GENBANK/DDBJ ID Number

| |
|---|
| CDL19544.1 |
| CDL23451.1 |
| CDL25123.1 |
| CDL39139.1 |
| CDL46167.1 |
| CDL57556.1 |
| CDL57557.1 |
| CDL58440.1 |
| CDL62829.1 |
| CDL63085.1 |
| CDL79639.1 |
| CDL85576.1 |
| CDM42435.1 |
| CDM57288.1 |
| CDM60749.1 |
| CDM60990.1 |
| CDM66632.1 |
| CDM91301.1 |
| CDN08347.1 |
| CDN42601.1 |
| CDN83560.1 |
| CDN91137.1 |
| CDQ16187.1 |
| CDR93058.1 |
| CDS53731.1 |
| CDS55128.1 |
| CDS59015.1 |
| CDS84404.1 |
| CDS84851.1 |
| CDT66748.1 |
| CDU33788.1 |
| CDU41160.1 |
| CDW92944.1 |
| CDX00216.1 |
| CDX11223.1 |
| CDX16126.1 |
| CDX17209.1 |
| CDX17653.1 |
| CDX18157.1 |
| CDX23096.1 |
| CDX26808.1 |
| CDX28868.1 |
| CDX31490.1 |
| CDX34075.1 |
| CDX36972.1 |
| CDX38569.1 |
| CDX38670.1 |
| CDX49350.1 |
| CDX53768.1 |
| CDX56980.1 |
| CDX58275.1 |
| CDX59705.1 |
| CDX62547.1 |
| CDY73639.1 |
| CDY74077.1 |
| CDY75840.1 |
| CDY77024.1 |
| CDY78583.1 |
| CDZ23447.1 |
| CDZ85765.1 |
| CED57567.1 |
| CEE01721.1 |
| CEF30993.1 |
| CEF31451.1 |
| CEH98691.1 |
| CEI18991.1 |
| CEI51711.1 |
| CEJ65416.1 |
| CEK22007.1 |
| CEK37314.1 |
| CEL88255.1 |
| CEN33873.1 |
| CEN34609.1 |
| CEN35800.1 |
| CEN39832.1 |
| CEN43042.1 |
| CEN51600.1 |

TABLE 8-continued

Representative Examples of Agmatinase
by EMBL/GENBANK/DDBJ ID Number

| |
|---|
| CEN51743.1 |
| CEN53478.1 |
| CEN53480.1 |
| CEN53702.1 |
| CEO41666.1 |
| CEO90406.1 |
| CEP33358.1 |
| CEQ02613.1 |
| CEY70465.1 |
| CFC48269.1 |
| CFT92190.1 |
| CFT96567.1 |
| CJA40003.1 |
| CJC36758.1 |
| CJF84864.1 |
| CJG89416.1 |
| CJI93354.1 |
| CJI95124.1 |
| CJN03702.1 |
| CJN67826.1 |
| COF22522.1 |
| COF38764.1 |
| COI45864.1 |
| COP15970.1 |
| COP30452.1 |
| COP45895.1 |
| COQ71690.1 |
| CPR16225.1 |
| CPR16252.1 |
| CPR21886.1 |
| CPR28567.1 |
| CPR28568.1 |
| CQR76249.1 |
| CRF98508.1 |
| CRH30681.1 |
| CRH35397.1 |
| CRH39702.1 |
| CRH69483.1 |
| CRI55920.1 |
| CRI56443.1 |
| CRL10051.1 |
| CRL61080.1 |
| CRL62208.1 |
| CRL90920.1 |
| CRL92325.1 |
| CRP39759.1 |
| CRP93373.1 |
| CRQ49718.1 |
| CRQ59532.1 |
| CRV25744.1 |
| CSB25877.1 |
| CSB76203.1 |
| CSC35023.1 |
| CSI87493.1 |
| CSK81664.1 |
| CSN19142.1 |
| CSP73809.1 |
| CSS26770.1 |
| CTQ00826.1 |
| CTQ01842.1 |
| CTQ07399.1 |
| CTQ11021.1 |
| CTQ21393.1 |
| CTQ33005.1 |
| CTQ42017.1 |
| CTQ47453.1 |
| CTQ50609.1 |
| CTQ53954.1 |
| CTQ63712.1 |
| CTQ76095.1 |
| CTR88335.1 |
| CTS05166.1 |
| CTS30798.1 |
| CTT77634.1 |
| CTT83409.1 |
| CTT95037.1 |
| CTU43832.1 |
| CTU68877.1 |
| CTV16782.1 |
| CTV23427.1 |
| CTV60644.1 |
| CTW91398.1 |
| CTZ55651.1 |
| CTZ68789.1 |
| CUB11509.1 |
| CUB13588.1 |
| CUB16299.1 |
| CUB23833.1 |
| CUB24713.1 |
| CUB31352.1 |
| CUB37524.1 |
| CUB38342.1 |
| CUB41881.1 |
| CUB48656.1 |
| CUB51818.1 |
| CUB57702.1 |
| CUH40798.1 |
| CUH92888.1 |
| CUJ17376.1 |
| CUJ29157.1 |
| CUJ95397.1 |
| CVA34134.1 |
| CVE90668.1 |
| CVG47751.1 |
| CZX11870.1 |
| CZX80257.1 |
| EAO57065.1 |
| EAP72459.1 |
| EAP93055.1 |
| EAQ63147.1 |
| EAQ97486.1 |
| EAQ99338.2 |
| EAR30280.1 |
| EAR49722.1 |
| EAR53967.1 |
| EAR60303.1 |
| EAS45732.1 |
| EAS66652.1 |
| EAT13839.1 |
| EAU53062.1 |
| EAW26172.1 |
| EAW41481.1 |
| EAY25698.1 |
| EAY29686.1 |
| EAY71091.1 |
| EBA17342.1 |
| EBA45829.1 |
| EBA46625.1 |
| EBA46696.1 |
| EBA49948.1 |
| EDK27088.1 |
| EDK34419.1 |
| EDL55746.1 |
| EDL67758.1 |
| EDM72574.1 |
| EDM85436.1 |
| EDN00141.1 |
| EDN58209.1 |
| EDN75782.1 |
| EDO61990.1 |
| EDO83906.1 |
| EDO88009.1 |
| EDP21555.1 |
| EDP46398.1 |
| EDP57830.1 |
| EDP99239.1 |
| EDQ32183.2 |
| EDQ32422.2 |
| EDQ33985.1 |
| EDQ34081.2 |
| EDS19662.1 |
| EDS72096.1 |
| EDS73897.1 |
| EDS80988.1 |

TABLE 8-continued

Representative Examples of Agmatinase
by EMBL/GENBANK/DDBJ ID Number

| |
|---|
| EDS83158.1 |
| EDS88464.1 |
| EDS93649.1 |
| EDT16696.1 |
| EDT25032.1 |
| EDT72172.1 |
| EDU60242.1 |
| EDU65565.1 |
| EDU92236.1 |
| EDW21378.1 |
| EDX36044.1 |
| EDX47360.1 |
| EDX72527.1 |
| EDY23983.1 |
| EDY34967.1 |
| EDY39135.1 |
| EDY82527.1 |
| EDZ41638.1 |
| EDZ41715.1 |
| EDZ42430.1 |
| EDZ44891.1 |
| EDZ45134.1 |
| EDZ47076.1 |
| EDZ51775.1 |
| EDZ60731.1 |
| EDZ60741.1 |
| EEA81924.1 |
| EEA96242.1 |
| EEA96590.1 |
| EEA96958.1 |
| EEB32402.1 |
| EEB44176.1 |
| EEB65944.1 |
| EEB71277.1 |
| EEB71305.1 |
| EEB77525.1 |
| EEB78979.1 |
| EEB83949.1 |
| EEB85264.1 |
| EEB85629.1 |
| EEC31786.1 |
| EEC32371.1 |
| EED32136.1 |
| EED33461.1 |
| EED96977.1 |
| EEE02117.1 |
| EEE06332.1 |
| EEE08690.1 |
| EEE34962.1 |
| EEE35534.1 |
| EEE35828.1 |
| EEE38756.1 |
| EEE38911.1 |
| EEE39080.1 |
| EEE41906.1 |
| EEE44992.1 |
| EEE45349.1 |
| EEE45625.1 |
| EEE46631.1 |
| EEF78555.1 |
| EEG29984.1 |
| EEG55452.1 |
| EEG85448.1 |
| EEH25515.1 |
| EEH27429.1 |
| EEI48479.1 |
| EEK13686.1 |
| EEK47650.1 |
| EEN89060.1 |
| EEO01852.1 |
| EEO17496.1 |
| EEP49793.1 |
| EEP50112.1 |
| EEP54377.1 |
| EEP83565.1 |
| EEQ48941.1 |
| EES48642.1 |

TABLE 8-continued

Representative Examples of Agmatinase
by EMBL/GENBANK/DDBJ ID Number

| |
|---|
| EET02842.1 |
| EET04446.1 |
| EET46812.1 |
| EET48304.1 |
| EET48468.1 |
| EEU96709.1 |
| EEV88951.1 |
| EEW39916.1 |
| EEW41136.1 |
| EEW57117.1 |
| EEW57168.1 |
| EEX09750.1 |
| EEX09880.1 |
| EEX09889.1 |
| EEX10564.1 |
| EEX10565.1 |
| EEX13167.1 |
| EEX13946.1 |
| EEX22145.1 |
| EEX36090.1 |
| EEX49424.1 |
| EEX69732.1 |
| EEX74040.1 |
| EEX77692.1 |
| EEY45419.1 |
| EEY72540.1 |
| EEY99072.1 |
| EEZ40965.1 |
| EFB71687.1 |
| EFB74416.1 |
| EFB90964.1 |
| EFC53923.1 |
| EFC82450.1 |
| EFC93346.1 |
| EFD51996.1 |
| EFE04795.2 |
| EFE06568.1 |
| EFE11218.1 |
| EFE24314.1 |
| EFE53195.1 |
| EFE61787.2 |
| EFE81272.2 |
| EFE96243.1 |
| EFF05370.2 |
| EFF11560.2 |
| EFF63745.1 |
| EFF65458.1 |
| EFF77651.1 |
| EFG05259.1 |
| EFG07008.1 |
| EFG47867.1 |
| EFG79255.1 |
| EFG80390.1 |
| EFH08237.1 |
| EFH16891.1 |
| EFI87351.1 |
| EFJ68586.1 |
| EFJ72104.1 |
| EFJ78632.1 |
| EFJ85217.1 |
| EFJ95125.1 |
| EFK02096.1 |
| EFK07239.1 |
| EFK16400.1 |
| EFK22733.1 |
| EFK27354.1 |
| EFK33116.1 |
| EFK43743.1 |
| EFK52585.1 |
| EFK66135.1 |
| EFK73841.1 |
| EFK92719.1 |
| EFK93271.1 |
| EFL53944.1 |
| EFL89152.1 |
| EFL90564.1 |
| EFM05246.1 |

TABLE 8-continued

Representative Examples of Agmatinase
by EMBL/GENBANK/DDBJ ID Number

| |
|---|
| EFM19908.1 |
| EFM24365.1 |
| EFM59353.1 |
| EFO29280.1 |
| EFO29703.1 |
| EFO59693.1 |
| EFP56876.1 |
| EFP71835.1 |
| EFQ06576.1 |
| EFQ61867.1 |
| EFR18236.1 |
| EFR40215.1 |
| EFS98037.1 |
| EFU36795.1 |
| EFU68774.1 |
| EFV39454.1 |
| EFV63707.1 |
| EFW12879.1 |
| EFW30568.1 |
| EFW49236.1 |
| EFW57058.1 |
| EFW59097.1 |
| EGA66010.1 |
| EGA71635.1 |
| EGB61887.1 |
| EGB66941.1 |
| EGB73848.1 |
| EGB86481.1 |
| EGB97943.1 |
| EGC01418.1 |
| EGC01999.1 |
| EGC96351.1 |
| EGC98049.1 |
| EGD34121.1 |
| EGE35458.1 |
| EGG31693.1 |
| EGI09325.1 |
| EGI14579.1 |
| EGI19907.1 |
| EGI45080.1 |
| EGI49386.1 |
| EGI74586.1 |
| EGI92001.1 |
| EGI92746.1 |
| EGJ06069.1 |
| EGK08600.1 |
| EGK10342.1 |
| EGK19205.1 |
| EGK34617.1 |
| EGK58217.1 |
| EGK59573.1 |
| EGK89404.1 |
| EGL19982.1 |
| EGO94614.1 |
| EGP19949.1 |
| EGQ26127.1 |
| EGQ26450.1 |
| EGU34334.1 |
| EGU40287.1 |
| EGU44010.1 |
| EGU44343.1 |
| EGU51393.1 |
| EGU98979.1 |
| EGY26111.1 |
| EGY53448.1 |
| EGY80770.1 |
| EGZ47428.1 |
| EHA17557.1 |
| EHA32192.1 |
| EHA61998.1 |
| EHB47773.1 |
| EHC12051.1 |
| EHC32561.1 |
| EHC45853.1 |
| EHC52512.1 |
| EHC62337.1 |
| EHC67687.1 |
| EHC75282.1 |
| EHC82043.1 |
| EHC82835.1 |
| EHC87961.1 |
| EHC99966.1 |
| EHD19777.1 |
| EHD20169.1 |
| EHD22253.1 |
| EHE87999.1 |
| EHH11803.1 |
| EHJ99584.1 |
| EHK55408.1 |
| EHK61318.1 |
| EHK77285.1 |
| EHM45588.1 |
| EHM49309.1 |
| EHN09006.1 |
| EHN12391.1 |
| EHP66623.1 |
| EHP82577.1 |
| EHQ34219.1 |
| EHT11452.1 |
| EHT99386.1 |
| EHU07090.1 |
| EHU07469.1 |
| EHU10270.1 |
| EHU20405.1 |
| EHU23876.1 |
| EHU27436.1 |
| EHU37208.1 |
| EHU40408.1 |
| EHU52683.1 |
| EHV55179.1 |
| EHY68648.1 |
| EIC82503.1 |
| EID63302.1 |
| EID67830.1 |
| EIE52962.1 |
| EIG78918.1 |
| EIG93520.1 |
| EIH12673.1 |
| EIH22144.1 |
| EIH45204.1 |
| EIH76840.1 |
| EII24708.1 |
| EII34469.1 |
| EII46301.1 |
| EIJ66488.1 |
| EIK61760.1 |
| EIK70683.1 |
| EIK72394.1 |
| EIK96204.1 |
| EIL52555.1 |
| EIM75905.1 |
| EIQ05553.1 |
| EIQ18545.1 |
| EIQ26058.1 |
| EIQ34462.1 |
| EIQ57268.1 |
| EIQ71651.1 |
| EIQ78422.1 |
| EIW91574.1 |
| EJE70690.1 |
| EJE72665.1 |
| EJF28964.1 |
| EJF37584.1 |
| EJF40496.1 |
| EJI91627.1 |
| EJI91646.1 |
| EJL04634.1 |
| EJL08772.1 |
| EJL13645.1 |
| EJL86644.1 |
| EJM95575.1 |
| EJO22140.1 |
| EJO55869.1 |
| EJO56522.1 |

TABLE 8-continued

Representative Examples of Agmatinase
by EMBL/GENBANK/DDBJ ID Number

| |
|---|
| EJP30929.1 |
| EJS87369.1 |
| EJS88033.1 |
| EJS88036.1 |
| EJT07171.1 |
| EJT86204.1 |
| EJU28108.1 |
| EJU32316.1 |
| EJU32348.1 |
| EJU33461.1 |
| EJU35725.1 |
| EJU55912.1 |
| EJW18947.1 |
| EJZ23180.1 |
| EJZ23191.1 |
| EJZ63478.1 |
| EKB46124.1 |
| EKB47998.1 |
| EKE71933.1 |
| EKF06697.1 |
| EKF20235.1 |
| EKF21363.1 |
| EKF42800.1 |
| EKF58465.1 |
| EKI50661.1 |
| EKJ96466.1 |
| EKM19531.1 |
| EKM27370.1 |
| EKM33126.1 |
| EKS07972.1 |
| EKT55065.1 |
| EKT55967.1 |
| EKT65147.1 |
| EKU51342.1 |
| EKX63786.1 |
| ELC14265.1 |
| ELC16835.1 |
| ELC37936.1 |
| ELC95205.1 |
| ELD97255.1 |
| ELE41729.1 |
| ELE53627.1 |
| ELE58433.1 |
| ELG86729.1 |
| ELI22617.1 |
| ELJ68846.1 |
| ELP54032.1 |
| ELP55275.1 |
| ELP55913.1 |
| ELP68231.1 |
| ELQ87920.1 |
| ELQ87969.1 |
| ELQ88013.1 |
| ELQ88771.1 |
| ELQ91334.1 |
| ELS26448.1 |
| ELS26841.1 |
| ELS27850.1 |
| ELT47152.1 |
| ELU52903.1 |
| ELW31521.1 |
| ELW85333.1 |
| ELY27700.1 |
| ELZ99543.1 |
| EMD08742.1 |
| EMI11336.1 |
| EMI14266.1 |
| EMP51369.1 |
| EMR07851.1 |
| EMS71620.1 |
| EMS97913.1 |
| EMT40199.1 |
| EMU59685.1 |
| EMU68325.1 |
| EMV17924.1 |
| EMW97460.1 |
| EMX18620.1 |
| EMX29475.1 |
| EMX36709.1 |
| EMX46863.1 |
| EMX83205.1 |
| ENA04653.1 |
| ENA38209.1 |
| ENA38530.1 |
| ENA43836.1 |
| ENC90022.1 |
| END51199.1 |
| END90131.1 |
| ENG95642.1 |
| ENH01174.1 |
| ENH07605.1 |
| ENY75730.1 |
| ENZ85537.1 |
| EOC16726.1 |
| EOD01693.1 |
| EOD42238.1 |
| EON87502.1 |
| EOQ46176.1 |
| EOQ52661.1 |
| EOR96368.1 |
| EOU48067.1 |
| EOU65286.1 |
| EOU78385.1 |
| EOU89739.1 |
| EOV04148.1 |
| EOV47238.1 |
| EOV55387.1 |
| EOV76750.1 |
| EOV94389.1 |
| EOW04340.1 |
| EOW16261.1 |
| EOW19941.1 |
| EOW61850.1 |
| EOW95130.1 |
| EOZ98682.1 |
| EPA97273.1 |
| EPA99157.1 |
| EPB97690.1 |
| EPC14082.1 |
| EPE98824.1 |
| EPF13748.1 |
| EPF18896.1 |
| EPR26903.1 |
| EPR73838.1 |
| EPR73839.1 |
| EPR76419.1 |
| EPR76420.1 |
| EPR77354.1 |
| EPX76657.1 |
| EPX79011.1 |
| EPX79012.1 |
| EPX79543.1 |
| EPX80066.1 |
| EPX81913.1 |
| EPX81981.1 |
| EPX84862.1 |
| EPX85788.1 |
| EPX87242.1 |
| EPZ50642.1 |
| EPZ55228.1 |
| EQC48483.1 |
| EQC49653.1 |
| EQF26369.1 |
| EQI88341.1 |
| EQK40602.1 |
| EQK42131.1 |
| EQN24780.1 |
| EQN91648.1 |
| EQO59510.1 |
| EQP47193.1 |
| EQQ03969.1 |
| EQV89274.1 |
| EQX25771.1 |
| EQX86240.1 |

TABLE 8-continued

Representative Examples of Agmatinase by EMBL/GENBANK/DDBJ ID Number

| |
|---|
| EQY17582.1 |
| EQY57338.1 |
| EQZ99174.1 |
| ERF77294.1 |
| ERG11045.1 |
| ERG42422.1 |
| ERG53670.1 |
| ERI00623.1 |
| ERI28937.1 |
| ERI30693.1 |
| ERI31190.1 |
| ERI32103.1 |
| ERJ05871.1 |
| ERJ12333.1 |
| ERK11299.1 |
| ERK12088.1 |
| ERL54400.1 |
| ERN41122.1 |
| ERN42498.1 |
| ERP09068.1 |
| ERT09144.1 |
| ERT14069.1 |
| ESA61590.1 |
| ESA67356.1 |
| ESA68726.1 |
| ESA72701.1 |
| ESA84978.1 |
| ESA92506.1 |
| ESB01864.1 |
| ESC99187.1 |
| ESD05523.1 |
| ESD21413.1 |
| ESD37525.1 |
| ESD70932.1 |
| ESD76697.1 |
| ESD90270.1 |
| ESE04815.1 |
| ESE83038.1 |
| ESE86248.1 |
| ESF53709.1 |
| ESG73922.1 |
| ESJ19424.1 |
| ESK15534.1 |
| ESK34333.1 |
| ESL70090.1 |
| ESM15735.1 |
| ESN17179.1 |
| ESQ21061.1 |
| ESQ72660.1 |
| ESR24857.1 |
| EST58097.1 |
| ESU79960.1 |
| ESW56111.1 |
| ETA01630.1 |
| ETA52029.1 |
| ETA68210.1 |
| ETC31136.1 |
| ETD59987.1 |
| ETE22279.1 |
| ETE48169.1 |
| ETK29277.1 |
| ETS33247.1 |
| ETT01045.1 |
| ETT07169.1 |
| ETW14464.1 |
| ETY41683.1 |
| ETZ09941.1 |
| EUB72243.1 |
| EUB74618.1 |
| EUB75427.1 |
| EUB84551.1 |
| EUB87030.1 |
| EUB94968.1 |
| EUB98403.1 |
| EUC15772.1 |
| EUC17426.1 |
| EUC19927.1 |
| EUC20682.1 |
| EUD05937.1 |
| EVU13232.1 |
| EWG73750.1 |
| EWH06794.1 |
| EWS97919.1 |
| EXB27436.1 |
| EXB47610.1 |
| EXL02912.1 |
| EXL08805.1 |
| EXU74154.1 |
| EYD75827.1 |
| EYD76005.1 |
| EYD76216.1 |
| EYD76391.1 |
| EYD83437.1 |
| EYR81340.1 |
| EYT23778.1 |
| EYU15951.1 |
| EYV12183.1 |
| EYV18352.1 |
| EYZ99018.1 |
| EZA32957.1 |
| EZD33879.1 |
| EZE09298.1 |
| EZE49621.1 |
| EZH78403.1 |
| EZJ36630.1 |
| EZJ49363.1 |
| EZJ71201.1 |
| EZJ83504.1 |
| EZJ83557.1 |
| EZK19944.1 |
| EZP32763.1 |
| EZP33753.1 |
| EZP41224.1 |
| EZP51786.1 |
| EZP65628.1 |
| EZQ15102.1 |
| GAA61384.1 |
| GAA61578.1 |
| GAA64202.1 |
| GAA65645.1 |
| GAA67376.1 |
| GAA68205.1 |
| GAA78318.1 |
| GAA80934.1 |
| GAB51338.1 |
| GAC32173.1 |
| GAC65341.1 |
| GAD00064.1 |
| GAD00717.1 |
| GAD03916.1 |
| GAJ68144.1 |
| GAK28093.1 |
| GAK75263.1 |
| GAK86396.1 |
| GAK86397.1 |
| GAK92924.1 |
| GAK92925.1 |
| GAK97920.1 |
| GAK99145.1 |
| GAL05071.1 |
| GAL11041.1 |
| GAL11042.1 |
| GAL16782.1 |
| GAL16859.1 |
| GAL19427.1 |
| GAL26771.1 |
| GAL26853.1 |
| GAL30714.1 |
| GAL30715.1 |
| GAL30716.1 |
| GAL32582.1 |
| GAL34679.1 |
| GAL36803.1 |
| GAL37656.1 |

TABLE 8-continued

Representative Examples of Agmatinase by EMBL/GENBANK/DDBJ ID Number

| |
|---|
| GAL45646.1 |
| GAL50932.1 |
| GAL56692.1 |
| GAL62430.1 |
| GAL66823.1 |
| GAL70387.1 |
| GAL75242.1 |
| GAL79182.1 |
| GAL90464.1 |
| GAL93895.1 |
| GAL94496.1 |
| GAM12739.1 |
| GAM57916.1 |
| GAM57917.1 |
| GAM65556.1 |
| GAM68524.1 |
| GAM76289.1 |
| GAP34694.1 |
| GAP62607.1 |
| GAP64452.1 |
| GAP73496.1 |
| GAR75760.1 |
| KAJ04750.1 |
| KAJ55629.1 |
| KCV83816.1 |
| KDA43421.1 |
| KDA56888.1 |
| KDA92361.1 |
| KDB06864.1 |
| KDB07503.1 |
| KDC51678.1 |
| KDF12959.1 |
| KDF13306.1 |
| KDG93655.1 |
| KDM49647.1 |
| KDM66049.1 |
| KDN30188.1 |
| KDO00731.1 |
| KDO01789.1 |
| KDR38345.1 |
| KDR39580.1 |
| KDR40471.1 |
| KDR42489.1 |
| KDR44448.1 |
| KDR96261.1 |
| KDU29241.1 |
| KDV28115.1 |
| KDV41545.1 |
| KDV63795.1 |
| KDW29938.1 |
| KDX21120.1 |
| KDX45706.1 |
| KEA07283.1 |
| KEA55087.1 |
| KEA56995.1 |
| KEA60549.1 |
| KEF38453.1 |
| KEI66155.1 |
| KEI66563.1 |
| KEI72808.1 |
| KEJ44932.1 |
| KEJ59125.1 |
| KEJ73413.1 |
| KEL65107.1 |
| KEN53758.1 |
| KEN65615.1 |
| KEN98030.1 |
| KEO08160.1 |
| KEO20889.1 |
| KEO30088.1 |
| KEQ06864.1 |
| KEQ11857.1 |
| KEQ16616.1 |
| KEQ56848.1 |
| KEQ57225.1 |
| KER03203.1 |
| KER05877.1 |
| KER71432.1 |
| KER73555.1 |
| KES24087.1 |
| KEX93107.1 |
| KEY59239.1 |
| KEZ05720.1 |
| KEZ05934.1 |
| KFA97525.1 |
| KFB10431.1 |
| KFB86391.1 |
| KFC05462.1 |
| KFC26266.1 |
| KFC50616.1 |
| KFC63916.1 |
| KFC75035.1 |
| KFC77790.1 |
| KFC78157.1 |
| KFC79266.1 |
| KFC88526.1 |
| KFC95287.1 |
| KFC98498.1 |
| KFD07808.1 |
| KFD17130.1 |
| KFD75089.1 |
| KFD81165.1 |
| KFE26876.1 |
| KFE29856.1 |
| KFE36379.1 |
| KFF88091.1 |
| KFI27333.1 |
| KFI27574.1 |
| KFI32532.1 |
| KFJ12154.1 |
| KFK48033.1 |
| KFK53897.1 |
| KFK83392.1 |
| KFL00125.1 |
| KFL53690.1 |
| KFM16262.1 |
| KFM16471.1 |
| KFM17679.1 |
| KFM18828.1 |
| KFM21122.1 |
| KFN01206.1 |
| KFX70429.1 |
| KGA58376.1 |
| KGB51681.1 |
| KGB58219.1 |
| KGB82923.1 |
| KGB93469.1 |
| KGB93751.1 |
| KGC15448.1 |
| KGD53502.1 |
| KGD58420.1 |
| KGD74931.1 |
| KGD99322.1 |
| KGE84568.1 |
| KGF68819.1 |
| KGF85749.1 |
| KGF92571.1 |
| KGF94969.1 |
| KGF98296.1 |
| KGG00684.1 |
| KGG08593.1 |
| KGG09329.1 |
| KGG13720.1 |
| KGG14534.1 |
| KGG20576.1 |
| KGG25389.1 |
| KGJ87252.1 |
| KGJ88564.1 |
| KGJ88903.1 |
| KGJ91830.1 |
| KGJ98195.1 |
| KGJ99182.1 |
| KGJ99826.1 |
| KGK11101.1 |

TABLE 8-continued

Representative Examples of Agmatinase
by EMBL/GENBANK/DDBJ ID Number

| |
|---|
| KGK24833.1 |
| KGL02631.1 |
| KGL61018.1 |
| KGL63588.1 |
| KGM06104.1 |
| KGM27860.1 |
| KGM47940.1 |
| KGM62448.1 |
| KGM71414.1 |
| KGM83358.1 |
| KGM85012.1 |
| KGM87119.1 |
| KGM89320.1 |
| KGP46486.1 |
| KGQ31158.1 |
| KGQ42403.1 |
| KGQ44024.1 |
| KGQ45909.1 |
| KGQ50254.1 |
| KGQ57329.1 |
| KGQ59396.1 |
| KGQ63143.1 |
| KGT92054.1 |
| KGT93837.1 |
| KGW03528.1 |
| KGW13295.1 |
| KGY09805.1 |
| KGY14274.1 |
| KHA72711.1 |
| KHD09963.1 |
| KHD12613.1 |
| KHD26206.1 |
| KHF30311.1 |
| KHF30312.1 |
| KHF32019.1 |
| KHI37342.1 |
| KHJ20007.1 |
| KHJ52626.1 |
| KHJ53009.1 |
| KHJ67587.1 |
| KHK58158.1 |
| KHL14438.1 |
| KHM50825.1 |
| KHN63731.1 |
| KHO62446.1 |
| KHS44854.1 |
| KHT65211.1 |
| KIA76172.1 |
| KIA79272.1 |
| KIC08591.1 |
| KIC11124.1 |
| KIC12067.1 |
| KIC20734.1 |
| KIC21142.1 |
| KIC38967.1 |
| KIC39253.1 |
| KIC42948.1 |
| KIC44583.1 |
| KIC48940.1 |
| KIC81372.1 |
| KID01688.1 |
| KID07131.1 |
| KID10239.1 |
| KID53398.1 |
| KIF44861.1 |
| KIF47533.1 |
| KIF60145.1 |
| KIG04148.1 |
| KIH04246.1 |
| KII17028.1 |
| KII76311.1 |
| KIK88030.1 |
| KIL14780.1 |
| KIL44046.1 |
| KIL49701.1 |
| KIL52719.1 |
| KIN13602.1 |

TABLE 8-continued

Representative Examples of Agmatinase
by EMBL/GENBANK/DDBJ ID Number

| |
|---|
| KIO35232.1 |
| KIO64041.1 |
| KIO64826.1 |
| KIO64882.1 |
| KIO74022.1 |
| KIP13348.1 |
| KIP19384.1 |
| KIP21434.1 |
| KIP28327.1 |
| KIP77591.1 |
| KIQ47214.1 |
| KIQ67877.1 |
| KIQ67879.1 |
| KIQ93804.1 |
| KIR21892.1 |
| KIS42217.1 |
| KIS44949.1 |
| KIS45178.1 |
| KIS78067.1 |
| KIT15205.1 |
| KIT26177.1 |
| KIT34215.1 |
| KIT53655.1 |
| KIU06086.1 |
| KIV63387.1 |
| KIV67945.1 |
| KIV69114.1 |
| KIV76036.1 |
| KIX18215.1 |
| KIX35343.1 |
| KIX40471.1 |
| KIX50426.1 |
| KIY38310.1 |
| KJC02192.1 |
| KJC05651.1 |
| KJC11069.1 |
| KJE27066.1 |
| KJE29094.1 |
| KJE37105.1 |
| KJE41321.1 |
| KJE56468.1 |
| KJF68712.1 |
| KJF74388.1 |
| KJF82240.1 |
| KJF95975.1 |
| KJF96789.1 |
| KJG26707.1 |
| KJG38238.1 |
| KJG58333.1 |
| KJH08952.1 |
| KJH75111.1 |
| KJH76892.1 |
| KJJ85191.1 |
| KJJ97017.1 |
| KJK05856.1 |
| KJK14771.1 |
| KJM40293.1 |
| KJM86390.1 |
| KJN20029.1 |
| KJR24917.1 |
| KJU79826.1 |
| KJV49964.1 |
| KJW32728.1 |
| KJW52977.1 |
| KJX12327.1 |
| KJX88802.1 |
| KJY81950.1 |
| KJY91595.1 |
| KJZ06665.1 |
| KJZ10778.1 |
| KJZ33490.1 |
| KJZ43182.1 |
| KJZ43642.1 |
| KJZ49391.1 |
| KJZ65470.1 |
| KJZ83769.1 |
| KJZ85311.1 |

TABLE 8-continued

Representative Examples of Agmatinase
by EMBL/GENBANK/DDBJ ID Number

| |
|---|
| KKA53929.1 |
| KKB03409.1 |
| KKC64603.1 |
| KKC79077.1 |
| KKD31623.1 |
| KKD58710.1 |
| KKD60086.1 |
| KKF35468.1 |
| KKI44370.1 |
| KKJ02095.1 |
| KKJ26483.1 |
| KKJ76863.1 |
| KKO14625.1 |
| KKT03014.1 |
| KKW50513.1 |
| KKX34306.1 |
| KKX57725.1 |
| KKY43328.1 |
| KKY65106.1 |
| KKY79844.1 |
| KKZ18900.1 |
| KKZ94380.1 |
| KLA23437.1 |
| KLA28450.1 |
| KLE26363.1 |
| KLI68355.1 |
| KLI96588.1 |
| KLL00327.1 |
| KLN47102.1 |
| KLN59734.1 |
| KLN96605.1 |
| KLQ26950.1 |
| KLS52970.1 |
| KLT72171.1 |
| KLU18616.1 |
| KLU18617.1 |
| KLU21135.1 |
| KLU63532.1 |
| KLV01110.1 |
| KLV04731.1 |
| KLV10916.1 |
| KLV65168.1 |
| KLW86529.1 |
| KLX57832.1 |
| KLX95653.1 |
| KLY12051.1 |
| KME68567.1 |
| KMJ45199.1 |
| KMJ52368.1 |
| KMK12313.1 |
| KMK65695.1 |
| KMK67024.1 |
| KML08951.1 |
| KML19553.1 |
| KML55768.1 |
| KML63754.1 |
| KMM44201.1 |
| KMM80744.1 |
| KMM88468.1 |
| KMN35332.1 |
| KMN52710.1 |
| KMN54483.1 |
| KMN64511.1 |
| KMN82524.1 |
| KMN90587.1 |
| KMO70998.1 |
| KMO75409.1 |
| KMP15844.1 |
| KMP32711.1 |
| KMP76811.1 |
| KMP97239.1 |
| KMQ03530.1 |
| KMQ27939.1 |
| KMQ80607.1 |
| KMT23186.1 |
| KMV32028.1 |
| KMV34546.1 |
| KMV68971.1 |
| KMV72039.1 |
| KMW56860.1 |
| KMW57564.1 |
| KMW60148.1 |
| KMW73818.1 |
| KMY86054.1 |
| KMZ11104.1 |
| KNA43182.1 |
| KNC12045.1 |
| KNC94638.1 |
| KND54403.1 |
| KND57608.1 |
| KND60713.1 |
| KNF09788.1 |
| KNF69260.1 |
| KNF81881.1 |
| KNH13933.1 |
| KNH29699.1 |
| KNH42940.1 |
| KNN85891.1 |
| KNW74428.1 |
| KNX42579.1 |
| KNX78696.1 |
| KNY25361.1 |
| KNY25362.1 |
| KNY34664.1 |
| KNY78419.1 |
| KNZ84105.1 |
| KNZ96650.1 |
| KOA27319.1 |
| KOA70223.1 |
| KOC89788.1 |
| KOC93579.1 |
| KOE81497.1 |
| KOE86385.1 |
| KOF22188.1 |
| KOO07592.1 |
| KOO13953.1 |
| KOP04210.1 |
| KOP34818.1 |
| KOR21593.1 |
| KOY02635.1 |
| KOY33005.1 |
| KOY45864.1 |
| KOY61141.1 |
| KPA10469.1 |
| KPA16733.1 |
| KPA20218.1 |
| KPA53392.1 |
| KPB01772.1 |
| KPC99823.1 |
| KPD03212.1 |
| KPD11463.1 |
| KPD14945.1 |
| KPD18730.1 |
| KPF43120.1 |
| KPF56119.1 |
| KPF72724.1 |
| KPG94733.1 |
| KPG95797.1 |
| KPH01583.1 |
| KPH10681.1 |
| KPH60166.1 |
| KPH81257.1 |
| KPL51015.1 |
| KPL87226.1 |
| KPL88374.1 |
| KPL99047.1 |
| KPM59181.1 |
| KPM65351.1 |
| KPM84873.1 |
| KPM96585.1 |
| KPN62270.1 |
| KPN70840.1 |
| KPN74193.1 |
| KPN90785.1 |

TABLE 8-continued

Representative Examples of Agmatinase
by EMBL/GENBANK/DDBJ ID Number

KPO18578.1
KPO36864.1
KPO46574.1
KPP84622.1
KPP85678.1
KPP85884.1
KPP89409.1
KPQ06101.1
KPQ08097.1
KPQ13684.1
KPQ14340.1
KPQ14479.1
KPQ21467.1
KPQ22810.1
KPQ29983.1
KPQ32046.1
KPQ36131.1
KPQ37310.1
KPR57622.1
KPU50749.1
KPU53876.1
KPU54584.1
KPU54773.1
KPU84621.1
KPW02372.1
KPW04291.1
KPZ52050.1
KPZ54771.1
KPZ63440.1
KPZ65777.1
KPZ67737.1
KPZ69053.1
KPZ72596.1
KQA23172.1
KQA98185.1
KQB15598.1
KQB16357.1
KQB91620.1
KQB98549.1
KQJ13932.1
KQJ46046.1
KST27455.1
KSX90871.1
KTH73166.1
KTM92472.1
KTO38350.1
KTO86996.1
KTP62451.1
KUH44100.1
KUI50798.1
KUQ52563.1
KUU48154.1
KWV87278.1
KWZ91247.1
KXG92414.1
KXH00366.1
KXH98341.1
KXI61250.1
KXJ38653.1
KXL66969.1
KXQ42781.1
KXX90622.1
KXY08066.1
KXY28981.1
KXY53137.1
KXY72091.1
KYR44907.1
KYS97777.1
KYV67952.1
KZD58224.1
KZD81457.1
KZD82131.1
KZE06157.1
KZJ59530.1
OAC43113.1
OAE40342.1
OAE92625.1

TABLE 8-continued

Representative Examples of Agmatinase
by EMBL/GENBANK/DDBJ ID Number

OAH32122.1
OAJ87923.1
OAO68288.1
OAO72922.1
OBX00501.1
OCS74956.1
OCS95951.1
OCV53559.1
ODH24471.1
OEG92891.1
OEH04368.1
OEH12481.1
OEH14141.1
OEH95893.1
OEI65538.1
OEN36597.1
OIN26435.1
OIR51681.1
OIX27476.1
SAD71408.1
SAE32773.1
SAI34905.1
SAY76569.1
SAZ57795.1
SBX90640.1
SBZ90882.1
SCM53106.1

Representative examples of ornithine decarboxylase (EC 4.1.1.17) are given below in Table 9 and identified by their EMBL/GENBANK/DDBJ ID numbers. Any of the bacteria given in Table 10 can be engineered with any version of the ornithine decarboxylase (EC 4.1.1.17) set forth in Table 3 and 9. For instance, the bacteria can be engineered with a version of the ornithine decarboxylase enzyme that has at least 50% nucleotide similarity with any of the versions of ornithine decarboxylase given in Table 9 (e.g., at least nucleotide 60% similarity, at least 70% nucleotide similarity, at least 80% nucleotide similarity, at least 90% nucleotide similarity, at least 91% nucleotide similarity, at least 92% nucleotide similarity, at least 93% nucleotide similarity, at least 94% nucleotide similarity, at least 95% nucleotide similarity, at least 96% nucleotide similarity, at least 97% nucleotide similarity, at least 98% nucleotide similarity, at least 99% nucleotide similarity, at least 99.5% nucleotide similarity, at least 99.9% nucleotide similarity, or 100% nucleotide similarity).

TABLE 9

Representative Examples of Ornithine Decarboxylase
by EMBL/GENBANK/DDBJ ID Number AAA62785.1
AAA66174.1
AAA69133.1
AAC22248.1
AAC73787.1
AAC76002.2
AAK65018.1
AAK65019.2
AAL19645.1
AAL21989.1
AAL54375.1
AAL94697.1
AAM32881.1
AAM86897.1
AAN53399.1
AAN57109.1
AAN66489.2
AAN79250.1

TABLE 9-continued

Representative Examples of Ornithine Decarboxylase by EMBL/GENBANK/DDBJ ID Number

| |
|---|
| AAN82001.1 |
| AAO90264.2 |
| AAS63636.1 |
| AAV42846.1 |
| AAW60223.1 |
| AAY39277.1 |
| AAY96264.1 |
| AAZ17903.1 |
| AAZ21026.1 |
| AAZ45335.1 |
| AAZ60071.1 |
| AAZ71105.1 |
| ABA04186.1 |
| ABA78141.1 |
| ABB12186.1 |
| ABB40870.1 |
| ABB75259.1 |
| ABC22493.1 |
| ABC92384.1 |
| ABD09230.1 |
| ABD53718.1 |
| ABD69850.1 |
| ABD82224.1 |
| ABD90359.1 |
| ABD98955.1 |
| ABE05711.1 |
| ABE06188.1 |
| ABE08804.1 |
| ABE29508.1 |
| ABE36633.1 |
| ABE38094.1 |
| ABE44334.1 |
| ABE49183.1 |
| ABE49327.1 |
| ABE56353.1 |
| ABE64149.1 |
| ABE73821.1 |
| ABF62084.1 |
| ABF76724.1 |
| ABE79243.1 |
| ABG12272.1 |
| ABG19485.1 |
| ABG64092.1 |
| ABI25841.1 |
| ABI41283.1 |
| ABI41448.1 |
| ABI59635.1 |
| ABI61420.1 |
| ABI64670.1 |
| ABI73241.1 |
| ABI88035.1 |
| ABJ07102.1 |
| ABJ08721.1 |
| ABJ70427.1 |
| ABK39746.1 |
| ABK49901.1 |
| ABK50089.1 |
| ABL98620.1 |
| ABM01537.1 |
| ABM03233.1 |
| ABM17184.1 |
| ABM33819.1 |
| ABM37329.1 |
| ABM42903.1 |
| ABM94883.1 |
| ABN63325.1 |
| ABN63550.1 |
| ABO25258.1 |
| ABO55514.1 |
| ABP59886.1 |
| ABP62042.1 |
| ABP74273.1 |
| ABP77387.1 |
| ABP83569.1 |
| ABQ13490.1 |
| ABQ18377.1 |
| ABQ31378.1 |
| ABQ33584.1 |
| ABQ35247.1 |
| ABQ46942.1 |
| ABQ77056.1 |
| ABQ77881.1 |
| ABQ94106.1 |
| ABR63972.1 |
| ABR71097.1 |
| ABS65893.1 |
| ABS77454.2 |
| ABV20152.1 |
| ABV20217.1 |
| ABV32717.1 |
| ABV39617.1 |
| ABV43142.1 |
| ABV93117.1 |
| ABX51330.1 |
| ABY29398.1 |
| ABY96818.1 |
| ACA15010.1 |
| ACA32083.1 |
| ACA67112.1 |
| ACA74794.1 |
| ACA92668.1 |
| ACB16558.1 |
| ACB17513.1 |
| ACB26370.1 |
| ACB26621.1 |
| ACB79112.1 |
| ACB94577.1 |
| ACC75475.1 |
| ACD09708.1 |
| ACE89117.1 |
| ACE92836.1 |
| ACE99495.1 |
| ACF00856.1 |
| ACF62498.1 |
| ACF64187.1 |
| ACG58193.1 |
| ACH49712.1 |
| ACH50260.1 |
| ACH63785.1 |
| ACI11630.1 |
| ACI98761.1 |
| ACI99115.1 |
| ACJ00377.1 |
| ACK48448.1 |
| ACK49205.1 |
| ACK81873.1 |
| ACK83165.1 |
| ACL55330.1 |
| ACL93832.1 |
| ACN14131.1 |
| ACP07980.1 |
| ACP26670.1 |
| ACQ92481.1 |
| ACR70548.1 |
| ACR80274.1 |
| ACS38696.1 |
| ACS39829.1 |
| ACS86807.1 |
| ACT08032.1 |
| ACT11922.1 |
| ACX89156.1 |
| ACY53777.1 |
| ACZ75768.1 |
| ADA66726.1 |
| ADE84258.1 |
| ADG60285.1 |
| ADI02315.1 |
| ADM40347.1 |
| ADM42835.1 |
| ADM42836.1 |
| ADM97227.1 |
| ADO10738.1 |
| ADO47055.1 |
| ADO49370.1 |

TABLE 9-continued

Representative Examples of Ornithine Decarboxylase by EMBL/GENBANK/DDBJ ID Number ADO84265.1
ADP99549.1
ADU45025.1
ADU70535.1
ADU91399.1
ADV11066.1
ADV56349.1
ADW75162.1
ADY12020.1
ADZ25852.1
ADZ25990.1
AEA25536.1
AEA80789.1
AEB13218.1
AEE17405.1
AEF20700.1
AEF54819.1
AEG05601.1
AEG07021.1
AEG09620.1
AEG09845.1
AEG48476.1
AEH50365.1
AEH86445.1
AEI07722.1
AEJ18813.1
AEK61463.1
AEM41039.1
AEP37160.1
AEV60919.1
AFJ59017.1
AFL53867.1
AFY17936.1
AFY20265.1
AGA64911.1
AGG15787.1
AGG70048.1
AGG70049.1
AGH98733.1
AGL50812.1
AGO56945.1
AGT07607.1
AHA66979.1
AHD10069.1
AHD10849.1
AHE50504.1
AHE58679.1
AHF70264.1
AHF74955.1
AHH20127.1
AHJ62296.1
AHK70374.1
AHM04085.1
AHM04146.1
AHM77647.1
AHM83238.1
AHY72323.1
AIJ07696.1
AIJ08459.1
AIQ92829.1
AIQ93098.1
AIR09930.1
AIT00368.1
AIZ81713.1
AIZ84023.1
AJE57512.1
AJF55421.1
AJF57769.1
AJG20615.1
AJI87080.1
AJK49051.1
AJQ96966.1
AKA84438.1
AKB12437.1
AKB14359.1
AKB18263.1
AKB21587.1
AKB25327.1
AKB28151.1
AKB32085.1
AKB37309.1
AKB40448.1
AKB43558.1
AKB47010.1
AKB51817.1
AKB55259.1
AKB56666.1
AKB61403.1
AKB64701.1
AKB68292.1
AKB72738.1
AKB75272.1
AKB78060.1
AKB81641.1
AKB84150.1
AKF49823.1
AKH27073.1
AKH69183.1
AKH99554.1
AKO77226.1
AKO97889.1
ALD27842.1
ALV76207.1
ALY14469.1
ALZ68204.1
ALZ69985.1
ANK35386.1
ANM83745.1
ANM85435.1
ANT16911.1
AOM43847.1
AOT33749.1
APF08471.1
APF13004.1
BAA35349.1
BAE77028.1
BAI71258.1
BAI72082.1
BAI76414.1
BAI96560.1
BAJ81775.1
BAL83346.1
BAN98715.1
BAQ17945.1
BAU72598.1
CAD78655.1
CAD84820.1
CAG69512.1
CAG73878.1
CAH22470.1
CAI97377.1
CAI98549.1
CAJ12264.1
CAK02040.1
CAK13937.1
CAL10580.1
CAL13549.1
CAL19626.1
CAL78631.1
CAL79901.1
CAM00591.1
CAM03603.1
CAO97896.1
CAQ81820.1
CAQ89917.1
CAQ90401.1
CAR02067.1
CAR04482.1
CAR06878.1
CAR09582.2
CAR14483.1
CAR16788.1
CAR19506.1
CAR36594.1

TABLE 9-continued

Representative Examples of Ornithine Decarboxylase by EMBL/GENBANK/DDBJ ID Number CAR40820.1
CAR54968.1
CAU96547.1
CAU99265.1
CAX18544.1
CAX22758.1
CAX24467.1
CAX61217.1
CAX67648.1
CAX67666.1
CAY75622.1
CBA19528.1
CBA28212.1
CBA29223.1
CBA33757.1
CBG87473.1
CBG91695.1
CBI76815.1
CBI78256.1
CBI78275.1
CBL06633.1
CBS85874.1
CBS86483.1
CBS89897.1
CBW16782.1
CBW19188.1
CBY25820.1
CBY25832.1
CBY28841.1
CCA93756.1
CCC57896.1
CCC96226.1
CCC98554.1
CCD02602.1
CCD40282.1
CCD85313.1
CCD87735.1
CCD96638.1
CCE00128.1
CCE04953.1
CCE05308.1
CCE97429.1
CCE98566.1
CCF20520.1
CCG07833.1
CCG39584.1
CCG86023.1
CCG93567.1
CCI82390.1
CCJ43149.1
CCJ73160.1
CCJ73613.1
CCJ79388.1
CCJ82552.1
CCJ86161.1
CCJ87942.1
CCJ89861.1
CCJ91600.1
CCJ97363.1
CCJ99535.1
CCK01641.1
CCK03853.1
CCK06057.1
CCK08478.1
CCK22783.1
CCK45849.1
CCK48255.1
CCM77346.1
CCO07100.1
CCQ09200.1
CCQ74399.1
CCT59416.1
CCU62281.1
CCU62303.1
CCV05533.1
CCV16052.1
CCW14223.1
CCW18613.1
CDF57711.1
CDF82218.1
CDF92784.1
CDF95827.1
CDG34413.1
CDG41242.1
CDI09982.1
CDK34386.1
CDK72259.1
CDK72653.1
CDK75666.1
CDK97758.1
CDK98655.1
CDL07277.1
CDL10022.1
CDL20226.1
CDL23839.1
CDL25819.1
CDL25820.1
CDL27267.1
CDL27268.1
CDL27269.1
CDL39170.1
CDL50778.1
CDL50819.1
CDL86182.1
CDL90667.1
CDM25489.1
CDM39302.1
CDM59281.1
CDM60694.1
CDN08374.1
CDO59353.1
CDP53980.1
CDQ16217.1
CDR81373.1
CDR83974.1
CDR89923.1
CDS49197.1
CDU34381.1
CDU39548.1
CDU41134.1
CDX11380.1
CDX28277.1
CDX31971.1
CDX32761.1
CDX44074.1
CDX54921.1
CDX58455.1
CDY74095.1
CEF30930.1
CEG53321.1
CEI15979.1
CEJ65390.1
CEK26252.1
CEK27948.1
CEL27520.1
CEL88226.1
CEP77894.1
CFQ53013.1
CFQ53087.1
CFQ53093.1
CFQ63135.1
CNJ42662.1
CNK09967.1
CPR14076.1
CPR26377.1
CPR26378.1
CQH28513.1
CQH50344.1
CRG52628.1
CRH30711.1
CRH35440.1
CRH39733.1
CRL10245.1
CRL11665.1

TABLE 9-continued

Representative Examples of Ornithine Decarboxylase by EMBL/GENBANK/DDBJ ID Number CRL87218.1
CRO16551.1
CRP80377.1
CRY55295.1
CRY56151.1
CRY73398.1
CRZ77491.1
CSA30444.1
CSB23271.1
CSB44423.1
CSB97832.1
CSC29054.1
CSC32042.1
CSC55030.1
CSC90483.1
CSC91956.1
CSI90225.1
CSI94697.1
CSK70247.1
CSL03024.1
CSL07641.1
CSM63721.1
CSM98897.1
CSN54919.1
CSP82502.1
CSP97222.1
CSR81748.1
CSS46262.1
CSS69716.1
CST05596.1
CTQ00658.1
CTQ07290.1
CTQ10899.1
CTQ21239.1
CTQ33367.1
CTQ42919.1
CTQ43401.1
CTQ48990.1
CTQ51582.1
CTQ64509.1
CTQ70679.1
CTQ77678.1
CTR81841.1
CTR87483.1
CTS06036.1
CTS29676.1
CTS78438.1
CTT62185.1
CTT62210.1
CTT77363.1
CTT83136.1
CTT84900.1
CTT94762.1
CTU09480.1
CTU43474.1
CTU46798.1
CTU67775.1
CTV17999.1
CTV22603.1
CTV49713.1
CTV56172.1
CTV59366.1
CTV99708.1
CTW90830.1
CTX56302.1
CTZ36862.1
CTZ54946.1
CTZ68478.1
CTZ90267.1
CUH38863.1
CUH97680.1
CUI46350.1
CUI65295.1
CUJ95194.1
CUK08178.1
EAA24580.1
EDL69175.1
EDM60163.1
EDN58782.1
EDQ31943.2
EDQ34501.1
EDR33413.1
EDS92093.1
EDU62245.1
EDU64911.1
EDU91579.1
EDU92556.1
EDX33853.1
EDX36097.1
EDX47281.1
EDX48079.1
EDY22541.1
EDY26086.1
EDZ45245.1
EDZ48441.1
EDZ60503.1
EEB70922.1
EEB72505.1
EEH90224.1
EEI47014.1
EEI67673.1
EEJ60488.1
EEJ72107.1
EEJ73250.1
EEN80026.1
EEO01571.1
EEO17726.1
EEQ24327.1
EEV22915.1
EEW41165.1
EEX49266.1
EEY45602.1
EEY99726.1
EFC91687.1
EFE96168.1
EFE96169.1
EFE97489.1
EFG55431.1
EFM19932.1
EFM60159.1
EFP71802.1
EFQ23396.1
EFQ65259.1
EFR18105.1
EFR18206.1
EFW49207.1
EFW49866.1
EFW55944.1
EFW57461.1
EFW59125.1
EFY04546.1
EFZ35827.1
EGC73182.1
EGD26721.1
EGF12882.1
EGF12883.1
EGF13575.1
EGF13579.1
EGI92040.1
EGI93253.1
EGI99407.1
EGJ01620.1
EGK15386.1
EGK19303.1
EGK26882.1
EGK26884.1
EGK34653.1
EGK34656.1
EGK40304.1
EGK58241.1
EGK62838.1
EGL98455.1
EGL98460.1
EGM68475.1

TABLE 9-continued

Representative Examples of Ornithine Decarboxylase by EMBL/GENBANK/DDBJ ID Number

| |
|---|
| EGM68534.1 |
| EGO94943.1 |
| EGP08625.1 |
| EGP13188.1 |
| EHC87901.1 |
| EHC94859.1 |
| EHC94874.1 |
| EHD22909.1 |
| EHE87725.1 |
| EHE90319.1 |
| EHP88849.1 |
| EHP90237.1 |
| EHU02113.1 |
| EHU20119.1 |
| EHU26736.1 |
| EHV55210.1 |
| EIC02033.1 |
| EIJ31771.1 |
| EIK63890.1 |
| EIK67948.1 |
| EIK70882.1 |
| EIQ05587.1 |
| EIQ18576.1 |
| EIQ26095.1 |
| EIQ71312.1 |
| EIQ76994.1 |
| EIQ78394.1 |
| EIZ02840.1 |
| EJI92011.1 |
| EJL03608.1 |
| EJL08507.1 |
| EJO49529.1 |
| EKI50690.1 |
| EKP99013.1 |
| EKP99014.1 |
| EKQ02803.1 |
| EKQ02804.1 |
| EKQ09991.1 |
| EKQ09992.1 |
| EKQ11508.1 |
| EKQ11509.1 |
| EKQ18817.1 |
| EKQ21433.1 |
| EKS52809.1 |
| ELS26426.1 |
| ELW31551.1 |
| EMS72676.1 |
| EMU59716.1 |
| EMU68355.1 |
| EMV17894.1 |
| EMW96757.1 |
| EMX18650.1 |
| EMX29506.1 |
| EMX36739.1 |
| EMX46897.1 |
| EMX83235.1 |
| ENA04683.1 |
| ENA38238.1 |
| ENA43866.1 |
| ENC90052.1 |
| END51232.1 |
| END90160.1 |
| ENG95671.1 |
| ENH01203.1 |
| ENH07634.1 |
| EOD01056.1 |
| EPA96228.1 |
| EPC15663.1 |
| EPC38567.1 |
| EPF66737.1 |
| EPX75972.1 |
| EPX79893.1 |
| EPX85529.1 |
| EPX86372.1 |
| EQC66601.1 |
| EQC67119.1 |
| ERJ07090.1 |
| ERJ12441.1 |
| ERL16034.1 |
| ERL56578.1 |
| ESN64144.1 |
| ESN64681.1 |
| ESR23196.1 |
| ESR27061.1 |
| ESS57441.1 |
| ESU78166.1 |
| ETA69456.1 |
| ETS92400.1 |
| EUB20316.1 |
| EUB71374.1 |
| EUB75197.1 |
| EUB84084.1 |
| EUB97023.1 |
| EUC12442.1 |
| EWC58917.1 |
| EWC60810.1 |
| EWG73717.1 |
| EWG77348.1 |
| EYD71048.1 |
| EYD71269.1 |
| EYD77132.1 |
| EYD83397.1 |
| EZJ36659.1 |
| EZJ49393.1 |
| EZJ71231.1 |
| EZJ83500.1 |
| EZK19977.1 |
| EZP30980.1 |
| EZP72267.1 |
| GAO78552.1 |
| GAP76203.1 |
| KDA56789.1 |
| KDE39162.1 |
| KDM66230.1 |
| KDM67094.1 |
| KDM68717.1 |
| KDR44432.1 |
| KDU29207.1 |
| KDW29935.1 |
| KDX21151.1 |
| KDX45737.1 |
| KEA62619.1 |
| KEC54001.1 |
| KEJ45027.1 |
| KEJ59156.1 |
| KEJ73445.1 |
| KEK27105.1 |
| KEK29881.1 |
| KEL65139.1 |
| KEN53788.1 |
| KEN65519.1 |
| KEN98059.1 |
| KEO08191.1 |
| KEO30074.1 |
| KEQ53465.1 |
| KER02947.1 |
| KEY57491.1 |
| KEZ18534.1 |
| KFC03280.1 |
| KFC05486.1 |
| KFC63691.1 |
| KFC69417.1 |
| KFC77644.1 |
| KFC79295.1 |
| KFC83942.1 |
| KFC88765.1 |
| KFC94984.1 |
| KFD06768.1 |
| KFD07842.1 |
| KFD17151.1 |
| KFE39747.1 |
| KFE40588.1 |
| KFL92212.1 |
| KGA92942.1 |

TABLE 9-continued

Representative Examples of Ornithine Decarboxylase by EMBL/GENBANK/DDBJ ID Number KGB23003.1
KGM59804.1
KGM62416.1
KGM68326.1
KGM71386.1
KGM77872.1
KGM80580.1
KGM83330.1
KGM84983.1
KGM87536.1
KGM88313.1
KHJ19976.1
KHN90703.1
KHQ55244.1
KID27997.1
KIH04277.1
KIQ45687.1
KIQ47241.1
KIQ68453.1
KIQ68551.1
KIR02360.1
KIR22223.1
KIS02883.1
KIT17643.1
KIV66814.1
KIV70876.1
KJL37417.1
KJL45196.1
KJW30930.1
KJX87011.1
KLU03251.1
KLY03824.1
KMK68540.1
KMM41085.1
KMM41943.1
KMO67617.1
KMO73993.1
KMO74679.1
KMQ72910.1
KMY85028.1
KMZ12404.1
KND54388.1
KND59806.1
KNE76189.1
KNF62494.1
KNF81913.1
KNF82765.1
KNH02424.1
KNH10085.1
KNX39995.1
KNX42257.1
KOA19269.1
KON65543.1
KPA20904.1
KPA88263.1
KPO11674.1
KPO18606.1
KPO45157.1
KPO46605.1
KPP86129.1
KPQ30708.1
KPW02487.1
KPZ58476.1
KPZ73698.1
KQJ13961.1
KQJ37165.1
KRK54316.1
KRK64371.1
KSH09715.1
KST27486.1
KTZ13476.1
KXL65724.1
KXQ42753.1
KYR53760.1
KYV67923.1
KYV72148.1
OAC43139.1
OAH24264.1
OAJ89982.1
OCS73051.1
OCV53530.1
ODH24445.1
OEI63490.1
OEI65510.1
OFJ34340.1
OIR53362.1
OJF06953.1
SAY77725.1
SEF59356.1

A variety of microbes (e.g., bacteria) can be engineered to produce GABA (e.g., by engineering one or more of the enzymes set forth in Table 2). For instance, any of the bacteria set forth in Table 10 can be engineered to produce GABA. In other words, a bacteria having a 16S rDNA nucleotide sequence that is at least 50% similar to that set forth in Table 10 below can be engineered (e.g., with one of the enzymes in Tables 3-9) to produce GABA. The bacteria may have a 16S rDNA sequence that is at least 60% similar, at least 70% similar, at least 80% similar, at least 90% N similar, at least 91% similar, at least 92% similar, at least 93% similar, at least 94% similar, at least 95% similar, at least 96% similar, at least 97% similar, at least 98% similar, at least 99% similar, at least 99.5% similar, or 100% similar to the 16S rDNA nucleotide sequence given in Table 10.

As set forth in Example 8, *E. coli* was engineered to overexpress glutamate decarboxylase, which without wishing to be bound by theory, led to the expression of GABA by the engineered *E. coli*. As shown in FIG. 6, the engineered *E. coli* was able to induce the growth of *E. gabavorous* KLE1738. GABA can be produced by intestinal epithelial cells and by some bacteria, such as *Escherichia coli* and *Listeria monocytogenes*, by decarboxylation of glutamate. In *E. coli*, the decarboxylation of glutamate can serve as a mechanism to decrease intracellular pH, and therefore in some embodiments GABA production generally occurs at a low pH.

Figure 6A:
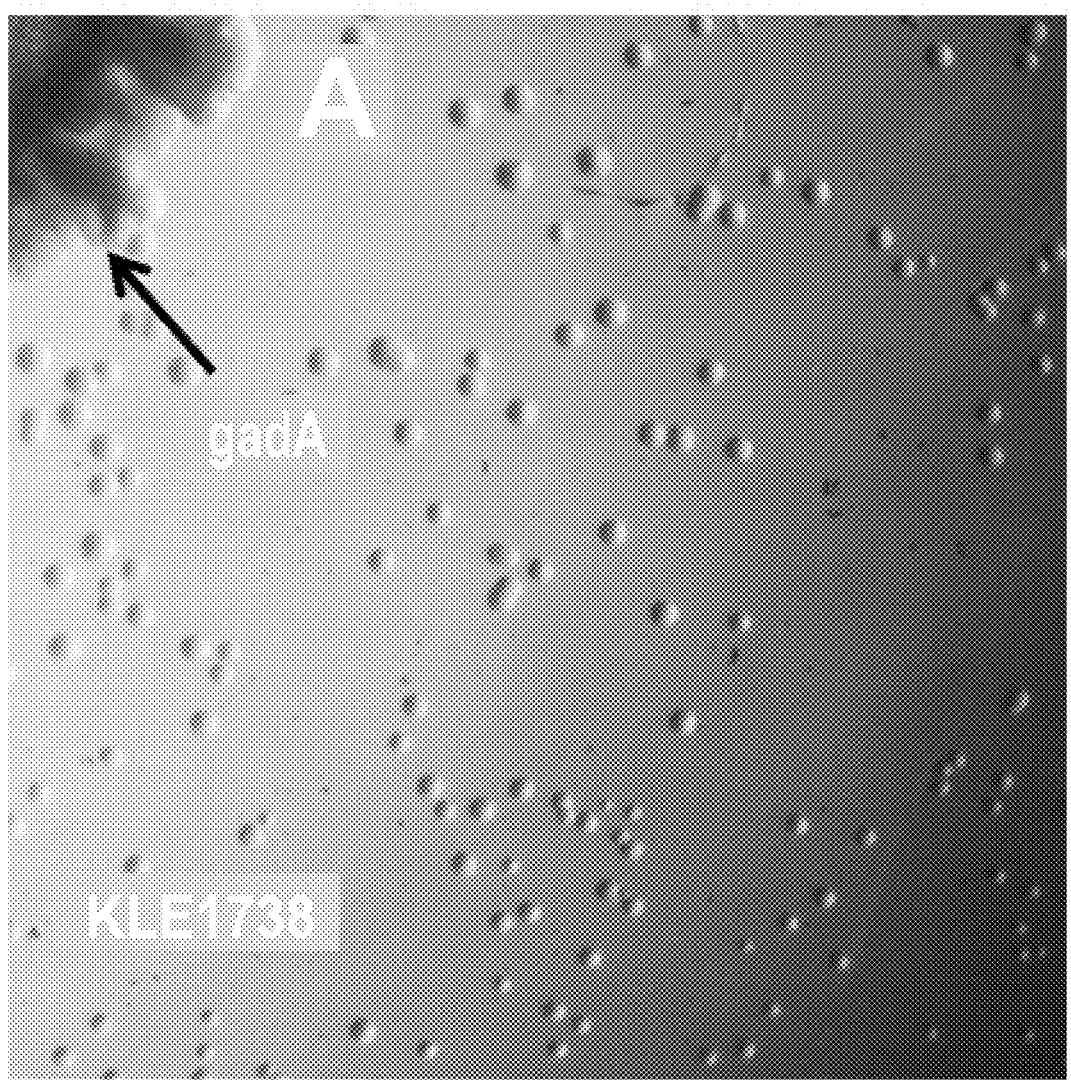
FIG. 6A shows the growth of *E. gabavorous* KLE1738 in the presence of *E. coli* that has been engineered to express glutamate decarboxylase gadA.
Figure 6B:
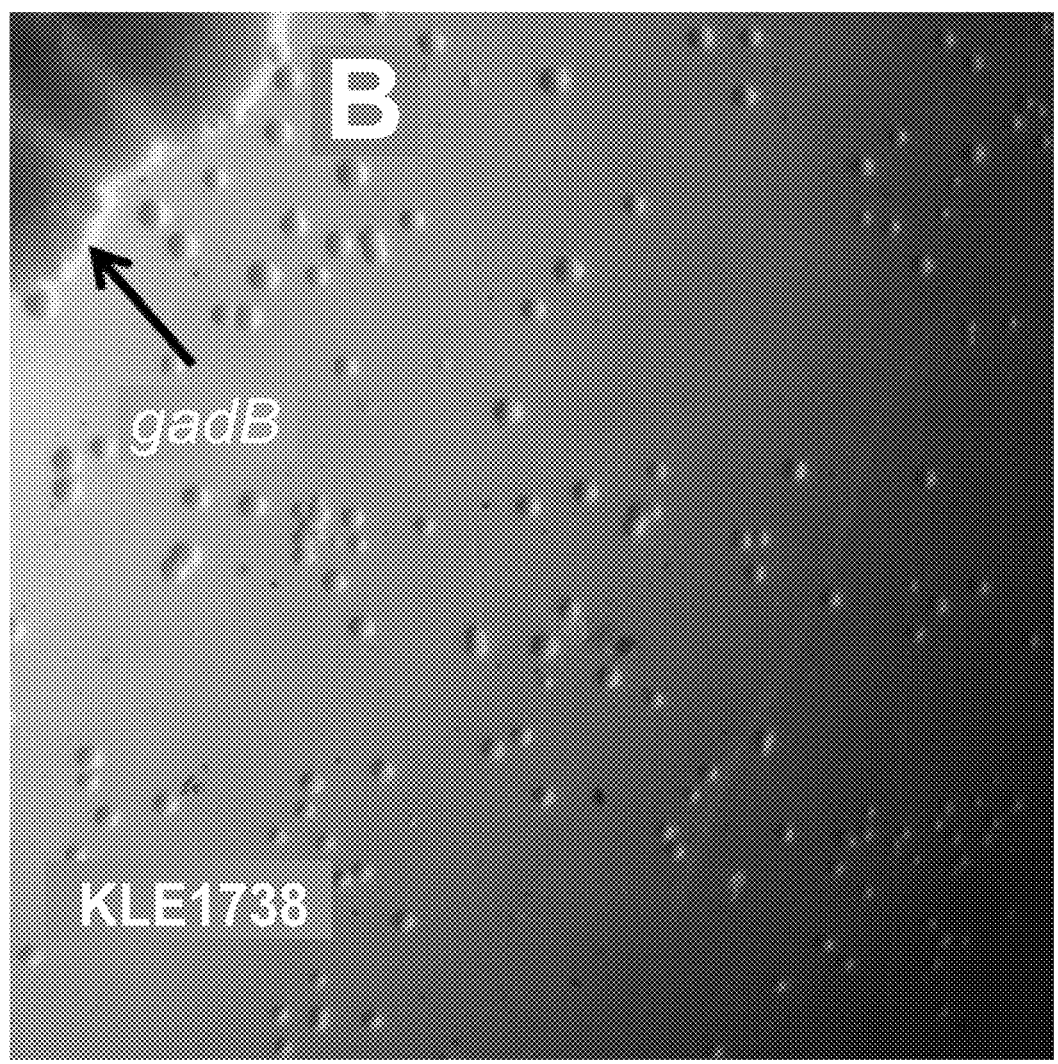
FIG. 6B shows the growth of *E. gabavorous* KLE1738 in the presence of *E. coli* that has been engineered to express glutamate decarboxylase gadB.
Figure 6C:
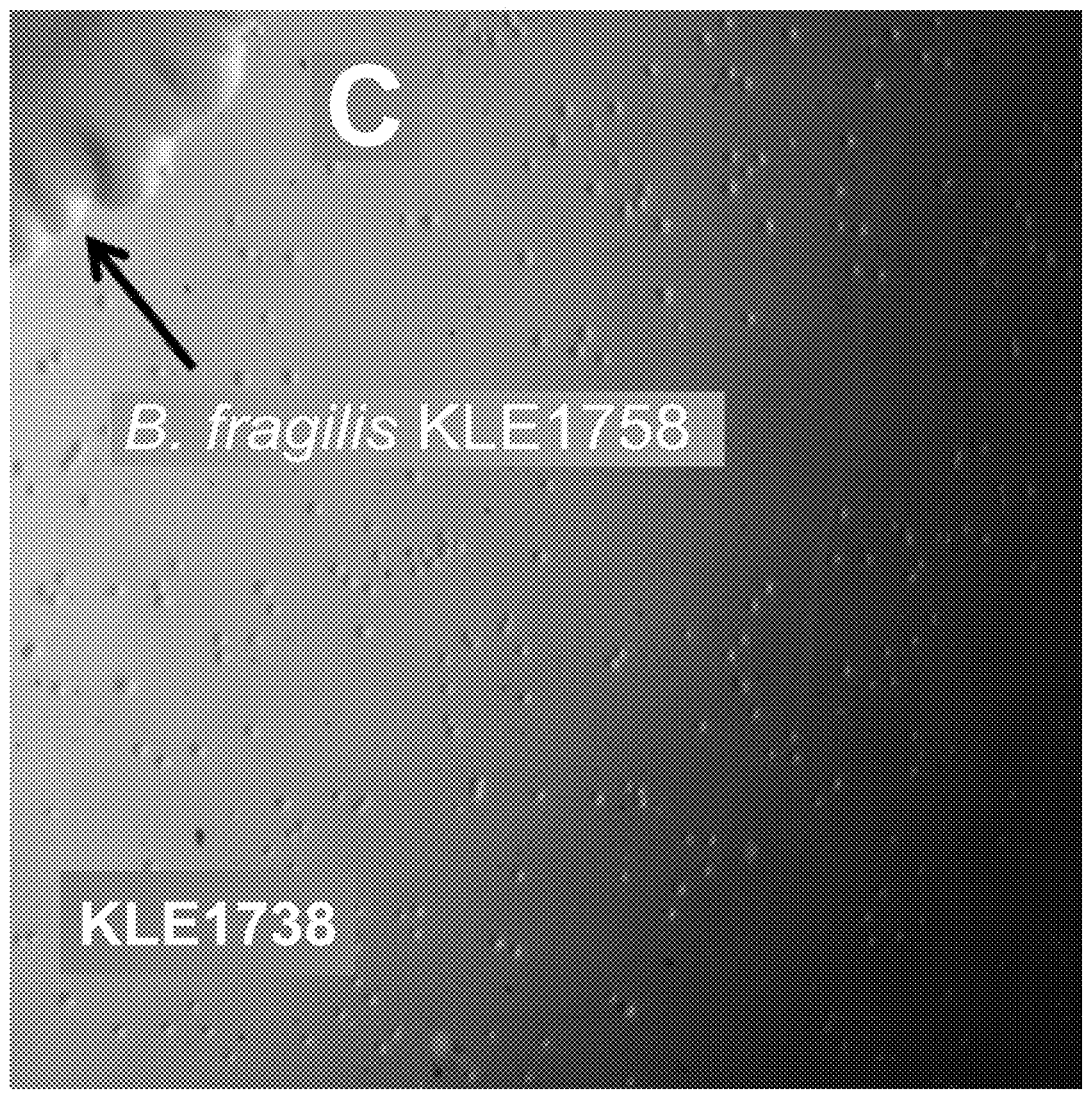
FIG. 6C shows the growth of *E. gabavorous* KLE1738 in the presence of *B. fragilis* KLE1758 that is known to produce GABA.
Figure 6D:
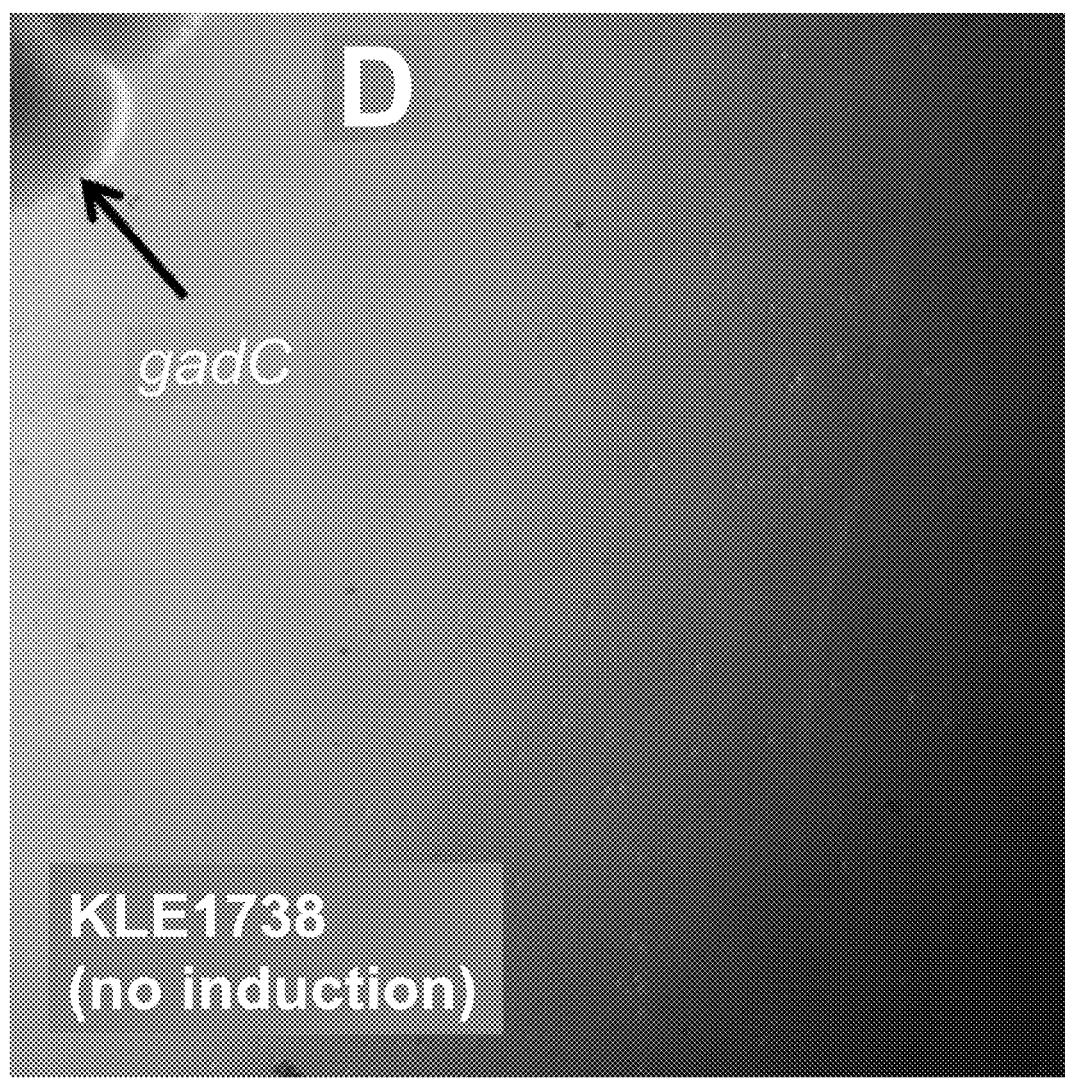
FIG. 6D shows the absence of growth of *E. gabavorous* KLE1738 in the presence of *E. coli* that has been engineered to express glutamate decarboxylase gadC.
Figure 6E:
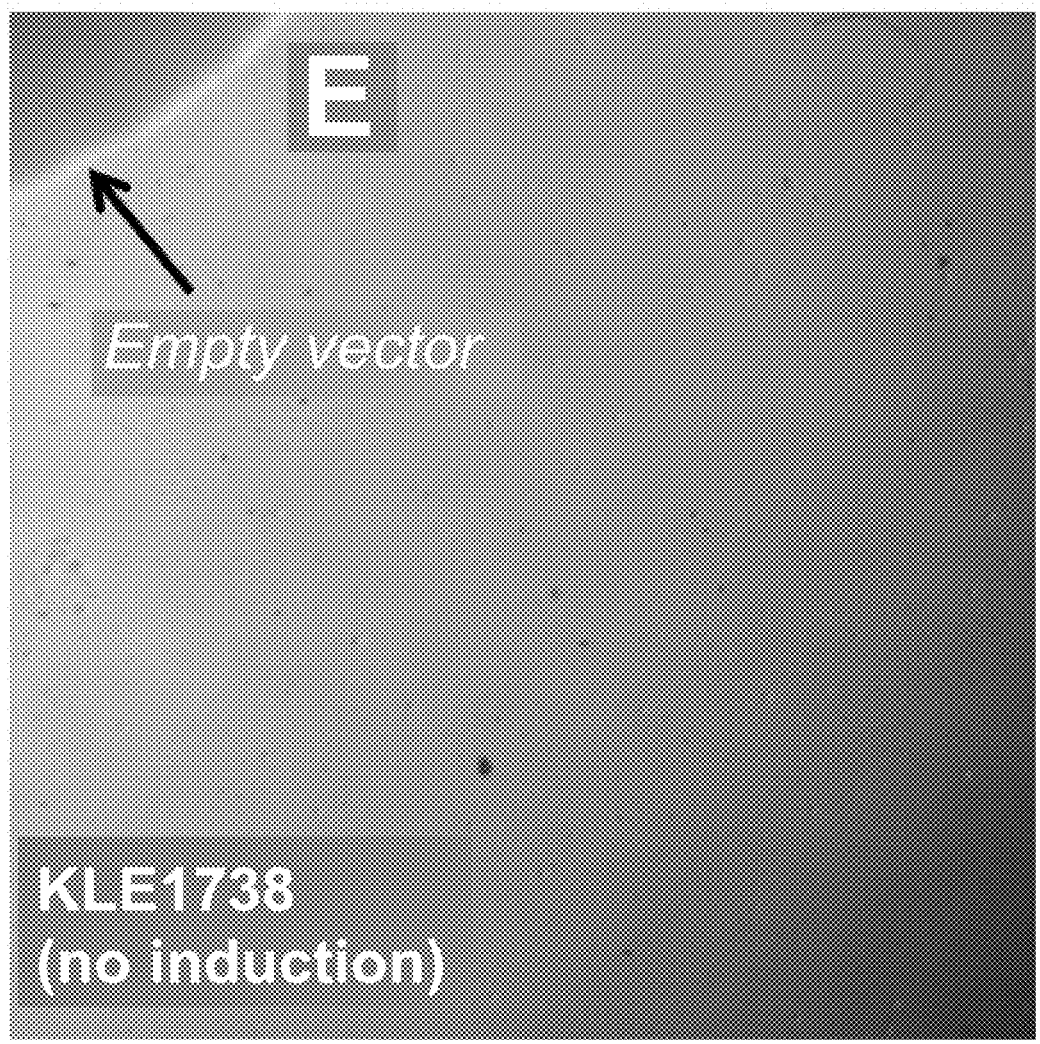
FIG. 6E shows the absence of growth of *E. gabavorous* KLE1738 in the presence empty vector.

As set forth in Example 8, Expression, e.g., overexpression of glutamate decarboxylase in *E. coli* (e.g., gadA or gadB), resulted in induction of *E. gabavorous* KLE1738 growth to levels seen with *B. fragilis* KLE1758. For instance, FIG. 6A shows induction of *E. gabavorous* KLE1738 in the presence of *E. coli* engineered to express glutamate decarboxylase gadA. Similarly, FIG. 6B shows induction of *E. gabavorous* KLE1738 in the presence of *E. coli* engineered to express glutamate decarboxylase gadB. As shown in FIG. 6C, the growth of *E. gabavorous* KLE1738 was qualitatively similar to that seen in the presence of *B. fragilis* KLE 1758. In contrast, as shown in FIG. 6D, when *E. coli* was engineered to express gadC, a GABA antiporter, no growth of *E. gabavorous* KLE1738 was observed. Similarly, no growth of *E. gabavorous* KLE1738 was observed in the presence of empty vehicle (FIG. 6E). Without wishing to be bound by theory the results of Example 8 demonstrate that bacteria can be engineered to produce GABA (e.g., via the expression or overexpression of glutamate decarboxylase). In some embodiments, the bacteria (e.g., *E. coli*) can be engineered to produce GABA inside the human gut.

In some embodiments, the present disclosure also provides compromising one or more repressors of GABA production, (e.g., gadX or gadW). In some embodiments, these repressors can regulate the pH restrictions of GABA production in *E. coli*, is a way to increase native GABA production. This can be achieved, for instance, via gene deletions, insertions, or substitutions, as known by those skilled in the art of molecular biology.

Altering the pH of growth media for KLE1738 did not change the GABA-dependency phenotype. Without wishing to be bound by theory, this suggests that engineering bacteria to overexpress glutamate decarboxylase is an effective way to produce GABA, as well as induce the growth of *E. gabavorous*.

In addition to *E. coli*, other bacteria can be engineered to produce GABA (e.g., at a physiologically relevant pH, such as between 4.5 and 7.5). For instance, any of the bacteria set forth in Table 10 can be engineered to produce GABA (e.g., at a physiologically relevant pH, such as between 4.5 and 7.5). For example, the bacteria can be engineered to contain DNA that codes for one or more enzymes set forth in Table 3-9. Set forth in Table 10 is also a sequence ID number for the 16S nucleotide sequence of the listed bacteria. In some embodiments, the bacteria that are engineered to produce GABA can have at least 90% 16S sequence similarity to the 16S sequences given in Table 10 (e.g., at least 91% similarity, at least 92% similarity, at least 93% similarity, at least 94% similarity, at least 95% similarity, at least 96% similarity, at least 97% similarity, at least 98% similarity, at least 99% similarity, at least 99.5% similarity, at least 99.9% similarity, or 100% similarity).

TABLE 10

Bacteria Capable of Being Engineered to Produce GABA

| Species | Seq. ID No. |
| --- | --- |
| Abiotrophia defectiva | 305 |
| Abiotrophia para-adiacens | 306 |
| Abiotrophia sp. | 307 |
| Acetanaerobacterium elongatum | 308 |
| Acetivibrio cellulolyticus | 309 |
| Acetivibrio ethanolgignens | 310 |
| Acetobacter aceti | 311 |
| Acetobacter fabarum | 312 |
| Acetobacter lovaniensis | 313 |
| Acetobacter malorum | 314 |
| Acetobacter orientalis | 315 |
| Acetobacter pasteurianus | 316 |
| Acetobacter pomorum | 317 |
| Acetobacter syzygii | 318 |
| Acetobacter tropicalis | 319 |
| Acetobacteraceae bacterium | 320 |
| Acholeplasma laidlawii | 321 |
| Achromobacter denitrificans | 322 |
| Achromobacter piechaudii | 323 |
| Achromobacter xylosoxidans | 324 |
| Acidaminococcus fermentans | 325 |
| Acidaminococcus initestini | 326 |
| Acidaminococcus sp. | 327 |
| Acidilobus saccharovorans | 328 |
| Acidithiobacillus ferrivorans | 329 |
| Acidovorax sp. | 330 |
| Acidovorax sp. | 331 |
| Acinetobacter baumannii | 332 |
| Acinetobacter calcoaceticus | 333 |
| Acinetobacter genomosp. | 334 |
| Acinetobacter haemolyticus | 335 |
| Acinetobacter johnsonii | 336 |
| Acinetobacter junii | 337 |
| Acinetobacter lwoffii | 338 |
| Acinetobacter parvus | 339 |
| Acinetobacter radioresistens | 340 |
| Acinetobacter schindleri | 341 |
| Acinetobacter sp. | 342 |

TABLE 10-continued

Bacteria Capable of Being Engineered to Produce GABA

| Species | Seq. ID No. |
| --- | --- |
| Acinetobacter sp. | 343 |
| Acinetobacter sp. | 344 |
| Acinetobacter sp. | 345 |
| Acinetobacter sp. | 346 |
| Acinetobacter sp. | 347 |
| Acinetobacter sp. | 348 |
| Actinobacillus minor | 349 |
| Actinobacillus pleuropneumoniae | 350 |
| Actinobacillus succinogenes | 351 |
| Actinobacillus succinogenes | 352 |
| Actinobacillus ureae | 353 |
| Actinobaculum massiliae | 354 |
| Actinobaculum schaalii | 355 |
| Actinobaculum sp. | 356 |
| Actinobaculum sp. | 357 |
| Actinomyces cardiffensis | 358 |
| Actinomyces europaeus | 359 |
| Actinomyces funkei | 360 |
| Actinomyces genomosp. | 361 |
| Actinomyces genomosp. | 362 |
| Actinomyces genomosp. | 363 |
| Actinomyces georgiae | 364 |
| Actinomyces israelii | 365 |
| Actinomyces massiliensis | 366 |
| Actinomyces meyeri | 367 |
| Actinomyces naeslundii | 368 |
| Actinomyces nasicola | 369 |
| Actinomyces neuii | 370 |
| Actinomyces odontolyticus | 371 |
| Actinomyces oricola | 372 |
| Actinomyces orihominis | 373 |
| Actinomyces oris | 374 |
| Actinomyces sp. | 375 |
| Actinomyces sp. | 376 |
| Actinomyces sp. | 377 |
| Actinomyces sp. | 378 |
| Actinomyces sp. | 379 |
| Actinomyces sp. | 380 |
| Actinomyces sp. | 381 |
| Actinomyces sp. | 382 |
| Actinomyces sp. | 383 |
| Actinomyces sp. | 384 |
| Actinomyces sp. | 385 |
| Actinomyces sp. | 386 |
| Actinomyces sp. | 387 |
| Actinomyces sp. | 388 |
| Actinomyces sp. | 389 |
| Actinomyces sp. | 390 |
| Actinomyces sp. | 391 |
| Actinomyces sp. | 392 |
| Actinomyces sp. | 393 |
| Actinomyces sp. | 394 |
| Actinomyces sp. | 395 |
| Actinomyces sp. | 396 |
| Actinomyces sp. | 397 |
| Actinomyces sp. | 398 |
| Actinomyces sp. | 399 |
| Actinomyces urogenitalis | 400 |
| Actinomyces viscosus | 401 |
| Adlercreutzia equolifaciens | 402 |
| Aerococcus sanguinicola | 403 |
| Aerococcus urinae | 404 |
| Aerococcus urinaeequi | 405 |
| Aerococcus viridans | 406 |
| Aeromicrobium marinum | 407 |
| Aeromicrobium sp. | 408 |
| Aeromonas allosaccharophila | 409 |
| Aeromonas enteropelogenes | 410 |
| Aeromonas hydrophila | 411 |
| Aeromonas jandaei | 412 |
| Aeromonas salmonicida | 413 |
| Aeromonas trota | 414 |
| Aeromonas veronii | 415 |
| Afipia genomosp. | 416 |
| Aggregatibacter actinomycetemcomitans | 417 |
| Aggregatibacter aphrophilus | 418 |

TABLE 10-continued

Bacteria Capable of Being Engineered to Produce GABA

| Species | Seq. ID No. |
|---|---|
| Aggregatibacter segnis | 419 |
| Agrobacterium radiobacter | 420 |
| Agrobacterium tumefaciens | 421 |
| Agrococcus jenensis | 422 |
| Akkermansia muciniphila | 423 |
| Alcaligenes faecalis | 424 |
| Alcaligenes sp. | 425 |
| Alcaligenes sp. | 426 |
| Alicyclobacillus acidocaldarius | 427 |
| Alicyclobacillus acidoterrestris | 428 |
| Alicyclobacillus contaminans | 429 |
| Alicyclobacillus cycloheptanicus | 430 |
| Alicyclobacillus herbarius | 431 |
| Alicyclobacillus pomorum | 432 |
| Alicyclobacillus sp. | 433 |
| Alistipes finegoldii | 434 |
| Alistipes indistinctus | 435 |
| Alistipes onderdonkii | 436 |
| Alistipes putredinis | 437 |
| Alistipes shahii | 438 |
| Alistipes sp. | 439 |
| Alistipes sp. | 440 |
| Alistipes sp. | 441 |
| Alkaliphilus metalliredigenes | 442 |
| Alkaliphilus oremlandii | 443 |
| Alloscardovia omnicolens | 444 |
| Alloscardovia sp. | 445 |
| Anaerobaculum hydrogeniformans | 446 |
| Anaerobiospirillum succiniciproducens | 447 |
| Anaerobiospirillum thomasii | 448 |
| Anaerococcus hydrogenalis | 449 |
| Anaerococcus lactolyticus | 450 |
| Anaerococcus octavius | 451 |
| Anaerococcus prevotii | 452 |
| Anaerococcus sp. | 453 |
| Anaerococcus sp. | 454 |
| Anaerococcus sp. | 455 |
| Anaerococcus sp. | 456 |
| Anaerococcus sp. | 457 |
| Anaerococcus sp. | 458 |
| Anaerococcus sp. | 459 |
| Anaerococcus sp. | 460 |
| Anaerococcus sp. | 461 |
| Anaerococcus tetradius | 462 |
| Anaerococcus vaginalis | 463 |
| Anaerofustis stercorihominis | 464 |
| Anaeroglobus geminatus | 465 |
| Anaerosporobacter mobilis | 466 |
| Anaerostipes caccae | 467 |
| Anaerostipes sp. | 468 |
| Anaerotruncus colihominis | 469 |
| Anaplasma marginale | 470 |
| Anaplasma phagocytophilum | 471 |
| Aneurinibacillus aneurinilyticus | 472 |
| Aneurinibacillus danicus | 473 |
| Aneurinibacillus migulanus | 474 |
| Aneurinibacillus terranovensis | 475 |
| Aneurybacillus thermoaerophilus | 476 |
| Anoxybacillus contaminans | 477 |
| Anoxybacillus flavithermus | 478 |
| Arcanobacterium haemolyticum | 479 |
| Arcanobacterium pyogenes | 480 |
| Arcobacter butzleri | 481 |
| Arcobacter cryaerophilus | 482 |
| Arthrobacter agilis | 483 |
| Arthrobacter arilaitensis | 484 |
| Arthrobacter bergerei | 485 |
| Arthrobacter globiformis | 486 |
| Arthrobacter nicotianae | 487 |
| Atopobium minutum | 488 |
| Atopobium parvulum | 489 |
| Atopobium rimae | 490 |
| Atopobium sp. | 491 |
| Atopobium sp. | 492 |
| Atopobium sp. | 493 |
| Atopobium sp. | 494 |
| Atopobium vaginae | 495 |
| Aurantimonas coralicida | 496 |
| Aureimonas altamirensis | 497 |
| Auritibacter ignavus | 498 |
| Averyella dalhousiensis | 499 |
| Bacillus aeolius | 500 |
| Bacillus aerophilus | 501 |
| Bacillus aestuarii | 502 |
| Bacillus alcalophilus | 503 |
| Bacillus amyloliquefaciens | 504 |
| Bacillus atrophaeus | 505 |
| Bacillus badius | 506 |
| Bacillus cereus | 507 |
| Bacillus circulans | 508 |
| Bacillus clausii | 509 |
| Bacillus coagulans | 510 |
| Bacillus firmus | 511 |
| Bacillus flexus | 512 |
| Bacillus fordii | 513 |
| Bacillus gelatini | 514 |
| Bacillus halmapalus | 515 |
| Bacillus halodurans | 516 |
| Bacillus herbersteinensis | 517 |
| Bacillus horti | 518 |
| Bacillus idriensis | 519 |
| Bacillus lentus | 520 |
| Bacillus licheniformis | 521 |
| Bacillus megaterium | 522 |
| Bacillus nealsonii | 523 |
| Bacillus niabensis | 524 |
| Bacillus niacini | 525 |
| Bacillus pocheonensis | 526 |
| Bacillus pumilus | 527 |
| Bacillus safensis | 528 |
| Bacillus simple | 529 |
| Bacillus sonorensis | 530 |
| Bacillus sp. | 531 |
| Bacillus sp. | 532 |
| Bacillus sp. | 533 |
| Bacillus sp. | 534 |
| Bacillus sp. | 535 |
| Bacillus sp. | 536 |
| Bacillus sp. | 537 |
| Bacillus sp. | 538 |
| Bacillus sp. | 539 |
| Bacillus sp. | 540 |
| Bacillus sp. | 541 |
| Bacillus sp. | 542 |
| Bacillus sp. | 543 |
| Bacillus sp. | 544 |
| Bacillus sp. | 545 |
| Bacillus sp. | 546 |
| Bacillus sp. | 547 |
| Bacillus sp. | 548 |
| Bacillus sp. | 549 |
| Bacillus sp. | 550 |
| Bacillus sp. | 551 |
| Bacillus sp. | 552 |
| Bacillus sp. | 553 |
| Bacillus sp. | 554 |
| Bacillus sphaericus | 555 |
| Bacillus sporothermodurans | 556 |
| Bacillus subtilis | 557 |
| Bacillus thermoamylovorans | 558 |
| Bacillus thuringiensis | 559 |
| Bacillus weihenstephanensis | 560 |
| Bacteroidales bacterium | 561 |
| Bacteroidales genomosp. | 562 |
| Bacteroidales genomosp. | 563 |
| Bacteroidales genomosp. | 564 |
| Bacteroidales genomosp. | 565 |
| Bacteroidales genomosp. | 566 |
| Bacteroidales genomosp. | 567 |
| Bacteroidales genomosp. | 568 |
| Bacteroidales genomosp. | 569 |
| Bacteroides acidifaciens | 570 |

TABLE 10-continued

Bacteria Capable of Being Engineered to Produce GABA

| Species | Seq. ID No. |
|---|---|
| Bacteroides barnesiae | 571 |
| Bacteroides caccae | 572 |
| Bacteroides cellulosilyticus | 573 |
| Bacteroides clarus | 574 |
| Bacteroides coagulans | 575 |
| Bacteroides coprocola | 576 |
| Bacteroides coprophilus | 577 |
| Bacteroides dorei | 578 |
| Bacteroides eggerthii | 579 |
| Bacteroides faecis | 580 |
| Bacteroides finegoldii | 581 |
| Bacteroides fluxus | 582 |
| Bacteroides fragilis | 583 |
| Bacteroides galacturonicus | 584 |
| Bacteroides helcogenes | 585 |
| Bacteroides heparinolyticus | 586 |
| Bacteroides intestinalis | 587 |
| Bacteroides massiliensis | 588 |
| Bacteroides nordii | 589 |
| Bacteroides oleiciplenus | 590 |
| Bacteroides ovatus | 591 |
| Bacteroides pectinophilus | 592 |
| Bacteroides plebeius | 593 |
| Bacteroides pyogenes | 594 |
| Bacteroides salanitronis | 595 |
| Bacteroides salyersiae | 596 |
| Bacteroides sp. | 597 |
| Bacteroides sp. | 598 |
| Bacteroides sp. | 599 |
| Bacteroides sp. | 600 |
| Bacteroides sp. | 601 |
| Bacteroides sp. | 602 |
| Bacteroides sp. | 603 |
| Bacteroides sp. | 604 |
| Bacteroides sp. | 605 |
| Bacteroides sp. | 606 |
| Bacteroides sp. | 607 |
| Bacteroides sp. | 608 |
| Bacteroides sp. | 609 |
| Bacteroides sp. | 610 |
| Bacteroides sp. | 611 |
| Bacteroides sp. | 612 |
| Bacteroides sp. | 613 |
| Bacteroides sp. | 614 |
| Bacteroides sp. | 615 |
| Bacteroides sp. | 616 |
| Bacteroides sp. | 617 |
| Bacteroides sp. | 618 |
| Bacteroides sp. | 619 |
| Bacteroides sp. | 620 |
| Bacteroides sp. | 621 |
| Bacteroides sp. | 622 |
| Bacteroides sp. | 623 |
| Bacteroides sp. | 624 |
| Bacteroides sp. | 625 |
| Bacteroides sp. | 626 |
| Bacteroides sp. | 627 |
| Bacteroides sp. | 628 |
| Bacteroides sp. | 629 |
| Bacteroides sp. | 630 |
| Bacteroides sp. | 631 |
| Bacteroides stercoris | 632 |
| Bacteroides thetaiotaomicron | 633 |
| Bacteroides uniformis | 634 |
| Bacteroides ureolyticus | 635 |
| Bacteroides vulgatus | 636 |
| Bacteroides xylanisolvens | 637 |
| Bacteroidetes bacterium | 638 |
| Bacteroidetes bacterium | 639 |
| Bacteroidetes bacterium | 640 |
| Barnesiella intestinihominis | 641 |
| Barnesiella viscericola | 642 |
| Bartonella bacilliformis | 643 |
| Bartonella grahamii | 644 |
| Bartonella henselae | 645 |
| Bartonella quintana | 646 |
| Bartonella tamiae | 647 |
| Bartonella washoensis | 648 |
| Bdellovibrio sp. | 649 |
| Bifidobacteriaceae genomosp. | 650 |
| Bifidobacterium adolescentis | 651 |
| Bifidobacterium angulatum | 652 |
| Bifidobacterium animalis | 653 |
| Bifidobacterium bifidum | 654 |
| Bifidobacterium breve | 655 |
| Bifidobacterium catenulatum | 656 |
| Bifidobacterium gallicum | 657 |
| Bifidobacterium infantis | 658 |
| Bifidobacterium kashiwanohense | 659 |
| Bifidobacterium longum | 660 |
| Bifidobacterium pseudocatenulatum | 661 |
| Bifidobacterium pseudolongum | 662 |
| Bifidobacterium scardovii | 663 |
| Bifidobacterium sp. | 664 |
| Bifidobacterium sp. | 665 |
| Bifidobacterium sp. | 666 |
| Bifidobacterium sp. | 667 |
| Bifidobacterium sp. | 668 |
| Bifidobacterium thermophilum | 669 |
| Bifidobacterium urinalis | 670 |
| Bilophila wadsworthia | 671 |
| Bisgaard Taxon | 672 |
| Bisgaard Taxon | 673 |
| Bisgaard Taxon | 674 |
| Bisgaard Taxon | 675 |
| Blastomonas natatoria | 676 |
| Blautia coccoides | 677 |
| Blautia glucerasea | 678 |
| Blautia glucerasei | 679 |
| Blautia hansenii | 680 |
| Blautia hydrogenotrophica | 681 |
| Blautia luti | 682 |
| Blautia producta | 683 |
| Blautia schinkii | 684 |
| Blautia sp. | 685 |
| Blautia stercoris | 686 |
| Blautia wexlerae | 687 |
| Brachybacterium alimentarium | 688 |
| Brachybacterium conglomeratum | 689 |
| Brachybacterium tyrofermentans | 690 |
| Brachyspira aalborgi | 691 |
| Brachyspira pilosicoli | 692 |
| Brachyspira sp. | 693 |
| Brachyspira sp. | 694 |
| Brachyspira sp. | 695 |
| Brevibacillus agri | 696 |
| Brevibacillus brevis | 697 |
| Brevibacillus centrosporus | 698 |
| Brevibacillus choshinensis | 699 |
| Brevibacillus invocatus | 700 |
| Brevibacillus laterosporus | 701 |
| Brevibacillus parabrevis | 702 |
| Brevibacillus reuszeri | 703 |
| Brevibacillus sp. | 704 |
| Brevibacillus thermoruber | 705 |
| Brevibacterium aurantiacum | 706 |
| Brevibacterium casei | 707 |
| Brevibacterium epidermidis | 708 |
| Brevibacterium frigoritolerans | 709 |
| Brevibacterium linens | 710 |
| Brevibacterium mcbrellneri | 711 |
| Brevibacterium paucivorans | 712 |
| Brevibacterium sanguinis | 713 |
| Brevibacterium sp. | 714 |
| Brevibacterium sp. | 715 |
| Brevundimonas subvibrioides | 716 |
| Bryantella formatexigens | 717 |
| Buchnera aphidicola | 718 |
| Bulleidia extructa | 719 |
| Butyricicoccus pullicaecorum | 720 |
| Butyricimonas virosa | 721 |
| Butyrivibrio crossotus | 722 |

TABLE 10-continued

Bacteria Capable of Being Engineered to Produce GABA

| Species | Seq. ID No. |
|---|---|
| Butyrivibrio fibrisolvens | 723 |
| Caldimonas manganoxidans | 724 |
| Caminicella sporogenes | 725 |
| Candidatus arthromitus | 726 |
| Candidatus sulcia | 727 |
| Capnocytophaga canimorsus | 728 |
| Capnocytophaga genomosp. | 729 |
| Capnocytophaga gingivalis | 730 |
| Capnocytophaga granulosa | 731 |
| Capnocytophaga ochracea | 732 |
| Capnocytophaga sp. | 733 |
| Capnocytophaga sp. | 734 |
| Capnocytophaga sp. | 735 |
| Capnocytophaga sp. | 736 |
| Capnocytophaga sp. | 737 |
| Capnocytophaga sp. | 738 |
| Capnocytophaga sp. | 739 |
| Capnocytophaga sputigena | 740 |
| Cardiobacterium hominis | 741 |
| Cardiobacterium valvarum | 742 |
| Carnobacterium divergens | 743 |
| Carnobacterium maltaromaticum | 744 |
| Catabacter hongkongensis | 745 |
| Catenibacterium mitsuokai | 746 |
| Catonella genomosp. | 747 |
| Catonella morbi | 748 |
| Catonella sp. | 749 |
| Cedecea davisae | 750 |
| Cellulosimicrobium funkei | 751 |
| Cetobacterium somerae | 752 |
| Chlamydiales bacterium | 753 |
| Chlamydiales bacterium | 754 |
| Chlamydiales bacterium | 755 |
| Chloroflexi genomosp. | 756 |
| Christensenella minuta | 757 |
| Chromobacterium violaceum | 758 |
| Chryseobacterium anthropi | 759 |
| Chryseobacterium gleum | 760 |
| Chryseobacterium hominis | 761 |
| Citrobacter amalonaticus | 762 |
| Citrobacter braakii | 763 |
| Citrobacter farmeri | 764 |
| Citrobacter freundii | 765 |
| Citrobacter gillenii | 766 |
| Citrobacter koseri | 767 |
| Citrobacter murliniae | 768 |
| Citrobacter rodentium | 769 |
| Citrobacter sedlakii | 770 |
| Citrobacter sp. | 771 |
| Citrobacter sp. | 772 |
| Citrobacter werkmanii | 773 |
| Citrobacter youngae | 774 |
| Cloacibacillus evryensis | 775 |
| Clostridiaceae bacterium | 776 |
| Clostridiaceae bacterium | 777 |
| Clostridiales bacterium | 778 |
| Clostridiales bacterium | 779 |
| Clostridiales bacterium | 780 |
| Clostridiales bacterium | 781 |
| Clostridiales bacterium | 782 |
| Clostridiales bacterium | 783 |
| Clostridiales bacterium | 784 |
| Clostridiales bacterium | 785 |
| Clostridiales genomosp. | 786 |
| Clostridiales sp. | 787 |
| Clostridiales sp. | 788 |
| Clostridiales sp. | 789 |
| Clostridium acetobutylicum | 790 |
| Clostridium aerotolerans | 791 |
| Clostridium aldenense | 792 |
| Clostridium aldrichii | 793 |
| Clostridium algidicarnis | 794 |
| Clostridium algidixylanolyticum | 795 |
| Clostridium aminovalericum | 796 |
| Clostridium amygdalinum | 797 |
| Clostridium argentinense | 798 |
| Clostridium asparagiforme | 799 |
| Clostridium baratii | 800 |
| Clostridium bartlettii | 801 |
| Clostridium beijerinckii | 802 |
| Clostridium bifermentans | 803 |
| Clostridium bolteae | 804 |
| Clostridium butyricum | 805 |
| Clostridium cadaveris | 806 |
| Clostridium carboxidivorans | 807 |
| Clostridium carnis | 808 |
| Clostridium celatum | 809 |
| Clostridium celerecrescens | 810 |
| Clostridium cellulosi | 811 |
| Clostridium chauvoei | 812 |
| Clostridium citroniae | 813 |
| Clostridium clariflavum | 814 |
| Clostridium clostridioforme | 815 |
| Clostridium coccoides | 816 |
| Clostridium cochlearium | 817 |
| Clostridium cocleatum | 818 |
| Clostridium colicanis | 819 |
| Clostridium colinum | 820 |
| Clostridium disporicum | 821 |
| Clostridium estertheticum | 822 |
| Clostridium falla | 823 |
| Clostridium favososporum | 824 |
| Clostridium felsineum | 825 |
| Clostridium frigidicarnis | 826 |
| Clostridium gasigenes | 827 |
| Clostridium ghonii | 828 |
| Clostridium glycolicum | 829 |
| Clostridium glycyrrhizinilyticum | 830 |
| Clostridium haemolyticum | 831 |
| Clostridium hathewayi | 832 |
| Clostridium hiranonis | 833 |
| Clostridium histolyticum | 834 |
| Clostridium hylemonae | 835 |
| Clostridium indolis | 836 |
| Clostridium innocuum | 837 |
| Clostridium irregulare | 838 |
| Clostridium isatidis | 839 |
| Clostridium kluyveri | 840 |
| Clostridium lactatifermentans | 841 |
| Clostridium lavalense | 842 |
| Clostridium leptum | 843 |
| Clostridium limosum | 844 |
| Clostridium magnum | 845 |
| Clostridium malenominatum | 846 |
| Clostridium mayombei | 847 |
| Clostridium methylpentosum | 848 |
| Clostridium nexile | 849 |
| Clostridium novyi | 850 |
| Clostridium orbiscindens | 851 |
| Clostridium oroticum | 852 |
| Clostridium paraputrificum | 853 |
| Clostridium phytofermentans | 854 |
| Clostridium piliforme | 855 |
| Clostridium putrefaciens | 856 |
| Clostridium quinii | 857 |
| Clostridium ramosum | 858 |
| Clostridium rectum | 859 |
| Clostridium saccharogumia | 860 |
| Clostridium saccharolyticum | 861 |
| Clostridium saccharolyticum | 862 |
| Clostridium sardiniense | 863 |
| Clostridium sartagoforme | 864 |
| Clostridium scindens | 865 |
| Clostridium septicum | 866 |
| Clostridium sordellii | 867 |
| Clostridium sp. | 868 |
| Clostridium sp. | 869 |
| Clostridium sp. | 870 |
| Clostridium sp. | 871 |
| Clostridium sp. | 872 |
| Clostridium sp. | 873 |
| Clostridium sp. | 874 |

TABLE 10-continued

Bacteria Capable of Being Engineered to Produce GABA

| Species | Seq. ID No. |
|---|---|
| Clostridium sp. | 875 |
| Clostridium sp. | 876 |
| Clostridium sp. | 877 |
| Clostridium sp. | 878 |
| Clostridium sp. | 879 |
| Clostridium sp. | 880 |
| Clostridium sp. | 881 |
| Clostridium sp. | 882 |
| Clostridium sp. | 883 |
| Clostridium sp. | 884 |
| Clostridium sphenoides | 885 |
| Clostridium spiroforme | 886 |
| Clostridium sporogenes | 887 |
| Clostridium sporosphaeroides | 888 |
| Clostridium stercorarium | 889 |
| Clostridium sticklandii | 890 |
| Clostridium straminisolvens | 891 |
| Clostridium subterminale | 892 |
| Clostridium sulfidigenes | 893 |
| Clostridium symbiosum | 894 |
| Clostridium tertium | 895 |
| Clostridium tetani | 896 |
| Clostridium thermocellum | 897 |
| Clostridium tyrobutyricum | 898 |
| Clostridium viride | 899 |
| Clostridium xylanolyticum | 900 |
| Collinsella aerofaciens | 901 |
| Collinsella intestinalis | 902 |
| Collinsella stercoris | 903 |
| Collinsella tanakaei | 904 |
| Comamonadaceae bacterium | 905 |
| Comamonadaceae bacterium | 906 |
| Comamonadaceae bacterium | 907 |
| Comamonadaceae bacterium | 908 |
| Comamonadaceae bacterium | 909 |
| Comamonas sp. | 910 |
| Conchiformibius kuhniae | 911 |
| Coprobacillus cateniformis | 912 |
| Coprobacillus sp. | 913 |
| Coprobacillus sp. | 914 |
| Coprococcus catus | 915 |
| Coprococcus comes | 916 |
| Coprococcus eutactus | 917 |
| Coprococcus sp. | 918 |
| Coriobacteriaceae bacterium | 919 |
| Coriobacteriaceae bacterium | 920 |
| Coriobacteriaceae bacterium | 921 |
| Corynebacterium accolens | 922 |
| Corynebacterium ammoniagenes | 923 |
| Corynebacterium appendicis | 924 |
| Corynebacterium argentoratense | 925 |
| Corynebacterium atypicum | 926 |
| Corynebacterium aurimucosum | 927 |
| Corynebacterium bovis | 928 |
| Corynebacterium canis | 929 |
| Corynebacterium casei | 930 |
| Corynebacterium confusum | 931 |
| Corynebacterium coyleae | 932 |
| Corynebacterium durum | 933 |
| Corynebacterium efficiens | 934 |
| Corynebacterium falsenii | 935 |
| Corynebacterium flavescens | 936 |
| Corynebacterium genitalium | 937 |
| Corynebacterium glaucum | 938 |
| Corynebacterium glucuronolyticum | 939 |
| Corynebacterium glutamicum | 940 |
| Corynebacterium hansenii | 941 |
| Corynebacterium imitans | 942 |
| Corynebacterium kroppenstedtii | 943 |
| Corynebacterium lipophiloflavum | 944 |
| Corynebacterium macginleyi | 945 |
| Corynebacterium mastitidis | 946 |
| Corynebacterium matruchotii | 947 |
| Corynebacterium minutissimum | 948 |
| Corynebacterium mucifaciens | 949 |
| Corynebacterium propinquum | 950 |
| Corynebacterium pseudodiphtheriticum | 951 |
| Corynebacterium pseudogenitalium | 952 |
| Corynebacterium pseudotuberculosis | 953 |
| Corynebacterium pyruviciproducens | 954 |
| Corynebacterium renale | 955 |
| Corynebacterium resistens | 956 |
| Corynebacterium riegelii | 957 |
| Corynebacterium simulans | 958 |
| Corynebacterium singulare | 959 |
| Corynebacterium sp. | 960 |
| Corynebacterium sp. | 961 |
| Corynebacterium sp. | 962 |
| Corynebacterium sp. | 963 |
| Corynebacterium sp. | 964 |
| Corynebacterium sundsvallense | 965 |
| Corynebacterium tuberculostearicum | 966 |
| Corynebacterium tuscaniae | 967 |
| Corynebacterium ulcerans | 968 |
| Corynebacterium ureicelerivorans | 969 |
| Corynebacterium variabile | 970 |
| Cronobacter malonaticus | 971 |
| Cronobacter sakazakii | 972 |
| Cronobacter turicensis | 973 |
| Cryptobacterium curtum | 974 |
| Cupriavidus metallidurans | 975 |
| Cytophaga xylanolytica | 976 |
| Deferribacteres sp. | 977 |
| Deferribacteres sp. | 978 |
| Deferribacteres sp. | 979 |
| Deinococcus radiodurans | 980 |
| Deinococcus sp. | 981 |
| Delftia acidovorans | 982 |
| Dermabacter hominis | 983 |
| Dermacoccus sp. | 984 |
| Desmospora activa | 985 |
| Desmospora sp. | 986 |
| Desulfitobacterium frappieri | 987 |
| Desulfitobacterium hafniense | 988 |
| Desulfobulbus sp. | 989 |
| Desulfotomaculum nigrificans | 990 |
| Desulfovibrio desulfuricans | 991 |
| Desulfovibrio fairfieldensis | 992 |
| Desulfovibrio piger | 993 |
| Desulfovibrio sp. | 994 |
| Desulfovibrio vulgaris | 995 |
| Dialister invisus | 996 |
| Dialister micraerophilus | 997 |
| Dialister microaerophilus | 998 |
| Dialister pneumosintes | 999 |
| Dialister propionicifaciens | 1000 |
| Dialister sp. | 1001 |
| Dialister succinatiphilus | 1002 |
| Dietzia natronolimnaea | 1003 |
| Dietzia sp. | 1004 |
| Dietzia sp. | 1005 |
| Dietzia timorensis | 1006 |
| Dorea formicigenerans | 1007 |
| Dorea longicatena | 1008 |
| Dysgonomonas gadei | 1009 |
| Dysgonomonas mossii | 1010 |
| Edwardsiella tarda | 1011 |
| Eggerthella lenta | 1012 |
| Eggerthella sinensis | 1013 |
| Eggerthella sp. | 1014 |
| Eggerthella sp. | 1015 |
| Eggerthella sp. | 1016 |
| Eikenella corrodens | 1017 |
| Enhydrobacter aerosaccus | 1018 |
| Enterobacter aerogenes | 1019 |
| Enterobacter asburiae | 1020 |
| Enterobacter cancerogenus | 1021 |
| Enterobacter cloacae | 1022 |
| Enterobacter cowanii | 1023 |
| Enterobacter hormaechei | 1024 |
| Enterobacter sp. | 1025 |
| Enterobacter sp. | 1026 |

TABLE 10-continued

Bacteria Capable of Being Engineered to Produce GABA

| Species | Seq. ID No. |
|---|---|
| Enterobacter sp. | 1027 |
| Enterobacter sp. | 1028 |
| Enterobacter sp. | 1029 |
| Enterobacteriaceae bacterium | 1030 |
| Enterobacteriaceae bacterium | 1031 |
| Enterobacteriaceae bacterium | 1032 |
| Enterococcus avium | 1033 |
| Enterococcus caccae | 1034 |
| Enterococcus casseliflavus | 1035 |
| Enterococcus durans | 1036 |
| Enterococcus faecalis | 1037 |
| Enterococcus faecium | 1038 |
| Enterococcus gallinarum | 1039 |
| Enterococcus gilvus | 1040 |
| Enterococcus hawaiiensis | 1041 |
| Enterococcus hirae | 1042 |
| Enterococcus italicus | 1043 |
| Enterococcus mundtii | 1044 |
| Enterococcus raffinosus | 1045 |
| Enterococcus sp. | 1046 |
| Enterococcus sp. | 1047 |
| Enterococcus sp. | 1048 |
| Enterococcus sp. | 1049 |
| Enterococcus thailandicus | 1050 |
| Eremococcus coleocola | 1051 |
| Erysipelothrix inopinata | 1052 |
| Erysipelothrix rhusiopathiae | 1053 |
| Erysipelothrix tonsillarum | 1054 |
| Erysipelotrichaceae bacterium | 1055 |
| Erysipelotrichaceae bacterium | 1056 |
| Escherichia albertii | 1057 |
| Escherichia coli | 1058 |
| Escherichia fergusonii | 1059 |
| Escherichia hermannii | 1060 |
| Escherichia sp. | 1061 |
| Escherichia sp. | 1062 |
| Escherichia sp. | 1063 |
| Escherichia vulneris | 1064 |
| Ethanoligenens harbinense | 1065 |
| Eubacteriaceae bacterium | 1066 |
| Eubacterium barkeri | 1067 |
| Eubacterium biforme | 1068 |
| Eubacterium brachy | 1069 |
| Eubacterium budayi | 1070 |
| Eubacterium callanderi | 1071 |
| Eubacterium cellulosolvens | 1072 |
| Eubacterium contortum | 1073 |
| Eubacterium coprostanoligenes | 1074 |
| Eubacterium cylindroides | 1075 |
| Eubacterium desmolans | 1076 |
| Eubacterium dolichum | 1077 |
| Eubacterium eligens | 1078 |
| Eubacterium fissicatena | 1079 |
| Eubacterium hadrum | 1080 |
| Eubacterium hallii | 1081 |
| Eubacterium infirmum | 1082 |
| Eubacterium limosum | 1083 |
| Eubacterium moniliforme | 1084 |
| Eubacterium multiforme | 1085 |
| Eubacterium nitritogenes | 1086 |
| Eubacterium nodatum | 1087 |
| Eubacterium ramulus | 1088 |
| Eubacterium rectale | 1089 |
| Eubacterium ruminantium | 1090 |
| Eubacterium saburreum | 1091 |
| Eubacterium saphenum | 1092 |
| Eubacterium siraeum | 1093 |
| Eubacterium sp. | 1094 |
| Eubacterium sp. | 1095 |
| Eubacterium sp. | 1096 |
| Eubacterium sp. | 1097 |
| Eubacterium sp. | 1098 |
| Eubacterium sp. | 1099 |
| Eubacterium sp. | 1100 |
| Eubacterium sp. | 1101 |
| Eubacterium sp. | 1102 |
| Eubacterium sp. | 1103 |
| Eubacterium sp. | 1104 |
| Eubacterium tenue | 1105 |
| Eubacterium tortuosum | 1106 |
| Eubacterium ventriosum | 1107 |
| Eubacterium xylanophilum | 1108 |
| Eubacterium yurii | 1109 |
| Ewingella americana | 1110 |
| Exiguobacterium acetylicum | 1111 |
| Facklamia hominis | 1112 |
| Faecalibacterium prausnitzii | 1113 |
| Filifactor alocis | 1114 |
| Filifactor villosus | 1115 |
| Finegoldia magna | 1116 |
| Flavobacteriaceae genomosp. | 1117 |
| Flavobacterium sp. | 1118 |
| Flavonifractor plautii | 1119 |
| Flexispira rappini | 1120 |
| Flexistipes sinusarabici | 1121 |
| Francisella novicida | 1122 |
| Francisella philomiragia | 1123 |
| Fulvimonas sp. | 1124 |
| Fusobacterium canifelinum | 1125 |
| Fusobacterium genomosp. | 1126 |
| Fusobacterium genomosp. | 1127 |
| Fusobacterium gonidiaformans | 1128 |
| Fusobacterium mortiferum | 1129 |
| Fusobacterium naviforme | 1130 |
| Fusobacterium necrogenes | 1131 |
| Fusobacterium necrophorum | 1132 |
| Fusobacterium nucleatum | 1133 |
| Fusobacterium periodonticum | 1134 |
| Fusobacterium russii | 1135 |
| Fusobacterium sp. | 1136 |
| Fusobacterium sp. | 1137 |
| Fusobacterium sp. | 1138 |
| Fusobacterium sp. | 1139 |
| Fusobacterium sp. | 1140 |
| Fusobacterium sp. | 1141 |
| Fusobacterium sp. | 1142 |
| Fusobacterium sp. | 1143 |
| Fusobacterium sp. | 1144 |
| Fusobacterium sp. | 1145 |
| Fusobacterium sp. | 1146 |
| Fusobacterium sp. | 1147 |
| Fusobacterium sp. | 1148 |
| Fusobacterium sp. | 1149 |
| Fusobacterium sp. | 1150 |
| Fusobacterium sp. | 1151 |
| Fusobacterium sp. | 1152 |
| Fusobacterium ulcerans | 1153 |
| Fusobacterium varium | 1154 |
| Gardnerella vaginalis | 1155 |
| Gemella haemolysans | 1156 |
| Gemella morbillorum | 1157 |
| Gemella morbillorum | 1158 |
| Gemella sanguinis | 1159 |
| Gemella sp. | 1160 |
| Gemella sp. | 1161 |
| Gemella sp. | 1162 |
| Gemella sp. | 1163 |
| Gemmiger formicilis | 1164 |
| Geobacillus kaustophilus | 1165 |
| Geobacillus sp. | 1166 |
| Geobacillus sp. | 1167 |
| Geobacillus stearothermophilus | 1168 |
| Geobacillus thermocatenulatus | 1169 |
| Geobacillus thermodenitrificans | 1170 |
| Geobacillus thermoglucosidasius | 1171 |
| Geobacillus thermoleovorans | 1172 |
| Geobacter bemidjiensis | 1173 |
| Gloeobacter violaceus | 1174 |
| Gluconacetobacter azotocaptans | 1175 |
| Gluconacetobacter diazotrophicus | 1176 |
| Gluconacetobacter entanii | 1177 |
| Gluconacetobacter europaeus | 1178 |

TABLE 10-continued

Bacteria Capable of Being Engineered to Produce GABA

| Species | Seq. ID No. |
|---|---|
| Gluconacetobacter hansenii | 1179 |
| Gluconacetobacter johannae | 1180 |
| Gluconacetobacter oboediens | 1181 |
| Gluconacetobacter xylinus | 1182 |
| Gordonia bronchialis | 1183 |
| Gordonia polyisoprenivorans | 1184 |
| Gordonia sp. | 1185 |
| Gordonia sputi | 1186 |
| Gordonia terrae | 1187 |
| Gordonibacter pamelaeae | 1188 |
| Gordonibacter pamelaeae | 1189 |
| Gracilibacter thermotolerans | 1190 |
| Gramella forsetii | 1191 |
| Granulicatella adiacens | 1192 |
| Granulicatella elegans | 1193 |
| Granulicatella paradiacens | 1194 |
| Granulicatella sp. | 1195 |
| Granulicatella sp. | 1196 |
| Granulicatella sp. | 1197 |
| Granulicatella sp. | 1198 |
| Granulicatella sp. | 1199 |
| Grimontia hollisae | 1200 |
| Haematobacter sp. | 1201 |
| Haemophilus aegyptius | 1202 |
| Haemophilus genomosp. | 1203 |
| Haemophilus genomosp. | 1204 |
| Haemophilus haemolyticus | 1205 |
| Haemophilus parahaemolyticus | 1206 |
| Haemophilus parainfluenzae | 1207 |
| Haemophilus paraphrophaemolyticus | 1208 |
| Haemophilus parasuis | 1209 |
| Haemophilus somnus | 1210 |
| Haemophilus sp. | 1211 |
| Haemophilus sp. | 1212 |
| Haemophilus sp. | 1213 |
| Haemophilus sp. | 1214 |
| Haemophilus sp. | 1215 |
| Haemophilus sp. | 1216 |
| Haemophilus sp. | 1217 |
| Haemophilus sp. | 1218 |
| Haemophilus sputorum | 1219 |
| Hafnia alvei | 1220 |
| Halomonas elongata | 1221 |
| Halomonas johnsoniae | 1222 |
| Halorubrum lipolyticum | 1223 |
| Helicobacter bilis | 1224 |
| Helicobacter canadensis | 1225 |
| Helicobacter cinaedi | 1226 |
| Helicobacter pullorum | 1227 |
| Helicobacter sp. | 1228 |
| Helicobacter winghamensis | 1229 |
| Heliobacterium modesticaldum | 1230 |
| Herbaspirillum seropedicae | 1231 |
| Herbaspirillum sp. | 1232 |
| Histophilus somni | 1233 |
| Holdemania filiformis | 1234 |
| Hydrogenoanaerobacterium saccharovorans | 1235 |
| Hyperthermus butylicus | 1236 |
| Hyphomicrobium sulfonivorans | 1237 |
| Hyphomonas neptunium | 1238 |
| Ignatzschineria indica | 1239 |
| Ignatzschineria sp. | 1240 |
| Ignicoccus islandicus | 1241 |
| Inquilinus limosus | 1242 |
| Janibacter limosus | 1243 |
| Janibacter melonis | 1244 |
| Janthinobacterium sp. | 1245 |
| Johnsonella ignava | 1246 |
| Jonquetella anthropi | 1247 |
| Kerstersia gyiorum | 1248 |
| Kingella denitrificans | 1249 |
| Kingella genomosp. | 1250 |
| Kingella kingae | 1251 |
| Kingella oralis | 1252 |
| Kingella sp. | 1253 |
| Klebsiella sp. | 1254 |
| Klebsiella sp. | 1255 |
| Klebsiella sp. | 1256 |
| Klebsiella sp. | 1257 |
| Klebsiella sp. | 1258 |
| Klebsiella sp. | 1259 |
| Klebsiella sp. | 1260 |
| Klebsiella sp. | 1261 |
| Klebsiella sp. | 1262 |
| Klebsiella sp. | 1263 |
| Klebsiella sp. | 1264 |
| Klebsiella variicola | 1265 |
| Kluyvera ascorbata | 1266 |
| Kluyvera cryocrescens | 1267 |
| Kocuria marina | 1268 |
| Kocuria palustris | 1269 |
| Kocuria rhizophila | 1270 |
| Kocuria rosea | 1271 |
| Kocuria varians | 1272 |
| Lachnobacterium bovis | 1273 |
| Lachnospira multipara | 1274 |
| Lachnospira pectinoschiza | 1275 |
| Lachnospiraceae bacterium | 1276 |
| Lachnospiraceae bacterium | 1277 |
| Lachnospiraceae bacterium | 1278 |
| Lachnospiraceae bacterium | 1279 |
| Lachnospiraceae bacterium | 1280 |
| Lachnospiraceae bacterium | 1281 |
| Lachnospiraceae bacterium | 1282 |
| Lachnospiraceae bacterium | 1283 |
| Lachnospiraceae bacterium | 1284 |
| Lachnospiraceae bacterium | 1285 |
| Lachnospiraceae bacterium | 1286 |
| Lachnospiraceae bacterium | 1287 |
| Lachnospiraceae bacterium | 1288 |
| Lachnospiraceae bacterium | 1289 |
| Lachnospiraceae bacterium | 1290 |
| Lachnospiraceae bacterium | 1291 |
| Lachnospiraceae bacterium | 1292 |
| Lachnospiraceae genomosp. | 1293 |
| Lactobacillus acidipiscis | 1294 |
| Lactobacillus acidophilus | 1295 |
| Lactobacillus alimentarius | 1296 |
| Lactobacillus amylolyticus | 1297 |
| Lactobacillus amylovorus | 1298 |
| Lactobacillus antri | 1299 |
| Lactobacillus brevis | 1300 |
| Lactobacillus buchneri | 1301 |
| Lactobacillus casei | 1302 |
| Lactobacillus catenaformis | 1303 |
| Lactobacillus coleohominis | 1304 |
| Lactobacillus coryniformis | 1305 |
| Lactobacillus crispatus | 1306 |
| Lactobacillus curvatus | 1307 |
| Lactobacillus delbrueckii | 1308 |
| Lactobacillus dextrinicus | 1309 |
| Lactobacillus farciminis | 1310 |
| Lactobacillus fermentum | 1311 |
| Lactobacillus gasseri | 1312 |
| Lactobacillus gastricus | 1313 |
| Lactobacillus genomosp. | 1314 |
| Lactobacillus genomosp. | 1315 |
| Lactobacillus helveticus | 1316 |
| Lactobacillus hilgardii | 1317 |
| Lactobacillus hominis | 1318 |
| Lactobacillus iners | 1319 |
| Lactobacillus jensenii | 1320 |
| Lactobacillus johnsonii | 1321 |
| Lactobacillus kalixensis | 1322 |
| Lactobacillus kefiranofaciens | 1323 |
| Lactobacillus kefiri | 1324 |
| Lactobacillus kimchii | 1325 |
| Lactobacillus leichmannii | 1326 |
| Lactobacillus mucosae | 1327 |
| Lactobacillus murinus | 1328 |
| Lactobacillus nodensis | 1329 |
| Lactobacillus oeni | 1330 |

TABLE 10-continued

Bacteria Capable of Being Engineered to Produce GABA

| Species | Seq. ID No. |
| --- | --- |
| Lactobacillus oris | 1331 |
| Lactobacillus parabrevis | 1332 |
| Lactobacillus parabuchneri | 1333 |
| Lactobacillus paracasei | 1334 |
| Lactobacillus parakefiri | 1335 |
| Lactobacillus pentosus | 1336 |
| Lactobacillus perolens | 1337 |
| Lactobacillus plantarum | 1338 |
| Lactobacillus pontis | 1339 |
| Lactobacillus reuteri | 1340 |
| Lactobacillus rhamnosus | 1341 |
| Lactobacillus rogosae | 1342 |
| Lactobacillus ruminis | 1343 |
| Lactobacillus sakei | 1344 |
| Lactobacillus salivarius | 1345 |
| Lactobacillus saniviri | 1346 |
| Lactobacillus senioris | 1347 |
| Lactobacillus sp. | 1348 |
| Lactobacillus sp. | 1349 |
| Lactobacillus sp. | 1350 |
| Lactobacillus sp. | 1351 |
| Lactobacillus sp. | 1352 |
| Lactobacillus sp. | 1353 |
| Lactobacillus sp. | 1354 |
| Lactobacillus sp. | 1355 |
| Lactobacillus sp. | 1356 |
| Lactobacillus sp. | 1357 |
| Lactobacillus sp. | 1358 |
| Lactobacillus sp. | 1359 |
| Lactobacillus sp. | 1360 |
| Lactobacillus sp. | 1361 |
| Lactobacillus sp. | 1362 |
| Lactobacillus sp. | 1363 |
| Lactobacillus sp. | 1364 |
| Lactobacillus sp. | 1365 |
| Lactobacillus tucceti | 1366 |
| Lactobacillus ultunensis | 1367 |
| Lactobacillus vaginalis | 1368 |
| Lactobacillus vini | 1369 |
| Lactobacillus vitulinus | 1370 |
| Lactobacillus zeae | 1371 |
| Lactococcus garvieae | 1372 |
| Lactococcus lactis | 1373 |
| Lactococcus raffinolactis | 1374 |
| Lactonifactor longoviformis | 1375 |
| Laribacter hongkongensis | 1376 |
| Lautropia mirabilis | 1377 |
| Lautropia sp. | 1378 |
| Leminorella grimontii | 1379 |
| Leminorella richardii | 1380 |
| Leptotrichia buccalis | 1381 |
| Leptotrichia genomosp. | 1382 |
| Leptotrichia goodfellowii | 1383 |
| Leptotrichia hofstadii | 1384 |
| Leptotrichia shahii | 1385 |
| Leptotrichia sp. | 1386 |
| Leptotrichia sp. | 1387 |
| Leptotrichia sp. | 1388 |
| Leptotrichia sp. | 1389 |
| Leptotrichia sp. | 1390 |
| Leptotrichia sp. | 1391 |
| Leptotrichia sp. | 1392 |
| Leuconostoc carnosum | 1393 |
| Leuconostoc citreum | 1394 |
| Leuconostoc gasicomitatum | 1395 |
| Leuconostoc inhae | 1396 |
| Leuconostoc kimchii | 1397 |
| Leuconostoc lactis | 1398 |
| Leuconostoc mesenteroides | 1399 |
| Leuconostoc pseudomesenteroides | 1400 |
| Listeria innocua | 1401 |
| Listeria ivanovii | 1402 |
| Luteococcus sanguinis | 1403 |
| Lutispora thermophila | 1404 |
| Lysinibacillus fusiformis | 1405 |
| Lysinibacillus sphaericus | 1406 |
| Macrococcus caseolyticus | 1407 |
| Mannheimia haemolytica | 1408 |
| Marvinbryantia formatexigens | 1409 |
| Massilia sp. | 1410 |
| Megamonas funiformis | 1411 |
| Megamonas hypermegale | 1412 |
| Megasphaera genomosp. | 1413 |
| Megasphaera genomosp. | 1414 |
| Megasphaera micronuciformis | 1415 |
| Megasphaera sp. | 1416 |
| Megasphaera sp. | 1417 |
| Metallosphaera sedula | 1418 |
| Methanobacterium formicicum | 1419 |
| Methanobrevibacter acididurans | 1420 |
| Methanobrevibacter arboriphilus | 1421 |
| Methanobrevibacter curvatus | 1422 |
| Methanobrevibacter cuticularis | 1423 |
| Methanobrevibacter filiformis | 1424 |
| Methanobrevibacter gottschalkii | 1425 |
| Methanobrevibacter millerae | 1426 |
| Methanobrevibacter olleyae | 1427 |
| Methanobrevibacter oralis | 1428 |
| Methanobrevibacter ruminantium | 1429 |
| Methanobrevibacter smithii | 1430 |
| Methanobrevibacter thaueri | 1431 |
| Methanobrevibacter woesei | 1432 |
| Methanobrevibacter wolinii | 1433 |
| Methanosphaera stadtmanae | 1434 |
| Methylobacterium extorquens | 1435 |
| Methylobacterium podarium | 1436 |
| Methylobacterium radiotolerans | 1437 |
| Methylobacterium sp. | 1438 |
| Methylobacterium sp. | 1439 |
| Methylocella silvestris | 1440 |
| Methylophilus sp. | 1441 |
| Microbacterium chocolatum | 1442 |
| Microbacterium flavescens | 1443 |
| Microbacterium gubbeenense | 1444 |
| Microbacterium lacticum | 1445 |
| Microbacterium oleivorans | 1446 |
| Microbacterium oxydans | 1447 |
| Microbacterium paraoxydans | 1448 |
| Microbacterium phyllosphaerae | 1449 |
| Microbacterium schleiferi | 1450 |
| Microbacterium sp. | 1451 |
| Microbacterium sp. | 1452 |
| Microbacterium testaceum | 1453 |
| Micrococcus antarcticus | 1454 |
| Micrococcus luteus | 1455 |
| Micrococcus lylae | 1456 |
| Micrococcus sp. | 1457 |
| Microcystis aeruginosa | 1458 |
| Mitsuokella jalaludinii | 1459 |
| Mitsuokella multacida | 1460 |
| Mitsuokella sp. | 1461 |
| Mitsuokella sp. | 1462 |
| Mobiluncus curtisii | 1463 |
| Mobiluncus mulieris | 1464 |
| Moellerella wisconsensis | 1465 |
| Mogibacterium diversum | 1466 |
| Mogibacterium neglectum | 1467 |
| Mogibacterium pumilum | 1468 |
| Mogibacterium timidum | 1469 |
| Mollicutes bacterium | 1470 |
| Moorella thermoacetica | 1471 |
| Moraxella catarrhalis | 1472 |
| Moraxella lincolnii | 1473 |
| Moraxella osloensis | 1474 |
| Moraxella sp. | 1475 |
| Moraxella sp. | 1476 |
| Morganella morganii | 1477 |
| Morganella sp. | 1478 |
| Morococcus cerebrosus | 1479 |
| Moryella indoligenes | 1480 |
| Mycobacterium sp. | 1481 |
| Mycobacterium sp. | 1482 |

TABLE 10-continued

Bacteria Capable of Being Engineered to Produce GABA

| Species | Seq. ID No. |
|---|---|
| *Mycobacterium* sp. | 1483 |
| *Mycobacterium* sp. | 1484 |
| *Mycobacterium* sp. | 1485 |
| *Mycobacterium* sp. | 1486 |
| *Mycobacterium* sp. | 1487 |
| *Mycobacterium* sp. | 1488 |
| *Mycobacterium* sp. | 1489 |
| *Mycobacterium* sp. | 1490 |
| *Mycobacterium* sp. | 1491 |
| *Mycobacterium* sp. | 1492 |
| *Mycobacterium* sp. | 1493 |
| *Mycobacterium* sp. | 1494 |
| *Mycobacterium* sp. | 1495 |
| *Mycoplasma agalactiae* | 1496 |
| *Mycoplasma amphoriforme* | 1497 |
| *Mycoplasma arthritidis* | 1498 |
| *Mycoplasma bovoculi* | 1499 |
| *Mycoplasma faucium* | 1500 |
| *Mycoplasma fermentans* | 1501 |
| *Mycoplasma flocculare* | 1502 |
| *Mycoplasma genitalium* | 1503 |
| *Mycoplasma hominis* | 1504 |
| *Mycoplasma orale* | 1505 |
| *Mycoplasma ovipneumoniae* | 1506 |
| *Mycoplasma penetrans* | 1507 |
| *Mycoplasma pneumoniae* | 1508 |
| *Mycoplasma putrefaciens* | 1509 |
| *Mycoplasma salivarium* | 1510 |
| *Mycoplasmataceae* genomosp. | 1511 |
| *Myroides odoratimimus* | 1512 |
| *Myroides* sp. | 1513 |
| *Neisseria bacilliformis* | 1514 |
| *Neisseria cinerea* | 1515 |
| *Neisseria elongata* | 1516 |
| *Neisseria flavescens* | 1517 |
| *Neisseria* genomosp. | 1518 |
| *Neisseria lactamica* | 1519 |
| *Neisseria macacae* | 1520 |
| *Neisseria mucosa* | 1521 |
| *Neisseria pharyngis* | 1522 |
| *Neisseria polysaccharea* | 1523 |
| *Neisseria sicca* | 1524 |
| *Neisseria* sp. | 1525 |
| *Neisseria* sp. | 1526 |
| *Neisseria* sp. | 1527 |
| *Neisseria* sp. | 1528 |
| *Neisseria* sp. | 1529 |
| *Neisseria* sp. | 1530 |
| *Neisseria* sp. | 1531 |
| *Neisseria subflava* | 1532 |
| *Neorickettsia risticii* | 1533 |
| *Neorickettsia sennetsu* | 1534 |
| *Nocardia brasiliensis* | 1535 |
| *Nocardia cyriacigeorgica* | 1536 |
| *Nocardia farcinica* | 1537 |
| *Nocardia puris* | 1538 |
| *Nocardia* sp. | 1539 |
| *Nocardiopsis dassonvillei* | 1540 |
| *Novosphingobium aromaticivorans* | 1541 |
| *Oceanobacillus caeni* | 1542 |
| *Oceanobacillus* sp. | 1543 |
| *Ochrobactrum anthropi* | 1544 |
| *Ochrobactrum intermedium* | 1545 |
| *Ochrobactrum pseudintermedium* | 1546 |
| *Odoribacter laneus* | 1547 |
| *Odoribacter splanchnicus* | 1548 |
| *Okadaella gastrococcus* | 1549 |
| *Oligella ureolytica* | 1550 |
| *Oligella urethralis* | 1551 |
| *Olsenella* genomosp. | 1552 |
| *Olsenella profusa* | 1553 |
| *Olsenella* sp. | 1554 |
| *Olsenella* sp. | 1555 |
| *Olsenella uli* | 1556 |
| *Opitutus terrae* | 1557 |
| *Oribacterium sinus* | 1558 |
| *Oribacterium* sp. | 1559 |
| *Oribacterium* sp. | 1560 |
| *Oribacterium* sp. | 1561 |
| *Oribacterium* sp. | 1562 |
| *Oribacterium* sp. | 1563 |
| *Oribacterium* sp. | 1564 |
| *Oribacterium* sp. | 1565 |
| *Oribacterium* sp. | 1566 |
| *Ornithinibacillus bavariensis* | 1567 |
| *Ornithinibacillus* sp. | 1568 |
| *Oscillibacter* sp. | 1569 |
| *Oscillibacter valericigenes* | 1570 |
| *Oscillospira guilliermondii* | 1571 |
| *Oxalobacter formigenes* | 1572 |
| *Paenibacillus barcinonensis* | 1573 |
| *Paenibacillus barengoltzii* | 1574 |
| *Paenibacillus chibensis* | 1575 |
| *Paenibacillus cookii* | 1576 |
| *Paenibacillus durus* | 1577 |
| *Paenibacillus glucanolyticus* | 1578 |
| *Paenibacillus lactis* | 1579 |
| *Paenibacillus lautus* | 1580 |
| *Paenibacillus pabuli* | 1581 |
| *Paenibacillus polymyxa* | 1582 |
| *Paenibacillus popilliae* | 1583 |
| *Paenibacillus* sp. | 1584 |
| *Paenibacillus* sp. | 1585 |
| *Paenibacillus* sp. | 1586 |
| *Paenibacillus* sp. | 1587 |
| *Paenibacillus* sp. | 1588 |
| *Paenibacillus* sp. | 1589 |
| *Paenibacillus* sp. | 1590 |
| *Paenibacillus timonensis* | 1591 |
| *Pantoea agglomerans* | 1592 |
| *Pantoea ananatis* | 1593 |
| *Pantoea brenneri* | 1594 |
| *Pantoea citrea* | 1595 |
| *Pantoea conspicua* | 1596 |
| *Pantoea septica* | 1597 |
| *Papillibacter cinnamivorans* | 1598 |
| *Parabacteroides distasonis* | 1599 |
| *Parabacteroides goldsteinii* | 1600 |
| *Parabacteroides gordonii* | 1601 |
| *Parabacteroides johnsonii* | 1602 |
| *Parabacteroides merdae* | 1603 |
| *Parabacteroides* sp. | 1604 |
| *Parabacteroides* sp. | 1605 |
| *Parachlamydia* sp. | 1606 |
| *Paracoccus denitrificans* | 1607 |
| *Paracoccus marcusii* | 1608 |
| *Paraprevotella clara* | 1609 |
| *Paraprevotella xylaniphila* | 1610 |
| *Parascardovia denticolens* | 1611 |
| *Parasutterella excrementihominis* | 1612 |
| *Parasutterella secunda* | 1613 |
| *Parvimonas micra* | 1614 |
| *Parvimonas* sp. | 1615 |
| *Pasteurella bettyae* | 1616 |
| *Pasteurella dagmatis* | 1617 |
| *Pasteurella multocida* | 1618 |
| *Pediococcus acidilactici* | 1619 |
| *Pediococcus pentosaceus* | 1620 |
| *Peptococcus niger* | 1621 |
| *Peptococcus* sp. | 1622 |
| *Peptococcus* sp. | 1623 |
| *Peptoniphilus asaccharolyticus* | 1624 |
| *Peptoniphilus duerdenii* | 1625 |
| *Peptoniphilus harei* | 1626 |
| *Peptoniphilus indolicus* | 1627 |
| *Peptoniphilus ivorii* | 1628 |
| *Peptoniphilus lacrimalis* | 1629 |
| *Peptoniphilus* sp. | 1630 |
| *Peptoniphilus* sp. | 1631 |
| *Peptoniphilus* sp. | 1632 |
| *Peptoniphilus* sp. | 1633 |
| *Peptoniphilus* sp. | 1634 |

TABLE 10-continued

Bacteria Capable of Being Engineered to Produce GABA

| Species | Seq. ID No. |
|---|---|
| Peptoniphilus sp. | 1635 |
| Peptoniphilus sp. | 1636 |
| Peptostreptococcaceae bacterium | 1637 |
| Peptostreptococcus anaerobius | 1638 |
| Peptostreptococcus micros | 1639 |
| Peptostreptococcus sp. | 1640 |
| Peptostreptococcus sp. | 1641 |
| Peptostreptococcus sp. | 1642 |
| Peptostreptococcus sp. | 1643 |
| Peptostreptococcus stomatis | 1644 |
| Phascolarctobacterium faecium | 1645 |
| Phascolarctobacterium sp. | 1646 |
| Phascolarctobacterium succinatutens | 1647 |
| Phenylobacterium zucineum | 1648 |
| Photorhabdus asymbiotica | 1649 |
| Pigmentiphaga daeguensis | 1650 |
| Planomicrobium koreense | 1651 |
| Plesiomonas shigelloides | 1652 |
| Porphyromonadaceae bacterium | 1653 |
| Porphyromonas asaccharolytica | 1654 |
| Porphyromonas endodontalis | 1655 |
| Porphyromonas gingivalis | 1656 |
| Porphyromonas levii | 1657 |
| Porphyromonas macacae | 1658 |
| Porphyromonas somerae | 1659 |
| Porphyromonas sp. | 1660 |
| Porphyromonas sp. | 1661 |
| Porphyromonas sp. | 1662 |
| Porphyromonas sp. | 1663 |
| Porphyromonas sp. | 1664 |
| Porphyromonas uenonis | 1665 |
| Prevotella albensis | 1666 |
| Prevotella amnii | 1667 |
| Prevotella bergensis | 1668 |
| Prevotella bivia | 1669 |
| Prevotella brevis | 1670 |
| Prevotella buccae | 1671 |
| Prevotella buccalis | 1672 |
| Prevotella copri | 1673 |
| Prevotella corporis | 1674 |
| Prevotella dentalis | 1675 |
| Prevotella denticola | 1676 |
| Prevotella disiens | 1677 |
| Prevotella genomosp. | 1678 |
| Prevotella genomosp. | 1679 |
| Prevotella genomosp. | 1680 |
| Prevotella genomosp. | 1681 |
| Prevotella genomosp. | 1682 |
| Prevotella heparinolytica | 1683 |
| Prevotella histicola | 1684 |
| Prevotella intermedia | 1685 |
| Prevotella loescheii | 1686 |
| Prevotella maculosa | 1687 |
| Prevotella marshii | 1688 |
| Prevotella melaninogenica | 1689 |
| Prevotella micans | 1690 |
| Prevotella multiformis | 1691 |
| Prevotella multisaccharivora | 1692 |
| Prevotella nanceiensis | 1693 |
| Prevotella nigrescens | 1694 |
| Prevotella oralis | 1695 |
| Prevotella oris | 1696 |
| Prevotella oulorum | 1697 |
| Prevotella pallens | 1698 |
| Prevotella ruminicola | 1699 |
| Prevotella salivae | 1700 |
| Prevotella sp. | 1701 |
| Prevotella sp. | 1702 |
| Prevotella sp. | 1703 |
| Prevotella sp. | 1704 |
| Prevotella sp. | 1705 |
| Prevotella sp. | 1706 |
| Prevotella sp. | 1707 |
| Prevotella sp. | 1708 |
| Prevotella sp. | 1709 |
| Prevotella sp. | 1710 |
| Prevotella sp. | 1711 |
| Prevotella sp. | 1712 |
| Prevotella sp. | 1713 |
| Prevotella sp. | 1714 |
| Prevotella sp. | 1715 |
| Prevotella sp. | 1716 |
| Prevotella sp. | 1717 |
| Prevotella sp. | 1718 |
| Prevotella sp. | 1719 |
| Prevotella sp. | 1720 |
| Prevotella sp. | 1721 |
| Prevotella sp. | 1722 |
| Prevotella sp. | 1723 |
| Prevotella sp. | 1724 |
| Prevotella sp. | 1725 |
| Prevotella sp. | 1726 |
| Prevotella sp. | 1727 |
| Prevotella sp. | 1728 |
| Prevotella sp. | 1729 |
| Prevotella sp. | 1730 |
| Prevotella sp. | 1731 |
| Prevotella sp. | 1732 |
| Prevotella sp. | 1733 |
| Prevotella sp. | 1734 |
| Prevotella sp. | 1735 |
| Prevotella sp. | 1736 |
| Prevotella sp. | 1737 |
| Prevotella sp. | 1738 |
| Prevotella sp. | 1739 |
| Prevotella sp. | 1740 |
| Prevotella sp. | 1741 |
| Prevotella sp. | 1742 |
| Prevotella sp. | 1743 |
| Prevotella sp. | 1744 |
| Prevotella sp. | 1745 |
| Prevotella sp. | 1746 |
| Prevotella stercorea | 1747 |
| Prevotella tannerae | 1748 |
| Prevotella timonensis | 1749 |
| Prevotella veroralis | 1750 |
| Prevotellaceae bacterium | 1751 |
| Prochlorococcus marinus | 1752 |
| Propionibacteriaceae bacterium | 1753 |
| Propionibacterium acidipropionici | 1754 |
| Propionibacterium acnes | 1755 |
| Propionibacterium avidum | 1756 |
| Propionibacterium freudenreichii | 1757 |
| Propionibacterium granulosum | 1758 |
| Propionibacterium jensenii | 1759 |
| Propionibacterium propionicum | 1760 |
| Propionibacterium sp. | 1761 |
| Propionibacterium sp. | 1762 |
| Propionibacterium sp. | 1763 |
| Propionibacterium sp. | 1764 |
| Propionibacterium sp. | 1765 |
| Propionibacterium thoenii | 1766 |
| Proteus mirabilis | 1767 |
| Proteus penneri | 1768 |
| Proteus sp. | 1769 |
| Proteus vulgaris | 1770 |
| Providencia alcalifaciens | 1771 |
| Providencia rettgeri | 1772 |
| Providencia rustigianii | 1773 |
| Providencia stuartii | 1774 |
| Pseudoclavibacter sp. | 1775 |
| Pseudoflavonifractor capillosus | 1776 |
| Pseudomonas aeruginosa | 1777 |
| Pseudomonas fluorescens | 1778 |
| Pseudomonas gessardii | 1779 |
| Pseudomonas mendocina | 1780 |
| Pseudomonas monteilii | 1781 |
| Pseudomonas poae | 1782 |
| Pseudomonas pseudoalcaligenes | 1783 |
| Pseudomonas putida | 1784 |
| Pseudomonas sp. | 1785 |
| Pseudomonas sp. | 1786 |

TABLE 10-continued

Bacteria Capable of Being Engineered to Produce GABA

| Species | Seq. ID No. |
|---|---|
| Pseudomonas sp. | 1787 |
| Pseudomonas stutzeri | 1788 |
| Pseudomonas tolaasii | 1789 |
| Pseudomonas viridiflava | 1790 |
| Pseudoramibacter alactolyticus | 1791 |
| Psychrobacter arcticus | 1792 |
| Psychrobacter cibarius | 1793 |
| Psychrobacter cryohalolentis | 1794 |
| Psychrobacter faecalis | 1795 |
| Psychrobacter nivimaris | 1796 |
| Psychrobacter pulmonis | 1797 |
| Psychrobacter sp. | 1798 |
| Pyramidobacter piscolens | 1799 |
| Ralstonia pickettii | 1800 |
| Ralstonia sp. | 1801 |
| Raoultella ornithinolytica | 1802 |
| Raoultella planticola | 1803 |
| Raoultella terrigena | 1804 |
| Rhodobacter sp. | 1805 |
| Rhodobacter sphaeroides | 1806 |
| Rhodococcus corynebacterioides | 1807 |
| Rhodococcus equi | 1808 |
| Rhodococcus erythropolis | 1809 |
| Rhodococcus fascians | 1810 |
| Rhodopseudomonas palustris | 1811 |
| Robinsoniella peoriensis | 1812 |
| Roseburia cecicola | 1813 |
| Roseburia faecalis | 1814 |
| Roseburia faecis | 1815 |
| Roseburia hominis | 1816 |
| Roseburia intestinalis | 1817 |
| Roseburia inulinivorans | 1818 |
| Roseburia sp. | 1819 |
| Roseburia sp. | 1820 |
| Roseiflexus castenholzii | 1821 |
| Roseomonas cervicalis | 1822 |
| Roseomonas mucosa | 1823 |
| Roseomonas sp. | 1824 |
| Roseomonas sp. | 1825 |
| Roseomonas sp. | 1826 |
| Roseomonas sp. | 1827 |
| Rothia aeria | 1828 |
| Rothia dentocariosa | 1829 |
| Rothia mucilaginosa | 1830 |
| Rothia nasimurium | 1831 |
| Rothia sp. | 1832 |
| Ruminobacter amylophilus | 1833 |
| Ruminococcaceae bacterium | 1834 |
| Ruminococcus albus | 1835 |
| Ruminococcus bromii | 1836 |
| Ruminococcus callidus | 1837 |
| Ruminococcus champanellensis | 1838 |
| Ruminococcus flavefaciens | 1839 |
| Ruminococcus gnavus | 1840 |
| Ruminococcus hansenii | 1841 |
| Ruminococcus lactaris | 1842 |
| Ruminococcus obeum | 1843 |
| Ruminococcus sp. | 1844 |
| Ruminococcus sp. | 1845 |
| Ruminococcus sp. | 1846 |
| Ruminococcus sp. | 1847 |
| Ruminococcus sp. | 1848 |
| Ruminococcus torques | 1849 |
| Saccharomonospora viridis | 1850 |
| Sarcina ventriculi | 1851 |
| Scardovia inopinata | 1852 |
| Scardovia wiggsiae | 1853 |
| Segniliparus rotundus | 1854 |
| Segniliparus rugosus | 1855 |
| Selenomonas artemidis | 1856 |
| Selenomonas dianae | 1857 |
| Selenomonas flueggei | 1858 |
| Selenomonas genomosp. | 1859 |
| Selenomonas genomosp. | 1860 |
| Selenomonas genomosp. | 1861 |
| Selenomonas genomosp. | 1862 |
| Selenomonas genomosp. | 1863 |
| Selenomonas genomosp. | 1864 |
| Selenomonas infeli | 1865 |
| Selenomonas noxia | 1866 |
| Selenomonas ruminantium | 1867 |
| Selenomonas sp. | 1868 |
| Selenomonas sp. | 1869 |
| Selenomonas sp. | 1870 |
| Selenomonas sp. | 1871 |
| Selenomonas sp. | 1872 |
| Selenomonas sp. | 1873 |
| Selenomonas sp. | 1874 |
| Selenomonas sp. | 1875 |
| Selenomonas sp. | 1876 |
| Selenomonas sp. | 1877 |
| Selenomonas sp. | 1878 |
| Selenomonas sp. | 1879 |
| Selenomonas sp. | 1880 |
| Selenomonas sputigena | 1881 |
| Serratia fonticola | 1882 |
| Serratia liquefaciens | 1883 |
| Serratia marcescens | 1884 |
| Serratia odorifera | 1885 |
| Serratia proteamaculans | 1886 |
| Shewanella putrefaciens | 1887 |
| Shuttleworthia satelles | 1888 |
| Shuttleworthia sp. | 1889 |
| Shuttleworthia sp. | 1890 |
| Simonsiella muelleri | 1891 |
| Slackia equolifaciens | 1892 |
| Slackia exigua | 1893 |
| Slackia faecicanis | 1894 |
| Slackia heliotrinireducens | 1895 |
| Slackia isoflavoniconvertens | 1896 |
| Slackia piriformis | 1897 |
| Slackia sp. | 1898 |
| Solobacterium moorei | 1899 |
| Sphingobacterium faecium | 1900 |
| Sphingobacterium mizutaii | 1901 |
| Sphingobacterium multivorum | 1902 |
| Sphingobacterium spiritivorum | 1903 |
| Sphingomonas echinoides | 1904 |
| Sphingomonas sp. | 1905 |
| Sphingomonas sp. | 1906 |
| Sphingomonas sp. | 1907 |
| Sphingomonas sp. | 1908 |
| Sphingopyxis alaskensis | 1909 |
| Spiroplasma insolitum | 1910 |
| Sporobacter termitidis | 1911 |
| Sporolactobacillus inulinus | 1912 |
| Sporolactobacillus nakayamae | 1913 |
| Sporosarcina newyorkensis | 1914 |
| Sporosarcina sp. | 1915 |
| Staphylococcaceae bacterium | 1916 |
| Staphylococcus aureus | 1917 |
| Staphylococcus auricularis | 1918 |
| Staphylococcus capitis | 1919 |
| Staphylococcus caprae | 1920 |
| Staphylococcus carnosus | 1921 |
| Staphylococcus cohnii | 1922 |
| Staphylococcus condimenti | 1923 |
| Staphylococcus epidermidis | 1924 |
| Staphylococcus equorum | 1925 |
| Staphylococcus fleurettii | 1926 |
| Staphylococcus haemolyticus | 1927 |
| Staphylococcus hominis | 1928 |
| Staphylococcus lugdunensis | 1929 |
| Staphylococcus pasteuri | 1930 |
| Staphylococcus pseudintermedius | 1931 |
| Staphylococcus saccharolyticus | 1932 |
| Staphylococcus saprophyticus | 1933 |
| Staphylococcus sciuri | 1934 |
| Staphylococcus sp. | 1935 |
| Staphylococcus sp. | 1936 |
| Staphylococcus sp. | 1937 |
| Staphylococcus succinus | 1938 |

TABLE 10-continued

Bacteria Capable of Being Engineered to Produce GABA

| Species | Seq. ID No. |
|---|---|
| *Staphylococcus vitulinus* | 1939 |
| *Staphylococcus warneri* | 1940 |
| *Staphylococcus xylosus* | 1941 |
| *Stenotrophomonas maltophilia* | 1942 |
| *Stenotrophomonas* sp. | 1943 |
| *Streptobacillus moniliformis* | 1944 |
| *Streptococcus agalactiae* | 1945 |
| *Streptococcus alactolyticus* | 1946 |
| *Streptococcus anginosus* | 1947 |
| *Streptococcus australis* | 1948 |
| *Streptococcus bovis* | 1949 |
| *Streptococcus canis* | 1950 |
| *Streptococcus constellatus* | 1951 |
| *Streptococcus cristatus* | 1952 |
| *Streptococcus downei* | 1953 |
| *Streptococcus dysgalactiae* | 1954 |
| *Streptococcus equi* | 1955 |
| *Streptococcus equinus* | 1956 |
| *Streptococcus gallolyticus* | 1957 |
| *Streptococcus* genomosp. | 1958 |
| *Streptococcus* genomosp. | 1959 |
| *Streptococcus* genomosp. | 1960 |
| *Streptococcus* genomosp. | 1961 |
| *Streptococcus* genomosp. | 1962 |
| *Streptococcus* genomosp. | 1963 |
| *Streptococcus* genomosp. | 1964 |
| *Streptococcus* genomosp. | 1965 |
| *Streptococcus gordonii* | 1966 |
| *Streptococcus infantarius* | 1967 |
| *Streptococcus infantis* | 1968 |
| *Streptococcus intermedius* | 1969 |
| *Streptococcus lutetiensis* | 1970 |
| *Streptococcus massiliensis* | 1971 |
| *Streptococcus milleri* | 1972 |
| *Streptococcus mitis* | 1973 |
| *Streptococcus mutans* | 1974 |
| *Streptococcus oligofermentans* | 1975 |
| *Streptococcus oralis* | 1976 |
| *Streptococcus parasanguinis* | 1977 |
| *Streptococcus pasteurianus* | 1978 |
| *Streptococcus peroris* | 1979 |
| *Streptococcus pneumoniae* | 1980 |
| *Streptococcus porcinus* | 1981 |
| *Streptococcus pseudopneumoniae* | 1982 |
| *Streptococcus pseudoporcinus* | 1983 |
| *Streptococcus ratti* | 1984 |
| *Streptococcus salivarius* | 1985 |
| *Streptococcus sanguinis* | 1986 |
| *Streptococcus sinensis* | 1987 |
| *Streptococcus* sp. | 1988 |
| *Streptococcus* sp. | 1989 |
| *Streptococcus* sp. | 1990 |
| *Streptococcus* sp. | 1991 |
| *Streptococcus* sp. | 1992 |
| *Streptococcus* sp. | 1993 |
| *Streptococcus* sp. | 1994 |
| *Streptococcus* sp. | 1995 |
| *Streptococcus* sp. | 1996 |
| *Streptococcus* sp. | 1997 |
| *Streptococcus* sp. | 1998 |
| *Streptococcus* sp. | 1999 |
| *Streptococcus* sp. | 2000 |
| *Streptococcus* sp. | 2001 |
| *Streptococcus* sp. | 2002 |
| *Streptococcus* sp. | 2003 |
| *Streptococcus* sp. | 2004 |
| *Streptococcus* sp. | 2005 |
| *Streptococcus* sp. | 2006 |
| *Streptococcus* sp. | 2007 |
| *Streptococcus* sp. | 2008 |
| *Streptococcus* sp. | 2009 |
| *Streptococcus* sp. | 2010 |
| *Streptococcus* sp. | 2011 |
| *Streptococcus* sp. | 2012 |
| *Streptococcus* sp. | 2013 |
| *Streptococcus* sp. | 2014 |
| *Streptococcus* sp. | 2015 |
| *Streptococcus* sp. | 2016 |
| *Streptococcus* sp. | 2017 |
| *Streptococcus* sp. | 2018 |
| *Streptococcus* sp. | 2019 |
| *Streptococcus* sp. | 2020 |
| *Streptococcus* sp. | 2021 |
| *Streptococcus* sp. | 2022 |
| *Streptococcus* sp. | 2023 |
| *Streptococcus* sp. | 2024 |
| *Streptococcus* sp. | 2025 |
| *Streptococcus* sp. | 2026 |
| *Streptococcus* sp. | 2027 |
| *Streptococcus* sp. | 2028 |
| *Streptococcus* sp. | 2029 |
| *Streptococcus* sp. | 2030 |
| *Streptococcus* sp. | 2031 |
| *Streptococcus* sp. | 2032 |
| *Streptococcus* sp. | 2033 |
| *Streptococcus* sp. | 2034 |
| *Streptococcus* sp. | 2035 |
| *Streptococcus* sp. | 2036 |
| *Streptococcus* sp. | 2037 |
| *Streptococcus* sp. | 2038 |
| *Streptococcus* sp. | 2039 |
| *Streptococcus* sp. | 2040 |
| *Streptococcus suis* | 2041 |
| *Streptococcus thermophilus* | 2042 |
| *Streptococcus uberis* | 2043 |
| *Streptococcus urinalis* | 2044 |
| *Streptococcus vestibularis* | 2045 |
| *Streptococcus viridans* | 2046 |
| *Streptomyces albus* | 2047 |
| *Streptomyces griseus* | 2048 |
| *Streptomyces* sp. | 2049 |
| *Streptomyces* sp. | 2050 |
| *Streptomyces* sp. | 2051 |
| *Streptomyces* sp. | 2052 |
| *Streptomyces* sp. | 2053 |
| *Streptomyces thermoviolaceus* | 2054 |
| *Subdoligranulum variabile* | 2055 |
| *Succinatimonas hippei* | 2056 |
| *Sutterella morbirenis* | 2057 |
| *Sutterella parvirubra* | 2058 |
| *Sutterella sanguinus* | 2059 |
| *Sutterella* sp. | 2060 |
| *Sutterella stercoricanis* | 2061 |
| *Sutterella wadsworthensis* | 2062 |
| *Synergistes* genomosp. | 2063 |
| *Synergistes* sp. | 2064 |
| Synergistetes bacterium | 2065 |
| Synergistetes bacterium | 2066 |
| Synergistetes bacterium | 2067 |
| Synergistetes bacterium | 2068 |
| Synergistetes bacterium | 2069 |
| *Syntrophococcus sucromutans* | 2070 |
| Syntrophomonadaceae genomosp. | 2071 |
| *Tannerella forsythia* | 2072 |
| *Tannerella* sp. | 2073 |
| *Tatlockia micdadei* | 2074 |
| *Tatumella ptyseos* | 2075 |
| *Tessaracoccus* sp. | 2076 |
| *Tetragenococcus halophilus* | 2077 |
| *Tetragenococcus koreensis* | 2078 |
| *Thermoanaerobacter pseudethanolicus* | 2079 |
| *Thermobifida fusca* | 2080 |
| *Thermofilum pendens* | 2081 |
| *Thermus aquaticus* | 2082 |
| *Tissierella praeacuta* | 2083 |
| *Trabulsiella guamensis* | 2084 |
| *Treponema* genomosp. | 2085 |
| *Treponema* genomosp. | 2086 |
| *Treponema* genomosp. | 2087 |
| *Treponema* genomosp. | 2088 |
| *Treponema phagedenis* | 2089 |
| *Treponema* sp. | 2090 |

TABLE 10-continued

Bacteria Capable of Being Engineered to Produce GABA

| Species | Seq. ID No. |
|---|---|
| Treponema sp. | 2091 |
| Treponema sp. | 2092 |
| Treponema sp. | 2093 |
| Treponema sp. | 2094 |
| Treponema sp. | 2095 |
| Treponema sp. | 2096 |
| Treponema sp. | 2097 |
| Treponema sp. | 2098 |
| Treponema sp. | 2099 |
| Treponema sp. | 2100 |
| Treponema sp. | 2101 |
| Treponema sp. | 2102 |
| Treponema sp. | 2103 |
| Treponema sp. | 2104 |
| Treponema sp. | 2105 |
| Treponema sp. | 2106 |
| Treponema sp. | 2107 |
| Treponema sp. | 2108 |
| Treponema sp. | 2109 |
| Treponema sp. | 2110 |
| Treponema sp. | 2111 |
| Tropheryma whipplei | 2112 |
| Trueperella pyogenes | 2113 |
| Tsukamurella paurometabola | 2114 |
| Tsukamurella tyrosinosolvens | 2115 |
| Turicibacter sanguinis | 2116 |
| Ureaplasma parvum | 2117 |
| Ureaplasma urealyticum | 2118 |
| Ureibacillus composti | 2119 |
| Ureibacillus suwonensis | 2120 |
| Ureibacillus terrenus | 2121 |
| Ureibacillus thermophilus | 2122 |
| Ureibacillus thermosphaericus | 2123 |
| Vagococcus fluvialis | 2124 |
| Veillonella atypica | 2125 |
| Veillonella dispar | 2126 |
| Veillonella genomosp. | 2127 |
| Veillonella montpellierensis | 2128 |
| Veillonella parvula | 2129 |
| Veillonella sp. | 2130 |
| Veillonella sp. | 2131 |
| Veillonella sp. | 2132 |
| Veillonella sp. | 2133 |
| Veillonella sp. | 2134 |
| Veillonella sp. | 2135 |
| Veillonella sp. | 2136 |
| Veillonella sp. | 2137 |
| Veillonella sp. | 2138 |
| Veillonella sp. | 2139 |
| Veillonella sp. | 2140 |
| Veillonella sp. | 2141 |
| Veillonella sp. | 2142 |
| Veillonella sp. | 2143 |
| Veillonella sp. | 2144 |
| Veillonellaceae bacterium | 2145 |
| Veillonellaceae bacterium | 2146 |
| Victivallaceae bacterium | 2147 |
| Victivallis vadensis | 2148 |
| Virgibacillus proomii | 2149 |
| Weissella beninensis | 2150 |
| Weissella cibaria | 2151 |
| Weissella confusa | 2152 |
| Weissella hellenica | 2153 |
| Weissella kandleri | 2154 |
| Weissella koreensis | 2155 |
| Weissella paramesenteroides | 2156 |
| Weissella sp. | 2157 |
| Wolinella succinogenes | 2158 |
| Xanthomonadaceae bacterium | 2159 |
| Xanthomonas campestris | 2160 |
| Xanthomonas sp. | 2161 |
| Xenophilus aerolatus | 2162 |
| Yokenella regensburgei | 2163 |
| Zimmermannella bifida | 2164 |
| Zymomonas mobilis | 2165 |
| Alistipes shahii | 2166 |
| Bacteroides caccae | 2167 |
| Bacteroides eggerthii | 2168 |
| Bacteroides sp. | 2169 |
| Bacteroides sp. | 2170 |
| Bacteroides sp. | 2171 |
| Bacteroides uniformis | 2172 |
| Bacteroides vulgatus | 2173 |
| Bacteroides vulgatus | 2174 |
| Bifidobacterium adolescentis | 2175 |
| Bifidobacterium pseudocatenulatum | 2176 |
| Blautia producta | 2177 |
| Blautia producta | 2178 |
| Blautia schinkii | 2179 |
| Clostridium bolteae | 2180 |
| Clostridium butyricum | 2181 |
| Clostridium disporicum | 2182 |
| Clostridium hathewayi | 2183 |
| Clostridium hylemonae | 2184 |
| Clostridium innocuum | 2185 |
| Clostridium innocuum | 2186 |
| Clostridium mayombei | 2187 |
| Clostridium nexile | 2188 |
| Clostridium orbiscindens | 2189 |
| Clostridium symbiosum | 2190 |
| Clostridium tertium | 2191 |
| Collinsella aerofaciens | 2192 |
| Coprobacillus sp. | 2193 |
| Coprococcus catus | 2194 |
| Coprococcus comes | 2195 |
| Dorea formicigenerans | 2196 |
| Dorea longicatena | 2197 |
| Enterococcus faecalis | 2198 |
| Erysipelotrichaceae bacterium | 2199 |
| Escherichia coli | 2200 |
| Escherichia coli | 2201 |
| Eubacterium eligens | 2202 |
| Eubacterium rectale | 2203 |
| Eubacterium rectale | 2204 |
| Faecalibacterium prausnitzii | 2205 |
| Faecalibacterium prausnitzii | 2206 |
| Lachnospiraceae bacterium | 2207 |
| Odoribacter splanchnicus | 2208 |
| Odoribacter splanchnicus | 2209 |
| Parabacteroides merdae | 2210 |
| Roseburia intestinalis | 2211 |
| Ruminococcus bromii | 2212 |
| Ruminococcus gnavus | 2213 |
| Ruminococcus obeum | 2214 |
| Ruminococcus torques | 2215 |
| Streptococcus thermophilus | 2216 |
| Escherichia coli | 2217 |
| Streptococcus thermophilus | 2218 |
| Escherichia coli | 2219 |

Therapeutic Compositions

Any of the GABA-producing bacteria described herein (e.g., natural bacteria or engineered bacteria), or any combination thereof (including combinations of natural and engineered bacteria) can be incorporated into a therapeutic composition. For instance, the therapeutic compositions can be administered to a patient in need thereof to treat or alleviate the symptom of a mental illness or central nervous system disease.

Purification of Strains

In some embodiments, bacteria are purified prior to incorporation into a therapeutic composition. For instance, bacteria can be purified so that the population of bacteria is substantially free of other bacteria (e.g., contains at least 90%, at least 91%, at least 92%, at least 93%, at least 94%, at least 95%, at least 96%, at least 97%, or at least 98%, at least 99% of the specific bacterial strain or strains desired in the composition).

In some embodiments, the therapeutic composition is a probiotic or a medical food comprising at least one GABA-producing bacterial strain. The strain can be administered, for instance, as a probiotic, as capsules, tablets, caplets, pills, troches, lozenges, powders, and/or granules. The strain can also be formulated as a medical food. The GABA-producing bacteria can also be administered as a fecal transplant or suppository.

In some embodiments, the dose of the therapeutic can contain $1\times10^4$, $1\times10^5$, $1\times10^6$, $1\times10^7$, $1\times10^8$, $1\times10^9$, $1\times10^{10}$, $1\times10^{11}$ or greater than $1\times10^{11}$ colony forming units (CFUs) of the desired bacterial species. For instance, the desired bacterial species can be GABA-producing bacteria, bacteria that are capable of inhibiting the growth of GABA-consuming bacteria, or a combination thereof.

In some embodiments, the therapeutic composition or dose unit comprises a pharmaceutically acceptable formulation, including an enteric coating or similar to survive the acidity of the stomach and enabled delivery into the small or large intestines, prebiotics (such as, but not limited to, amino acids (including arginine, glutamate, and omithine), biotin, fructooligosaccharide, galactooligosaccharides, hemicelluloses (e.g., arabinoxylan, xylan, xyloglucan, and glucomannan), inulin, chitin, lactulose, mannan oligosaccharides, oligofructose-enriched inulin, gums (e.g., guar gum, gum arabic and carregenaan), oligofructose, oligodextrose, tagatose, resistant maltodextrins (e.g., resistant starch), transgalactooligosaccharide, pectins (e.g., xylogalactouronan, citrus pectin, apple pectin, and rhamnogalacturonan-1), dietary fibers (e.g., soy fiber, sugarbeet fiber, pea fiber, corn bran, and oat fiber) and xylooligosaccharides, polyamines (such as but not limited to spermidine and putrescine), an effective amount of an anti-bacterial agent, anti-fungal agent, anti-viral agent, or anti-parasitic agent, or any combinations of the above. For instance, the therapeutic composition can also be in the form of a yogurt containing one or more purified strains of GABA-producing bacteria.

Disease Indications

In one or more embodiments of any of the above-aspects, the mental illness or disease of the central nervous system that can be treated by administration of a therapeutic composition described herein is selected from depression, bipolar disorder, schizophrenia, anxiety, anxiety disorders, addiction, social phobia, major depressive disorder, treatment-resistant major depressive disorder (TR-MDD), major depressive disorder and its subtypes (melancholic depression, atypical depression, catatonic depression, postpartum depression, and seasonal affective disorder), Neurodegenerative amyloid disorders (Parkinson's, Alzheimer's, and Huntington's diseases) orthostatic tremor, Lafora disease, restless leg syndrome, neuropathic pain, pain disorders, dementia, epilepsy, stiff-person syndrome, premenstrual dysphoric disorder, autism spectrum disorder, sleep disorders, and attention deficit hyperactivity disorder (ADHD).

In some embodiments, the method further comprises decreasing at least one symptom of a mental disorder or disease of the central nervous system in the subject selected from the group consisting of: fatigue, insomnia, motor dysfunction, stress, persistent anxiety, persistent sadness, social withdrawal, substance withdrawal, irritability, thoughts of suicide, thoughts of self-harm, restlessness, low sex drive, lack of focus, loss of appetite, seizures, memory loss, anger, bouts of emotional reactivity, confusion, pain, and muscle spasms.

Methods of Treatment

The therapeutic compositions described herein can be administered to a patient in need thereof, for instance for the treatment of a mental illness or disease of the central nervous system. In some embodiments, the method of treatment can comprise first diagnosing a patient who can benefit from treatment by a therapeutic composition described herein. In some embodiments, the method further comprises administering to the patient a therapeutic composition described herein.

Patient Diagnosis

In some embodiments, the process of identifying a subject with a mental illness or disease of the central nervous system can be carried out by a trained psychologist, psychiatrist, or neurologist. For instance, a psychiatrist, psychologist, or neurologist can diagnose a subject with a mental illness or disease of the central nervous system evaluating the subject's behavior for symptoms of the mental illness or disease of the central nervous system. One of skill in the art will understand that mental illness can also be identified in a subject with the aid of the *Diagnostic and Statistical Manual of Mental Disorders* (DSM-5), (American Psychiatric Association).

In one or more embodiments, the process of identifying a subject with a mental illness or disease of the central nervous system can comprise diagnosing the subject with a mental illness or disease of the central nervous system. In some embodiments, the mental illness or disease of the central nervous system is identified or diagnosed using fMRI. In some embodiments, mental illness or disease of the central nervous system can be identified with standard psychological and neurological surveys, or in other methods known to experts in the field.

In some embodiments, a subject in need of treatment with a therapeutic composition described herein can be identified by identifying low levels of GABA in the subject's blood, serum, stool, or other bodily fluid. In some embodiments, the amount of GABA in the subject's stool (e.g., the initial amount of GABA in the subject's stool) is below about 8 µg GABA per gram of stool. The amount of GABA can be measured using the wet or dry weight of stool by LC/MS or another technique known in the art. In some embodiments, the amount of GABA in the subject's blood or serum (e.g., the initial amount of GABA in the subject's blood or serum) is below about 10 µg/L+/−5 µg/L GABA per gram of blood or serum (e.g., as measured by LC/MS). In some embodiments, the amount of GABA in the prefrontal cortex, or other areas of the brain, is below about 1.0 mM/kg, as measured by proton magnetic resonance (PMR), or another similar technique.

In some embodiments, the percentage of GABA-producing bacteria in the subject's gut (e.g., the initial amount) represents about 10% of total 16S sequences as measured by sequencing using such methods as 16S rDNA gene Illumina sequencing or quantitative PCR. In some embodiments, the percentage of GABA-producing bacteria in the subject's gut represents about 9%, about 8%, about 7%, about 6%, about 5%, about 4%, about 3%, about 2%, about 1%, or less than about 1% of the total 16S sequences measured in the subject's gut.

Determination of the initial amount of GABA in a subject's blood, serum, regions of the brain, or stool can help identify subjects that can benefit from treatment by administration of GABA-producing bacteria. In some embodiments, a subject with an initial amount of GABA in the serum or blood below 10 µg/L GABA can benefit from administration of GABA-producing bacteria. In some embodiments, a subject with an initial amount of GABA in the serum or blood below 100 µg, below 50 µg, below 25 µg, below 20 µg, below 15 µg, below 10 µg, below 9 µg, below 8 µg, below 7 µg, below 6 µg, below 5 µg, below 4 µg, below 3 µg, below 2 µg, below 1 µg, below 0.5 µg, below 0.1 µg, below 0.01 µg, below 10 ng, or below 1 ng, or below 0.1 ng per L of blood or serum can benefit from administration of a GABA-producing bacteria.

In some embodiments, a subject with an initial amount of GABA in the brain, in regions such as the prefrontal cortex (or other areas of the brain), of about 1.0 mM/kg can benefit from treatment by administration of GABA-producing bacteria. In some embodiments, a subject with an initial amount of GABA in the brain, in such regions as the prefrontal cortex (or other areas of the brain), of below 100 mM, below 50 mM, below 25 mM, below 20 mM, below 15 mM, below 10 mM, below 9 mM, below 8 mM, below 7 mM, below 6 mM, below 5 mM, below 4 mM, below 3 mM, below 2 mM, below 1 mM, below 0.5 mM, below 0.1 mM, or below 0.01 mM, or below 0.001 mM GABA can benefit from treatment by administration of GABA-producing bacteria.

In some embodiments, a subject with an initial amount of GABA in stool below 8 µg GABA per gram of stool (wet or dry weight) can benefit from administration of GABA-producing bacteria. In some embodiments, a subject with an initial amount of GABA in the stool below 100 µg, below 50 µg, below 25 µg, below 20 µg, below 15 µg, below 10 µg, below 9 µg, below 8 µg, below 7 µg, below 6 µg, below 5 µg, below 4 µg, below 3 µg, below 2 µg, below 1 µg, below 0.5 µg, below 0.1 µg, below 0.01 µg, below 10 ng, or below 1 ng, or below 0.1 ng per gram of stool can benefit from administration of a GABA-producing bacteria.

In some embodiments of any of the above aspects, the amount of GABA is increased 0.1, 1, 5, 10, 20, 30, 40, 50, 60, 70, 80, 90, 100, 500, 1000, 2000, 3000, 4000, 5000, or more percent in the subject's stool relative to the initial amount of GABA in the subject's stool, e.g., as measured in step (b) of any of the above-aspects. In some embodiments, the amount of GABA is increased 0.1, 1, 5, 10, 20, 30, 40, 50, 60, 70, 80, 90, 100, 500, 1000, 2000, 3000, 4000, 5000, or more percent in the subject's blood or serum relative to the initial amount of GABA in the subject's blood or serum, e.g., as measured in step (b) of any of the above-aspects. In some embodiments, the amount of GABA is increased 0.1, 1, 5, 10, 20, 30, 40, 50, 60, 70, 80, 90, 100, 500, 1000, 2000, 3000, 4000, 5000, or more percent in regions of the subject's brain, such as, but not limited to the prefrontal cortex, relative to the initial amount of GABA in the subject's brain, e.g., as measured in step (b) of any of the above-aspects. In some embodiments, at least one GABA-producing bacteria is increased 0.1, 1, 5, 10, 20, 30, 40, 50, 60, 70, 80, 90, 100, 500, 1000, 2000, 3000, 4000, 5000, or more percent in the subject's stool relative to the initial amount of GABA-producing bacteria in the subject's stool, e.g., as measured in step (b) in any of the above-aspects. In some embodiments, the level of expression of at least one GABA producing enzyme is increased 0.1, 1, 5, 10, 20, 30, 40, 50, 60, 70, 80, 90, 100, 500, 1000, 2000, 3000, 4000, 5000, or more percent in the subject's stool relative to the initial level of expression of GABA-producing enzymes in the subject's stool, as measured by qPCR or some other appropriate method, known to those familiar in the field.

In some embodiments of the disclosure, the amount of GABA-consuming bacteria can be reduced, e.g., reduced in the subject's stool, blood serum, and the like. The GABA-consuming bacteria can be, for instance, *Evtepia gabavorous* or *Firmicutes bacterium* MGS:114. In some embodiments, GABA-consuming bacteria can be reduced by 0.1, 1, 5, 10, 20, 30, 40, 50, 60, 70, 80, 90, 100, 500, 1000, 2000, 3000, 4000, 5000, or more percent.

Accordingly, the present disclosure provides for the treatment of mental illness or disease of the central nervous system comprising administering to the subject GABA-producing bacteria, or prebiotics to stimulate growth or GABA production capabilities of GABA producing bacteria.

Methods of Culturing GABA-Consuming Bacteria

In some embodiments, the present disclosure provides a method of culturing bacteria that require GABA for survival and replication. In some cases, these bacteria were previously uncultured or unculturable. In some cases, the bacteria are cultured by supplying endogenous GABA to the growth medium. In some embodiments, the bacteria are cultured by co-culturing the bacteria with a different bacterium capable of producing GABA (e.g., a bacterium as described above).

In some embodiments, the previously uncultured bacterium is *E. gabavorous*. *E. gabavorous* can be cultured on a suitable substrate such as agar. In some embodiments, the agar can contain added GABA. In some embodiments, the present disclosure provides a method of culturing *E. gabavorous* comprising co-culturing *E. gabavorous* with another bacterial strain, said strain is capable of producing GABA, for instance at conditions that are physiologically relevant and found in to the human gastrointestinal tract (e.g., pH less between about 4.5 and about 7.5).

Without wishing to be bound by theory, some previously unculturable bacteria (e.g., *E. gabavorous*) may be able to grow in proximity to cultivable organisms producing growth factors necessary for bacteria to survive or grow. Accordingly, the present disclosure teaches the discovery and culture of *E. gabavorous* in the presence of GABA as a necessary growth factor.

*E. gabavorous* was identified as a late-growing colony in spatial proximity to *Bacteroides fragilis* KLE1758. It was found that growth of *E. gabavorous* KLE1738 was induced in the presence of supernatant derived from *Bacteroides fragilis* KLE1758. Chemical analysis via HPLC and NMR of *Bacteroides fragilis* KLE1738 supernatant revealed GABA as the necessary growth factor for *E. gabavorous*.

As set forth in FIG. 1, and Example 2, *E. gabavorous* was initially found because it grew in the presence of *Bacteroides fragilis* KLE1758. It was proposed that *Bacteroides fragilis* KLE1758 produces a growth factor that is necessary for the growth and survival of *E. gabavorous*. FIG. 1A shows a photograph of an agar plate containing colonies of bacteria after treatment with human stool. The inset at the top right shows a close-up of a colony of KLE1758 along with a colony of 1738 that is growing in the immediate proximity. FIG. 1B shows a colony of KLE1758 that is capable of supporting multiple colonies of KLE1738 on an agar plate with no other bacteria. Without wishing to be bound by theory, *Bacteroides fragilis* KLE1758 can support the growth of *E. gabavorous* KLE1738. Without wishing to be bound by theory, *Bacteroides fragilis* KLE1758 and *E. gabavorous* KLE1738 can co-exist in a symbiotic relationship in which *E. gabavorous* KLE1738 can consume the GABA that is produced by *Bacteroides fragilis* KLE1758.

As shown in FIG. 2 and Examples 3-4, the supernatant from a 48-hour culture of *Bacteroides fragilis* KLE1758 was found to support the growth of *E. gabavorous* KLE1738, whereas standard agar was not. After a series of purification and isolation steps of the KLE1758 supernatant, it was discovered that GABA was responsible for the growth of *E. gabavorous* KLE1738. FIG. 2A shows that *E. gabavorous* KLE1738 grew in the presence of supernatant of *Bacteroides fragilis*. However, FIG. 2B shows that *E. gabavorous* KLE1738 did not grow in the presence of sterile vehicle on standard agar. After a first fractionation of the *Bacteroides* fragilis KLE1758 spent medium, it was found that the most polar fragment was capable of inducing the growth of *E. gabavorous* KLE1738 (FIG. 2C), but that less polar fragments could not induce growth (FIG. 2D). FIGS. 2E and 2F show close-up views demonstrating that the most polar fraction of the *Bacteroides fragilis* KLE1758 supernatant could induce growth of *E. gabavorous* KLE1738 (FIG. 2E), whereas less polar fragments could not (FIG. 2F). As shown in FIG. 2G, only GABA was identified as being capable of inducing growth of *E. gabavorous* KLE1738.

The 16S nucleotide sequence of *E. gabavorous* KLE1738 is given in Seq. ID No. 2286.

The genetic sequence of *E. gabavorous* KLE1738 was identified as set forth in Example 5. The annotated genome (2,500,009 bp) of *E. gabavorous* is given in the attached Sequence Listing comprising SEQ. ID Nos. 1-2288 and is given in SEQ ID Nos. 2218-2285. Without wishing to be bound by theory, the genome revealed no obvious entry points for metabolism of common sugars or other carbon sources.

Without wishing to be bound by theory, it was discovered that transport systems for common sugars or other carbon sources were also incomplete. Without wishing to be bound by theory, their absence suggests a recent loss of function. *E. gabavorous* is predicted to have a limited set of transporters, including those for methionine, branched-chain amino acids, dipeptides, oligopeptides, and choline/betaine, as predicted in Table 10.

TABLE 10

Predicted Transport Systems in *E. gabavorous*.

| Category | Subsystem | Role |
| --- | --- | --- |
| Amino Acids and Derivatives | Polyamine Metabolism | ABC transporter, periplasmic spermidine putrescine-binding protein PotD (TC 3.A.1.11.1) |
| Amino Acids and Derivatives | Polyamine Metabolism | Spermidine Putrescine ABC transporter permease component PotB (TC 3.A.1.11.1) |
| Amino Acids and Derivatives | Polyamine Metabolism | Spermidine Putrescine ABC transporter permease component PotC (TC 3.A.1.11.1) |
| Amino Acids and Derivatives | Methionine Biosynthesis | Methionine ABC transporter ATP-binding protein |
| Amino Acids and Derivatives | Methionine Biosynthesis | Methionine ABC transporter permease protein |
| Amino Acids and Derivatives | Methionine Biosynthesis | Methionine ABC transporter substrate-binding protein |
| Amino Acids and Derivatives | Methionine Degradation | Methionine ABC transporter ATP-binding protein |
| Amino Acids and Derivatives | Methionine Degradation | Methionine ABC transporter permease protein |
| Amino Acids and Derivatives | Methionine Degradation | Methionine ABC transporter substrate-binding protein |
| Clustering-based subsystems | PhoR-PhoB two-component regulatory system | Phosphate ABC transporter, periplasmic phosphate-binding protein PstS (TC 3.A.1.7.1) |
| Membrane Transport | ABC transporter dipeptide (TC 3.A.1.5.2) | Dipeptide-binding ABC transporter, periplasmic substrate-binding component (TC 3.A.1.5.2) |
| Membrane Transport | ABC transporter oligopeptide (TC 3.A.1.5.1) | Oligopeptide ABC transporter, periplasmic oligopeptide-binding protein OppA (TC 3.A.1.5.1) |
| Membrane Transport | ABC transporter branched-chain amino acid (TC 3.A.1.4.1) | Branched-chain amino acid ABC transporter, amino acid-binding protein (TC 3.A.1.4.1) |
| Phosphorus Metabolism | High affinity phosphate transporter and control of PHO regulon | Phosphate ABC transporter, periplasmic phosphate-binding protein PstS (TC 3.A.1.7.1) |
| Phosphorus Metabolism | Phosphate metabolism | Phosphate ABC transporter, periplasmic phosphate-binding protein PstS (TC 3.A.1.7.1) |
| Stress Response | Choline and Betaine Uptake and Betaine Biosynthesis | L-proline glycine betaine ABC transport system permease protein ProV (TC 3.A.1.12.1) |
| Stress Response | Choline and Betaine Uptake and Betaine Biosynthesis | Glycine betaine ABC transport system, glycine-betaine-binding protein OpuAC |
| Stress Response | Choline and Betaine Uptake and Betaine Biosynthesis | Glycine betaine ABC transport system, permease protein OpuAB |
| Stress Response | Choline and Betaine Uptake and Betaine Biosynthesis | L-proline glycine betaine binding ABC transporter protein ProX (TC 3.A.1.12.1) |
| Sulfur Metabolism | Alkanesulfonate assimilation | ABC-type nitrate/sulfonate/bicarbonate transport system, ATPase component |
| Sulfur Metabolism | Alkanesulfonate assimilation | Alkanesulfonates ABC transporter ATP-binding protein |

Without wishing to be bound by theory, these amino acids are not usually capable of supporting bacterial growth as single carbon sources, unlike serine, threonine, glutamate, and others. This is supported by the inability of *E. gabavorous* to grow on the tested amino acids.

Figure 3:
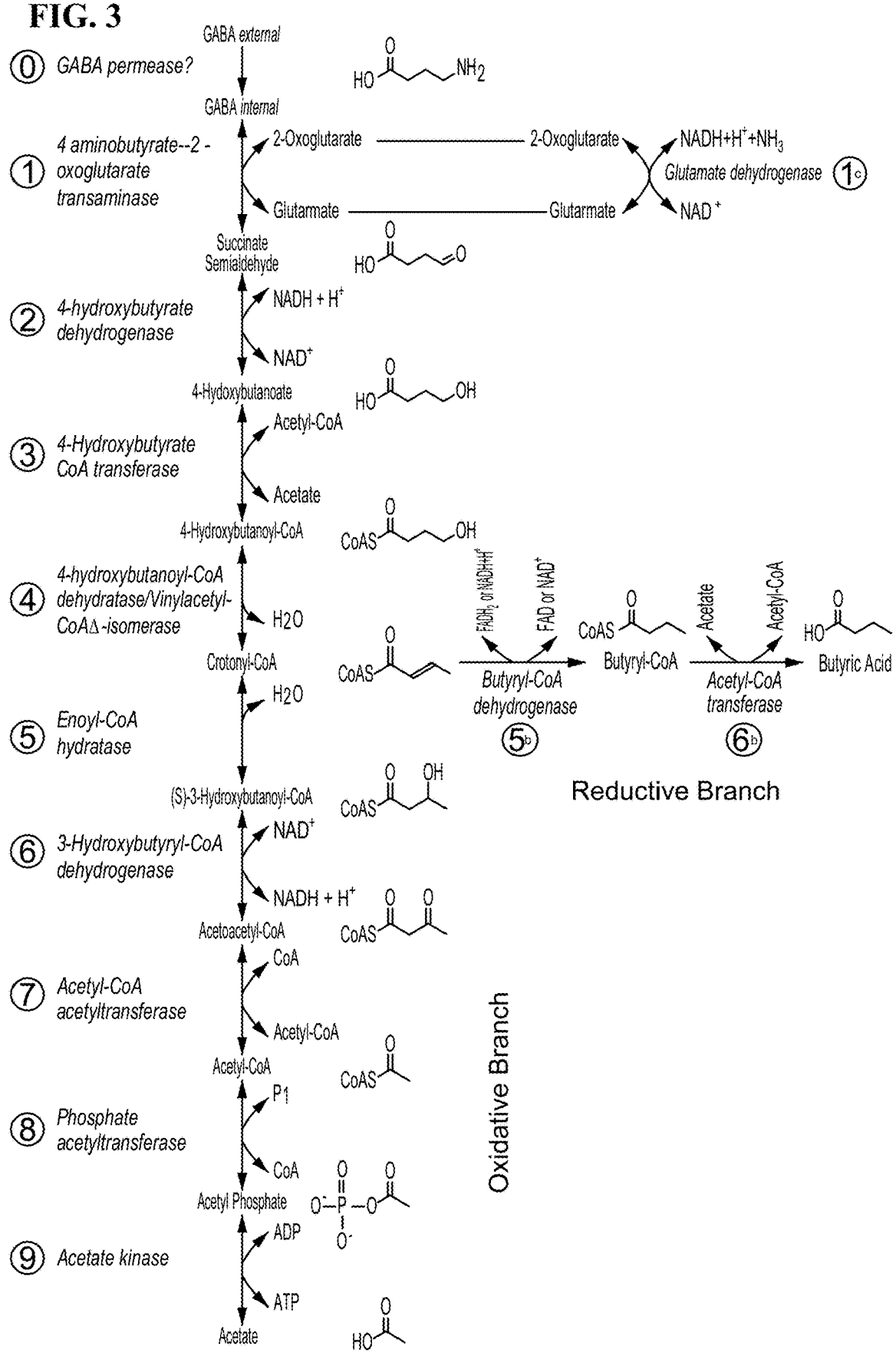
FIG. 3 shows a proposed GABA metabolism of *E. gabavorous* KLE1738.

Without wishing to be bound by theory, the metabolic pathway of *E. gabavorous* is proposed to be similar to that of *Clostridium aminobutyricum*, as set forth in FIG. 3, as all enzymes in this pathway were identified in the *E. gabavorous* genome (Table 11).

colonies of *E. gabavorous* that do form will necessarily grow in close spatial proximity to GABA-producers.

Because GABA production by some bacteria, including *E. coli*, only occurs at a very low pH (e.g., at a pH not relevant to the human gut), the assay method set forth herein was adapted to control the pH of the media, enabling identification of organisms capable of producing GABA at a pH between about 4.5 and about 7.5. Without wishing to be bound by theory, the pH of between about 4.5 and about 7.5 is the relevant pH within the human gut. Accordingly,

TABLE 11

Enzymes in *E. gabavorous* GABA fermentation pathway, predicted by RAST

| Enzyme # | Contig | Start | Stop | Length (bp) | Function |
|---|---|---|---|---|---|
| 1 | KLE1738_5 | 26729 | 28084 | 1356 | Gamma-aminobutyrate: alpha-ketoglutarate aminotransferase (EC 2.6.1.19) |
| 2 | KLE1738_5 | 25576 | 26688 | 1113 | NAD-dependent 4-hydroxybutyrate dehydrogenase (EC 1.1.1.61) |
| 3 | KLE1738_2 | 195690 | 197033 | 1344 | 4-hydroxybutyrate: acetyl-CoA CoA transferase (EC 2.8.1.-) |
| 3 | KLE1738_28 | 9343 | 10665 | 1323 | 4-hydroxybutyrate: acetyl-CoA CoA transferase (EC 2.8.1.-) |
| 3 | KLE1738_5 | 24249 | 25547 | 1299 | 4-hydroxybutyrate: acetyl-CoA CoA transferase (EC 2.8.1.-) |
| 3 | KLE1738_7 | 87690 | 86401 | 1290 | 4-hydroxybutyrate: acetyl-CoA CoA transferase (EC 2.8.1.-) |
| 4 | KLE1738_5 | 22352 | 23902 | 1551 | 4-hydroxybutanoyl-CoA dehydratase (EC 4.2.1.-)/Vinylacetyl-CoA Delta-isomerase (EC 5.3.3.3) |
| 5 | KLE1738_6 | 2958 | 2092 | 867 | Enoyl-CoA hydratase (EC 4.2.1.17) |
| 5 | KLE1738_11 | 1132 | 356 | 777 | Enoyl-CoA hydratase (EC 4.2.1.17) |
| 6 | KLE1738_6 | 4710 | 5762 | 1053 | 3-hydroxybutyryl-CoA dehydrogenase (EC 1.1.1.35) |
| 6 | KLE1738_8 | 87921 | 88769 | 849 | 3-hydroxybutyryl-CoA dehydrogenase (EC 1.1.1.35) |
| 7 | KLE1738_14 | 4910 | 6139 | 1230 | Acetyl-CoA acetyltransferase (EC 2.3.1.9) |
| 7 | KLE1738_19 | 28638 | 27382 | 1257 | Acetyl-CoA acetyltransferase (EC 2.3.1.9) |
| 8 | KLE1738_13 | 26709 | 25738 | 972 | Phosphate acetyltransferase (EC 2.3.1.8) |
| 9 | KLE1738_1 | 119924 | 121141 | 1218 | Acetate kinase (EC 2.7.2.1) |
| 1b | KLE1738_30 | 8650 | 9999 | 1350 | NADP-specific glutamate dehydrogenase (EC 1.4.1.4) |
| 5b | KLE1738_6 | 4303 | 3083 | 1221 | Butyryl-CoA dehydrogenase (EC 1.3.8.1) |
| 6b | KLE1738_1 | 158124 | 159767 | 1644 | Acetyl-CoA: acetoacetyl-CoA transferase (EC 2.8.3.8) |

Figure 4A:
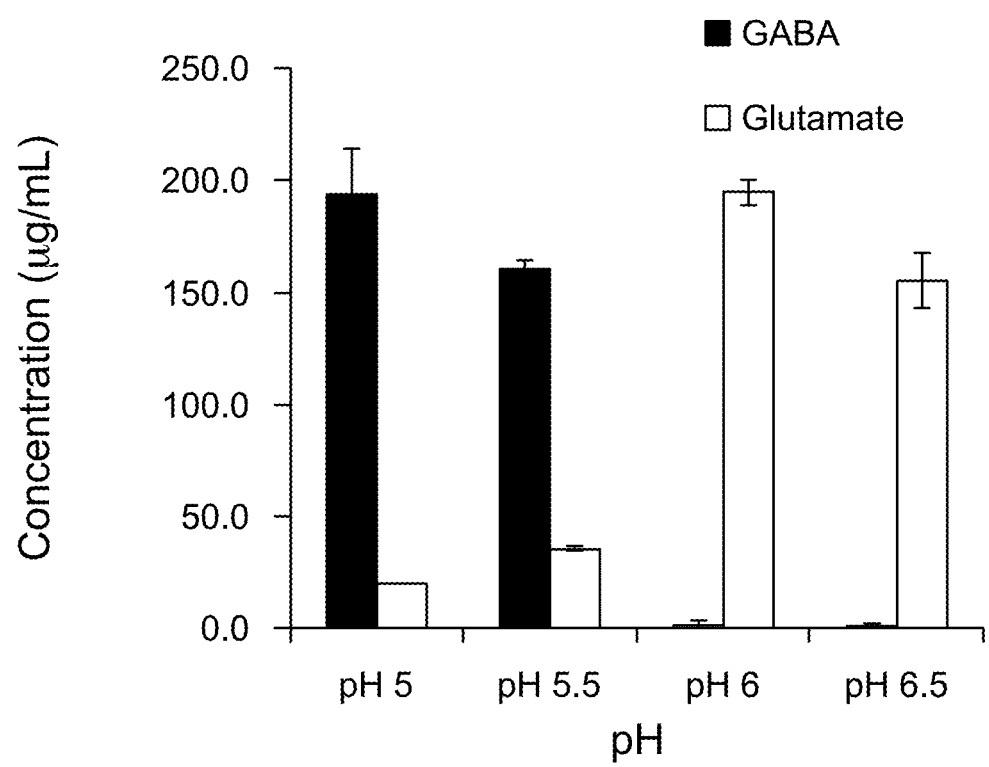
FIG. 4a shows GABA production of *B. fragilis* KLE1758 is observed only at a pH of 5.5 and below, highlighting the importance of acidic pH on GABA production for certain strains or species of bacteria.

The pH dependency of *B. fragilis* KLE1758's ability to produce GABA was investigated. As set forth in Example 6, *B. fragilis* KLE1758 was grown at various pH values, and the supernatant from that growth was analyzed using LCMS. As shown in FIG. 4A, GABA is produced primarily at relatively lower pH (e.g., about 5.5 and below), compared with glutamate.

Accordingly, it was found that *B. fragilis* KLE1758 can produce GABA at low pH, whereas it was found to produce primarily glutamate at relatively high pH. As set forth in Example 6 and FIG. 4A, at a pH of about 5 and about 5.5, *B. fragilis* KLE1758 produced considerably more GABA than glutamate. However, at a pH of about 6 and about 6.5, *B. fragilis* KLE1758 was found to produce primarily glutamate and relatively low quantities of GABA.

Biological Screens for GABA-Producers

The present disclosure also teaches methods of identifying bacteria that can produce GABA. Given the strict requirement of GABA for the growth of *E. gabavorous*, the present disclosure provides methods of screening for bacteria capable of producing GABA using, for instance. *E. gabavorous* and/or other GABA-dependent bacterial growth as a bioassay. Importantly, by using buffered media (e.g., buffered agar), the assay technique set forth herein can be used to identify bacteria that are capable of producing bacteri at various pH values (e.g., between about 5.5 to about 7.5).

As set forth in Example 7, a sample that is thought to contain GABA-producing bacteria, such as a human stool sample, can be mixed with molten agar. The agar, containing the bacterial sample, can then be streaked with a dilute solution of *E. gabavorous*. As shown herein, *E. gabavorous* cannot grow in the absence of GABA, and therefore any bacteria that can produce GABA at these pH values can in some embodiments be capable of producing GABA in the human gut.

In other words, by controlling the pH of the growth medium (e.g., by buffering the molten agar), the present disclosure can allow one to distinguish between GABA-producers that are capable of producing GABA at a physiologically relevant pH (e.g., between about 4.5 to about 7.5) from bacteria that are not able to produce GABA at a physiological relevant pH (e.g., bacteria that can only produce substantial quantities of GABA below pH of about 4.5).

Figure 4B:
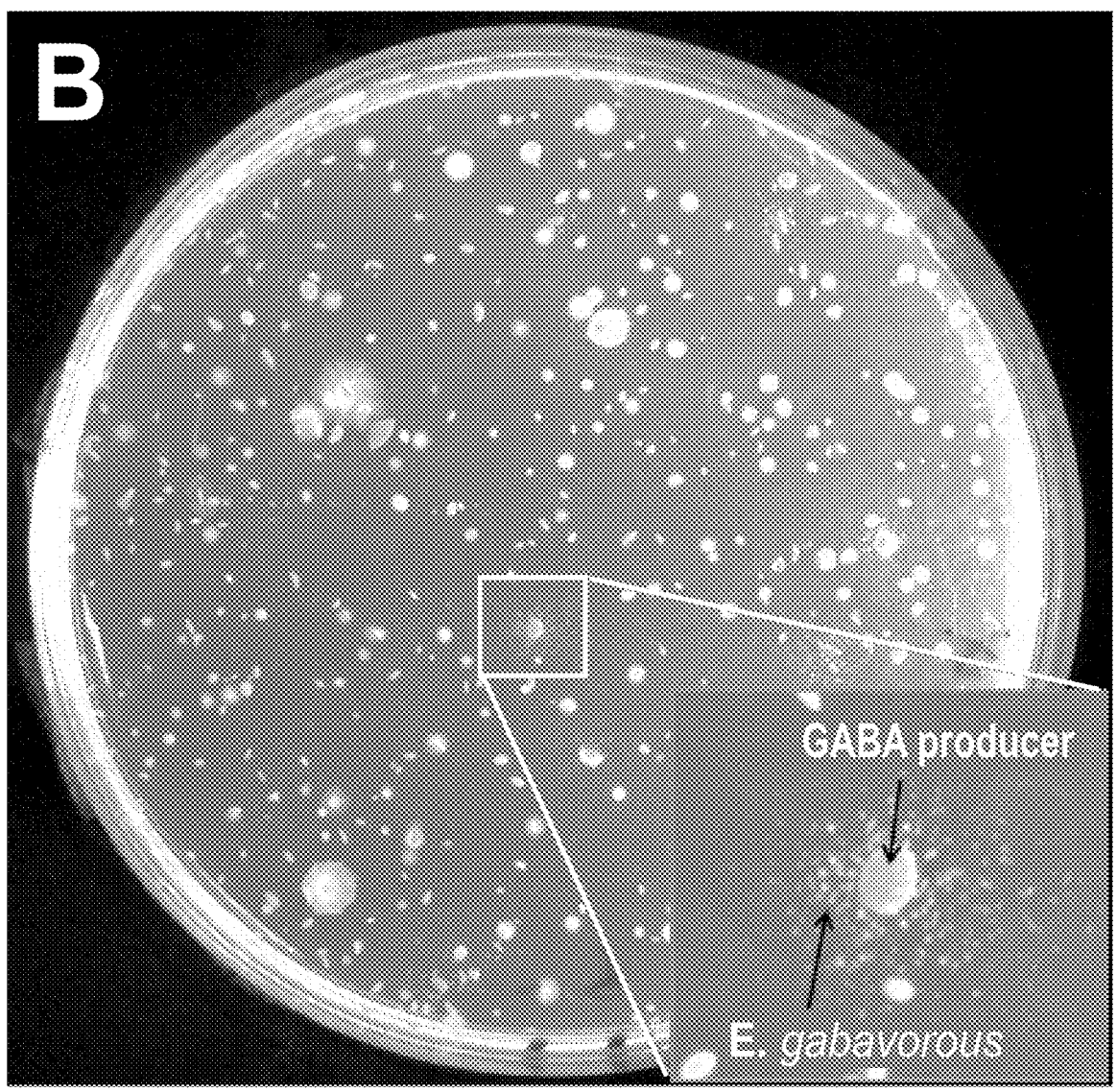
FIG. 4B shows an assay for the identification of GABA-producing bacteria, capable of producing GABA at a pH between 4.5 and 7.5, using the GABA-requirement of *E. gabavorous* KLE1738. The medium was heavily buffered to maintain a pH of the desired range and identify strains of bacteria capable of producing GABA at a pH physiologically relevant to the human gut.
Figure 4C:
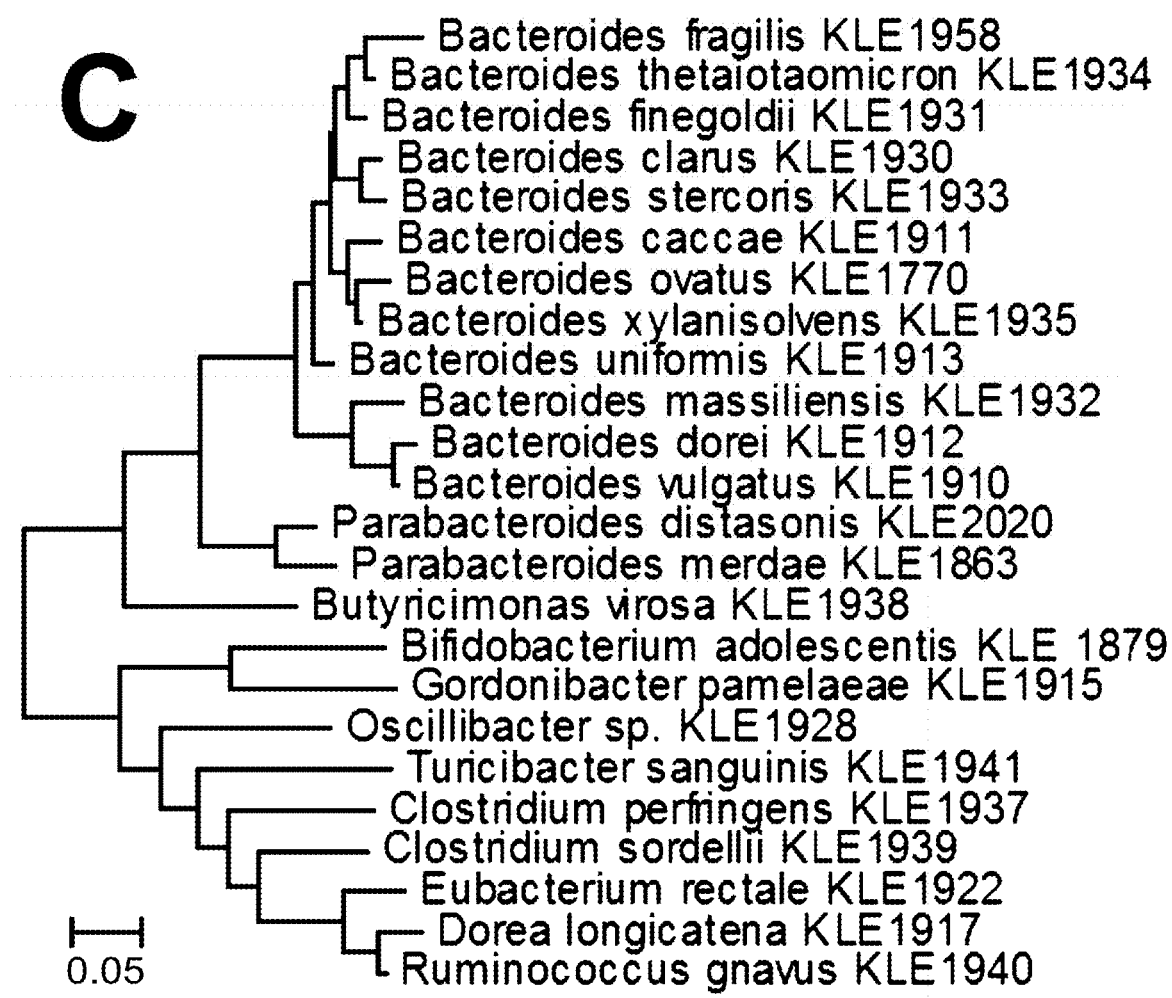
FIG. 4C shows a phylogenetic tree of GABA producers, capable of producing GABA at a pH of about 4.5 to about 7.5, identified by the methods herein.

Using this method, a number of representatives from multiple genera, including, but not limited to, *Bacteroides. Bifidobacterium, Blautia, Coprococcus, Gordonibacter, Dorea*, and *Clostridium* were identified. FIG. 4B shows a representative agar plate showing growth of *E. gabavorous* in the presence of a GABA-producing bacteria. FIG. 4C shows a phylogenetic tree of GABA-producing bacteria that were identified using this method.

Figure 5:
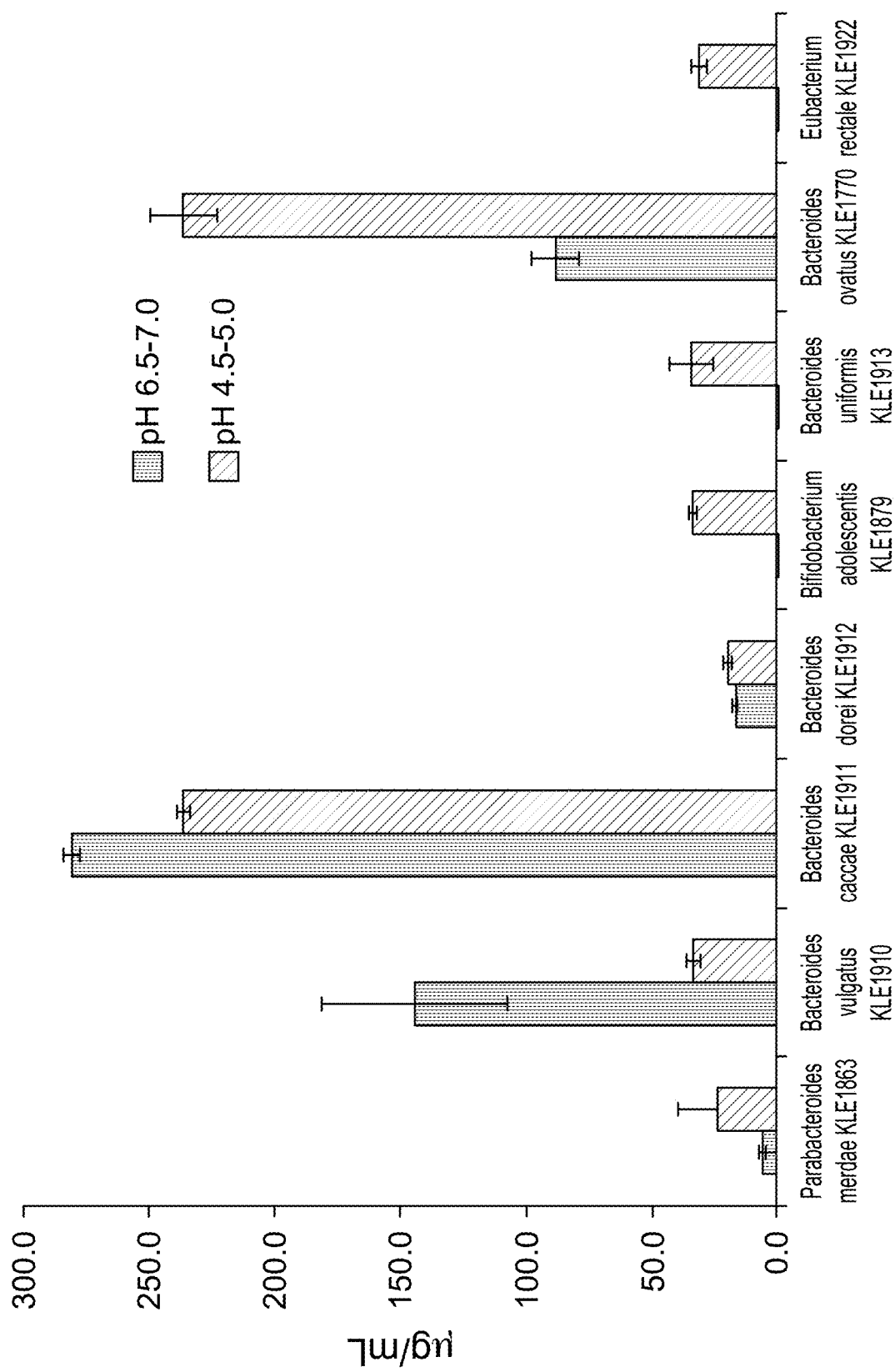
FIG. 5 shows GABA production capabilities of several strains identified using the screen described in Example 7. The ability of organisms to produce GABA at a range of pH conditions is highlighted.

FIG. 5 shows the GABA production capabilities of certain strains of GABA producers identified using the techniques described herein. As set forth in FIG. 5, eight strains of GABA producers were grown in buffered media (e.g., between about pH 4.5 and about pH 5.0; and between about pH 6.5 and about pH 7.0). Using the method described in Example 6, the GABA-producing capabilities of the GABA-producing bacteria at various pH values were investigated. As set forth in FIG. 5, certain bacteria (e.g., *B. dorei* KLE1912) produced relatively similar quantities of GABA at lower pH (e.g., between about 4.5 and about 5.0). In contrast, certain bacteria produced different amounts of GABA depending on the pH (e.g., *B. vulgatus* KLE1910 and

*B. ovatus* KLE1770). Notably, as shown for *B. vulgatus* KLE1910 and *B. ovatus* KLE1770, some bacteria were found to produce relatively more GABA at lower pH than at higher pH, whereas some bacteria were found to produce relatively more GABA at higher pH than at lower pH.

In some embodiments of the method of identifying bacteria capable of producing GABA, the substrate is agar. In some embodiments, the step of contacting the substrate with *E. gabavorous* comprises streaking the agar with a dilute solution of *E. gabavorous*. The GABA-producing colonies are then identified by growth induction of *E. gabavorous*. As set forth above, growth *E. gabavorous* is used to determine if a bacterial strain produces GABA. However, one of skill in the art will understand that any bacteria that has a strict requirement of GABA for growth and survival can likewise be used as described above to identify bacteria that can produce GABA.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Unless otherwise noted, all materials were obtained from commercial suppliers and were used without further purification. Anhydrous solvents were obtained from Sigma-Aldrich (Milwaukee, Wis.) and used directly.

Unless otherwise specified, PCR was performed using the general bacterial primers 27F (5'-AGAGTTGATCMTGGCTCAG-3') (set forth in Seq ID No. 2287) and 1492R (5'-TACGGYTACCTTGTACGACTT-3') (set forth in Seq ID No. 2288) to amplify the 16S rRNA gene. The PCR reaction mixture was 12.5 µL GoTaq Master Mix (Promega), 1 µL 10 µM 27F and 1492R primers, 9.5 µL Nuclease Free Water (Promega), and 1 µL of a colony resuspended in 100 µL sterilized distilled water. The amplification conditions were one cycle of 95° C. for 5 min; 30 cycles of 95° C. for 30 s, 55° C. for 30 s; 72° C. for 90 s; and finally one cycle of 72° C. for 7 min. Amplification of PCR reactions were then confirmed using gel electrophoresis on a 0.8% agarose gel loaded saturated with ethidium bromide. Successful PCRs were sequenced by Macrogen Corporation using the 27F primer using the Applied Biosystems 3730xl DNA analyzer. Quality control for sequences was performed using DNA Baser (www.DnaBaser.com), in which ends were trimmed until there were more than 75% good bases (defined by having a QV score of higher than 25) in an 18 base window. Identification of phylogenetic neighbors and calculation of pairwise sequence similarity were carried out using the EzTaxon server.

Example 1: Human Stool Collection

Stool samples from a healthy human donor were collected using a commercially available stool collection vessel. Within 5 minutes of collection, 1 gram of stool was resuspended in 9 mL of sterile 20% glycerol in PBS and homogenized for 30 seconds using a vortex. 1 mL aliquots of this mixture were loaded in cryotubes and stored at −80° C. for cultivation.

Example 2: Cultivation of Helper-Uncultured Pairs from Human Stool Samples

All cultivation work was performed in a Coy Anaerobic Vinyl chamber with an atmosphere of 5% hydrogen, 10% $CO_2$, 85% nitrogen. Anaerobically, serial dilutions of thawed stool samples were prepared in PBS and bead spread (7-10 beads/plate) on 1× Fastidious Anaerobic Agar (Accumedia) plates with 2.5% yeast extract (FAAy). Plates were incubated at 37° C. anaerobically for one week, and each day appearance of colonies were tracked by spotting the outside of the plates with different colored markers. At the end of the week, serial dilutions of late forming colonies (appearance after 4-7 days) were prepared in PBS and bead spread on FAAy plates. Nearby (<2 cm), early forming colonies (appearance after 1-3 days) were then resuspended in PBS at a high density. Five µL of this suspension were spotted on the plates with their respective spread-candidate dependent and incubated for up to one week in the chamber, and observed daily. Growth induction of the dependent organism around the spotted helper indicated a positive hit.

A fecal sample from a healthy human donor was diluted and spread-plated on rich medium, and newly formed colonies were noted daily for a week. Late forming colonies (3-7 days) were diluted and spread on a nutrient agar plate, and a heavy inoculum of a neighboring, early forming colony (1-2 days) was spotted, as shown in FIG. 1A. Using this method, a number of helper-uncultured pairs were identified, in which the spread-plated uncultured isolate formed a gradient of growth around the spotted culturable helper.

One isolate, *E. gabavorous* KLE1738 (93.22% similar to *Flavonifractor plauttii* ATCC 29863 by 16S rRNA gene sequence), was dependent on *Bacteroides fragilis* KLE1758 (100% similar to *Bacteroides fragilis* ATCC 25852 by 16S rRNA gene sequence) for growth (FIG. 1B). *E. gabavorous*, is a gram positive organism of the Clostridia class.

Example 3: Determination of GABA as Growth Factor for *E. gabavorous*

Figure 2A:
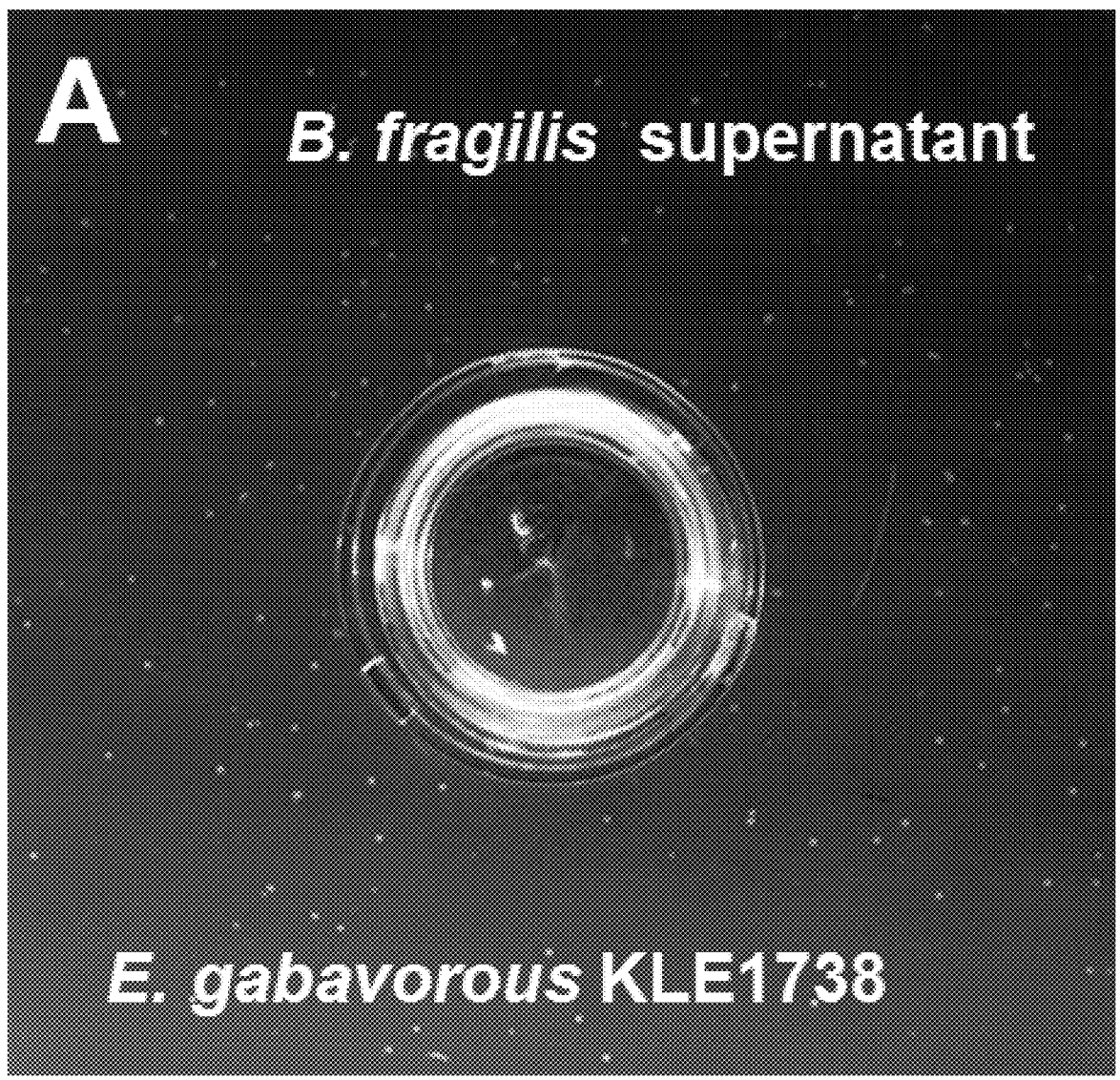
FIG. 2A shows the growth of *Evtepia gabavorous* KLE1738 in the presence of the supernatant from *Bacteroides fragilis*.
Figure 2B:
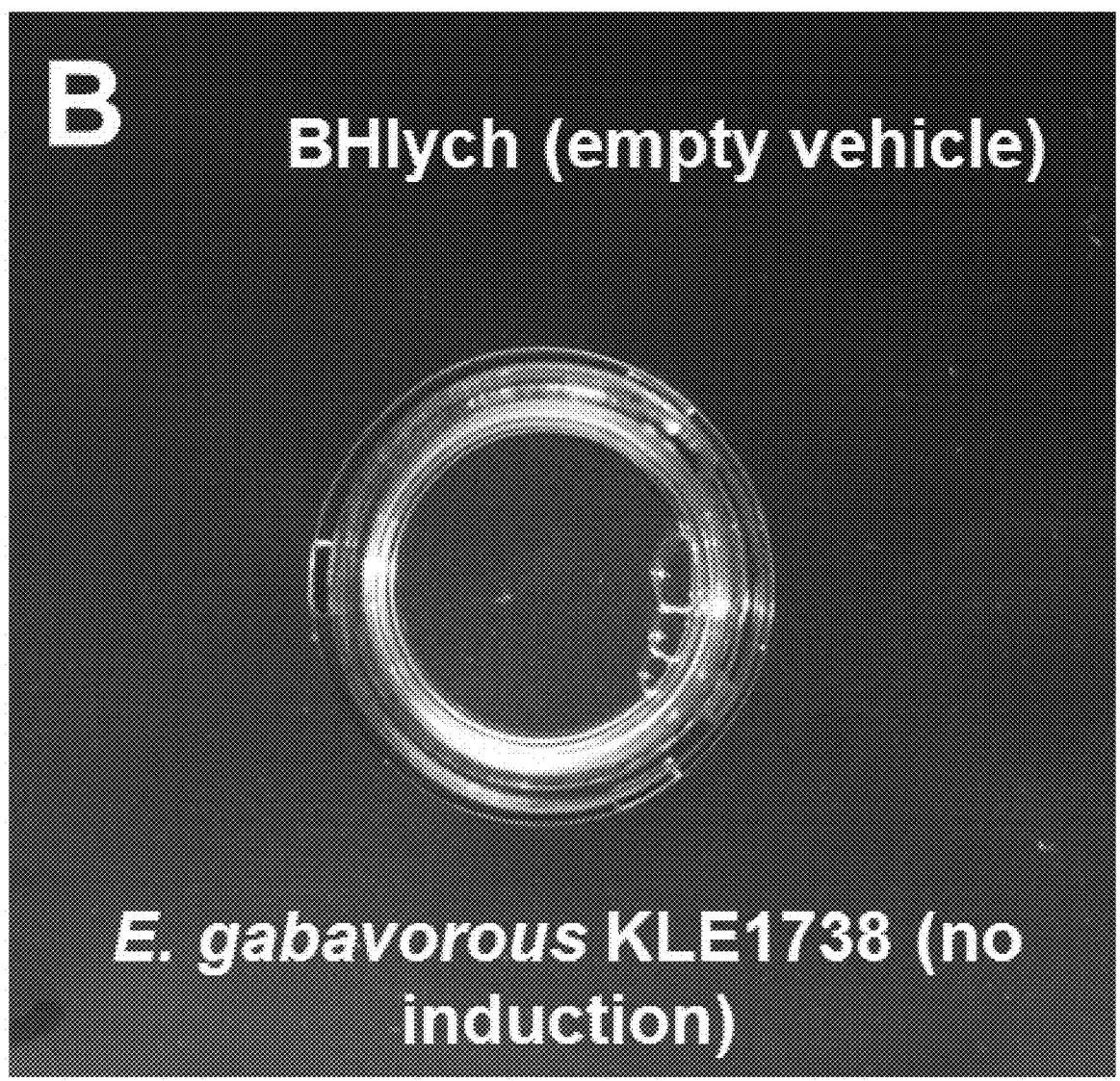
FIG. 2B shows a lack of growth of *Evtepia gabavorous* KLE1738 in the presence of the empty vehicle.
Figure 2C:
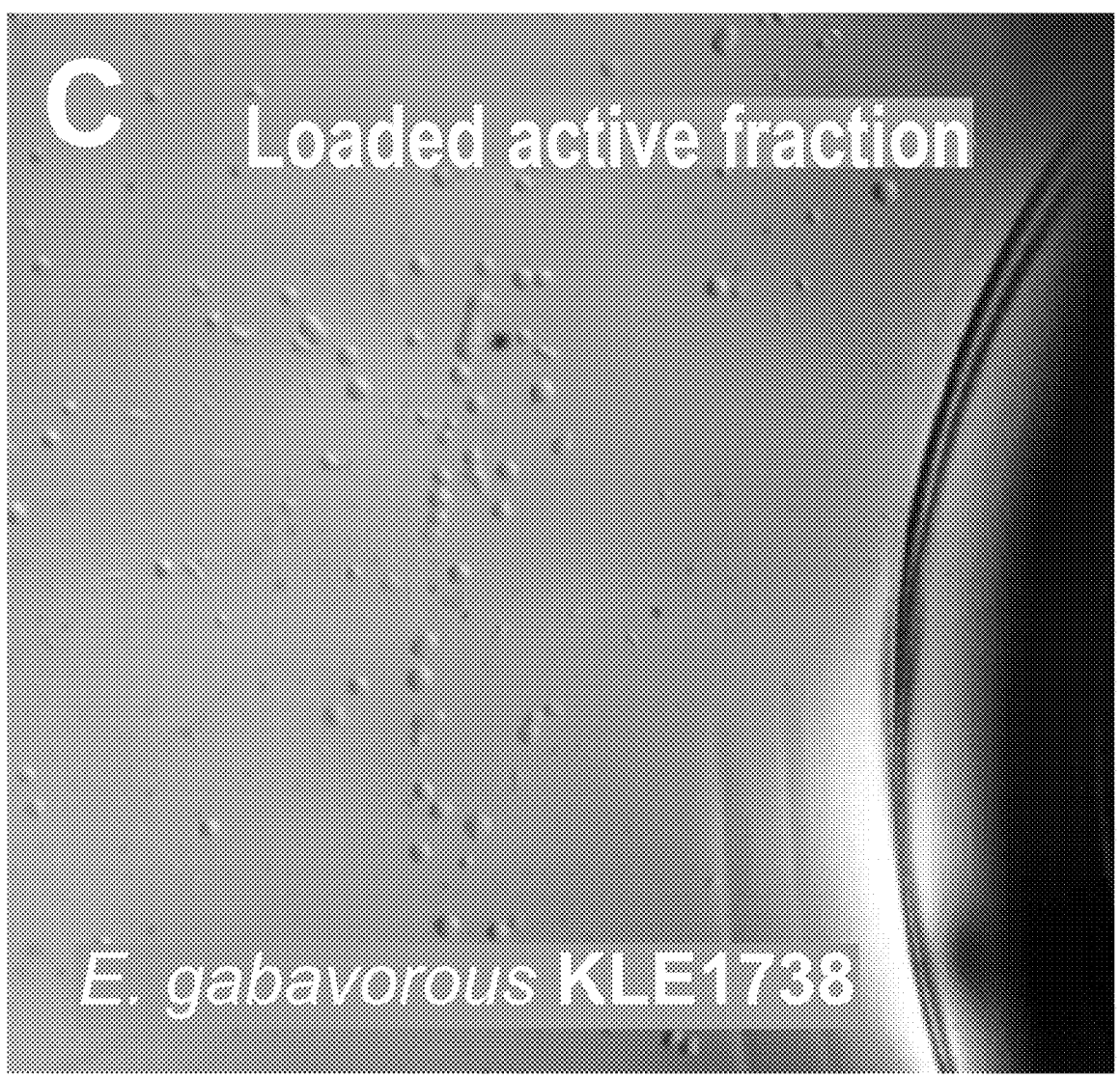
FIG. 2C shows the growth of *Evtepia gabavorous* in the presence of the most polar fraction of the supernatant from *Bacteroides fragilis* KLE1758.
Figure 2D:
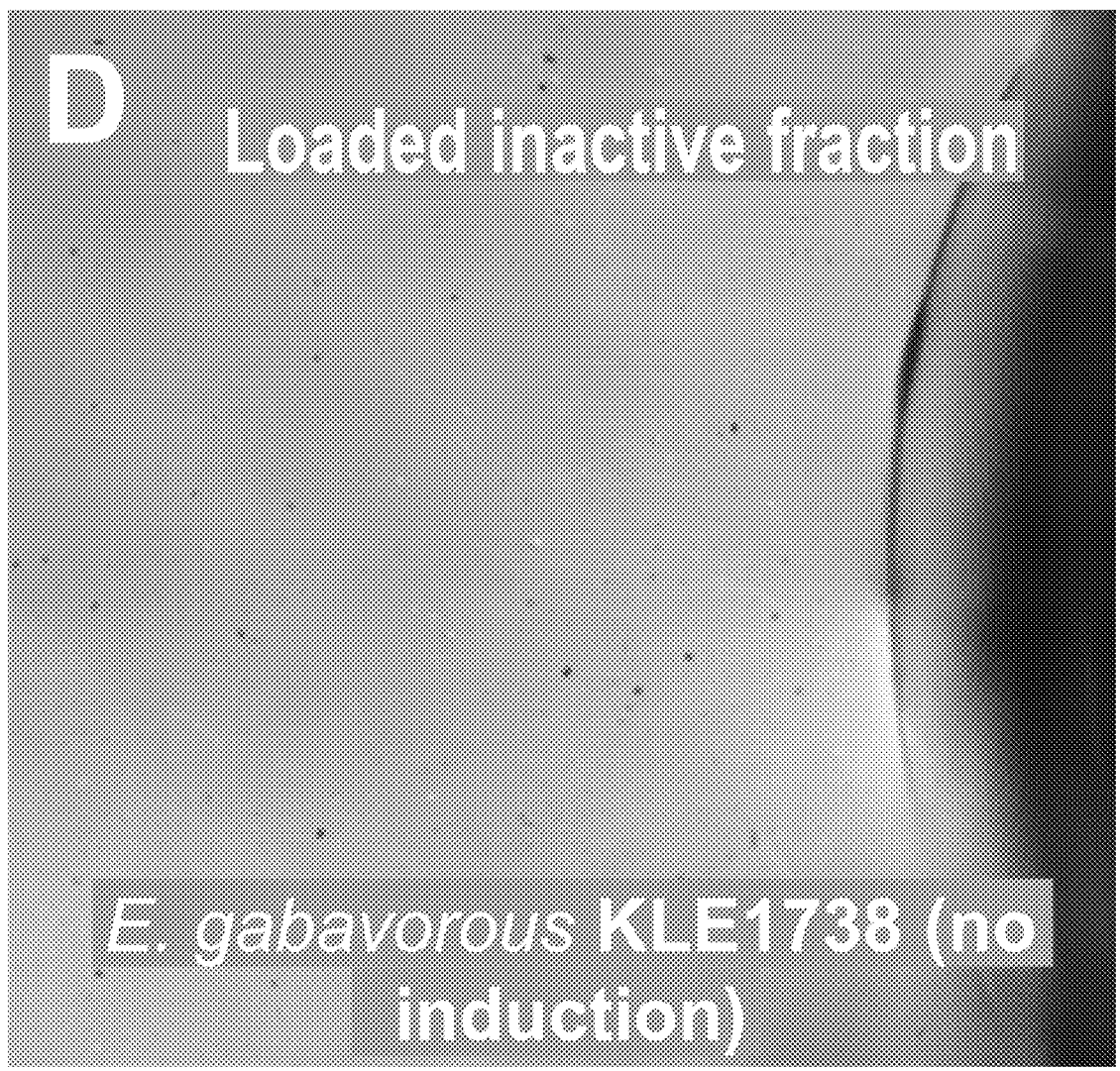
FIG. 2D shows a close-view of the lack of growth of *Evtepia gabavorous* KLE1738 in the presence of the empty vehicle.
Figure 2E:
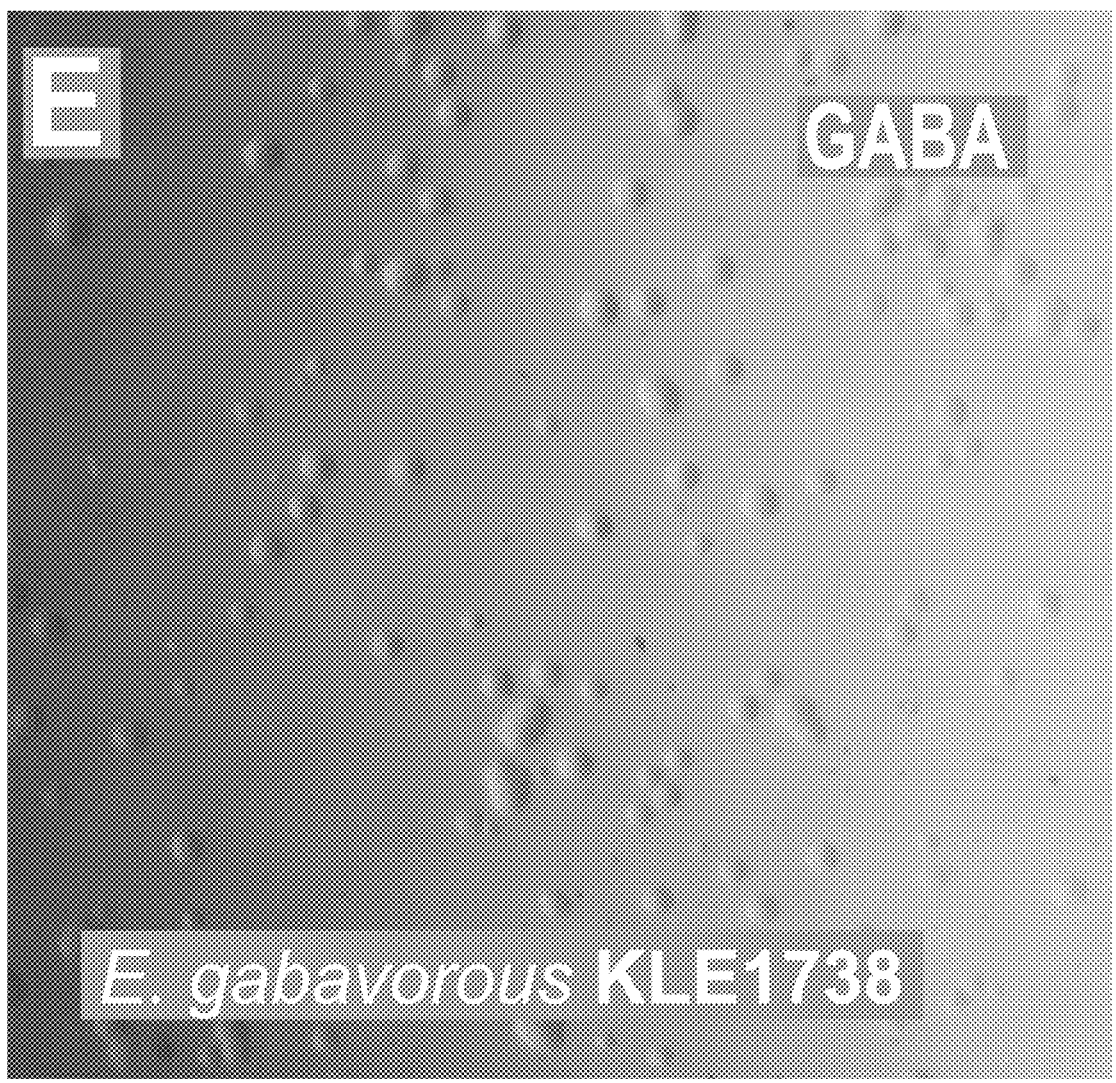
FIG. 2E shows a close-view of the growth of *Evtepia gabavorous* KLE1738 in the presence of the supernatant from *Bacteroides fragilis* KLE1758.
Figure 2F:
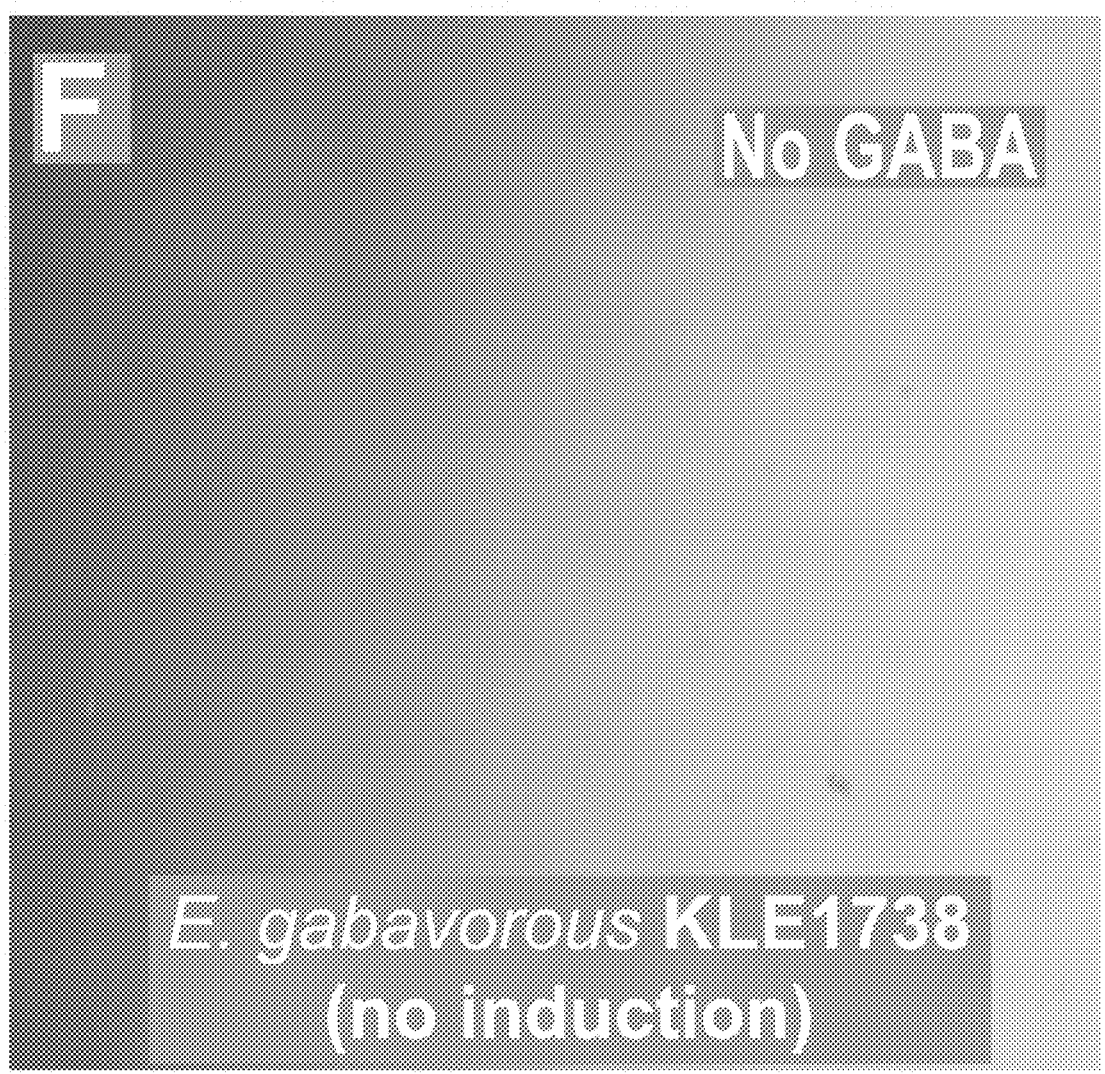
FIG. 2F shows a close-view of the lack of growth of *Evtepia gabavorous* KLE1738 in the presence of the empty vehicle (bacterial media).

The supernatant of a 48-hour culture of *B. fragilis* KLE1758 grown in rich medium induced growth of *E. gabavorous* as shown in FIGS. 2A and 2B, enabling bioassay-driven purification of the growth factor. The supernatant was solvent-partitioned with ethyl acetate, and the water residue fraction induced the growth of *E. gabavorous*. The water fraction was then purified using HP-20 column chromatography, and the most polar fraction induced the growth of *E. gabavorous* as shown in FIG. 2C. This active fraction was then further fractionated by preparative HPLC. HPLC yielded one active fraction, and NMR showed that it contained 10 compounds, primarily GABA, threonine, lactic acid, valine, glutamine, malonic acid, succinic acid, and alanine. All compounds were spotted on plates where *E. gabavorous* was spread, and only GABA caused growth induction, as shown in FIGS. 2E-F. The compounds were identified by NMR analysis including $^1H$, $^{13}C$, $^1H$-$^1H$ COSY, TOCY, HSQC, and HMBC NMR experiments to identify the constituents in the fraction. All NMR experiments were carried out on a Varian INOVA 600 MHz NMR spectrometer equipped with an indirect detection probe.

Example 4: Testing Other Compounds for Induction of E. gabavorous

Multiple compounds were tested for the ability to induce the growth of E. gabavorous as shown in FIG. 2G. Stocks of each compound (purchased from Sigma, excluding the ATCC Mineral and Vitamin mixes) were prepared dependent on solubility in water at the concentrations shown in FIG. 2G. Five µL of the stocks were then spotted on FAAy plates spread with E. gabavorous, and incubated anaerobically for one week, and any growth was observed. No compounds induced growth but GABA.

Example 5: Whole Genome Sequencing and Annotation

DNA from cells of E. gabavorous grown 48 hours anaerobically on FAAy plates with 1.0 mg/mL GABA was isolated for genome sequencing using the PowerSoil® DNA Isolation Kit (Mo Bio, San Diego, Calif.) to manufacturer specifications, yielding ~5.0 µg of high quality DNA. Genomic sequencing and de novo assembly was performed by the Genomic Core at Tufts University in Boston, Mass. The genome of E. gabavorous was sequenced on an Illumina MiSeq using MiSeq V2 500 cycles chemistry with a paired-end 250 bases format. Briefly, 100 ng of genomic DNA was sheared on a Covaris M220 to an average fragment size of around 600 bases. Using the fragmented DNA as input, a sequencing library was prepared with Illumina TruSeq Nano DNA Sample Preparation Kit per the manufacturer instruction. Base calling and demultiplexing was performed on the raw data from the MiSeq using CASAVA and fastq files were generated. De novo assembly of the genome was performed using Edena V3.131028 with a customized parameter optimization pipeline. The best assembled genome, as assessed by the contig statistic, was reported. Assembly yielded 68 contigs (n), with all contigs having a sequence length longer than 200 bases (n:200). 7 contigs with a larger value than the N50 (119748), and the minimal contig length is 355 (min). The N20, N50 and N20 are 33403, 119748 and 204670, respectively. The largest contig length (max) was 344080, and the estimated genome size is 2500009. The draft genome was annotated using the RAST server and the KAAS (KEGG Automatic Annotation Server) analysis tool of the KEGG (Kyoto Encyclopedia of Genes and Genomes) database. The genome of E. gabavorous was annotated using RAST, and the genomes of CAG:113 and E. gabavorous were compared using RAST.

Example 6: Quantification of Glutamate and GABA Production in B. fragilis

The absolute amount of glutamate and GABA contained in the B. fragilis KLE1758 supernatant was determined by HPLC, using a fluorophore to aid in detection. Specifically, free amines were labeled for analysis by reacting with the AccQ reagent (Waters) according to manufacturer's protocols. A calibration curve was generated from stock solutions (10 mg/mL) that were prepared by dissolving GABA (2.0 mg) in water (200 µL), glutamate (Glu) (10.2 mg) in water (1020 µL) and cysteic acid (CSA) (16.9 mg) in water (1690 µL). These were serially diluted to generate a concentration gradient. Specifically, stocks were made to final concentrations of 0.1 mg/mL, 0.05 mg/mL, 0.01 mg/mL and 0.001 mg/mL. An aliquot of a given stock solution, was added to the AccQ reaction buffer (25 µL final), followed by the addition of the acetonitrile-dissolved AccQ reagent (25 µL). This was reacted for ten minutes at 55-60° C., and then transferred directly to an LCMS vial, fitted with a glass insert. Reaction concentrations of the amino acids were: 20 ng/µL, 10 ng/µL, 5 ng/µL, 2.5 ng/µL, 1 ng/µL, 0.5 ng/µL, 1 ng/µL and 0 ng/µL (control). These samples were injected (10 µL) on an Agilent LCMS, using a gradient of solvent A (water/0.1% formic acid) and B (acetonitrile/0.1% formic acid) over the following time course: 1) 0-40 minutes linear gradient of 2% B to 98% B; 2) 40-45 min isocratic at 98% B; 3) 45-45.5 min linear gradient of 98% B to 2% B; 4) 45.5-55 min isocratic at 2% B. The CSA-AccA derivative eluted at 9.5 min, the Glu-AccQ derivative eluted at 12.1 min and the GABA-AccQ derivative at 12.5 min. The area under the curve, in extracted ion (EIC) mode (m/z=274 for GABA-AccQ, 318 for Glu-AccQ and 340 for CSA-AccQ), was used to develop a calibration curve by plotting area against amount of original Glu, CSA or GABA (in ng) injected. An average of two runs for each tested concentration was used to generate the calibration curve. In the case of GABA and Glu, CSA was added to all reactions, to a final concentration of 2.5 µg/mL, and used as an internal standard.

Triplicate cultures of B. fragilis KLE1758 were grown in BHIych anaerobically for 48 hours, the cells centrifuged, and the supernatant was filtered through a 0.2 µm filter. Samples were stored at 4° C. until analysis. To analyze the samples, an aliquot (2 µL) of each sample was added to AccQ reaction buffer (16 µL), CSA internal standard (2 µL of a 50 µg/mL solution in buffer), followed by the addition of the AccQ reagent (20 µL). These samples were heated to 55° C. for ten minutes, and then transferred directly into an LCMS vial fitted with a glass insert. An aliquot of each sample (10 µL) was injected onto the LCMS, and separated following the same injection program as used for the calibration curve. The total EIC area under curves representing GABA, Glu and CSA was determined using ChemStation software (Agilent). Each injection represented 25% of the original media concentration, therefore the total amount of sample determined (in ng) was multiplied by a factor of four to determine the original concentration (in ng/µL=µg/mL). All areas were normalized to the area under the curve of the internal standard (CSA), which was held at constant concentration throughout the experiment. The results are given in FIG. 4A.

Example 7: Co-Culture Screen for GABA Producers Using E. gabavorous

GABA secretion can allow bacteria to survive acid stress. Decarboxylation of glutamate produces GABA, which is exported from the cell in a protonated form, alkalinizing the cytoplasm. E. coli, as well as some Lactobacillus and Bifidobacterium strains were shown to produce GABA, but these organisms are typically found at a low abundance in the human intestinal tract, and in the case of E. coli, is dependent on low pH (e.g., about 4.2 and below). Bacteroides fragilis, the helper of E. gabavorous, is a common gut bacterium, but it was found that similarly to E. coli. GABA production by Bacteroides fragilis KLE1758 is only observed at a pH less than about 5.5 as shown in FIG. 4A. GABA is shown in left-hand columns and glutamate is shown in right-hand columns at each pH value. Without wishing to be bound by theory, it was therefore considered useful to identify microorganisms capable of producing GABA at a physiologically relevant pH for the human large intestine (e.g., pH of about 5.5 to about 7.5, or about pH 5.7 to about 7.4).

To accomplish this, the strict GABA requirement of *E. gabavorous* was utilized to screen for bacteria capable of secreting GABA on heavily buffered medium. Metabolic byproducts of bacterial growth may lower the pH of the medium in the absence of buffer. Stool sample was mixed with molten agar and poured in Petri plates in an anaerobic chamber, and *E. gabavorous* was spread on top of the agar once solidified. By looking for zones of growth induction of *E. gabavorous*, and measuring the pH of the agar, bacteria that produce GABA at a pH of between about 6.0 and about 7.0 were identified, as well as those producing GABA at a pH of about 4.5 to about 5.0, as shown in FIG. 4B. The full 16S rRNA gene was amplified and sequenced using the 27F and 1492R universal primers, and annotation with EZTaxon revealed a number of representatives from multiple genera, including *Bacteroides, Bifidobacterium, Blautia, Coprococcus, Gordonibacter, Dorea,* and *Clostridium* (FIG. 4C). Of these, only *Bifidobacterium adolescentis* was previously reported to produce GABA.

Example 8: Using an Engineered *Escherichia coli* Strain to Produce GABA and Induce the Growth of *E. gabavorous*

GABA can be produced by intestinal epithelial cells and by some bacteria, such as *Escherichia coli* and *Listeria monocytogenes*, by decarboxylation of glutamate. In *E. coli*, the decarboxylation of glutamate serves as a mechanism to decrease intracellular pH, and GABA production generally occurs at a low pH. To survey whether *E. coli* could be engineered to produce GABA. *E. coli* colones harboring native glutamate decarboxylases (gadA, gadB), or the GABA antiporter. (gadC) in the pCA24N IPTG inducible high-copy number vector, were tested for GABA production via co-cultivation assay with *E. gabavorous*. Overexpression of glutamate decarboxylase in *E. coli* (gadA or gadB), resulted in induction of KLE1738 growth to levels seen with *B. fragilis*, while expression of the GABA antiporter, gadC, did not (FIG. 6). Altering the pH of growth media for KLE1738 did not change the GABA-dependency phenotype. Without wishing to be bound by theory, this suggests that engineering bacteria to overexpress glutamate decarboxylase or other GABA producing enzymes, constitutively or inducibly, is an effective way to produce GABA, as well as induce the growth of *E. gabavorous*.

EQUIVALENTS

While the present disclosure has been described in conjunction with the specific embodiments set forth above, many alternatives, modifications and other variations thereof will be apparent to those of ordinary skill in the art. All such alternatives, modifications and variations are intended to fall within the spirit and scope of the present disclosure.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11116804B2). An electronic copy of the "Sequence Listing" will also be available from the USPTO upon request and payment of the fee set forth in 37 CFR 1.19(b)(3).

The invention claimed is:

1. A therapeutic composition comprising at least one purified bacterial population that produces GABA at a pH range of between 4.5 and 7.5, the at least one purified bacterial population consisting of bacteria comprising a 16s rDNA sequence at least 98% identical to a 16s rDNA sequence selected from the group consisting of SEQ ID Nos. 1-4, 8, 10, 12, 16-18, 28-29 and 81.

2. The therapeutic composition of claim 1, wherein the at least one bacterial population consists of bacteria comprising a 16S rDNA sequence at least 99% identical to a 16S rDNA sequence selected from the group consisting of SEQ ID Nos. 1-4, 8, 10, 12, 16-18, 28-29 and 81.

3. The therapeutic composition of claim 1, wherein the at least one purified bacterial population consists of bacteria selected from the group consisting of: *Bacteroides* caccae; *Bacteroides clarus; Bacteroides* dorei; *Bacteroides* finegoldii; *Bacteroides* stercoris; *Bacteroides uniformis; Bacteroides* xylanisolvens; *Butyricimonas virosa; Clostridium perfringens; Clostridium sordellii; Parabacteroides distasonis; Parabacteroides merdae; Ruminococcus gnavus; Bacteroides salyersiae*, and combinations thereof.

4. The therapeutic composition of claim 1, wherein the at least one purified bacterial population consists of bacteria comprising a DNA sequence which encodes an enzyme selected from: glutamate decarboxylase; putrescine aminotransferase; gamma-aminobutyraldehyde dehydrogenase; arginine decarboxylase; agmatinase; ornithine decarboxylase; or a combination thereof.

5. The therapeutic composition of claim 4, wherein the glutamate decarboxylase; putrescine aminotransferase; gamma-aminobutyraldehyde dehydrogenase; arginine decarboxylase; agmatinase; ornithine decarboxylase; or a combination thereof, is encoded by a DNA sequence at least 50% identical in DNA sequence to any one of Seq. ID. Nos. 275-304.

6. The therapeutic composition of claim 4, wherein the glutamate decarboxylase is encoded by a DNA sequence at least 50% identical in DNA sequence to a sequence selected from SEQ ID Nos. 275-279.

7. The therapeutic composition of claim 4, wherein the ornithine decarboxylase is encoded by a DNA sequence at least 50% identical to a sequence selected from the group consisting of SEQ ID Nos. 300-304, the gamma-aminobutyraldehyde dehydrogenase is encoded by a DNA sequence at least 50% identical to a sequence selected from the group consisting of SEQ ID Nos. 285-289, and the putrescine aminotransferase is encoded by a DNA sequence at least 50% identical to a sequence selected from the group consisting of SEQ ID Nos. 280-284.

8. The therapeutic composition of claim 4, wherein the arginine decarboxylase is encoded by a DNA sequence at least 50% identical to a sequence selected from the group consisting of SEQ ID Nos. 290-294, the agmatinase is encoded by a DNA sequence at least 50% identical to a sequence selected from the group consisting of SEQ ID Nos. 295-299 and the gamma aminobutyraldehyde dehydrogenase is encoded by a DNA sequence at least 50% identical to a sequence selected from the group consisting of SEQ ID Nos. 285-289.

9. The therapeutic composition of claim 1, wherein the composition is in the form of a capsule, a tablet, a caplet, a pill, a troche, a lozenge, a powders, a granule, a medical food, a fecal transplant or a combination thereof.

10. The therapeutic composition of claim 1, wherein the bacteria are capable of producing GABA via expression of any combination of glutamate decarboxylase, putrescine aminotransferase, gamma-aminobutyraldehyde dehydrogenase, arginine decarboxylase, agmatinase, and/or ornithine decarboxylase.

11. The therapeutic composition of claim 1, further comprising a purified bacterial strain that is cytotoxic or cytostatic to a GABA-consuming bacteria.

12. The therapeutic composition of claim 11, wherein the GABA-consuming bacteria is *Evtepia gabavorous* or *Firmicutes bacterium* MGS:114.

13. The therapeutic composition of claim 1, further comprising a prebiotic capable of stimulating the growth or GABA-production levels of a GABA-producing bacteria.

14. The therapeutic composition of claim 1, wherein the at least one purified bacterial population consists of *Bacteroides* caccae, *Bacteroides* clarus, *Bacteroides* dorei, *Bacteroides* finegoldii, *Bacteroides* stercoris, *Bacteroides* salyersiae, *Bacteroides* uniformis, *Bacteroides* xylanisolvens, *Parabacteroides merdae*, Parabacteriodes *distasonis*, and combinations thereof.

15. The composition of claim 1, wherein the composition is a probiotic.

16. The composition of claim 1, further comprising a prebiotic.

17. A composition in the form of a prebiotic, probiotic or a medical food, the composition comprising at least one purified bacterial population that produces GABA at a pH range of between 4.5 and 7.5, the at least one purified bacterial population consisting of bacteria comprising a 16s rDNA sequence at least 98% identical to a 16s rDNA sequence selected from the group consisting of SEQ ID Nos. 1-4, 8, 10, 12, 16-18, 28-29 and 81.

18. The composition of claim 17, wherein the prebiotic, probiotic, or medical food is in the form of capsules, tablets, caplets, pills, troches, lozenges, powders, granules, or yoghurt.

* * * * *